US011479598B2

(12) United States Patent
Wec et al.

(10) Patent No.: US 11,479,598 B2
(45) Date of Patent: Oct. 25, 2022

(54) ANTI-YELLOW FEVER ANTIBODIES, AND METHODS OF THEIR GENERATION AND USE

(71) Applicant: Mabloc, LLC, Washington, DC (US)

(72) Inventors: Anna Wec, Lebanon, NH (US); Laura Walker, Norwich, VT (US)

(73) Assignee: Mabloc, Inc., Washington, DC (US)

( * ) Notice: Subject to any disclaimer, the term of this patent is extended or adjusted under 35 U.S.C. 154(b) by 0 days.

(21) Appl. No.: 17/103,844

(22) Filed: Nov. 24, 2020

(65) Prior Publication Data

US 2021/0253675 A1    Aug. 19, 2021

Related U.S. Application Data

(60) Provisional application No. 62/940,049, filed on Nov. 25, 2019.

(51) Int. Cl.
*C07K 16/10* (2006.01)
*A61P 31/14* (2006.01)
*A61K 39/42* (2006.01)

(52) U.S. Cl.
CPC .............. *C07K 16/10* (2013.01); *A61K 39/42* (2013.01); *A61P 31/14* (2018.01); *C07K 2317/76* (2013.01); *C07K 2317/92* (2013.01)

(58) Field of Classification Search
CPC .......... C07K 16/10; A61P 31/14; A61K 39/42
See application file for complete search history.

(56) References Cited

U.S. PATENT DOCUMENTS

| 6,596,541 B2 | 7/2003 | Murphy et al. |
| 2004/0101920 A1 | 5/2004 | Radziejewski et al. |
| 2011/0311515 A1 | 12/2011 | Bouche et al. |
| 2012/0128669 A1 | 5/2012 | Depla et al. |

FOREIGN PATENT DOCUMENTS

| CN | 110343173 A | 10/2019 |
| CN | 110343174 A | 10/2019 |
| WO | 2005/103081 A2 | 11/2005 |
| WO | 2019200160 A1 | 10/2019 |
| WO | 2021108448 A1 | 6/2021 |

OTHER PUBLICATIONS

Lamminmaki et al. "Crystal structure of a recombinant anti-estradiol Fab fragment in complex with 17beta-estradiol", JBC 2001, 276:36687-36694 (Year: 2001).*
Rudikoff etal . "Single amino acid altering antigen-binding specificity", Proc Natl Acad Sci USA 1982 vol. 79 p. 1979 (Year: 1979).*
MacCallum et al. "Antibody-antigen Interactions: Contact Analysis and Binding Site Topography", J. Mol. Biol. (1996) 262, 732-745 (Year: 1996).*
Pascalis et al. "Grafting of "Abbreviated" Complementarity-Determining Regions Containing Specificity-Determining Residues Essential for Ligand Contact to Engineer a Less Immunogenic Humanized Monoclonal Antibody", The Journal of Immunology (2002) 169, 3076-3084 (Year: 2002).*
Casset et al. "A peptide mimetic of an anti-CD4 monoclonal antibody by rational design", BBRC 2003, 307:198-205 (Year: 2003).*
Vajdos et al. "Comprehensive functional maps of the antigen-binding site of an anti-ErbB2 antibody obtained with shotgun scanning mutagenesis", J. Mol. Biol. (2002) 320, 415-428 (Year: 2002).*
Chen et al. "Selection and analysis of an optimized anti-VEGF antibody: crystal structure of an affinity-matured Fab in complex with antigen", J. Mol. Bio. (1999) 293, 865-881 (Year: 1999).*
Wu et al. "Humanization of a murine monoclonal antibody by simultaneous optimization of framework and CDR residues", J. Mol. Biol. (1999) 294, 151-162 (Year: 1999).*
Padlan et al. "Structure of an antibody-antigen complex: crystal structure of the HyHEL-10 Fab-lysozyme complex", PNAS 1989, 86:5938-5942 (Year: 1989).*
Altschul et al. (1990) "Basic Local Alignment Search Tool", Journal of Molecular Biology, 215(3):403-410.
Altschul et al. (1997) "Gapped BLAST and PSI-BLAST: A New Generation of Protein Database Search Programs", Nucleic Acids Research, 25(17):3389-3402.
Bitonti et al. (2006) "Pulmonary Administration of Therapeutic Proteins Using an Immunoglobulin Transport Pathway", Advanced Drug Delivery Reviews, 58(9-10):1106-1118.
Bornholdt et al. (Mar. 2016) "Isolation of Potent Neutralizing Antibodies from a Survivor of the 2014 Ebola Virus Outbreak", Science, 351(6277):1078-1083.
Daffis et al. (2005) "Antibody Responses Against Wild-type Yellow Fever Virus and the 17D Vaccine Strain: Characterization with Human Monoclonal Antibody Fragments and Neutralization Escape Variants", Virology, 337:262-272.
Ehring Hanno (1999) "Hydrogen Exchange/Electrospray Ionization Mass Spectrometry Studies of Structural Features of Proteins and Protein/Protein Interactions", Analytical Biochemistry, 267(2):252-259.
Engen et al. (May 1, 2001) "A Powerful New Approach That Goes Beyond Deciphering Protein Structures", Analytical Chemistry, 73(9):256A-265A.
Gonnet et al. (Jun. 5, 1992) "Exhaustive Matching of the Entire Protein Sequence Database", Science, 256(5062):1443-1445.
Hochleitner et al. (2000) "Characterization of a Discontinuous Epitope of the Human Immunodeficiency Virus (HIV) Core Protein p24 by Epitope Excision and Differential Chemical Modification Followed by Mass Spectrometric Peptide Mapping Analysis", Protein Science, 9(3):487-496.

(Continued)

*Primary Examiner* — Amy E Juedes
*Assistant Examiner* — Peter Johansen
(74) *Attorney, Agent, or Firm* — Mintz, Levin, Cohn, Ferris, Glovsky & Popeo, P.C.

(57) ABSTRACT

Antibodies and antigen-binding fragments thereof specific to the YFV E protein and with neutralizing potency against YFV are provided. These antibodies and antigen-binding fragments are useful in treating YFV.

14 Claims, 24 Drawing Sheets

Specification includes a Sequence Listing.

(56) References Cited

OTHER PUBLICATIONS

Junghans et al. (Mar. 1, 1990) "Anti-Tac-H, a Humanized Antibody to the Interleukin 2 Receptor with New Features for Immunotherapy in Malignant and Immune Disorders", Cancer Research, 50(5):1495-1502.
Kufer et al. (May 1, 2004) "A Revival of Bispecific Antibodies", Trends in Biotechnology, 22(5):238-244.
Langer Robert (Sep. 28, 1990) "New Methods of Drug Delivery", Science, 249:1527-1533.
Lu et al. (Jan. 8, 2019) "Double Lock of a Human Neutralizing and Protective Monoclonal Antibody Targeting the Yellow Fever Virus Envelope", Cell Reports, 26(2):438-446.
Maillet et al. (Jun. 2008) "Aerodynamical, Immunological and Pharmacological Properties of the Anticancer Antibody Cetuximab Following Nebulization", Pharmaceutical Research, 25(6):1318-1326.
McGuinness et al. (2017) "An Overview of Yellow Fever Virus Disease", The Neurohospitalist, 7(4):157-158.
Pugachev et al. (Jan. 2004) "High Fidelity of Yellow Fever Virus RNA Polymerase", Journal of Virology, 78(2):1032-1038.
Reineke Ulrich (2004) "Antibody Epitope Mapping Using Arrays of Synthetic Peptides", Methods in Molecular Biology, 248:443-463.
Taylor et al. (1992) "A Transgenic Mouse that Expresses A Diversity of Human Sequence Heavy and Light Chain Immunoglobulin", Nucleic Acids Research, 20(23):6287-6295.
Tiller et al. (Jan. 1, 2008) "Efficient Generation of Monoclonal Antibodies from Single Human B Cells by Single Dell RT-PCR and Expression Vector Cloning", Journal of Immunological Methods, 329(1-2):112-124.
Tutt et al. (Jul. 1, 1991) "Trispecific F(ab')3 Derivatives that use Cooperative Signaling via the TCR/CD3 Complex and CD2 to Activate and Redirect Resting Cytotoxic T Cells", Journal of Immunology, 147(1):60-69.

UNIPROT (Jul. 21, 1986) "Genome Polyprotein", Accession No. P03314, 30 pages.
UNIPROT (Nov. 28, 2006) "Genome Polyprotein", Accession No. Q6DV88, 25 pages.
Vajdos et al. (Jul. 5, 2002) "Comprehensive Functional Maps of the Antigen-Binding Site of an Anti-ErbB2 Antibody Obtained with Shotgun Scanning Mutagenesis", Journal of Molecular Biology, 320(2):415-428.
Volk et al. (Nov. 10, 2009) "Structure of Yellow Fever Virus Envelope Protein Domain III", Virology, 394(1):12-18.
Vratskikh et al. (Jun. 2013) "Dissection of Antibody Specificities Induced by Yellow Fever Vaccination", PLOS Pathogens, e1003458, 9(6):1-12.
Wu et al. (1987) "Receptor-Mediated in Vitro Gene Transformation by a Soluble DNA Carrier System", The Journal of Biological Chemistry, 262(10):4429-4432.
Zhang et al. (2017) "Structures and Functions of the Envelope Glycoprotein in Flavivirus Infections", Viruses, 9(11):338(14 pages).
Gietz et al. (2007) "High-efficiency Yeast Transformation Using the LiAc/SS Carrier DNA/PEG Method", Nature Protocols, 2(1):31-34.
Gietz et al. (2007) "Large-scale High-efficiency Yeast Transformation Using the LiAc/SS Carrier DNA/PEG Method", Nature Protocols, 2(1):38-41.
International Search Report and Written Opinion corresponding to International Application No. PCT/US2020/062084 dated Apr. 19, 2021.
Calvert et al. "A Humanized Monoclonal Antibody Neutralizes Yellow Fever Virus Strain 17D-204 in Vitro but does not Protect a Mouse Model from Disease", Antiviral Research 131:92-99 (Jul. 2016).
Dondelinger et al. "Understanding the Significance and Implications of Antibody Numbering and Antigen-Binding Surace/Residue Definition", Frontiers in Immunology 9:2278 (Oct. 16, 2018).

\* cited by examiner

ANTI-YELLOW FEVER ANTIBODIES, AND METHODS OF THEIR GENERATION AND USE

CROSS-REFERENCE TO RELATED APPLICATIONS

This application claims priority to U.S. Provisional Application No. 62/940,049, filed Nov. 25, 2019, which is hereby incorporated by reference in its entirety.

REFERENCE TO A "SEQUENCE LISTING," A TABLE, OR A COMPUTER PROGRAM LISTING APPENDIX SUBMITTED AS AN ASCII FILE

The Sequence Listing written in file MAB-01001WO_SequenceListing_ST25.txt, created May 7, 2021, 499,368 bytes, machine format IBM-PC, MS Windows operating system, is hereby incorporated by reference.

FIELD OF THE DISCLOSURE

The disclosure relates to anti-Yellow Fever Virus (YFV) antibodies and antigen-binding fragments thereof, and compositions containing such antibodies and antigen-binding fragments thereof, and therapeutic and diagnostic uses for the antibodies, antigen-binding fragments, and compositions.

BACKGROUND OF THE DISCLOSURE

Yellow Fever Virus (YFV) is a mosquito-borne flavivirus found in tropical and subtropical areas of Africa and South America. It is transmitted to humans primarily through the bite of infected *Aedes* or *Haemagogus* mosquito species and has three distinct transmission cycles: 1) jungle or sylvatic cycle; 2) African savannah (intermediate) cycle; and 3) urban cycle. (see the World Wide Web website at cdc.gov/yellowfever/transmission/index.html). While many people infected with YFV are asymptomatic, others develop symptoms such as fever, chills, headache, low back pain, myalgia, loss of appetite, nausea, vomiting, and/or fatigue following an incubation period of 3-6 days. (see the World Wide Web website at who.int/news-room/fact-sheets/detail/yellow-fever). Roughly 15% of people infected develop a severe form of YFV that includes high fever, bleeding diatheses, abdominal pain, renal failure, cardiovascular instability, and liver failure; up to 50% of patients with the severe form of YFV will die. (McGuinness et al, Neurohospitalist 2017, 7(4); 157-158).

YFV has a RNA genome of 10,862 nucleotides that encode three structural and seven non-structural proteins. From the 5' terminus, the order of the encoded proteins is: C; prM/M; E; NS1; NS2A; NS2B; NS3; NS4A; NS4B and NS5. The three structural proteins include the C (capsid) protein, the membrane protein, M, and the envelope protein, E. The envelope protein plays an important role in cell tropism, virulence, and immunity.

Live attenuated 17D vaccine is considered one of the safest and most efficacious vaccines developed to date. However, despite the availability of the vaccine, Yellow Fever remains a serious public health issue. There are some data suggesting immunity, though protective, may wane over time in certain populations. Additionally, YFV outbreaks in non-endemic countries (such as the 11 imported cases in China in 2016) and concurrent outbreaks exhausting stockpiles of 17D have underscored the importance of developing a treatment.

Indeed, to date there are currently no approved YFV treatments (the only course being supportive therapy) and, despite decades of research, the development of safe and effective therapeutic antibodies against YFV has remained elusive. The YFV E-specific serum antibody response has been shown to be overwhelmingly mediated by antibodies targeting domain I (DI) and/or domain II (DII) of the E protein, whereas antibodies targeting domain III (DIII) are absent or present at very low titers (DVratskikh et al. PLoS pathogens 9, e1003458 (2013)). Correspondingly, the six YFV E-specific human monoclonal antibodies described to date all target overlapping epitopes within DII of the E protein (Lu et al. Cell Reports 26, 438-446 e435 (2019); Daffis et al. Virology 337, 262-272 (2005)). Recently, the crystal structure of one of these mAbs (5A) in complex with a soluble YFV E dimer was determined, which showed that this mAb binds to a conserved neutralizing epitope within DII of one E monomer (Lu et al. Cell Reports 26, 438-446 e435 (2019)). Therefore, there remains a need for highly specific, high affinity, and highly potent neutralizing anti-YFV antibodies and antigen-binding fragments thereof.

SUMMARY OF THE DISCLOSURE

The disclosure pertains to the discovery of antibodies and antigen-binding fragments thereof that bind to YFV protein and exhibit neutralizing potency, in particular antibodies binding to the domain III (DIII) of the E protein that exhibit high neutralization potency. The antibodies of the present disclosure may also cross-react with other flaviviruses, e.g., display binding reactivity to DENV-2, DENV-4, WNV, and/or ZIKV E proteins. An extensive panel of YFV-specific monoclonal antibodies is described. Binding studies demonstrated that the neutralizing antibody response to YFV-17D is primarily mediated by antibodies that recognize FL proximal epitopes within DII of the YFV E protein. A small set of DIII-targeting antibodies having potent neutralizing activity was also identified. Additionally, binding assays revealed that YFV-17D vaccination appears to induce a subset of antibodies that display broad flavivirus binding activity, the majority of which target the highly conserved FL and show little to no cross-neutralizing activity. Neutralization studies showed a proportion of antibodies display highly potent neutralizing activity. Altogether, the panel of antibodies described herein provides promising therapeutic candidates and a framework for the rational design of YFV vaccines.

Such antibodies may be useful when administered prophylactically (prior to exposure to the virus and infection with the virus) to lessen the severity, or duration of a primary infection with YFV, or ameliorate at least one symptom associated with the infection. The antibodies may be used alone or in conjunction with a second agent useful for treating an YFV infection. In certain embodiments, the antibodies may be given therapeutically (after exposure to and infection with the virus) either alone, or in conjunction with a second agent to lessen the severity or duration of the primary infection, or to ameliorate at least one symptom associated with the infection. In certain embodiments, the antibodies may be used prophylactically as stand-alone therapy to protect patients who are at risk for acquiring an infection with YFV, such as those described above. Any of these patient populations may benefit from treatment with the antibodies of the disclosure, when given alone or in conjunction with a second agent, including for example, an anti-viral therapy, or other anti-viral vaccines.

In certain embodiments are provided isolated antibodies or antigen-binding fragments thereof that specifically bind to YFV, wherein at least one of a CDRH1, a CDRH2, a CDRH3, a CDRL1, a CDRL2, and a CDRL3 amino acid sequence of such antibodies or the antigen-binding fragments thereof is at least 70% identical; at least 75% identical; 80% identical; at least 85% identical; at least 90% identical; at least 95% identical; at least 96% identical; at least 97% identical; at least 98% identical; at least 99%; and/or all percentages of identity in between; to at least one of the CDRH1, CDRH2, CDRH3, CDRL1, CDRL2, and/or CDRL3 amino acid sequences as disclosed in Table 3 of an antibody selected from Antibody Number 1 through Antibody Number 152 as disclosed in Table 3.

The antibody or the antigen-binding fragment thereof may also have one or more of the following characteristics: a) the antibodies or antigen-binding fragments thereof display a clean or low polyreactivity profile; b) the antibodies or antigen-binding fragments thereof display an in vitro neutralization potency ($IC_{50}$) of between about 0.5 microgram/milliliter (µg/ml) to about 5 µg/ml; between about 0.05 µg/ml to about 0.5 µg/ml; or less than about 0.05 mg/ml; c) the antibodies or antigen-binding fragments thereof bind YFV-17D particles; or d) the antibody or antigen-binding fragment thereof binds to an envelope protein of YFV. In certain embodiments, the isolated antibodies or antigen-binding fragments thereof comprise at least two; at least three; or 4 of characteristics a) through d) above.

In certain other embodiments, the isolated antibodies or antigen-binding fragments thereof comprise: a) the CDRH1 amino acid sequence of any one of the antibodies designated Antibody Number 1 through Antibody Number 152 as disclosed in Table 3; b) the CDRH2 amino acid sequence of any one of the antibodies designated Antibody Number 1 through Antibody Number 152 as disclosed in Table 3; c) the CDRH3 amino acid sequence of any one of the antibodies designated Antibody Number 1 through Antibody Number 152 as disclosed in Table 3; d) the CDRL1 amino acid sequence of any one of the antibodies designated Antibody Number 1 through Antibody Number 152 as disclosed in Table 3; e) the CDRL2 amino acid sequence of any one of the antibodies designated Antibody Number 1 through Antibody Number 152 as disclosed in Table 3; f) the CDRL3 amino acid sequence of any one of the antibodies designated Antibody Number 1 through Antibody Number 152 as disclosed in Table 3; and/or g) any combination of two or more of a), b), c), d), e), and f).

In certain other embodiments, the isolated antibodies or antigen-binding fragments thereof are selected from the group consisting of antibodies that are at least 70% identical; at least 75% identical; 80% identical; at least 85% identical; at least 90% identical; at least 95% identical; at least 96% identical; at least 97% identical; at least 98% identical; at least 99%; and/or all percentages of identity in between; to any one of the antibodies designated as Antibody Number 1 through Antibody Number 152 as disclosed in Table 3.

In certain other embodiments, the isolated antibodies or antigen-binding fragments thereof comprise: a) a heavy chain (HC) amino acid sequence of any one of the antibodies designated Antibody Number 1 through Antibody Number 152 as disclosed in Table 3; and/or b) a light chain (LC) amino acid sequence of any one of the antibodies designated Antibody Number 1 through Antibody Number 152 as disclosed in Table 3.

The disclosure also contemplates nucleic acids encoding the described anti-YFV antibodies and expression vectors comprising said nucleic acids, as well as host cells that express such antibodies via the nucleic acids and/or expression vectors.

In one embodiment is provided isolated nucleic acid sequences encoding antibodies or antigen-binding fragments thereof disclosed herein.

In other embodiments are provided expression vectors comprising isolated nucleic acid sequences encoding antibodies or antigen-binding fragments disclosed herein.

In other embodiments are provided host cells transfected, transformed, or transduced with nucleic acid sequences encoding antibodies or antigen-binding fragments disclosed herein or expression vectors comprising isolated nucleic acid sequences encoding antibodies or antigen-binding fragments disclosed herein.

In other embodiments are provided pharmaceutical compositions comprising one or more of the isolated antibodies or antigen-binding fragments thereof disclosed herein; and a pharmaceutically acceptable carrier and/or excipient.

In other embodiments are provided pharmaceutical compositions comprising one or more nucleic acid sequences encoding antibodies or antigen-binding fragments disclosed herein, or one or more expression vectors comprising nucleic acid sequences encoding antibodies or antigen-binding fragments disclosed herein; and a pharmaceutically acceptable carrier and/or excipient.

In other embodiments are provided expression vectors comprising nucleic acid sequences encoding antibodies or antigen-binding fragments disclosed herein; or a host cell comprising nucleic acid sequences encoding antibodies or antigen-binding fragments disclosed herein.

The disclosure further contemplates methods of prevention and/or treatment using the described anti-YFV antibodies (or nucleic acids encoding or expression vectors comprising such nucleic acids).

In one embodiment is provided methods of treating or preventing a Yellow Fever Virus (YFV) infection, or at least one symptom associated with YFV infection, comprising administering to a patient in need thereof or suspected of being in need thereof: a) one or more antibodies or antigen-binding fragments thereof according to other embodiments disclosed herein; b) one or more nucleic acid sequences encoding antibodies or antigen-binding fragments disclosed herein; an expression vector comprising nucleic acid sequences encoding antibodies or antigen-binding fragments disclosed herein; or a host cell comprising an expression vector comprising nucleic acid sequences encoding antibodies or antigen-binding fragments disclosed herein; or c) a pharmaceutical composition according to other embodiments disclosed herein; such that the YFV infection is treated or prevented, or the at least one symptom associated with YFV infection is treated, alleviated, or reduced in severity.

In other embodiments the methods further comprise administering to the patient a second therapeutic agent.

In embodiments the second therapeutic agent is selected from: an antiviral agent; a vaccine specific for YFV; a vaccine specific for a flavivirus; an siRNA specific for a YFV antigen; and a second antibody specific for a YFV antigen.

In certain embodiments are provided pharmaceutical compositions for use in preventing a YFV infection in a patient in need thereof or suspected of being in need thereof, or for treating a patient suffering from an YFV infection, or for ameliorating at least one symptom or complication associated with the infection, wherein the infection is either prevented, or at least one symptom or complication associated with the infection is prevented, ameliorated, or lessened in severity and/or duration as a result of such use. In certain embodiments are provided pharmaceutical compositions for use in preventing a YFV infection in a patient in need thereof or suspected of being in need thereof. In certain embodiments are provided pharmaceutical compositions for use in treating a patient suffering from an YFV infection. In certain embodiments are provided pharmaceutical compositions for use in ameliorating at least one symptom or complication associated with the infection. In certain embodiments the infection is prevented. In certain embodiments at least one symptom or complication associated with the infection is prevented, ameliorated, or lessened in severity and/or duration as a result of such use.

In certain embodiments are provided pharmaceutical compositions for use in treating or preventing a YFV infection, or at least one symptom associated with said YFV infection, in a patient in need thereof or suspected of being in need thereof, wherein the infection is either prevented, or at least one symptom or complication associated with the infection is prevented, ameliorated, or lessened in severity and/or duration as a result of such use.

In certain other embodiments are provided uses of the pharmaceutical compositions in the manufacture of a medicament for preventing a YFV infection in a patient in need thereof, or for treating a patient suffering from a YFV infection, or for ameliorating at least one symptom or complication associated with the infection, wherein the infection is either prevented, or at least one symptom or complication associated with the infection is prevented, ameliorated, or lessened in severity and/or duration.

In certain other embodiments are provided uses of the pharmaceutical compositions in the manufacture of a medicament for preventing a YFV infection, or at least one symptom associated with said YFV infection, in a patient in need thereof or suspected of being in need thereof, wherein the infection is either prevented, or at least one symptom or complication associated with the infection is prevented, ameliorated, or lessened in severity and/or duration as a result of such use.

In certain other embodiments, an antobody that binds to the YFV E-Protein is provided. This antibody can bind to at least one of an epitope within FL of Domain II of the YFV E protein, proximal to the FL of Domain II of the YFV E protein, and to a protein in Domain III of YFV. This antibody can also have one or more of the following characteristics: a) the antibodies or antigen-binding fragments thereof display a clean or low polyreactivity profile; b) the antibodies or antigen-binding fragments thereof display an in vitro neutralization potency ($IC_{50}$) of between about 0.5 microgram/milliliter (µg/ml) to about 5 µg/ml; between about 0.05 µg/ml to about 0.5 µg/ml; or less than about 0.05 mg/ml; c) the antibodies or antigen-binding fragments thereof bind YFV-17D particles; and d) the antibody or antigen-binding fragment thereof binds to an envelope protein of YFV.

BRIEF DESCRIPTION OF THE FIGURES

FIG. 1A: Serum neutralizing activity against YFV-17D at day −5 (pre-vaccination), 10, 14, 28, 90, 180, 270, and 360 post-vaccination. Averages±SD (n=6) from two independent experiments are shown. FIG. 1B: Neutralization $IC_{50}$s of serum samples at each time point post-vaccination, expressed as reciprocal serum dilution.

FIG. 2A through FIG. 2D show characterization of the YFV-17D vaccination-induced plasmablast responses at days 10 and 14. FIG. 2A: Frequency of plasmablasts among $CD19^+CD20^{-/lo}$ B cells in peripheral blood at days 0, 10, and 14 post-vaccination. Plasmablasts are defined herein as $CD19^+CD3^-CD8^-CD14^-CD16^-CD20^{-/lo}CD38^{hi}CD27^{hi}$ cells. FIG. 2B: Percentage of PB-derived mAbs that showed ELISA binding reactivity to whole YFV-17D particles at 100 nM. FIG. 2C: Neutralizing activity of PB-derived mAbs against YFV-17D at 100 nM and 10 nM concentrations. Green dots indicate the number of nucleotide substitutions in $V_H+V_L$. FIG. 2D: Proportion of YFV-17D reactive PB-derived mAbs with the indicated neutralization potencies ($IC_{50}$s).

FIG. 5A: YFV E reactivity of $swIg^+$ B cells at each sampling time point. Fluorescence activated cell sorting (FACS) plots shown are gated on $CD19^+CD20^+IgD^-IgM^-$ B cells. YFV E was labeled with two different colors to reduce background binding. FIG. 5B: Percentage of $swIg^+$ B cells at each sampling time point that display YFV E reactivity.

FIG. 6A: VH germline gene usage of YFV E-specific mAbs isolated from each sampling time point. VH germline gene frequencies of unselected human MBC repertoires ("Unselected") are also included for comparison. Sequencing data for unselected human MBCs was obtained from multiple high-throughput sequencing studies. FIG. 6B: VL germline gene usage of mAbs utilizing the VH3-72 germline gene. MAbs from all sampling time points were pooled for this analysis. The numbers in the center of the pies denote the total number of VH3-72 mAbs. FIG. 6C: Length distribution of CDR H3 in YFV E-specific mAbs utilizing the VH3-72 germline gene, mAbs utilizing all other VH germline genes, or unselected Abs from MBCs. FIG. 6D: SHM loads (expressed as number of nucleotide substitutions in VH) of YFV E-specific mAbs utilizing the VH3-72 germline gene or all other VH germline genes. FIG. 6E: Apparent binding affinities of mAbs utilizing the VH3-72 germline gene or all other VH germline genes to the YFV E protein, as determined by BLI. Black bars indicate medians. Avid $KD^{App}$s are plotted for the mAbs isolated from day 14 MBCs because only a small subset of these mAb showed detectable binding to YFV E in a monovalent orientation. Statistical comparisons were made using the Mann-Whitney test (* $P<0.001$,  $P<0.01$, *$P<0.05$).

FIG. 7A through 7D illustrate antibodies targeting epitopes within or proximal to the FL dominate the memory B cell response to YFV-17D vaccination. FIG. 7A: Proportion of mAbs in each of the major competition groups at each sampling time point. FIG. 7B: VH3-72 utilizing mAbs are shaded according to the competition group; natively paired light chain germline genes are indicated. FIG. 7C: Proportion of mAbs that compete with 4G2 and use the VH3-72 germline gene. FIG. 7D: Apparent affinities of 4G2-competing mAbs that either use the VH3-72 germline gene or all other germline genes. Statistical comparisons were made using the Mann-Whitney test (** P<0.01).

FIG. 8A: Proportion of mAbs with neutralization $IC_{50}$s (less than 1, 1-10, greater than 10-100, and greater than 100 nM) against YFV-17D in each epitope bin. n.n—non-binder. FIG. 8B: Neutralization $IC_{50}$s of individual mAbs against YFV-17D across the indicated epitope bins. Black bars indicate medians. FIG. 8C: Proportion of highly potent neutralizing antibodies ($IC_{50}$<1 nM) targeting the indicated antigenic sites on YFV E. The number in the center of the pie indicates the number of highly potent neutralizing antibodies. FIG. 8D: VH and VL germline gene usage of 5A-only or 5A/ADI-45107 competitor neutralizing antibodies. MAbs from both donors were combined for all analyses shown.

FIG. 9A: Proportion of mAbs that react with one or more of the flavivirus E proteins tested (YFV, DENV-1, DENV-2, ZIKV, and WNV). Recombinant E protein binding was measured in an avid orientation by BLI. Numbers in the center of the pies indicate the number of mAbs analyzed. FIG. 9B: Proportion of cross-reactive mAbs that recognize the indicated antigenic sites. Cross-reactive mAbs from both donors were combined for this analysis. FIG. 9C: Heatmap showing the cross-reactivity profiles of 50 mAbs that showed binding to at least one flavivirus E protein aside from YFV E. Apparent affinities ($KD^{App}$s) were determined in avid orientation using BLI. A heat map showing virus neutralizing to activity against YFV-17D and ZIKV is shown below the binding heat map. Competition group assignments for the individual mAbs are indicated at the top of the heatmap. N.B., non-binding; n.n., non-neutralizing; neut., neutralization.

DETAILED DESCRIPTION OF THE DISCLOSURE

Figure 1A:
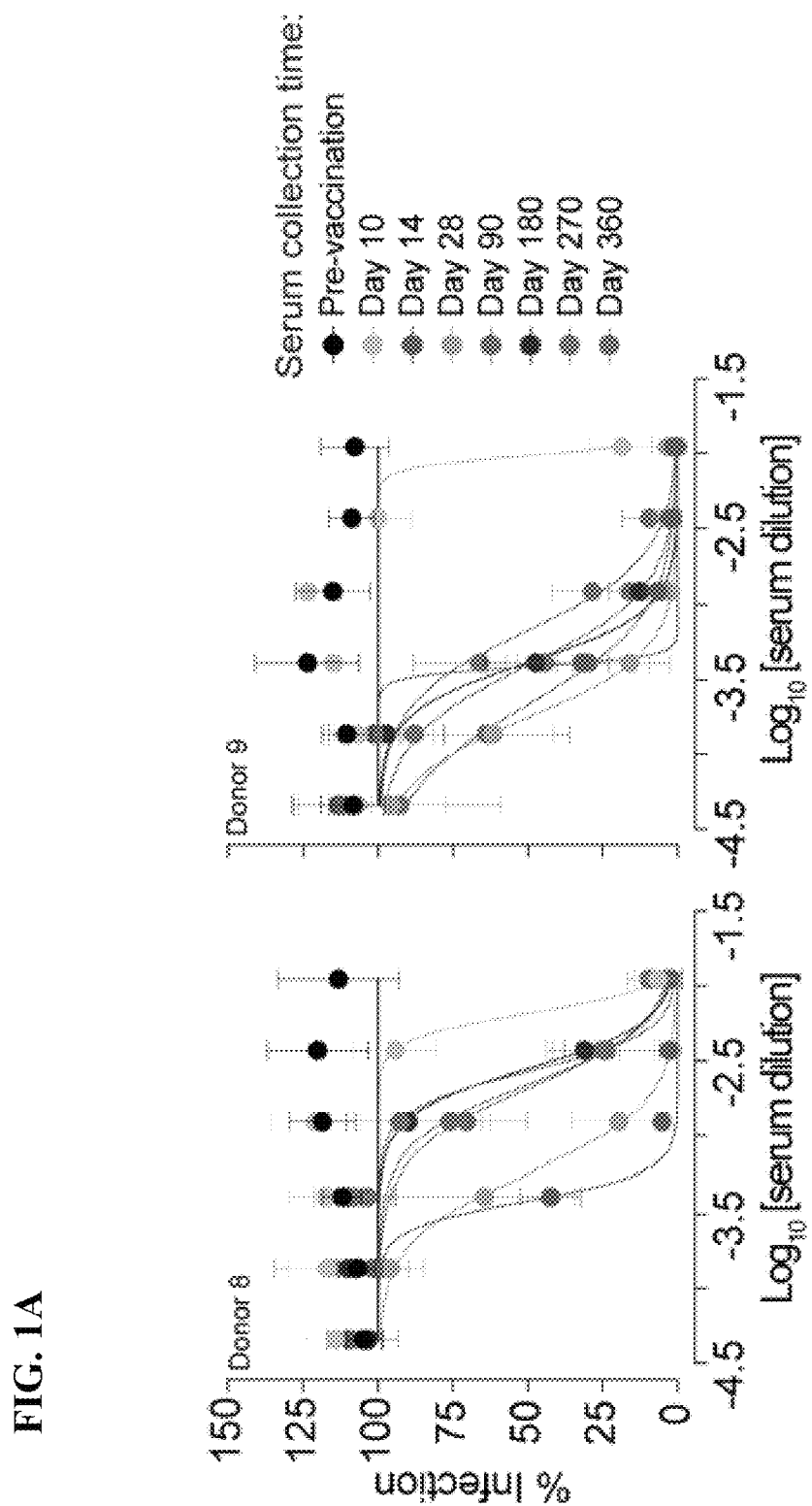
FIG. 1A and FIG. 1B illustrate donor serum analysis following YVF-14D vaccination.

An in-depth understanding of the human antibody response to YFV infection will aid the development and evaluation of YFV vaccine and therapeutic and/or prophylactic antibodies for the treatment and/or prevention of YFV infection. A high-throughput antibody isolation platform was used to dissect the human memory B cell response to YFV in two vaccinated adult donors and highly potent and selective YFV-neutralizing antibodies were isolated and characterized.

High-throughput epitope mapping studies revealed that epitopes within or proximal to the FL on DII of the YFV E protein are immunodominant. While many of the mAbs that bound to FL-specific epitopes were non-neutralizing, most of the mAbs that targeted FL-proximal epitopes overlapping the 5A epitope showed neutralizing activity. Furthermore, the vast majority of potent nAbs recognized this antigenic site suggesting that the nAb response induced by YFV-17D vaccination is primarily mediated by this class of Abs. A subset of these mAbs displayed exceptionally potent neutralizing activity, with $IC_{50}$ s that were about 10 times lower than previously described YFV mAbs. Given the recent YFV outbreaks in Brazil and the Democratic Republic of Congo, coupled with YFV-17D vaccine supply shortages and the lack of effective treatments for YFV disease, these mAbs represent promising candidates for prophylaxis and/or therapy Accordingly, disclosed herein are highly selective and potent anti-YFV antibodies, as well as possible vaccine candidates, for the treatment and/or prophylaxis of YFV infection. Additionally, the reagents disclosed here provide a useful set of tools for the evaluation of clinical trials, which will be critical for selecting the optimal YFV vaccination or antibody-based therapeutic strategy from those currently under investigation.

Unless defined otherwise, all technical and scientific terms used herein have the same meaning as commonly understood by one of ordinary skill in the art to which this disclosure belongs. In this specification and in the claims that follow, reference will be made to a number of terms that shall be defined to have the following meanings:

The terminology used herein is for the purpose of describing particular embodiments only and is not intended to be limiting. As used herein, the singular forms "a", "an" and "the" are intended to include the plural forms as well, unless the context clearly indicates otherwise.

"Optional" or "optionally" means that the subsequently described event or circumstance can or cannot occur, and that the description includes instances where the event or circumstance occurs and instances where it does not.

The term "about" when used before a numerical designation, e.g., temperature, time, amount, concentration, and such other, including a range, indicates approximations which may vary by (+) or (−) 10%, 5%, 1%, or any subrange or subvalue there between. Preferably, the term "about" when used with regard to an amount means that the amount may vary by +/−10%.

"Comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this disclosure.

"Yellow Fever Virus", also referred to as "YFV", is an RNA virus typically spread by the bite of infected *Aedes* or *Haemagogus* species mosquito bites.

The term "YFV-17D" refers to the attenuated YFV vaccine strain developed by passaging a wild-type Asibi strain in chicken and mouse tissue. There are three 17D substrains in current production: 17DD manufactured in Brazil, 17D-213 manufactured in Russia, and 17D-204 manufactured in China, France, Senegal, and the USA. While the mechanism of attenuation is poorly understood, it is hypothesized that the limited genetic diversity of the 17D vaccine virus attributes to vaccine attenuation and safety. There is evidence that replication of 17D is not as error-prone as wild-type RNA viruses. See Pugachev et al., J Virol. 78(2):1032-8 (2004).

The term "envelope protein" or "E protein" refers to the structural YFV protein that is a primary immunogen that plays a central role in receptor binding and membrane fusion. The structure of the E protein ectodomain (the soluble N-terminal portion consisting of 395 residues) includes three distinct structural domains, referred to as domains I, II, and III. (Volk et al., Virology 2009, 394(1): 12-18). Domain II contains a S-S bridge stabilized loop at its distal end that functions as a highly conserved fusion loop (FL). When a virus enters a target host cell, the FL of Domain II is exposed and inserts into the host cellular membrane. (Zhang et al., Viruses 2017, 9(11): 338). In some embodiments, the antibodies and antigen-binding fragments thereof bind to the FL of Domain II YFV E protein. In other embodiments, the antibodies and antigen-binding fragments thereof bind to Domain III of the YFV E protein.

The development of an effective YFV therapeutic has presented a number of unique challenges. The in-depth analysis of the human antibody response to the YFV vaccine performed here provides insights for the development of such a therapeutic treatment. The antibody repertoire analysis disclosed herein reveals that the majority of neutralizing YFV-specific antibodies target FL-proximal epitopes overlapping the 5A epitope, whereas a small number of potent neutralizing antibodies targeted the DIII domain—a region of the E protein that, until now, was not the epitope for any effective anti-YFV antibodies.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. The term "epitope" also refers to a site on an antigen to which B and/or T cells respond. It also refers to a region of an antigen that is bound by an antibody. Epitopes may be defined as structural or functional. Functional epitopes are generally a subset of the structural epitopes and have those residues that directly contribute to the affinity of the interaction. Epitopes may also be conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics. The term "antibody" (or "Ab"), as used herein, is intended to refer to immunoglobulin molecules comprised of four polypeptide chains, two heavy (H) chains and two light (L) chains interconnected by disulfide bonds (i.e., "full antibody molecules"), as well as multimers thereof (e.g. IgM) or antigen-binding fragments thereof.

The terms "antigen-binding portion", "antigen-binding fragment", and the like, as used herein, include any naturally occurring, enzymatically obtainable, synthetic, or genetically engineered polypeptide or glycoprotein that specifically binds an antigen to form a complex. In certain embodiments, the terms "antigen-binding portion" or "antibody fragment", as used herein, refer to one or more fragments of an antibody that retains the ability to bind to YFV.

An antibody fragment may include a Fab fragment, a F(ab')$_2$ fragment, a Fv fragment, a dAb fragment, a fragment containing a CDR, or an isolated CDR. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and (optionally) constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR, which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present disclosure include: (i) $V_H$-$C_H1$; (ii) $V_H$-$C_H2$; (iii) $V_H$-$C_H3$; (iv) $V_H$-$C_H1$-$C_H2$; (V) $V_H$-$C_H1$-$C_H2$-$C_H3$; (vi) $V_H$-$C_H2$-$C_H3$; (vii) $V_H$-CL; (viii) $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids, which result in a flexible or semi-flexible linkage between adjacent variable and/or constant domains in a single polypeptide molecule. Moreover, an antigen-binding fragment of an antibody of the present disclosure may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be mono-specific or multi-specific (e.g., bi-specific). A multi-specific antigen-binding fragment of an antibody will typically comprise at least two different variable domains, wherein each variable domain is capable of specifically binding to a separate antigen or to a different epitope on the same antigen. Any multi-specific antibody format, including the exemplary bi-specific antibody formats disclosed herein, may be adapted for use in the context of an antigen-binding fragment of an antibody of the present disclosure using routine techniques available in the art.

Each heavy chain is comprised of a heavy chain variable region ("HCVR" or "$V_H$") and a heavy chain constant region (comprised of domains $C_H1$, $C_H2$, and $C_H3$). Each light chain is comprised of a light chain variable region ("LCVR or "$V_L$") and a light chain constant region (CO. The $V_H$ and $V_L$ regions can be further subdivided into regions of hypervariability, termed complementarity determining region (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In certain embodiments of the disclosure, the FRs of the antibody (or antigen binding fragment thereof) may be identical to the human germline sequences, or may be naturally or artificially modified. An amino acid consensus sequence may be defined based on a side-by-side analysis of two or more CDRs. Accordingly, the CDRs in a heavy chain are designated "CDRH1", "CDRH2", and "CDRH3", respectively, and the CDRs in a light chain are designated "CDRL1", "CDRL2", and "CDRL3".

In some embodiments, the antibody or antigen-binding fragment thereof contains a CDRL3 binding domain comprising a consensus motif having the sequence $QQX_1X_2X_3X_4X_5X_6T$. $X_1$ is Y, F, or A, $X_2$ is N, H, or Y, $X_3$ is R, S, T, or D, $X_4$ is D, F, Y, W, or P, $X_5$ is P or S, $X_6$ is Y, F, K, or W. The following clones include this consensus motif: ADI-50211; ADI-48899; ADI-45136; ADI-45078; ADI-49162; ADI-49141; ADI-42844; ADI-48910; ADI-45074; ADI-49041; ADI-50220; ADI-42172; ADI-42178; ADI-50218; and ADI-49194.

In some embodiments, the present disclosure provides an antibody comprising a YFV binding domain, CDRL3, wherein the CDRL3 binding domain comprises a consensus motif, the consensus motif comprising the sequence $QX_1X_2X_3X_4TX_5X_6T$, wherein $X_1$ is Q or H, $X_2$ is A or S, $X_3$ is S or Y, $X_4$ is T or S, $X_5$ is R or P, and $X_6$ is Y, L, W, or R. The following clones include this consensus motif: ADI-42201; ADI-45164; ADI-46729; ADI-42223; ADI-46718; ADI-45076; ADI-48968; ADI-45156; ADI-50536; and ADI-50537.

In some embodiments, the present disclosure provides an antibody comprising a YFV binding domain, CDRL3, wherein the CDRL3 binding domain comprises a consensus motif, the consensus motif comprising the sequence $GTWDX_1SX_2X_3SAGX_4V$ (SEQ ID NO:1006), wherein $X_1$ is S or T, $X_2$ is S or no amino acid, $X_3$ is L or P, and $X_4$ is K, G, or R. The following clones include this consensus motif: ADI-45083; ADI-42225; ADI-42210; ADI-42198; ADI-42809; ADI-42830; ADI-42818; ADI-42151; and ADI-50533.

In some embodiments, the present disclosure provides an antibody comprising a YFV binding domain, CDRH3, wherein the CDRH3 binding domain comprises a consensus motif, the consensus motif comprising the sequence $AX_1X_2YDSX_3X_4YYX_5X_6X_7X_8$ (SEQ ID NO:1007), wherein $X_1$ is K or R, $X_2$ is Y, F, T, A, G, Y, or H, $X_3$ is S, N, or R, $X_4$ is A or G, $X_5$ is W or Y, $X_6$ is F, L, I, A, or E, $X_7$ is D, E, or H, and $X_8$ is Y, H, or S. The following clones include this consensus motif: ADI-45085; ADI-50211; ADI-45078; ADI-49162; ADI-45136; ADI-42172; ADI-49194; ADI-50203; ADI-42178; ADI-48908; ADI-42844; ADI-48910; and ADI-49168.

In some embodiments, the present disclosure provides an antibody comprising a YFV binding domain, CDRL2, wherein the CDRL2 binding domain comprises a consensus motif, the consensus motif comprising the sequence $X_1X_2X_3X_4RPS$, wherein $X_1$ is D or E, $X_2$ is N, V, or D, $X_3$ is K, N, D, or S, and $X_4$ is K, E, or R. The following clones include this consensus motif: ADI-49039; ADI-42229; ADI-45097; ADI-45083; ADI-42225; ADI-49139; ADI-48969; ADI-48900; ADI-42786; ADI-42210; ADI-42198; ADI-49154; ADI-49188; ADI-42188; ADI-42809; ADI-46596; ADI-42830; ADI-46591; ADI-48955; ADI-42818; ADI-46586; ADI-42151; ADI-45140; ADI-46722; ADI-45128; ADI-45127; ADI-46739; ADI-46724; ADI-50539; ADI-42114; ADI-50533; and ADI-49205.

In some embodiments, present disclosure provides an antibody comprising a YFV binding domain, CDRL2, wherein the CDRL2 binding domain comprises a consensus motif, the consensus motif comprising the sequence $X_1X_2X_3X_4LX_5X_6$, wherein $X_1$ is A, G, or R, $X_2$ is A or T, $X_3$ is S or T, $X_4$ is T, G, S, or I, $X_5$ is Q or R, and $X_6$ is S or R. The following clones include this consensus motif: ADI-49133; ADI-49033; ADI-48895; ADI-42201; ADI-42230; ADI-48916; ADI-42211; ADI-5164; ADI-42191; ADI-49145; ADI-46729; ADI-42189; ADI-46718; ADI-45076; ADI-48968; ADI-50203; ADI-42227; ADI-48894; ADI-50218; ADI-45156; ADI-50536; ADI-50537; ADI-46737; ADI-45123; and ADI-50200.

In some embodiments, present disclosure provides an antibody comprising a YFV binding domain, CDRL2, wherein the CDRL2 binding domain comprises a consensus motif, the consensus motif comprising the sequence $X_1X_2SX_3RAX_4$, wherein $X_1$ is G, D, R, or A, $X_2$ is A or S, $X_3$ is S, T, or N, and $X_4$ is T or A. The following clones include this consensus motif: ADI-49147; ADI-50201; ADI-45113; ADI-50219; ADI-48897; ADI-42194; ADI-42847; ADI-48908; ADI-42231; ADI-42233; ADI-45148; ADI-42187; ADI-42787; ADI-49141; ADI-42213; ADI-42192; ADI-49590; ADI-48462; ADI-42200; ADI-42181; ADI-49037; ADI-49137; and ADI-42817.

In some embodiments, the present disclosure provides an antibody comprising a YFV binding domain, CDRL2, wherein the CDRL2 binding domain comprises a consensus motif, the consensus motif comprising the sequence $X_1VX_2X_3RPS$ (SEQ ID NO:1008), wherein $X_1$ is D, E, or R, $X_2$ is S, T, N, or A, and $X_3$ is N, K, or Q. The following clones include this consensus motif: ADI-42228; ADI-42190; ADI-49183; ADI-49189; ADI-50205; ADI-50531; ADI-49138; ADI-45154; ADI-49161; ADI-49561; ADI-42219; ADI-48435; ADI-45161; ADI-42193; ADI-42149; ADI-42216; ADI-42810; ADI-48890; ADI-42206; ADI-48950; and ADI-42124.

In some embodiments, the present disclosure provides an antibody comprising a YFV binding domain, CDRL2, wherein the CDRL2 binding domain comprises a consensus motif, the consensus motif comprising the sequence $X_1ASX_2LEX_3$ (SEQ ID NO:1009), wherein $X_1$ is R, Q, or K, $X_2$ is T, S, G, R, or I, and $X_3$ is T or S. The following clones include this consensus motif: ADI-42831; ADI-42821; ADI-45085; ADI-50211; ADI-48899; ADI-49168; ADI-45136; ADI-45078; ADI-42844; ADI-48910; ADI-49041; ADI-42172; ADI-42178; ADI-49032; and ADI-49194.

In some embodiments, the present disclosure provides an antibody comprising a YFV binding domain, CDRH2, wherein the CDRH2 binding domain comprises a consensus motif, the consensus motif comprising the sequence $X_1X_2X_3HX_4X_5X_6X_7X_8YX_9PX_{10}X_{11}X_{12}S$ (SEQ ID NO:1010), wherein $X_1$ is D, E, or S, $X_2$ is I or V, $X_3$ is F or Y, $X_4$ is X or T, $X_5$ is G or E, $X_6$ is S, G, or T, $X_7$ is T or A, $X_8$ is N, S, H, K, or T, $X_9$ is N or S, $X_{10}$ is S or F, $X_{11}$ is L or V, and $X_{12}$ of K or E. The following clones include this consensus motif: ADI-45083; ADI-42225; ADI-49139; ADI-48900; ADI-42232; ADI-42786; ADI-42210; ADI-42198; ADI-49154; ADI-42188; ADI-42809; ADI-42818; ADI-42151; ADI-46722; ADI-46742; ADI-49141; ADI-46739; ADI-46724; ADI-50539; ADI-48951; ADI-50538; and ADI-50533.

In some embodiments, the present disclosure provides an antibody comprising a YFV binding domain, CDRH2, wherein the CDRH2 binding domain comprises a consensus motif, the consensus motif comprising the sequence $X_1X_2X_3X_4DX_5X_6X_7KX_8X_9ADSX_{10}X_{11}G$ (SEQ ID NO:1011), wherein $X_1$ is V or L, $X_2$ is I or M, $X_3$ is 5, W, or L, $X_4$ is F or Y, $X_5$ is E or G, $X_6$ is S or T, $X_7$ is K, N, or Y, $X_8$ is F, W, or Y, $X_9$ is Y or F, $X_{10}$ is V or L, and $X_{11}$ is K or R. The following clones include this consensus motif: ADI-45097; ADI-42144; ADI-49138; ADI-45154; ADI-49561; ADI-42189; ADI-42844; ADI-45161; ADI-48462; ADI-42172; ADI-42178; ADI-42217; ADI-46737; ADI-49205; ADI-45151; and ADI-46728.

In some embodiments, the present disclosure provides an antibody comprising a YFV binding domain, CDRL1, wherein the CDRL1 binding domain comprises a consensus motif, the consensus motif comprising the sequence $RX_1SX_2X_3X_4X_5X_6X_7X_8X_9$, wherein $X_1$ is A or T, $X_2$ is Q or R, $X_3$ is S or T, $X_4$ is I or V, $X_5$ is S or T, $X_6$ is S, N, T, F, D, or G, $X_7$ is N, Y, W, F, or K, $X_8$ is L or V, and $X_9$ is A or N. The following clones include this consensus motif: ADI-49147; ADI-50201; ADI-45113; ADI-42201; ADI-42194; ADI-42847; ADI-45085; ADI-48908; ADI-50211; ADI-42231; ADI-45164; ADI-48899; ADI-46729; ADI-49168; ADI-49040; ADI-45136; ADI-45078; ADI-46718; ADI-49141; ADI-42844; ADI-42192; ADI-48910; ADI-42200; ADI-50203; ADI-42181; ADI-49041; ADI-50220; ADI-42172; ADI-42178; ADI-49032; ADI-49137; ADI-42817; ADI-45156; ADI-50536; ADI-50537; and ADI-49194.

In some embodiments, the present disclosure provides an antibody comprising a YFV binding domain, CDRL1, wherein the CDRL1 binding domain comprises a consensus motif, the consensus motif comprising the sequence $SGSX_1SNX_2GX_3X_4X_5VX_6$ (SEQ ID NO:1012), wherein $X_1$ is N or S, $X_2$ is I or F, $X_3$ is S or N, $X_4$ is N, Y, S, or D, $X_5$ is Y, F, or D, and $X_6$ is S or A. The following clones include this consensus motif: ADI-49039; ADI-42229; ADI-45097; ADI-45083; ADI-42225; ADI-48900; ADI-42786; ADI-42210; ADI-42198; ADI-49154; ADI-42188; ADI-42809; ADI-46596; ADI-42830; ADI-46591; ADI-48955; ADI-42818; ADI-46586; ADI-42151; ADI-45140; ADI-46722; ADI-45128; ADI-46739; ADI-46724; ADI-50539; ADI-42114; and ADI-50533.

In some embodiments, the present disclosure provides an antibody comprising a YFV binding domain, CDRL1, wherein the CDRL1 binding domain comprises a consensus motif, the consensus motif comprising the sequence $X_1GTX_2X_3DX_4GX_5X_6X_7X_8VS$ (SEQ ID NO:1013), wherein $X_1$ is A or T, $X_2$ is S, G, or R, $X_3$ is S or T, $X_4$ is V, F, or I, $X_5$ is G or A, $X_6$ is Y, D, or F, $X_7$ K or N, and $X_8$ is Y or F. The following clones include this consensus motif: ADI-48969; ADI-42228; ADI-42190; ADI-49183; ADI-49189; ADI-50205; ADI-50531; ADI-49138; ADI-45154; ADI-49161; ADI-49561; ADI-42219; ADI-48435; ADI-45161; ADI-45127; ADI-42149; ADI-42216; ADI-42810; ADI-48890; ADI-42206; ADI-48950; ADI-42124; and ADI-49205.

In some embodiments, the present disclosure provides an antibody comprising a YFV binding domain, CDRH1, wherein the CDRH1 binding domain comprises a consensus motif, the consensus motif comprising the sequence: X1X2FX3X4X5X6X7X8, wherein X1 is F, Y, or L, X2 is T, A, S, or N, X3 is S, or T, X4 is S, T, or R, X5 is Y or L, X6 is G, A, T, W, S, or D, X7 is M, I, or L, and X8 is H, S, N, or T. The following clones include this consensus motif: ADI-45090; ADI-49044; ADI-45113; ADI-42144; ADI-50026; ADI-45075; ADI-42230; ADI-42154; ADI-45085; ADI-42211; ADI-50211; ADI-42231; ADI-42233; ADI-49168; ADI-42187; ADI-49561; ADI-42219; ADI-50535; ADI-45136; ADI-42189; ADI-48435; ADI-46718; ADI-42844; ADI-45161; ADI-48910; ADI-48462; ADI-42200; ADI-50203; ADI-42149; ADI-42172; ADI-42178; ADI-50197; ADI-42810; ADI-50218; ADI-45156; ADI-50536; ADI-50537; ADI-46737; ADI-42114; ADI-49194; ADI-42124; and ADI-46728.

In some embodiments, the present disclosure provides an antibody comprising a YFV binding domain, CDRH1, wherein the CDRH1 binding domain comprises a consensus motif, the consensus motif comprising the sequence: $X_1SIX_2X_3X_4X_5X_6WX_7$, wherein $X_1$ is G or I, $X_2$ is S or T, $X_3$ is S, T, G, or no amino acid, $X_4$ is D, S, T, or G, $X_5$ is Y, N, or D, $X_6$ is Wo r Y, and $X_7$ is S or T. The following clones include this consensus motif: ADI-45083; ADI-42225; ADI-48900; ADI-42786; ADI-42210; ADI-49188; ADI-42188; ADI-42818; ADI-42151; ADI-48913; ADI-46722; ADI-49141; ADI-46741; ADI-46739; ADI-50539; ADI-50538; and ADI-50533.

In some embodiments, the present disclosure provides an antibody comprising a YFV binding domain, CDRH1, wherein the CDRH1 binding domain comprises a consensus motif, the consensus motif comprising the sequence: FX1FSDX2YMX3 (SEQ ID NO:1014), wherein X1 is I or T, X2 is H or Y, and X3 is A or D. The following clones include this consensus motif: ADI-42191; ADI-49040; ADI-42223; ADI-42193; ADI-48968; ADI-42212; ADI-45126; ADI-42141; ADI-49140; ADI-48894; ADI-42226; ADI-49137; ADI-48890; ADI-42206; and ADI-49030.

Substitution of one or more CDR residues or omission of one or more CDRs is also possible. Antibodies have been described in the scientific literature in which one or two CDRs can be dispensed with for binding. Padlan et al. (1995 FASEB J. 9:133-139) analyzed the contact regions between antibodies and their antigens, based on published crystal structures, and concluded that only about one fifth to one third of CDR residues actually contact the antigen. Padlan also found many antibodies in which one or two CDRs had no amino acids in contact with an antigen (see also, Vajdos et al. 2002 J Mol Biol 320:415-428).

CDR residues not contacting antigen can be identified based on previous studies (for example residues H60-H65 in CDRH2 are often not required), from regions of Kabat CDRs lying outside Chothia CDRs, by molecular modeling and/or empirically. If a CDR or residue(s) thereof is omitted, it is usually substituted with an amino acid occupying the corresponding position in another human antibody sequence or a consensus of such sequences. Positions for substitution within CDRs and amino acids to substitute can also be selected empirically.

The fully human monoclonal antibodies disclosed herein may comprise one or more amino acid substitutions, insertions and/or deletions in the framework and/or CDR regions of the heavy and light chain variable domains as compared to the corresponding germline sequences. Such mutations can be readily ascertained by comparing the amino acid sequences disclosed herein to germline sequences available from, for example, public antibody sequence databases. The present disclosure includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present disclosure may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present disclosure.

The present disclosure also includes fully monoclonal antibodies comprising variants of any of the CDR amino acid sequences disclosed herein having one or more conservative substitutions. For example, the present disclosure includes antibodies having CDR amino acid sequences with, e.g., 10 or fewer, 8 or fewer, 6 or fewer, 4 or fewer, etc. conservative amino acid substitutions relative to any of the CDR amino acid sequences disclosed herein. In some embodiments, the anti-YFV antibodies and antigen-binding fragments disclosed are human antibodies. The term "human antibody", as used herein, is intended to include antibodies having variable and constant regions derived from human germline immunoglobulin sequences. The human antibodies of the disclosure may include amino acid residues not encoded by human germline immunoglobulin sequences (e.g., mutations introduced by random or site-specific mutagenesis in vitro or by somatic mutation in vivo), for example in the CDRs and in particular CDR3.

In some embodiments, the anti-YFV antibodies and antigen-binding fragments disclosed are recombinant antibodies. The term "recombinant" generally refers to any protein, polypeptide, or cell expressing a gene of interest that is produced by genetic engineering methods. The term "recombinant" as used with respect to a protein or polypeptide, means a polypeptide produced by expression of a recombinant polynucleotide. The proteins used in the immunogenic compositions of the disclosure may be isolated from a natural source or produced by genetic engineering methods.

The antibodies of the disclosure may, in some embodiments, be recombinant human antibodies. The term "recombinant human antibody", as used herein, is intended to include all antibodies, including human or humanized antibodies, that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

In some embodiments, the anti-YFV antibodies and antigen-binding fragments thereof are isolated antibodies. An "isolated antibody", as used herein, refers to an antibody that is substantially free of other antibodies having different antigenic specificities (e.g., an isolated antibody that specifically binds YFV, or a fragment thereof, is substantially free of Abs that specifically bind antigens other than YFV). In some embodiments, the anti-YFV antibodies and antigen-binding fragments specifically bind to the YFV E protein, e.g., the FL of DII domain or DIII. The term "specifically binds," or "binds specifically to", or the like, means that an antibody or antigen-binding fragment thereof forms a complex with an antigen that is relatively stable under physiologic conditions. Specific binding can be characterized by an equilibrium dissociation constant of at least about $1 \times 10^{-6}$ M or less (e.g., a smaller $K_D$ denotes a tighter binding). Methods for determining whether two molecules specifically bind are well known in the art and include, for example, equilibrium dialysis, surface plasmon resonance, and the like. As described herein, antibodies have been identified by surface plasmon resonance, e.g., BIACORE™, biolayer interferometry measurements using, e.g., a ForteBio Octet HTX instrument (Pall Life Sciences), which bind specifically to YFV. Moreover, multi-specific antibodies that bind to YFV protein and one or more additional antigens, or a bi-specific that binds to two different regions of YFV are nonetheless considered antibodies that "specifically bind", as used herein. In certain embodiments, the antibodies disclosed herein display equilibrium dissociation constants (and hence specificities) of about $1 \times 10^{-6}$ M; about $1 \times 10^{-7}$ M; about $1 \times 10^{-8}$ M; about $1 \times 10^{-9}$ M; about $1 \times 10^{-10}$ M; between about $1 \times 10^{-6}$ M and about $1 \times 10^{-7}$ M; between about $1 \times 10^{-7}$ M and about $1 \times 10^{-8}$ M; between about $1 \times 10^{-8}$ M and about $1 \times 10^{-9}$ M; between about $1 \times 10^{-9}$ M and about $1 \times 10^{-10}$ M; or between about $1 \times 10^{-9}$ M and about $1 \times 10^{-10}$ M.

In some embodiments, the anti-YFV antibodies and antigen-binding fragments are high affinity binders. The term "high affinity" refers to those mAbs having a binding affinity to YFV, expressed as $K_D$, of at least $10^{-9}$M; more preferably $10^{-10}$ M, more preferably $10^{-11}$ M, more preferably $10^{-12}$M as measured by surface plasmon resonance, e.g., BIACORE™, biolayer interferometry measurements using, e.g., a ForteBio Octet HTX instrument (Pall Life Sciences), or solution-affinity ELISA.

By the term "slow off rate", "Koff" or "kd" is meant an antibody that dissociates from YFV, with a rate constant of $1\times10^{-3}$ $s^{-1}$ or less, preferably $1\times10^{-4}$ $s^{-1}$ or less, as determined by surface plasmon resonance, e.g., BIACORE™ or a ForteBio Octet HTX instrument (Pall Life Sciences).

The specific embodiments, antibody or antibody fragments of the disclosure may be conjugated to a therapeutic moiety ("immunoconjugate"), such as an antibiotic, a second anti-YFV antibody, a vaccine, or a toxoid, or any other therapeutic moiety useful for treating a YFV infection.

Also contemplated are antibodies and antigen-binding fragments substantially identical to the antibodies provided herein. The term "substantial identity", or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 90%, and more preferably at least about 95%, 96%, 97%, 98% or 99% of the nucleotide bases, as measured by any well-known algorithm of sequence identity, such as FASTA, BLAST or GAP, as discussed below. Accordingly, nucleic acid sequences that display a certain percentage "identity" share that percentage identity, and/or are that percentage "identical" to one another. A nucleic acid molecule having substantial identity to a reference nucleic acid molecule may, in certain instances, encode a polypeptide having the same or substantially similar amino acid sequence as the polypeptide encoded by the reference nucleic acid molecule.

In some embodiments, the antibody or antibody binding fragment thereof comprises at least one of a CDRH1, a CDRH2, a CDRH3, a CDRL1, a CDRL2, and a CDRL3 amino acid sequence of such antibodies or the antigen-binding fragments thereof are at least 70% identical; at least 75% identical; 80% identical; at least 85% identical; at least 90% identical; at least 95% identical; at least 96% identical; at least 97% identical; at least 98% identical; at least 99%; and/or all percentages of identity in between; to at least one the CDRH1, a CDRH2, a CDRH3, a CDRL1, a CDRL2, and/or a CDRL3 amino acid sequences as disclosed in Table 3 of an antibody selected from Antibody Number 1 through Antibody Number 152 as disclosed in Table 3.

In certain embodiments, the antibodies and antigen-binding fragments thereof comprise the CDRH3 amino acid sequence of any one of the antibodies designated Antibody Number 1 through Antibody Number 152 as disclosed in Table 3.

In certain embodiments, the antibodies and antigen-binding fragments thereof comprise the CDRH2 amino acid sequence of any one of the antibodies designated Antibody Number 1 through Antibody Number 152 as disclosed in Table 3.

In certain embodiments, the antibodies and antigen-binding fragments thereof comprise the CDRH1 amino acid sequence of any one of the antibodies designated Antibody Number 1 through Antibody Number 152 as disclosed in Table 3.

In certain embodiments, the antibodies and antigen-binding fragments thereof comprise the CDRL3 amino acid sequence of any one of the antibodies designated Antibody Number 1 through Antibody Number 152 as disclosed in Table 3.

In certain embodiments, the antibodies and antigen-binding fragments thereof comprise the CDRL2 amino acid sequence of any one of the antibodies designated Antibody Number 1 through Antibody Number 152 as disclosed in Table 3.

In certain embodiments, the antibodies and antigen-binding fragments thereof comprise the CDRL1 amino acid sequence of any one of the antibodies designated Antibody Number 1 through Antibody Number 152 as disclosed in Table 3.

In some embodiments, an anti-YFV antibody and antigen-binding fragment thereof is at least 70% identical; at least 75% identical; 80% identical; at least 85% identical; at least 90% identical; at least 95% identical; at least 96% identical; at least 97% identical; at least 98% identical; at least 99%; and/or all percentages of identity in between; to any one of the antibodies designated as Antibody Number 1 through Antibody Number 152 as disclosed in Table 3.

In certain embodiments, the antibodies and antigen-binding fragments thereof comprise a heavy chain (HC) amino acid sequence of any one of the antibodies designated Antibody Number 1 through Antibody Number 152 as disclosed in Table 3.

In certain embodiments, the inventive antibodies and antigen-binding fragments thereof comprise a light chain (LC) amino acid sequence of any one of the antibodies designated Antibody Number 1 through Antibody Number 152 as disclosed in Table 3. In certain embodiments, the inventive antibodies and antigen-binding fragments thereof comprise a heavy chain (HC) amino acid sequence and a light chain (LC) amino acid sequence of any one of the antibodies designated Antibody Number 1 through Antibody Number 152 as disclosed in Table 3.

In certain embodiments, the antibodies and antigen-binding fragments thereof are each selected from the group consisting of the antibodies designated as Antibody Number 1 through Antibody Number 152 as disclosed in Table 3.

Also provided are nucleic acids encoding the antibodies described herein. In certain embodiments, isolated nucleic acid sequences are provided that encode antibodies that specifically bind to YFV and antigen-binding fragments thereof, wherein at least one of the CDRH1, CDRH2, CDRH3, CDRL1, CDRL2, and/or CDRL3 amino acid sequences of the antibody or the antigen-binding fragment thereof is at least 70% identical; at least 75% identical; 80% identical; at least 85% identical; at least 90% identical; at least 95% identical; at least 96% identical; at least 97% identical; at least 98% identical; at least 99%; and/or all percentages of identity in between; to at least one the CDRH1, CDRH2, CDRH3, CDRL1, CDRL2, and/or CDRL3 amino acid sequences as disclosed in Table 3 of an antibody selected from Antibody Number 1 through Antibody Number 152 as disclosed in Table 3.

In certain embodiments, isolated nucleic acid sequences are provided that encode the antibodies and antigen-binding fragments thereof, wherein such nucleic acid sequences comprise sequences that encode the CDRH3 amino acid sequence of any one of the antibodies designated Antibody Number 1 through Antibody Number 152 as disclosed in Table 3.

In certain embodiments, isolated nucleic acid sequences are provided that encode the antibodies and antigen-binding fragments thereof, wherein such nucleic acid sequences comprise sequences that encode the CDRH2 amino acid sequences of any one of the antibodies designated Antibody Number 1 through Antibody Number 152 as disclosed in Table 3.

In certain embodiments, isolated nucleic acid sequences are provided that encode the antibodies and antigen-binding fragments thereof, wherein such nucleic acid sequences comprise sequences that encode the CDRH1 amino acid sequences of any one of the antibodies designated Antibody Number 1 through Antibody Number 152 as disclosed in Table 3.

In certain embodiments, isolated nucleic acid sequences are provided that encode the antibodies and antigen-binding fragments thereof, wherein such nucleic acid sequences comprise sequences that encode the CDRL3 amino acid sequences of any one of the antibodies designated Antibody Number 1 through Antibody Number 152 as disclosed in Table 3.

In certain embodiments, isolated nucleic acid sequences are provided that encode the antibodies and antigen-binding fragments thereof, wherein such nucleic acid sequences comprise sequences that encode the CDRL2 amino acid sequences of any one of the antibodies designated Antibody Number 1 through Antibody Number 152 as disclosed in Table 3.

In certain embodiments, isolated nucleic acid sequences are provided that encode the antibodies and antigen-binding fragments thereof, wherein such nucleic acid sequences comprise sequences that encode the CDRL1 amino acid sequences of any one of the antibodies designated Antibody Number 1 through Antibody Number 152 as disclosed in Table 3.

In certain embodiments, isolated nucleic acid sequences are provided that encode the antibodies and antigen-binding fragments thereof, wherein such nucleic acid sequences comprise sequences that encode the heavy chain (HC) amino acid sequences of any one of the antibodies designated Antibody Number 1 through Antibody Number 152 as disclosed in Table 3

In certain embodiments, isolated nucleic acid sequences are provided that encode the antibodies and antigen-binding fragments thereof, wherein such nucleic acid sequences comprise sequences that encode the heavy chain (LC) amino acid sequences of any one of the antibodies designated Antibody Number 1 through Antibody Number 152 as disclosed in Table 3. As applied to polypeptides, the term "substantial identity" or "substantially identical" means that two peptide sequences, when optimally aligned, such as by the programs GAP or BESTFIT using default gap weights, share at least 90% sequence identity, even more preferably at least 95%, 98% or 99% sequence identity. Accordingly, amino acid sequences that display a certain percentage "identity" share that percentage identity, and/or are that percentage "identical" to one another. Accordingly, amino acid sequences that display a certain percentage "identity" share that percentage identity, and/or are that percentage "identical" to one another.

In certain embodiments, the disclosed antibody amino acid sequences are, e.g.: at least 70% identical; at least 75% identical; 80% identical; at least 85% identical; at least 90% identical; at least 95% identical; at least 96% identical; at least 97% identical; at least 98% identical; at least 99%; and/or all percentages of identity in between; to other sequences and/or share such percentage identities with one another (or with certain subsets of the herein-disclosed antibody sequences).

Preferably, residue positions, which are not identical, differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent or degree of similarity may be adjusted upwards to correct for the conservative nature of the substitution. Means for making this adjustment are well known to those of skill in the art. (See, e.g., Pearson (1994) Methods Mol. Biol. 24: 307-331). Examples of groups of amino acids that have side chains with similar chemical properties include 1) aliphatic side chains: glycine, alanine, valine, leucine and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartate and glutamate, and 7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443 45. A "moderately conservative" replacement is any change having a nonnegative value in the PAM250 log-likelihood matrix.

Sequence similarity for polypeptides is typically measured using sequence analysis software. Protein analysis software matches similar sequences using measures of similarity assigned to various substitutions, deletions and other modifications, including conservative amino acid substitutions. For instance, GCG software contains programs such as GAP and BESTFIT which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA with default or recommended parameters; a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the disclosure to a database containing a large number of sequences from different organisms is the computer program BLAST, especially BLASTP or TBLASTN, using default parameters. (See, e.g., Altschul et al. (1990) J. Mol. Biol. 215: 403 410 and (1997) Nucleic Acids Res. 25:3389 402).

In certain embodiments, the antibody or antibody fragment for use in the method of the disclosure may be mono-specific, bi-specific, or multi-specific. Multi-specific antibodies may be specific for different epitopes of one target polypeptide or may contain antigen-binding domains specific for epitopes of more than one target polypeptide.

As disclosed herein, anti-YFV antibodies may be obtained from human B cells using techniques available to the artisan, and, for example, as described in the EXAMPLES below. Methods for generating human antibodies in transgenic animals, such as mice, are also known in the art and may be employed in order to derive antibodies in accordance with the present disclosure. Any such known methods can be used in the context of the present disclosure to make human antibodies that specifically bind to YFV (see, for example, U.S. Pat. No. 6,596,541).

In certain embodiments, the antibodies of the instant disclosure possess affinities ($K_D$) ranging from about $1.0 \times 10^{-7}$M to about $1.0 \times 10^{-12}$M, when measured by binding to antigen either immobilized on solid phase or in solution phase. In certain embodiments, the antibodies of the disclosure possess affinities ($K_D$) ranging from about $1 \times 10^{-7}$ M to about $6 \times 10^{-10}$ M, when measured by binding to antigen either immobilized on solid phase or in solution phase. In certain embodiments, the antibodies of the disclosure possess affinities ($K_D$) ranging from about $1 \times 10^{-7}$ M to about $9 \times 10^{-10}$M, when measured by binding to antigen either immobilized on solid phase or in solution phase.

In addition to the specific anti-YFV antibodies and antibody fragments disclosed herein, the present disclosure also contemplates variants of those antibodies and antibody fragments that maintain bioequivalency. Such variant antibodies and antibody fragments comprise one or more additions, deletions, or substitutions of amino acids when compared to parent sequence, but exhibit biological activity that is essentially equivalent to that of the described antibodies. Likewise, the antibody-encoding DNA sequences of the present disclosure encompass sequences that comprise one or more additions, deletions, or substitutions of nucleotides when compared to the disclosed sequence, but that encode an antibody or antibody fragment that is essentially bioequivalent to an antibody or antibody fragment of the disclosure.

Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single does or multiple dose. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, and potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and/or in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of the antibodies of the disclosure may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antibodies may include antibody variants comprising amino acid changes, which modify the glycosylation characteristics of the antibodies, e.g., mutations that eliminate or remove glycosylation.

Biological and Biophysical Characteristics of the Antibodies

In certain embodiments, the inventive antibodies and antigen-binding fragments thereof specifically bind to YFV, wherein at least one of the CDRH1, CDRH2, CDRH3, CDRL1, CDRL2, and/or CDRL3 amino acid sequences is at least 70% identical; at least 75% identical; 80% identical; at least 85% identical; at least 90% identical; at least 95% identical; at least 96% identical; at least 97% identical; at least 98% identical; at least 99%; and/or all percentages of identity in between; to the corresponding CDRH1, CDRH2, CDRH3, CDRL1, CDRL2, and/or CDRL3 amino acid sequence as disclosed in Table 3 of an antibody selected from Antibody Number 1 through Antibody Number 152 as disclosed in Table 3.

In some embodiments, the anti-YFV antibodies and antigen-binding fragments thereof are neutralizing antibodies, i.e., exhibit neutralizing potency. A "neutralizing antibody", as used herein (or an "antibody that neutralizes YFV activity" or "an antibody with neutralizing activity"), refers to an antibody whose binding to an antigen, e.g., the YFV E protein as the case may be as disclosed herein, results in inhibition of at least one biological activity. For example, an antibody of the disclosure may aid in blocking the fusion of YFV to a host cell, or prevent syncytia formation, or prevent the primary disease caused by YFV. Alternatively, an antibody of the disclosure may demonstrate the ability to ameliorate at least one symptom of the YFV infection. This inhibition of the biological activity of YFV can be assessed by measuring one or more indicators of YFV biological activity by one or more of several standard in vitro assays (such as a neutralization assay, as described herein) or in vivo assays known in the art (for example, animal models to look at protection from challenge with YFV following administration of one or more of the antibodies described herein).

In certain embodiments, the antibodies and antigen-binding fragments thereof display an in vitro neutralization potency ($IC_{50}$) of between about 0.5 microgram/milliliter (µg/ml) to about 5 µg/ml; between about 0.05 µg/ml to about 0.5 µg/ml; or less than about 0.05 mg/ml.

The term "$IC_{50}$" refers to the "half maximal inhibitory concentration", which value measures the effectiveness of compound (e.g. anti-YFV antibody) inhibition towards a biological or biochemical utility. This quantitative measure indicates the quantity required for a particular inhibitor to inhibit a given biological process by half. In certain embodiments, YFV neutralization potencies for anti-YFV neutralizing antibodies disclosed herein are expressed as neutralization $IC_{50}$ values. Of the anitbodies described herein, generally the antibodies binding to DIII of the YFV E protein possess the highest neutralization potency.

In some embodiments, the antibodies and antigen-binding fragments thereof cross-react with DENV-2, DENV-4, WNV, or ZIKV E proteins, i.e., bind to YFV E protein and an E protein from one or more of the other flaviviruses. In certain embodiments, such antibodies and antigen-binding fragments thereof bind to DENV-2, DENV-4, WNV, YFV, and ZIKV E proteins with high apparent avid affinities ($K_D^{Apps}$<10 nM). In certain embodiments, the cross-reactive antibodies or antigen-binding fragments thereof have neutralizing activity against YFV-17D and another flavivirus. In certain embodiments, the cross-reactive antibodies and antigen-binding fragments thereof bind to the FL epitope. In certain embodiments, the cross-reactive antibodies and antigen-binding fragments thereof bind to DIII. In a certain embodiment, the cross-reactive antibody is ADI-48905.

Epitope Binning and Related Technologies

As described above and as demonstrated in the EXAMPLES, Applicant has characterized the epitopic binning of the inventive antibodies and antigen-binding fragments thereof. In addition to the methods for conducting such characterization, various other techniques are available to the artisan that can be used to carry out such characterization or to otherwise ascertain whether an antibody "interacts with one or more amino acids" within a polypeptide or protein. Exemplary techniques include, for example, a routine cross-blocking assay such as that described Antibodies, Harlow and Lane (Cold Spring Harbor Press, Cold Spring Harb., N.Y.) can be performed. Other methods include alanine scanning mutational analysis, peptide blot analysis (Reineke (2004) Methods Mol Biol 248:443-63), peptide cleavage analysis crystallographic studies and NMR analysis. In addition, methods such as epitope excision, epitope extraction and chemical modification of antigens can be employed (Tomer (2000) Protein Science 9: 487-496). Another method that can be used to identify the amino acids within a polypeptide with which an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water and exchangeable protons within amino acids that are protected by the antibody complex undergo deuterium-to-hydrogen back-exchange at a slower rate than exchangeable protons within amino acids that are not part of the interface. As a result, amino acids that form part of the protein/antibody interface may retain deuterium and therefore exhibit relatively higher mass compared to amino acids not included in the interface. After dissociation of the antibody, the target protein is subjected to protease cleavage and mass spectrometry analysis, thereby revealing the deuterium-labeled residues that correspond to the specific amino acids with which the antibody interacts. See, e.g., Ehring (1999) Analytical Biochemistry 267 (2):252-259; Engen and Smith (2001) Anal. Chem. 73:256A-265A.

As the artisan will understand, an epitope can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5 or 8-10 amino acids in a unique spatial conformation.

Modification-Assisted Profiling (MAP), also known as Antigen Structure-based Antibody Profiling (ASAP) is a method that categorizes large numbers of monoclonal antibodies (mAbs) directed against the same antigen according to the similarities of the binding profile of each antibody to chemically or enzymatically modified antigen surfaces (US 2004/0101920). Each category may reflect a unique epitope either distinctly different from or partially overlapping with an epitope represented by another category. This technology allows rapid filtering of genetically identical antibodies, such that characterization can be focused on genetically distinct antibodies. When applied to hybridoma screening, MAP may facilitate identification of rare hybridoma clones that produce mAbs having the desired characteristics. MAP may be used to sort the antibodies of the disclosure into groups of antibodies binding different epitopes.

As the artisan understands, one can easily determine whether an antibody binds to the same epitope as, or competes for binding with, a reference anti-YFV antibody by using routine methods available in the art. For example, to determine if a test antibody binds to the same epitope as a reference YFV antibody of the disclosure, the reference antibody is allowed to bind to a YFV protein or peptide under saturating conditions. Next, the ability of a test antibody to bind to the YFV molecule is assessed. If the test antibody is able to bind to YFV following saturation binding with the reference anti-YFV antibody, it can be concluded that the test antibody binds to a different epitope than the reference anti-YFV antibody. On the other hand, if the test antibody is not able to bind to the YFV molecule following saturation binding with the reference anti-YFV antibody, then the test antibody may bind to the same epitope as the epitope bound by the reference anti-YFV antibody of the disclosure.

To determine if an antibody competes for binding with a reference anti-YFV antibody, the above-described binding methodology is performed in two orientations: In a first orientation, the reference antibody is allowed to bind to a YFV molecule under saturating conditions followed by assessment of binding of the test antibody to the YFV molecule. In a second orientation, the test antibody is allowed to bind to a YFV molecule under saturating conditions followed by assessment of binding of the reference antibody to the YFV molecule. If, in both orientations, only the first (saturating) antibody is capable of binding to the YFV molecule, then it is concluded that the test antibody and the reference antibody compete for binding to YFV. As will be appreciated by a person of ordinary skill in the art, an antibody that competes for binding with a reference antibody may not necessarily bind to the identical epitope as the reference antibody, but may sterically block binding of the reference antibody by binding an overlapping or adjacent epitope.

Two antibodies bind to the same or overlapping epitope if each competitively inhibits (blocks) binding of the other to the antigen. That is, a 1-, 5-, 10-, 20- or 100-fold excess of one antibody inhibits binding of the other by at least 50% but preferably 75%, 90% or even 99% as measured in a competitive binding assay (see, e.g., Junghans et al., Cancer Res. (1990) 50:1495-1502). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, surface plasmon resonance, flow cytometry or any other quantitative or qualitative antibody-binding assay available in the art.

Immunoconjugates

The disclosure encompasses a human YFV monoclonal antibody conjugated to a therapeutic moiety ("immunoconjugate"), such as an agent that is capable of reducing the severity of primary infection with YFV, or to ameliorate at least one symptom associated with YFV infection, including fever, muscle pains, headache, vomiting, diarrhea, bleeding, or the severity thereof. Such an agent may be a second different antibody to YFV, or a vaccine. The type of therapeutic moiety that may be conjugated to the anti-YFV antibody will take into account the condition to be treated and the desired therapeutic effect to be achieved. Alternatively, if the desired therapeutic effect is to treat the sequelae or symptoms associated with YFV infection, or any other condition resulting from such infection, such as, but not limited to, disseminated intravascular coagulation, acute kidney failure, and acute respiratory distress syndrome, it may be advantageous to conjugate an agent appropriate to treat the sequelae or symptoms of the condition, or to alleviate any side effects of the antibodies of the disclosure. Examples of suitable agents for forming immunoconjugates are known in the art, see for example, WO 05/103081.

Multi-Specific Antibodies

The antibodies of the present disclosure may be monospecific, bi-specific, or multi-specific. Multi-specific antibodies may be specific for different epitopes of one target polypeptide or may contain antigen-binding domains specific for more than one target polypeptide. See, e.g., Tutt et al., 1991, J. Immunol. 147:60-69; Kufer et al., 2004, Trends Biotechnol. 22:238-244. The antibodies of the present disclosure can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment to produce a bi-specific or a multi-specific antibody with a second binding specificity.

Therapeutic Administration and Formulations

The disclosure provides therapeutic compositions comprising the inventive anti-YFV antibodies or antigen-binding fragments thereof. The administration of therapeutic compositions in accordance with the disclosure will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of each of the antibodies of the disclosure may vary depending upon the age and the size of a subject to be administered, target disease, conditions, route of administration, and the like. When the antibodies of the present disclosure are used for treating a YFV infection, or for treating one or more symptoms associated with a YFV infection, such as the fever, nausea, or muscle aches associated with a YFV infection in a patient, or for lessening the severity of the disease, it is advantageous to administer each of the antibodies of the present disclosure intravenously or subcutaneously. Normally, each of the antibodies would be administered at a single dose of about 0.01 to about 30 mg/kg body weight, more preferably about 0.1 to about 20 mg/kg body weight, or about 0.1 to about 15 mg/kg body weight, or about 0.02 to about 7 mg/kg body weight, about 0.03 to about 5 mg/kg body weight, or about 0.05 to about 3 mg/kg body weight, or about 1 mg/kg body weight, or about 3.0 mg/kg body weight, or about 10 mg/kg body weight, or about 20 mg/kg body weight. Multiple doses may be administered as necessary. Depending on the severity of the condition, the frequency and the duration of the treatment can be adjusted. In certain embodiments, the antibodies or antigen-binding fragments thereof of the disclosure can be administered as an initial dose of at least about 0.1 mg to about 800 mg, about 1 to about 600 mg, about 5 to about 300 mg, or about 10 to about 150 mg, to about 100 mg, or to about 50 mg. In certain embodiments, the initial dose may be followed by administration of a second or a plurality of subsequent doses of the antibodies or antigen-binding fragments thereof in an amount that can be approximately the same or less than that of the initial dose, wherein the subsequent doses are separated by at least 1 day to 3 days; at least one week, at least 2 weeks; at least 3 weeks; at least 4 weeks; at least 5 weeks; at least 6 weeks; at least 7 weeks; at least 8 weeks; at least 9 weeks; at least 10 weeks; at least 12 weeks; or at least 14 weeks.

Various delivery systems are known and can be used to administer the pharmaceutical composition of the disclosure, e.g., encapsulation in liposomes, microparticles, microcapsules, recombinant cells capable of expressing the mutant viruses, receptor mediated endocytosis (see, e.g., Wu et al. (1987) J. Biol. Chem. 262:4429-4432). Methods of introduction include, but are not limited to, intradermal, transdermal, intramuscular, intraperitoneal, intravenous, subcutaneous, intranasal, epidural and oral routes. The composition may be administered by any convenient route, for example by infusion or bolus injection, by absorption through epithelial or mucocutaneous linings {e.g., oral mucosa, nasal mucosa, rectal and intestinal mucosa, etc.) and may be administered together with other biologically active agents. Administration can be systemic or local. It may be delivered as an aerosolized formulation (See US2011/0311515 and US2012/0128669). The delivery of agents useful for treating respiratory diseases by inhalation is becoming more widely accepted (See A. J. Bitonti and J. A. Dumont, (2006), Adv. Drug Deliv. Rev, 58:1 106-1 1 18). In addition to being effective at treating local pulmonary disease, such a delivery mechanism may also be useful for systemic delivery of antibodies (See Maillet et al. (2008), Pharmaceutical Research, Vol. 25, No. 6, 2008).

The pharmaceutical composition can be also delivered in a vesicle, in particular a liposome (see, for example, Langer (1990) Science 249:1527-1533).

In certain situations, the pharmaceutical composition can be delivered in a controlled release system. In one embodiment, a pump may be used. In another embodiment, polymeric materials can be used. In yet another embodiment, a controlled release system can be placed in proximity of the composition's target, thus requiring only a fraction of the systemic dose.

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

A pharmaceutical composition of the present disclosure can be delivered subcutaneously or intravenously with a standard needle and syringe. In addition, with respect to subcutaneous delivery, a pen delivery device readily has applications in delivering a pharmaceutical composition of the present disclosure. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present disclosure. Examples include, but certainly are not limited to AUTOPEN™ (Owen Mumford, Inc., Woodstock, UK), DISETRONIC™ pen (Disetronic Medical Systems, Burghdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (Sanofi-Aventis, Frankfurt, Germany), to name only a few. Examples of disposable pen delivery devices having applications in subcutaneous delivery of a pharmaceutical composition of the present disclosure include, but certainly are not limited to the SOLOSTAR™ pen (Sanofi-Aventis), the FLEXPEN™ (Novo Nordisk), and the KWIKPEN™ (Eli Lilly), the SURECLICK™ Autoinjector (Amgen, Thousand Oaks, Calif.), the PENLET™ (Haselmeier, Stuttgart, Germany), the EPIPEN (Dey, L.P.) and the HUMIRA™ Pen (Abbott Labs, Abbott Park, Ill.), to name only a few.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 5 to about 500 mg per dosage form in a unit dose; especially in the form of injection, it is preferred that the aforesaid antibody is contained in about 5 to about 100 mg and in about 10 to about 250 mg for the other dosage forms.

Administration Regimens

In some embodiments, a therapeutically effective amount of an anti-YFV antibody or antigen-binding fragment thereof is provided to a subject in feed thereof, e.g., infected with YFV or at risk for infection with YFV. By the phrase "therapeutically effective amount" is meant an amount that produces the desired effect for which it is administered. The exact amount will depend on the purpose of the treatment, and will be ascertainable by one skilled in the art using known techniques (see, for example, Lloyd (1999) The Art, Science and Technology of Pharmaceutical Compounding).

According to certain embodiments, multiple doses of an antibody to YFV may be administered to a subject over a defined time course. The methods according to this aspect of the disclosure comprise sequentially administering to a subject multiple doses of an antibody to YFV. As used herein, "sequentially administering" means that each dose of antibody to YFV is administered to the subject at a different point in time, e.g., on different days separated by a predetermined interval (e.g., hours, days, weeks or months). The present disclosure includes methods which comprise sequentially administering to the patient a single initial dose of an antibody to YFV, followed by one or more secondary doses of the antibody to YFV and optionally followed by one or more tertiary doses of the antibody to YFV.

The terms "initial dose," "secondary doses," and "tertiary doses," refer to the temporal sequence of administration of the antibody to YFV. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of antibody to YFV, but generally may differ from one another in terms of frequency of administration. In certain embodiments, however, the amount of antibody to YFV contained in the initial, secondary and/or tertiary doses vary from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

In one exemplary embodiment of the present disclosure, each secondary and/or tertiary dose is administered 1 to 26 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, 15, 15½, 16, 16½, 17, 17½, 18, 18½, 19, 19½, 20, 20½, 21, 21½, 22, 22½, 23, 23½, 24, 24½, 25, 25½, 26, 26½, or more) weeks after the immediately preceding dose. The phrase "the immediately preceding dose," as used herein, means, in a sequence of multiple administrations, the dose of antibody to YFV which is administered to a patient prior to the administration of the very next dose in the sequence with no intervening doses.

The methods according to this aspect of the disclosure may comprise administering to a patient any number of secondary and/or tertiary doses of an antibody to YFV. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient 1 to 2 weeks after the immediately preceding dose. Similarly, in embodiments involving multiple tertiary doses, each tertiary dose may be administered at the same frequency as the other tertiary doses. For example, each tertiary dose may be administered to the patient 2 to 4 weeks after the immediately preceding dose. Alternatively, the frequency at which the secondary and/or tertiary doses are administered to a patient can vary over the course of the treatment regimen. The frequency of administration may also be adjusted during the course of treatment by a physician depending on the needs of the individual patient following clinical examination.

Accordingly, in certain embodiments are provided pharmaceutical compositions comprising: one or more of the inventive antibodies or antigen-binding fragments thereof disclosed herein and throughout and a pharmaceutically acceptable carrier and/or one or more excipients. In certain other embodiments are provided pharmaceutical compositions comprising: one or more nucleic acid sequences encoding one or more inventive antibodies or antigen-binding fragments thereof; or one or more the expression vectors harboring such nucleic acid sequences; and a pharmaceutically acceptable carrier and/or one or more excipients.

Therapeutic Uses of the Antibodies

The anti-YFV antibodies disclosed herein may be used to treat a subject with YFV and/or prevent YFV infection.

As used herein, the terms "treat," "treatment" and "treating" refer to the reduction or amelioration of the progression, severity, and/or duration of a YFV infection, or a symptom or condition related thereto (such as fever, chills, headache, low back pain, myalgia, loss of appetite, nausea, vomiting, fatigue, or a combination thereof) resulting from the administration of one or more therapies (including, but not limited to, the administration of one or more prophylactic or therapeutic agents). In certain embodiments, such terms refer to the reduction or inhibition of the replication of YFV, the inhibition or reduction in the spread of YFV to other subjects, the inhibition or reduction of infection of a cell with YFV, or the amelioration of one or more symptoms associated with a YFV infection.

As used herein, the terms "prevent," "preventing," and "prevention" refer to the prevention or inhibition of the development or onset of a YFV infection or condition related thereto in a subject, the prevention or inhibition of the progression of a YFV infection or a condition related thereto resulting from the administration of a therapy (e.g., a prophylactic or therapeutic agent), the prevention of a symptom of a YFV infection or condition related thereto, or the administration of a combination of therapies (e.g., a combination of prophylactic or therapeutic agents). As used herein, the terms "ameliorate" and "alleviate" refer to a reduction or diminishment in the severity a condition or any symptoms thereof.

Due to their binding to and interaction with YFV, it is believed that the inventive antibodies and antigen-binding fragments thereof are useful—without wishing to be bound to any theory—for preventing fusion of the virus with the host cell membrane, for preventing cell to cell virus spread, and for inhibition of syncytia formation. Alternatively, the antibodies of the present disclosure may be useful for ameliorating at least one symptom associated with the infection, such as fever, diarrhea, and bleeding, or for lessening the severity, duration, and/or frequency of the infection. The antibodies of the disclosure are also contemplated for prophylactic use in patients at risk for developing or acquiring a YFV infection. It is contemplated that the antibodies of the disclosure may be used alone, or in conjunction with a second agent, or third agent for treating YFV infection, or for alleviating at least one symptom or complication associated with the YFV infection, such as fever, nausea, or muscle aches associated with, or resulting from such an infection. The second or third agents may be delivered concurrently with the antibodies of the disclosure, or they may be administered separately, either before or after the antibodies of the disclosure. The second or third agent may be an anti-viral, an NSAID or other agents to reduce fever or pain, another second but different antibody that specifically binds YFV, an agent (e.g. an antibody) that binds to another YFV antigen, a vaccine against YFV, and an siRNA specific for a YFV antigen.

In yet a further embodiment of the disclosure the present antibodies are used for the preparation of a pharmaceutical composition for treating patients suffering from a YFV infection. In yet another embodiment of the disclosure the present antibodies are used for the preparation of a pharmaceutical composition for reducing the severity of a primary infection with YFV, or for reducing the duration of the infection, or for reducing at least one symptom associated with the YFV infection. In a further embodiment of the disclosure the present antibodies are used as adjunct therapy with any other agent useful for treating an YFV infection, including an antiviral, a toxoid, a vaccine, a second YFV antibody, or any other antibody specific for a YFV antigen, or any other palliative therapy known to those skilled in the art.

Accordingly, in certain embodiments are provided methods of treating or preventing a YFV infection, or at least one symptom associated with YFV infection, comprising administering to a patient in need thereof or suspected of being in need thereof one or more of the inventive antibodies or antigen-binding fragments thereof disclosed herein and throughout, such as, e.g., one or more of the anti-YFV antibodies disclosed in Table 3, such that the YFV infection is treated or prevented, or the at least one symptom associated with YFV infection is treated, alleviated, or reduced in severity.

In certain other embodiments are provided methods of treating or preventing a YFV infection, or at least one symptom associated with YFV infection, comprising administering to a patient in need thereof or suspected of being in need thereof a nucleic acid sequence encoding one or more of the inventive antibodies or antigen-binding fragments thereof, such nucleic acid sequence encoding an amino acid sequence disclosed in Table 3 and compliments thereof, such that the YFV infection is treated or prevented, or the at least one symptom associated with YFV infection is treated, alleviated, or reduced in severity.

In additional embodiments are provided methods of treating or preventing a YFV infection, or at least one symptom associated with YFV infection, comprising administering to a patient in need thereof or suspected of being in need thereof a host cell harboring a nucleic acid sequence or an expression vector comprising such a nucleic acid sequence, wherein such nucleic acid sequences encode an amino acid sequence selected from sequences disclosed in Table 3 and compliments thereof, such that the YFV infection is treated or prevented, or the at least one symptom associated with YFV infection is treated, alleviated, or reduced in severity.

In additional embodiments are provided methods of treating or preventing a YFV infection, or at least one symptom associated with YFV infection, comprising administering to a patient in need thereof or suspected of being in need thereof a pharmaceutical composition comprising either: one or more of the inventive antibodies or antigen-binding fragments thereof as disclosed in Table 3; one or more nucleic acid sequences or an expression vectors comprising such a nucleic acid sequence, wherein such nucleic acid sequences encode amino acid sequences selected from sequences disclosed in Table 3 and compliments thereof; one or more host cells harboring one or more nucleic acid sequences or expression vectors comprising such one or more nucleic acid sequences, wherein such nucleic acid sequences encode amino acid sequences selected from sequences disclosed in Table 3 and compliments thereof; and a pharmaceutically acceptable carrier and/or one or more excipients, such that the YFV infection is treated or prevented, or the at least one symptom associated with YFV infection is treated, alleviated, or reduced in severity.

In certain embodiments are provided methods of treating or preventing a YFV infection, or at least one symptom associated with said YFV infection, comprising administering to a patient in need thereof or suspected of being in need thereof one or more of the inventive antibodies or antigen-binding fragments thereof disclosed herein and throughout, such as, e.g., one or more of the anti-YFV antibodies disclosed in Table 3, such that the YFV infection is treated or prevented, or the at least one symptom associated with YFV infection is treated, alleviated, or reduced in severity.

In certain other embodiments are provided methods of treating or preventing a YFV infection, or at least one symptom associated with said YFV infection, comprising administering to a patient in need thereof or suspected of being in need thereof a nucleic acid sequence encoding one or more of the inventive antibodies or antigen-binding fragments thereof, such nucleic acid sequences encoding amino acid sequences disclosed in Table 3 and compliments thereof, such that the YFV infection is treated or prevented, or the at least one symptom associated with YFV infection is treated, alleviated, or reduced in severity.

In additional embodiments are provided methods of treating or preventing a YFV infection, or at least one symptom associated with said YFV infection, comprising administering to a patient in need thereof or suspected of being in need thereof a host cell harboring a nucleic acid sequence or an expression vector comprising such a nucleic acid sequence, wherein such nucleic acid sequences encode amino acid sequences selected from sequences disclosed in Table 3 and compliments thereof, such that the YFV infection is treated or prevented, or the at least one symptom associated with YFV infection is treated, alleviated, or reduced in severity.

In additional embodiments are provided methods of treating or preventing a YFV infection, or at least one symptom associated with said YFV infection, comprising administering to a patient in need thereof or suspected of being in need thereof a pharmaceutical composition comprising either: one or more of the inventive antibodies or antigen-binding fragments thereof as disclosed in Table 3; one or more nucleic acid sequences or an expression vectors comprising such a nucleic acid sequence, wherein such nucleic acid sequences encode amino acid sequences selected from sequences disclosed in Table 3 and compliments thereof; one or more host cells harboring one or more nucleic acid sequences or an expression vectors comprising such one or more nucleic acid sequences, wherein such nucleic acid sequences encode amino acid sequences selected from sequences disclosed in Table 3 and compliments thereof; and a pharmaceutically acceptable carrier and/or one or more excipients, such that the YFV infection is treated or prevented, or the at least one symptom associated with YFV infection is treated, alleviated, or reduced in severity.

Combination Therapies

As noted above, according to certain embodiments, the disclosed methods comprise administering to the subject one or more additional therapeutic agents in combination with an antibody to YFV. As used herein, the expression "in combination with" means that the additional therapeutic agents are administered before, after, or concurrent with the pharmaceutical composition comprising the anti-YFV antibody. The term "in combination with" also includes sequential or concomitant administration of the anti-YFV antibody and a second therapeutic agent.

For example, when administered "before" the pharmaceutical composition comprising the anti-YFV antibody, the additional therapeutic agent may be administered about 72 hours, about 60 hours, about 48 hours, about 36 hours, about 24 hours, about 12 hours, about 10 hours, about 8 hours, about 6 hours, about 4 hours, about 2 hours, about 1 hour, about 30 minutes, about 15 minutes or about 10 minutes prior to the administration of the pharmaceutical composition comprising the anti-YFV antibody. When administered "after" the pharmaceutical composition comprising the anti-YFV antibody, the additional therapeutic agent may be administered about 10 minutes, about 15 minutes, about 30 minutes, about 1 hour, about 2 hours, about 4 hours, about 6 hours, about 8 hours, about 10 hours, about 12 hours, about 24 hours, about 36 hours, about 48 hours, about 60 hours or about 72 hours after the administration of the pharmaceutical composition comprising the anti-YFV antibodies. Administration "concurrent" or with the pharmaceutical composition comprising the anti-YFV antibody means that the additional therapeutic agent is administered to the subject in a separate dosage form within less than 5 minutes (before, after, or at the same time) of administration of the pharmaceutical composition comprising the anti-YFV antibody, or administered to the subject as a single combined dosage formulation comprising both the additional therapeutic agent and the anti-YFV antibody.

Combination therapies may include an anti-YFV antibody of the disclosure and any additional therapeutic agent that may be advantageously combined with an antibody of the disclosure, or with a biologically active fragment of an antibody of the disclosure.

For example, a second or third therapeutic agent may be employed to aid in reducing the viral load in the liver, such as an antiviral. The antibodies may also be used in conjunction with other therapies, as noted above, including a toxoid, a vaccine specific for YFV, a second antibody specific for YFV, or an antibody specific for another YFV antigen.

Diagnostic Uses of the Antibodies

The inventive anti-YFV antibodies and antigen-binding fragments thereof may also be used to detect and/or measure YFV in a sample, e.g., for diagnostic purposes. It is envisioned that confirmation of an infection thought to be caused by YFV may be made by measuring the presence of the virus through use of any one or more of the antibodies of the disclosure. Exemplary diagnostic assays for YFV may comprise, e.g., contacting a sample, obtained from a patient, with an anti-YFV antibody of the disclosure, wherein the YFV antibody is labeled with a detectable label or reporter molecule or used as a capture ligand to selectively isolate the virus containing the protein from patient samples. Alternatively, an unlabeled YFV antibody can be used in diagnostic applications in combination with a secondary antibody which is itself detectably labeled. The detectable label or reporter molecule can be a radioisotope, such as $^3$H, $^{14}$C, $^{32}$P, $^{35}$S, or $^{125}$I; a fluorescent or chemiluminescent moiety such as fluorescein isothiocyanate, or rhodamine; or an enzyme such as alkaline phosphatase, β-galactosidase, horseradish peroxidase, or luciferase. Specific exemplary assays that can be used to detect or measure YFV in a sample include enzyme-linked immunosorbent assay (ELISA), radioimmunoassay (RIA), and fluorescence-activated cell sorting (FACS).

Samples that can be used in YFV diagnostic assays according to the present disclosure include any tissue or fluid sample obtainable from a patient, which contains detectable quantities of YFV protein, or fragments thereof, under normal or pathological conditions. Generally, levels of YFV in a particular sample obtained from a healthy patient (e.g., a patient not afflicted with a disease or condition associated with the presence of YFV) will be measured to initially establish a baseline, or standard, level of YFV protein. This baseline level of YFV can then be compared against the levels of YFV measured in samples obtained from individuals suspected of having an YFV infection, or symptoms associated with such infection.

EXAMPLES

The human antibody response to YFV was comprehensively profiled by isolating and characterizing 152 YFV-specific monoclonal antibodies from the memory B cells of two flavivirus-naive donors following immunization with YFV-17D, and these antibodies were then used to map the antigenic topology of YFV. The anti-YFV antibodies obtained were found to bind several antigenic sites, most commonly targeting an epitope within or proximal to the FL of Domain II of the YFV E protein and, thus, providing support for the development of YFV antibodies that target Domain II. However, a second less common class of antibodies with highly potent neutralizing activity were found to target DIII of the virus. Such DIII-directed antibodies may be particularly valuable in the context of therapeutic application of monoclonal antibodies or cocktails as this epitope is subdominant in the natural immune response. Taken together, these results have implications for the design and evaluation of YFV vaccine and antibody-based therapeutic candidates and offer new options for passive prophylaxis.

Study design: Two flavivirus-naïve healthy adult donors ("Donor 8" and "Donor 9") were immunized with the YFV-17D vaccine (Stamaril; Sanofi) and blood samples were collected at 10, 14, 28, 90, 180, 270, and 360 days post-vaccination. Serum neutralizing activity against YFV-17D appeared in both donors by day 14 post-vaccination and persisted through the course of the study (FIG. 1A). Pre-vaccination sera from both donors lacked reactivity with YFV-17D and showed no detectable neutralizing activity against YFV-17D (data not shown) and also lacked reactivity with E and NS1 proteins from other commonly circulating flaviviruses, i.e., dengue virus serotypes 1-4 (DENV1-4), JEV, TBEV, West Nile virus (WNV) and Zika virus (ZIKV), confirming that both donors were likely flavivirus-naïve at the time of vaccination (data not shown).

Figure 2A:
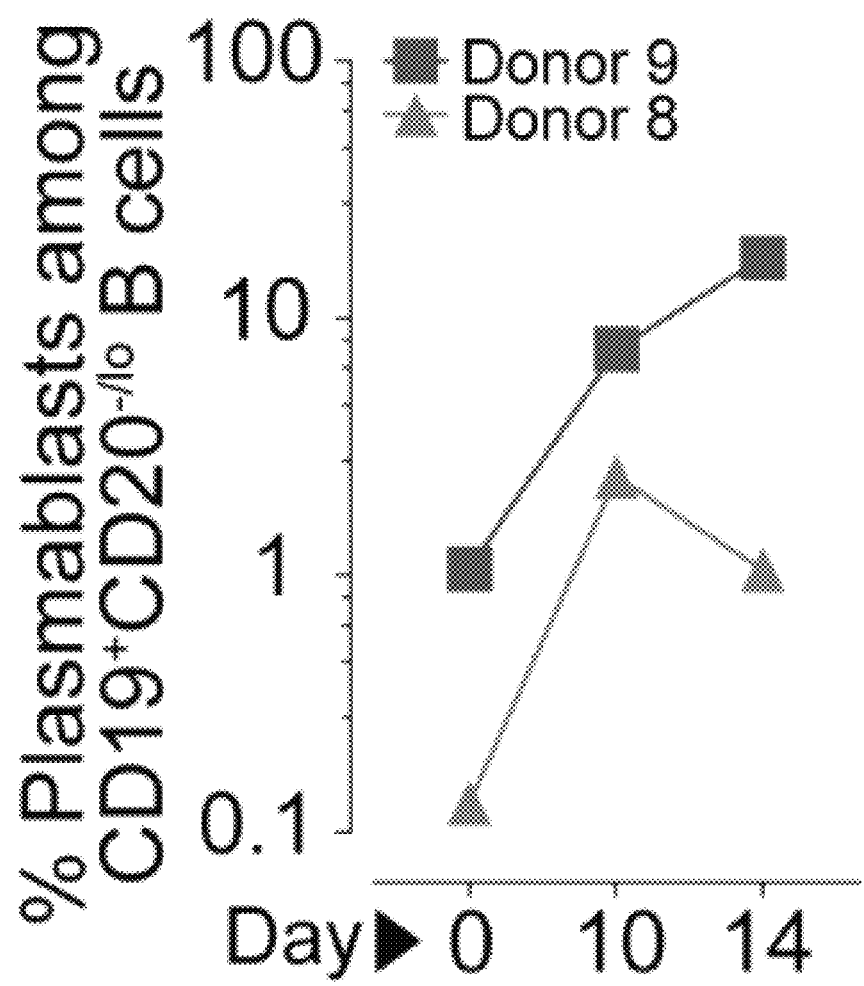

Molecular and Functional Characterization of YFV-17D Induced Plasmablast Response Plasmablast responses in both donors were monitored at 10 and 14 days post-vaccination. In both donors, expanded plasmablast populations were observed at both 10 and 14-day time points that were approximately 10-fold greater than pre-vaccination levels (FIG. 2A). Approximately 300 plasmablasts from each donor were sorted and amplified the corresponding VH and VL regions by single-cell PCR. 161 and 210 natively-paired antibodies were cloned from Donor 8 and Donor 9, respectively, and expressed as full-length IgGs in an engineered strain of Saccharomyces cerevisiae. Sequence analysis showed the plasmablast responses were highly diverse in both donors, with only about 15% of clones belonging to expanded clonal lineages (data not shown). A large fraction of plasmablast-derived antibodies from both donors contained high levels of somatic hypermutation (SHM), suggesting efficient recruitment of MBCs into the PB response (data not shown). The median level of SHM in the PB-derived mAbs was significantly higher on Day 10 than Day 14. Correspondingly, a larger proportion of mAbs cloned from day 14 PBs lacked SHM, suggesting an increased recruitment of cells from the naïve B cell compartment at this time point (data not shown).

Figure 3:
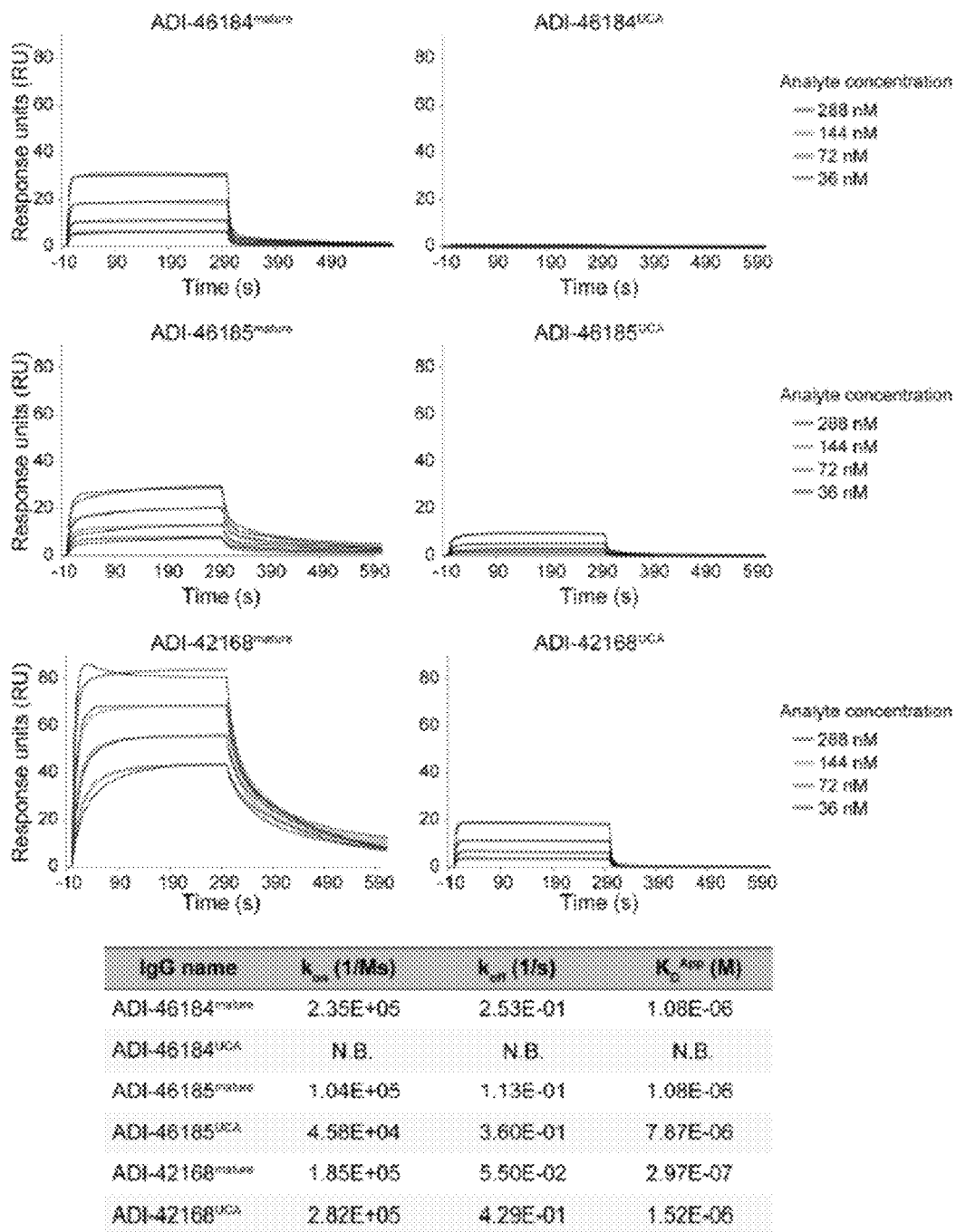
FIG. 3 illustrates the binding activity of germline-reverted plasmablast monoclonal antibodies. Binding traces and affinities of three somatically mutated PB-derived mAbs (ADI-46184, ADI-46185, and ADI-42168) and their corresponding UCAs, as determined by Biacore. UCA, unmutated common ancestor.

To analyze whether the somatic mutations in the PB-derived mAbs contribute to binding activity, inferred unmutated common ancestor (UCA) mAbs were generated from three somatically mutated PB clones and their binding affinities to a recombinant YFV E protein were measured. In all three cases, the UCA mAbs showed substantially reduced binding affinities compared to the mature mAbs, suggesting that somatic mutations in the PB mAbs are important for recognition of YFV E (FIG. 3).

Figure 2B:
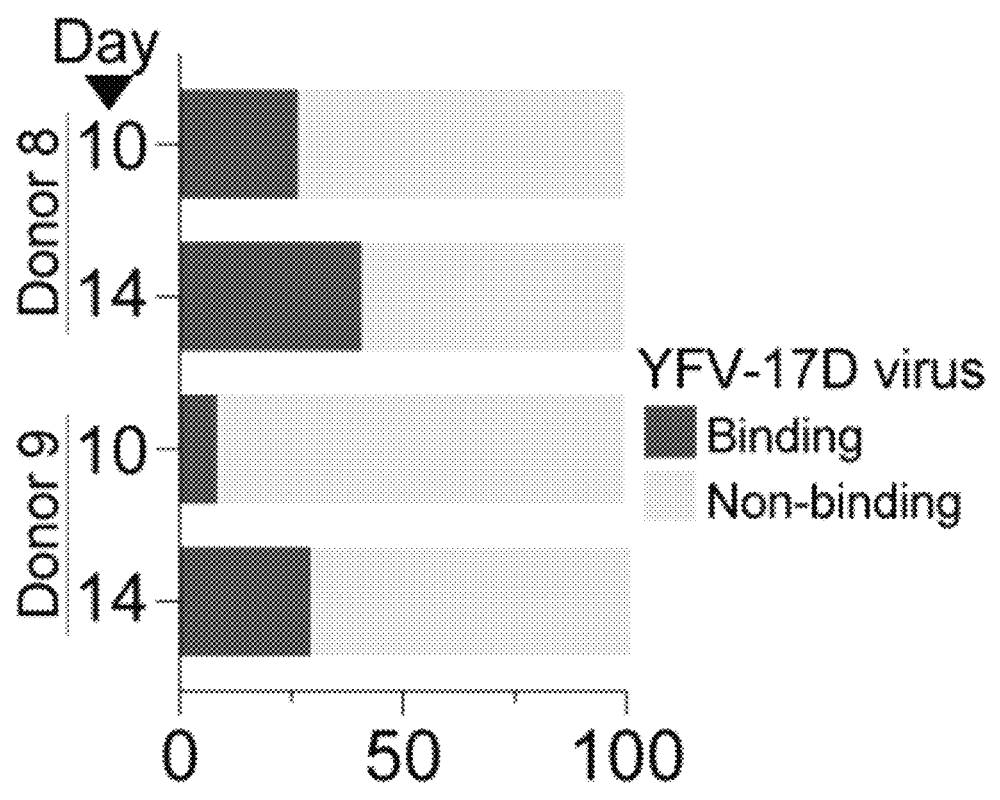
Figure 2C:
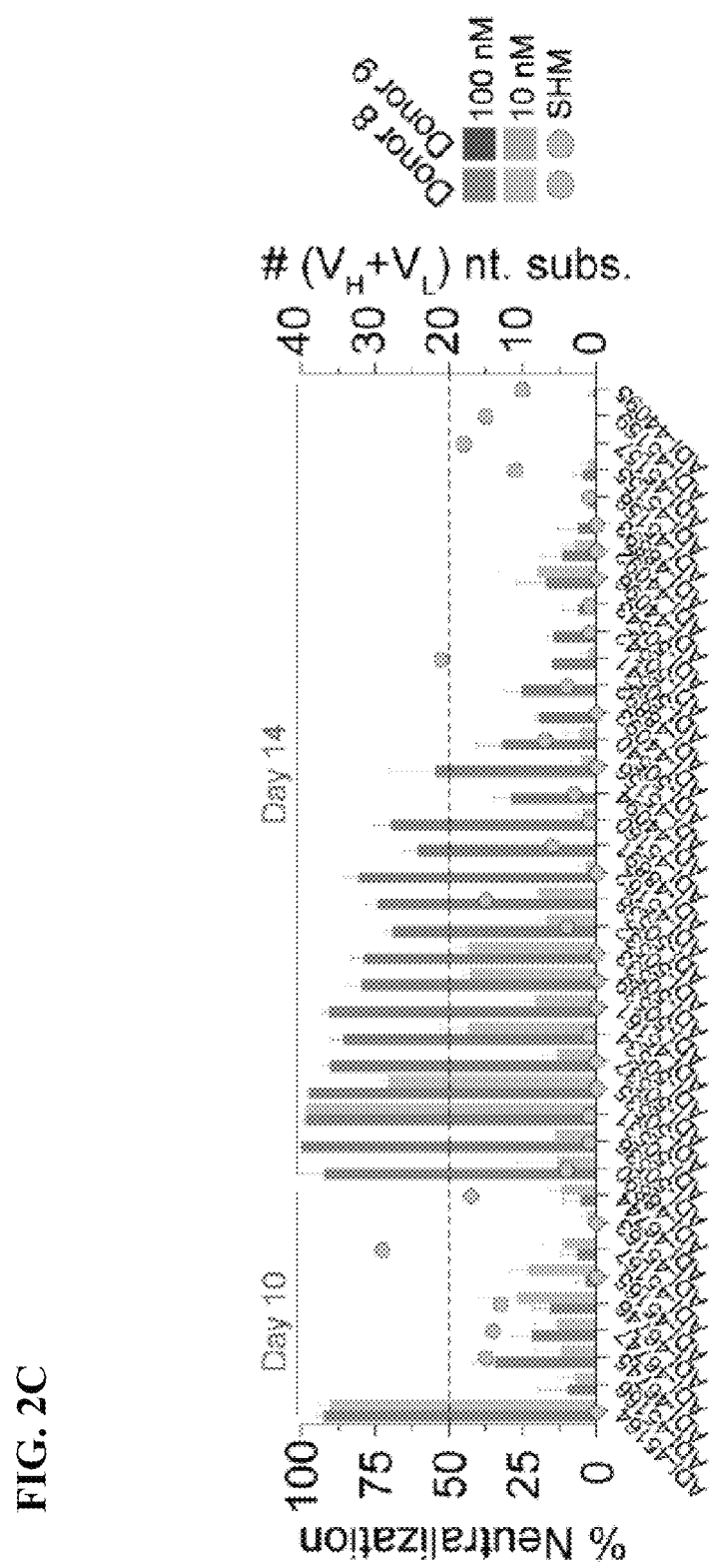
Figure 2D:
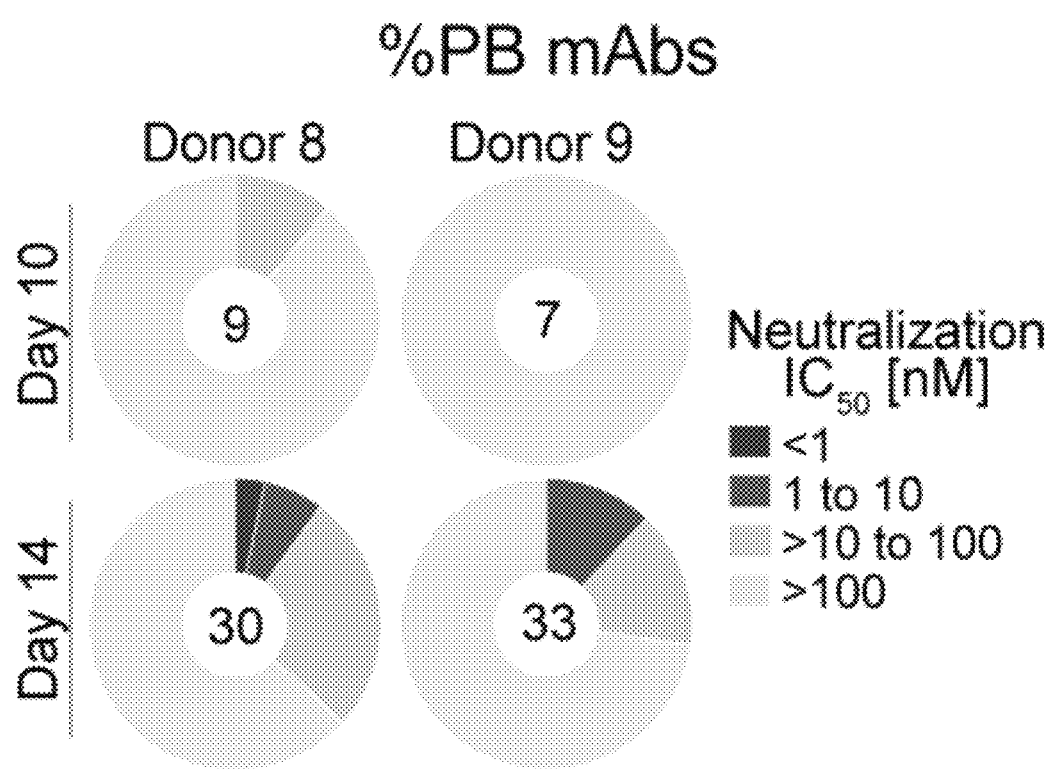
Figure 4:
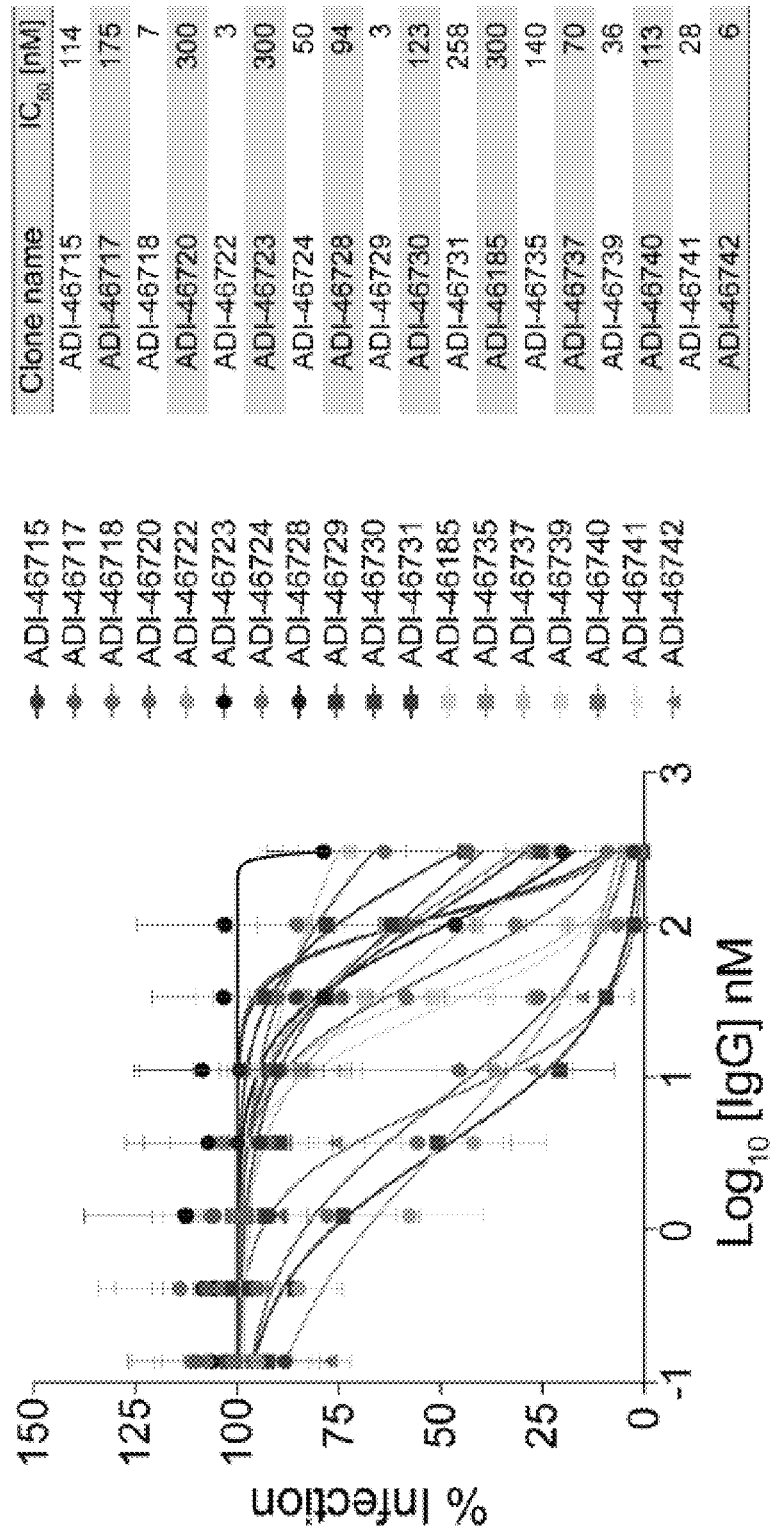
FIG. 4 shows neutralization screening of PB-derived mAbs. Representative YFV-17D neutralization titration curves for PB mAbs screened by micro-titer neutralization assay. Averages±SD (n=6) from two independent experiments are shown.

PB-derived mAbs were then tested for binding reactivity to YFV-17D particles using a sandwich ELISA assay (FIG. 2B). The frequency of YFV-17D binding mAbs isolated from day 10 and 14 PBs ranged from 8-41%. 45 and 46 YFV-17D binding mAbs were recovered from the expanded PB populations in Donor 8 and 9, respectively, and then analyzed the neutralizing activities of the mAbs in a microtiter neutralization assay at 100 and 10 nM concentrations. Neutralizing activities ranged from complete neutralization at 10 nM to no detectable neutralization at 100 nM (FIG. 2C). A higher fraction of mAbs isolated from day 14 PBs displayed neutralizing activity compared to those isolated from day 10 PBs, which is consistent with the increased serum neutralizing activity on day 14 versus day 10 in both donors (data not shown). Neutralization titration experiments on the mAbs displaying at least 50% infection inhibition at 100 nM revealed that 9-12% of YFV-17D binding mAbs isolated from day 14 PBs displayed medium to high neutralizing activity ($IC_{50}s \leq 10$ nM) (FIG. 2D and FIG. 4). Sequence analysis showed that 12.5-33% of the PB-derived nAbs utilized VH4-4/VL1-51 germline gene pairing, suggesting recognition of a common antigenic site (data not shown).

Figure 1B:
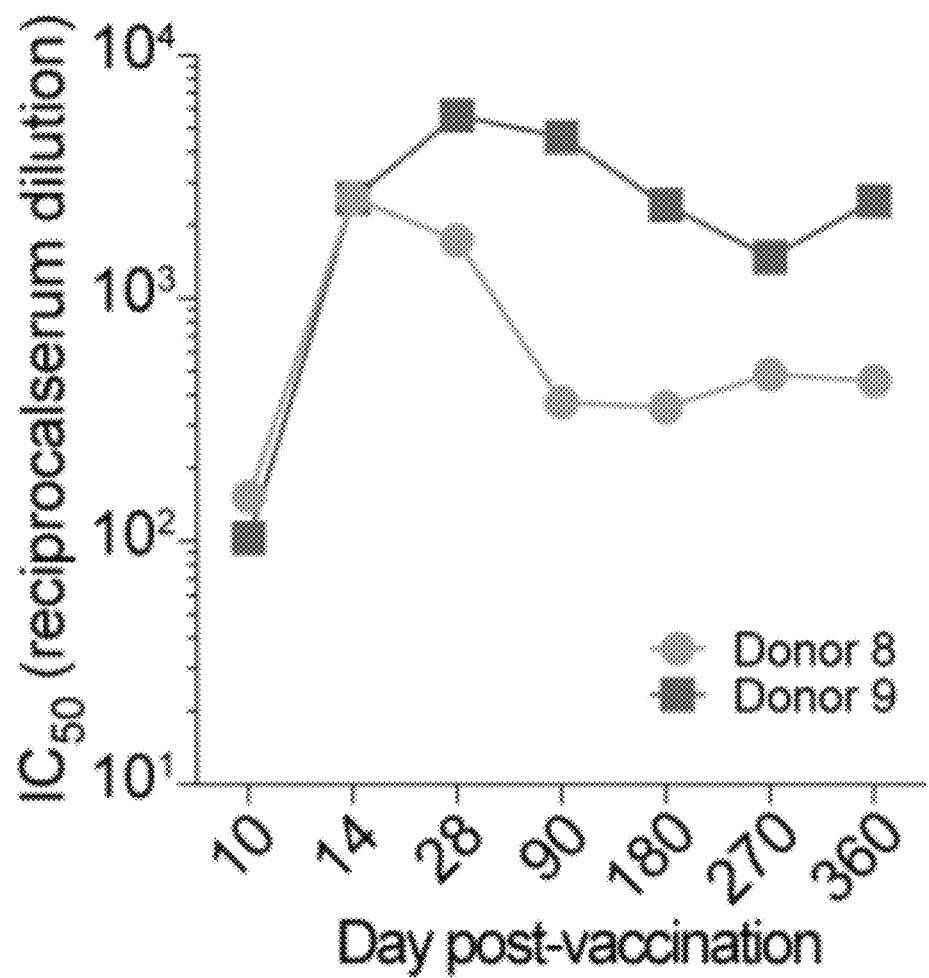

About 50% and 22% of the neutralizing antibodies isolated from donor 8 and 9, respectively, lacked somatic mutations, indicating that YFV-17D neutralizing antibodies are present in the naïve B cell repertoire and suggesting that YFV-17D vaccination induces PB responses that originate from both naïve and MBCs, and only a minority of these B cells encode Abs that display neutralizing activity. See FIGS. 1A and 1B.

Molecular and Functional Characterization of YFV-17D Induced MBC Response

Figure 5A:
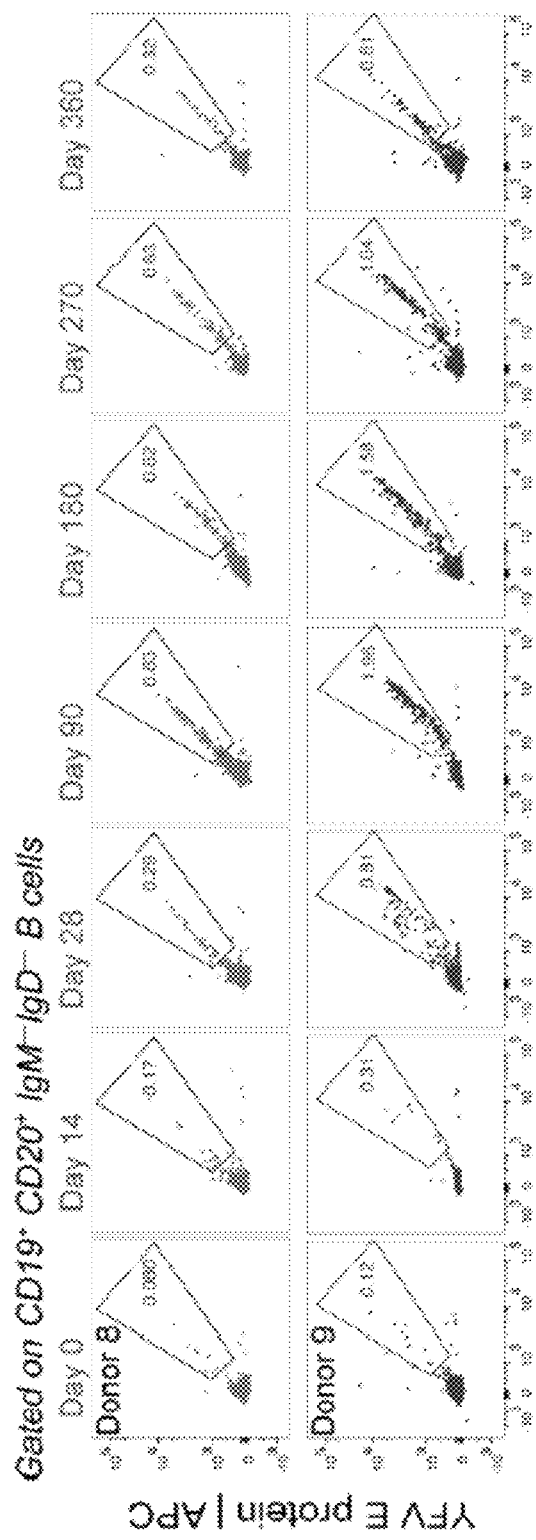
FIGS. 5A and 5B show the presence of $swIg^+$ B cells that display reactivity to YFV-17D.
Figure 5B:
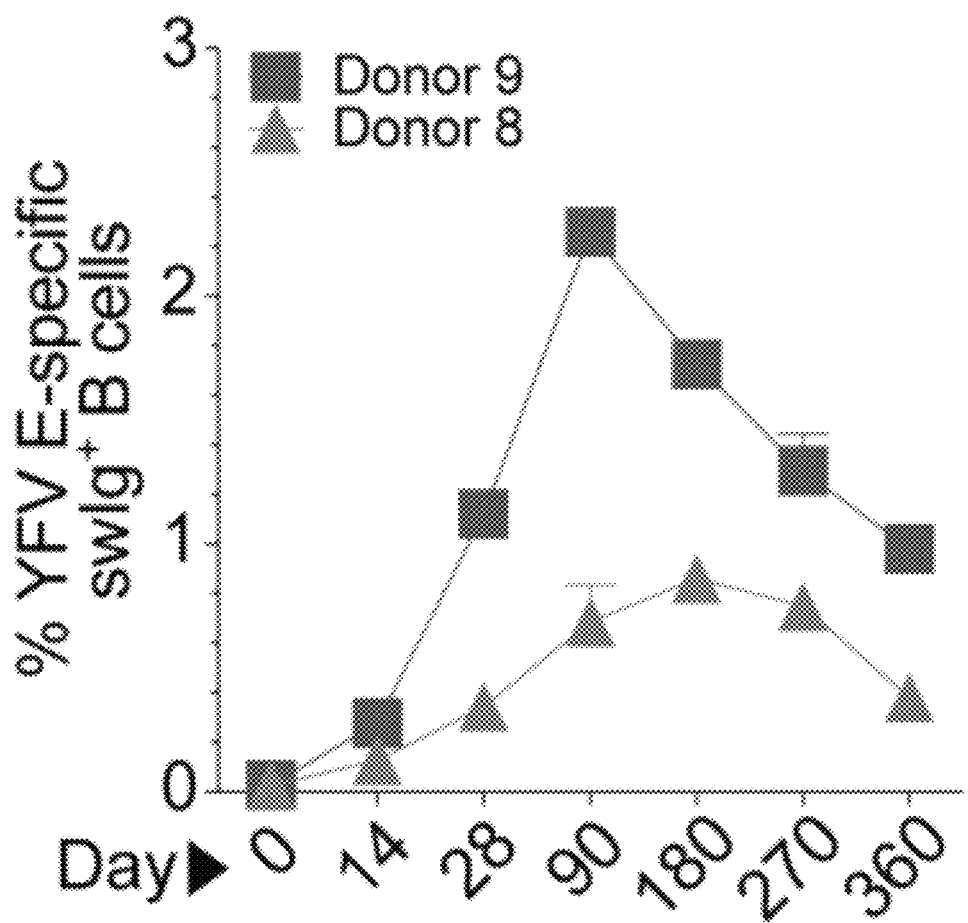

MBC responses in both donors were monitored by collecting PBMCs at days 14, 28, 90, 180, 270, and 360 post-vaccination and purified B cells were stained with a panel of previously described B cell surface markers (CD19, CD20, CD27, IgM, IgD, CD21, and CD71) and a fluorescently-labeled recombinant YFV E protein (FIG. 5A). YFV E-specific swIg+ MBCs emerged in both donors by Days 14-28, peaked between Days 90 and 180, and slowly declined between Days 180 and 360 (FIG. 5B).

Figure 8A:
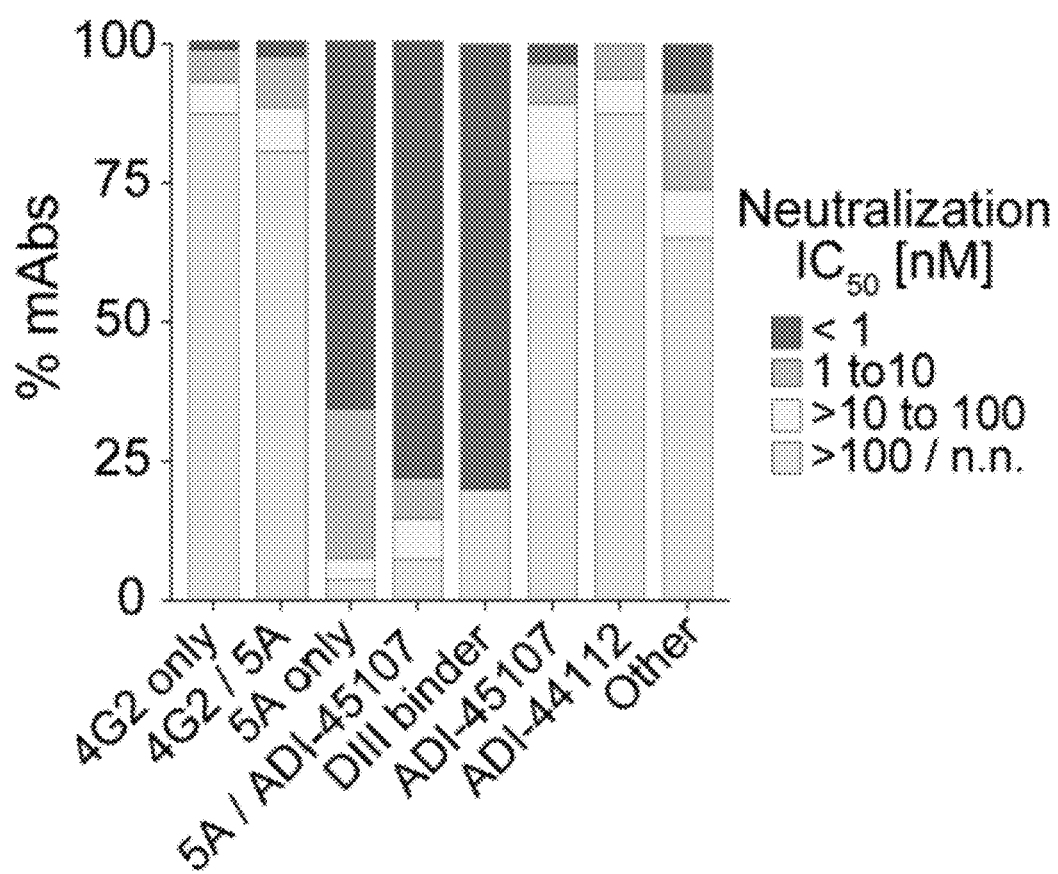
FIG. 8A through 8D illustrate a majority of highly potent neutralizing antibodies recognize FL-proximal epitopes.
Figure 8B:
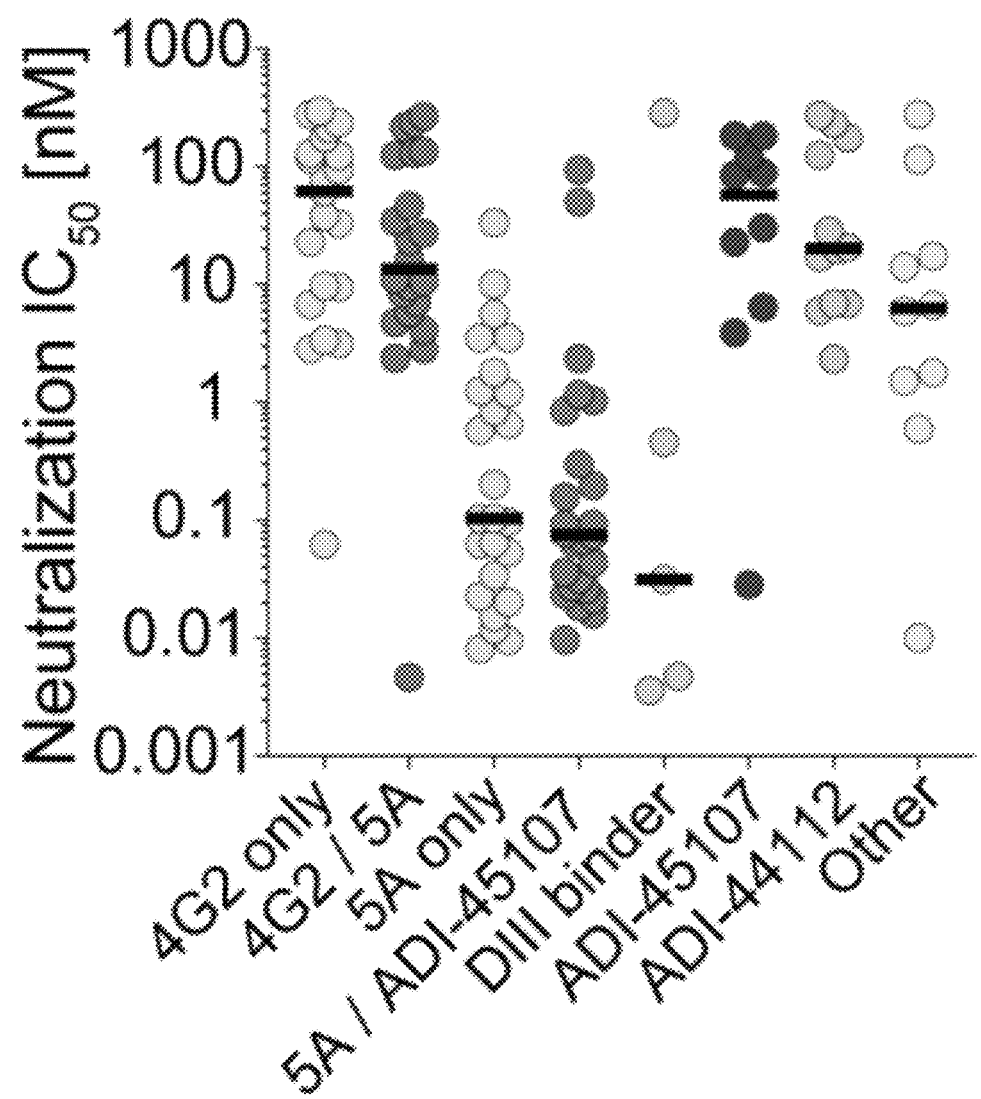
Figure 8C:
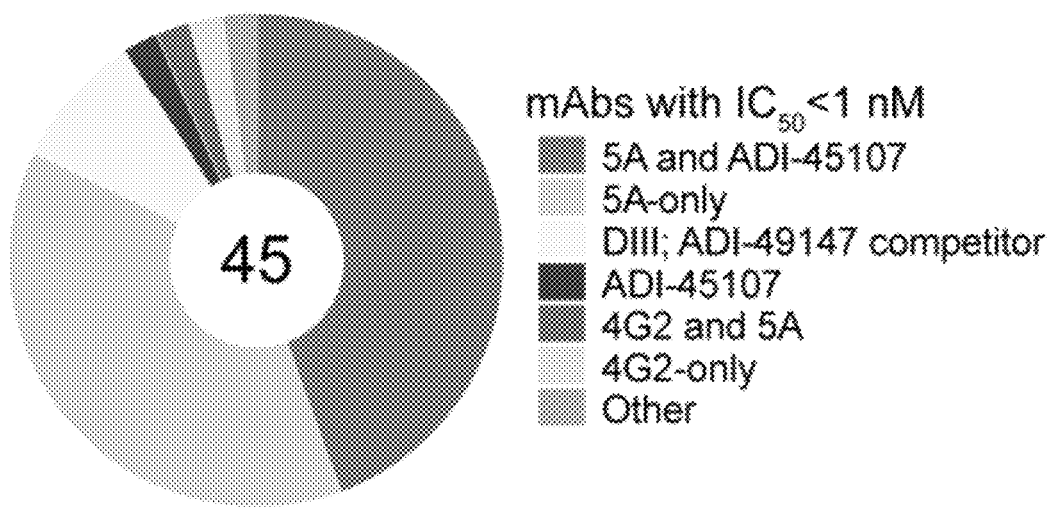
Figure 8D:
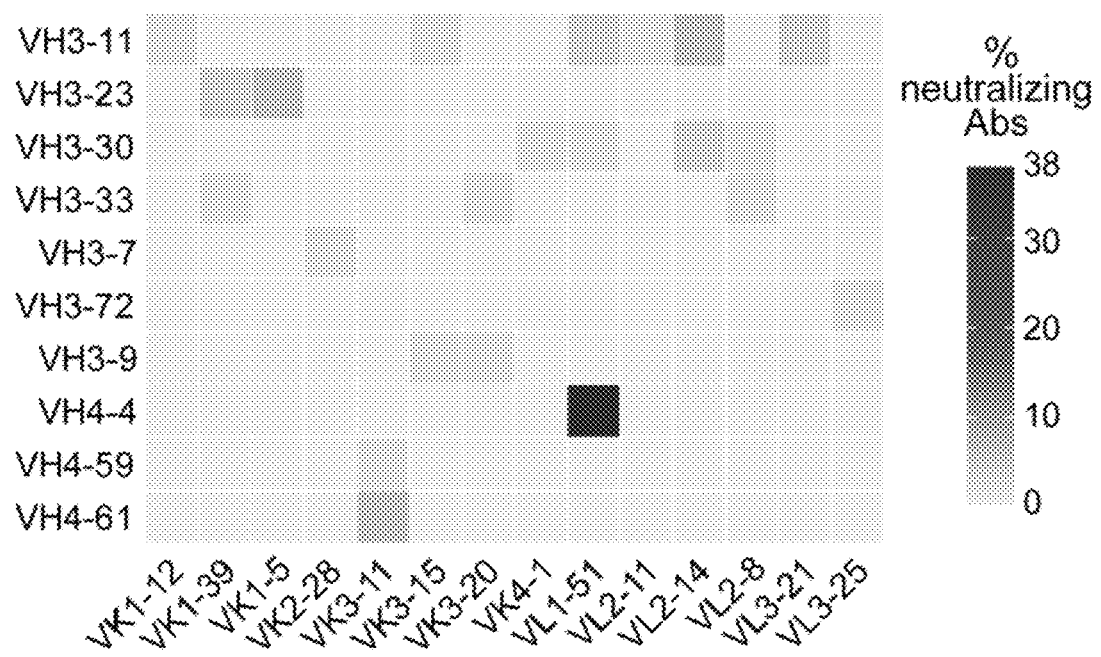
Figure 9A:
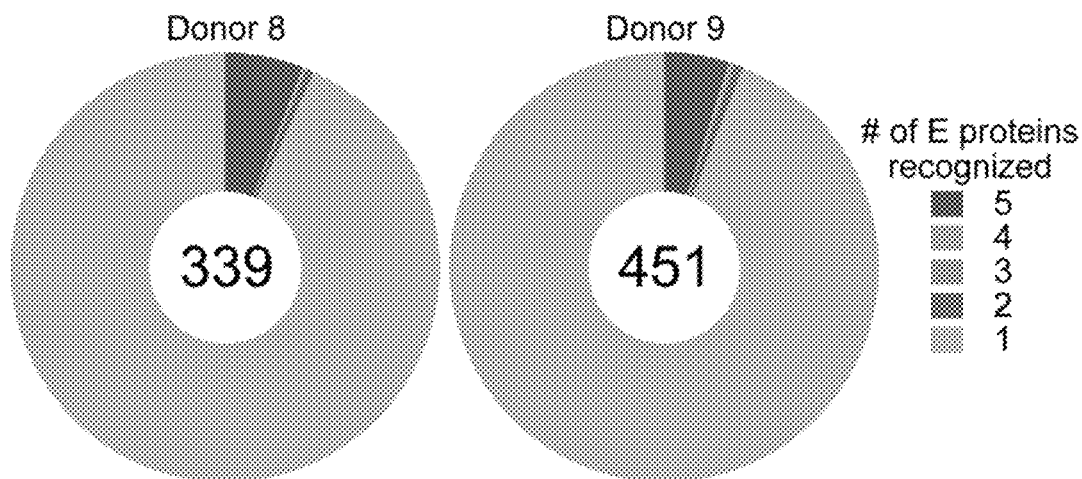
FIG. 9A through 9C shows a subset of monoclonal antibodies show broad flavivirus cross-reactivity.
Figure 9B:
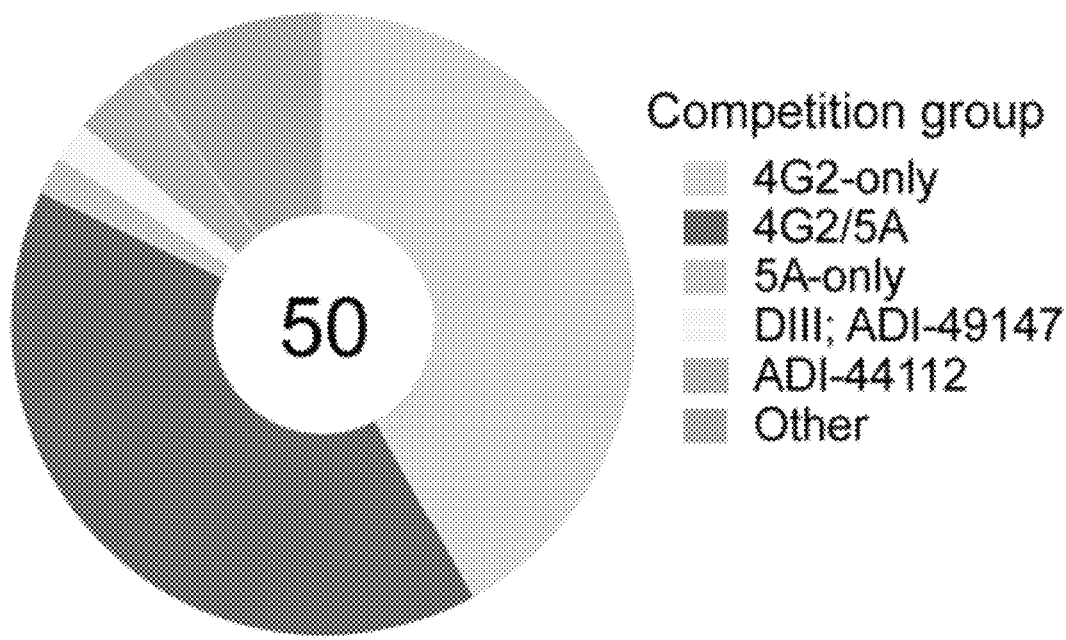
Figure 9C:
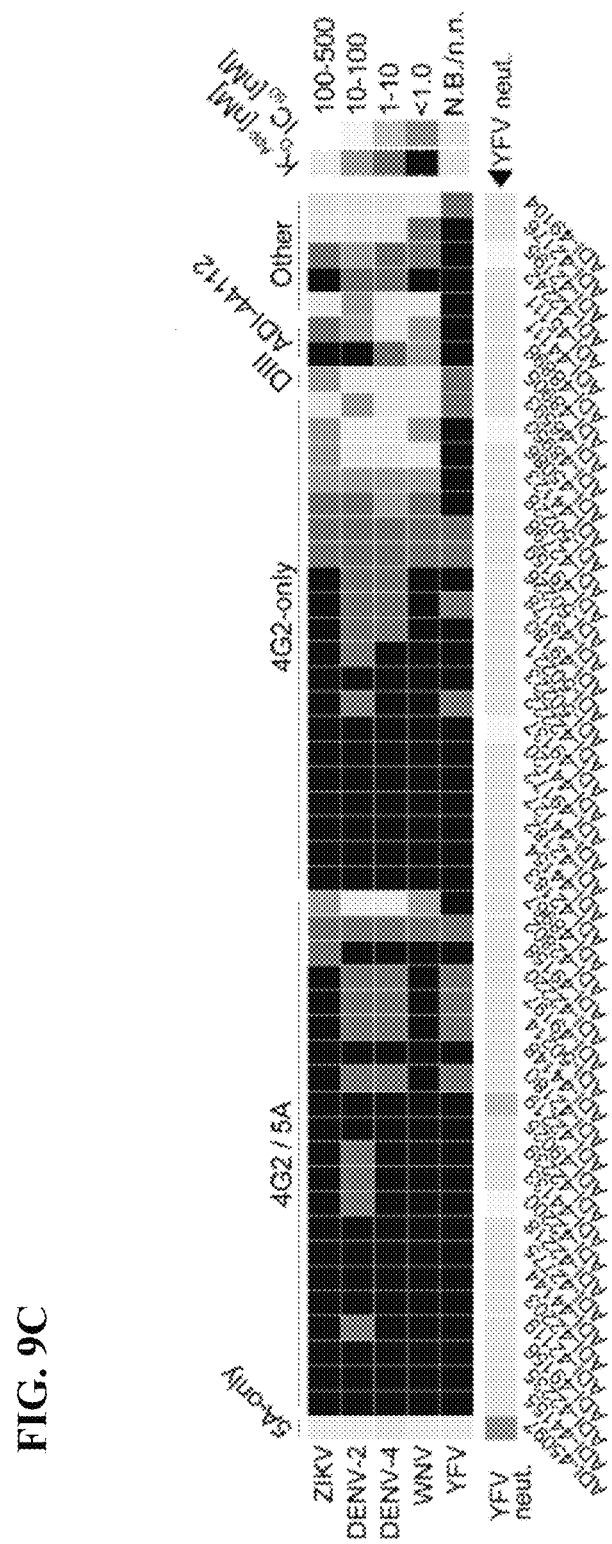

Between 100-400 YFV E-reactive B cells were sorted from both donors at each sampling time point. Naïve B cell-derived non-binding mAbs were captured via the sorting strategy employed but excluded from subsequent analyses. Analysis of the B cell surface markers expressed on the single-cell sorted, YFV E-reactive B cells revealed that the MBC response to YFV E was highly heterogenous at all time points (data not shown). At the earliest sampling time point (day 14), activated naïve B cells and IgM+CD27+ MBCs dominated the response in both donors, but these B cell populations waned rapidly over time. By day 90, less than 15% of the YFV E-specific response was comprised of IgM+CD27+ MBCs, and by day 360, only about 5% of YFV E-specific B cells belonged to this MBC population (FIG. 8B). In contrast, the swIg+ MBC population—which was comprised of both CD27+ and CD27− B cells—expanded between day 14 and day 90 and then remained stable throughout the course of the study. The MBC response observed following YFV-17D vaccination was also observed following natural infection with PUUV (data not shown).

SHM loads, apparent binding affinities ($K_D^{Apps}$), and neutralization potencies of the YFV E-specific mAbs were tracked at each sampling time point. In both donors, the median level of SHM was low at day 14—with over 50% of Abs lacking somatic mutations—and increased gradually over a 6-9-month time period, plateauing in both donors by 9 months post-vaccination, with a median of 9 and 7 nucleotide substitutions in $V_H$ for donor 8 and 9, respectively (data not shown). Binding studies with a recombinant YFV E protein showed that the $K_D^{Apps}$ of the MBC-derived mAbs were very weak at early time points and progressively improved for 6-9 months following vaccination (data not shown). On days 14 and 28 post-vaccination, the majority of YFV E-specific mAbs displayed $K_D^{Apps}>50$ nM, whereas by day 180, about 50% of the YFV E-specific mAbs displayed $K_D^{Apps}<5$ nM. In parallel with the increase in affinity, the emergence of highly potent neutralizing antibodies ($IC_{50}<1$ nM) were observed beginning at day 90 (data not shown). These neutralizing antibodies were derived from multiple MBC subsets, including atypical IgM+ and/or IgD+ MBCs (data not shown). Table 2 summarizes affinity and neutralization data for the isolated and characterized neutralizing mAbs.

Ongoing B cell activation was assessed by analyzing expression of CD71 and CD21 on YFV E-specific MBCs. CD71 was expressed on 75-85% YFV E-specific B cells at day 14 and remained elevated for about 6 months in both donors (data not shown). In both donors, YFV E-specific CD21$^{lo}$ cells were present at high frequencies on days 14 and 28 post-vaccination, comprising about 40-80% of the YFV E-specific response, and then declined rapidly by day 90. While there was a high degree of overlap between the CD71+ and CD21$^{lo}$ populations, with 50-80% of YFV E-specific activated B cells (defined as CD71+ and/or CD21$^{lo}$) displaying a CD71+CD21$^{lo}$ phenotype at day 14, by day 28-90, the CD71+CD21$^{lo}$ population waned to <50% of the activated B cell response in both donors and the majority of YFV E-specific activated B cells displayed either a CD71+CD21+ or CD71−CD21$^{lo}$ phenotype and were heterogenous with regard to isotype and CD27 expression (data not shown).

Isolation and Characterization of Anti-YFV Antibodies

Approximately 152 neutralizing monoclonal antibodies were isolated and characterized. Antibody variable heavy (VH) and variable light (VL) chain genes were rescued by single-cell PCR. Tiller et al. (2008) J Immunol Methods 329, 112-124. Cognate heavy and light chain pairs were subsequently cloned and expressed as full-length IgGs in an engineered strain of *Saccharomyces cerevisiae* for further characterization. Bornholdt et al., (2016) Science 351, 1078-1083.

Figure 6A:
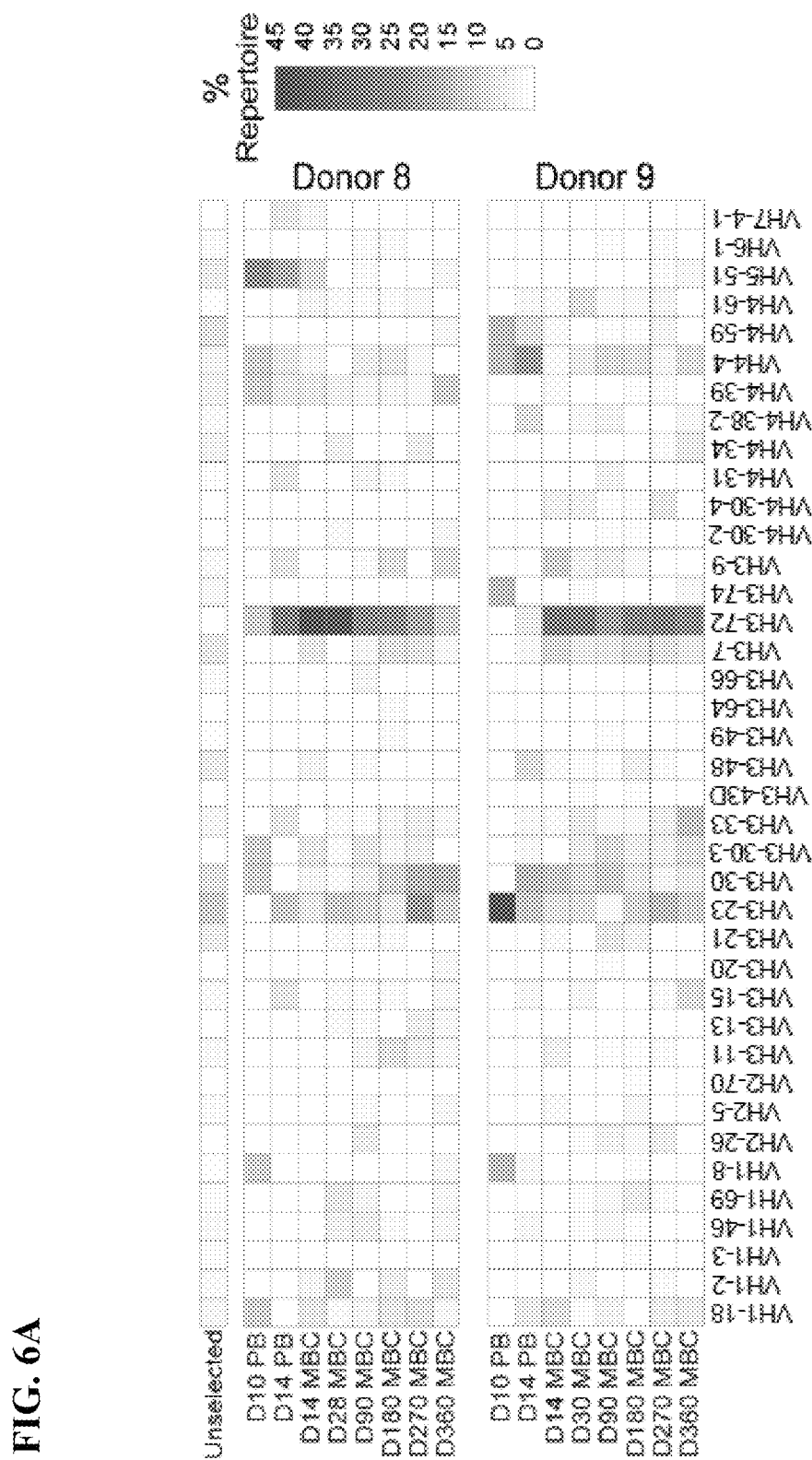
FIGS. 6A through 6E illustrate that YFV E-specific antibodies show preferential usage of the VH3-72 germline gene.
Figure 6B:
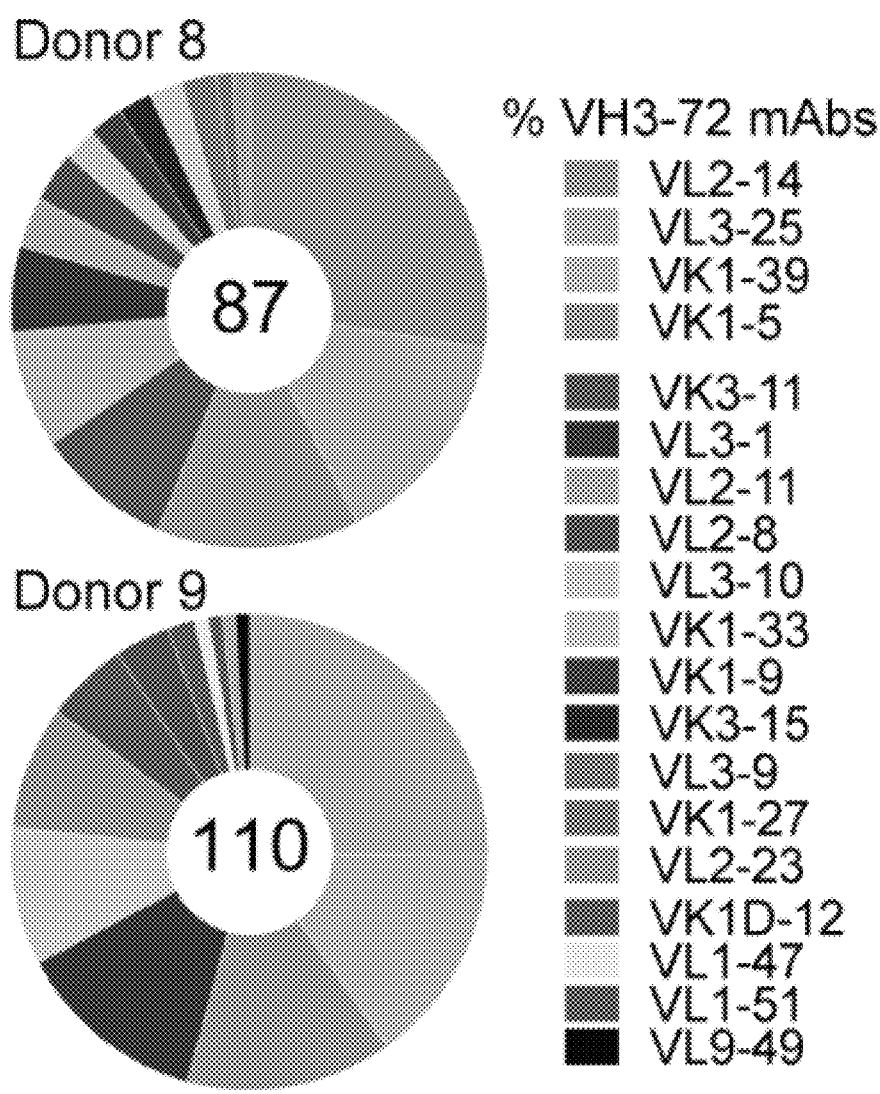
Figure 6C:
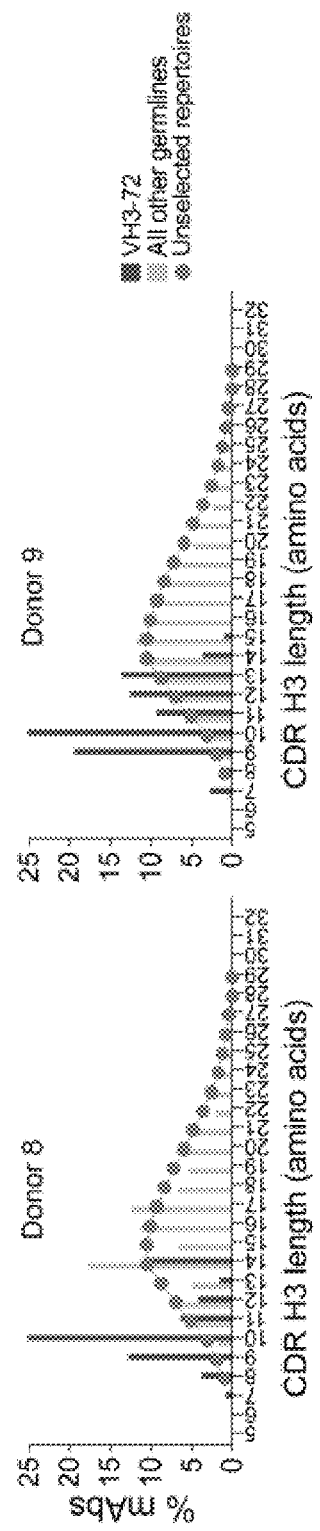
Figure 6D:
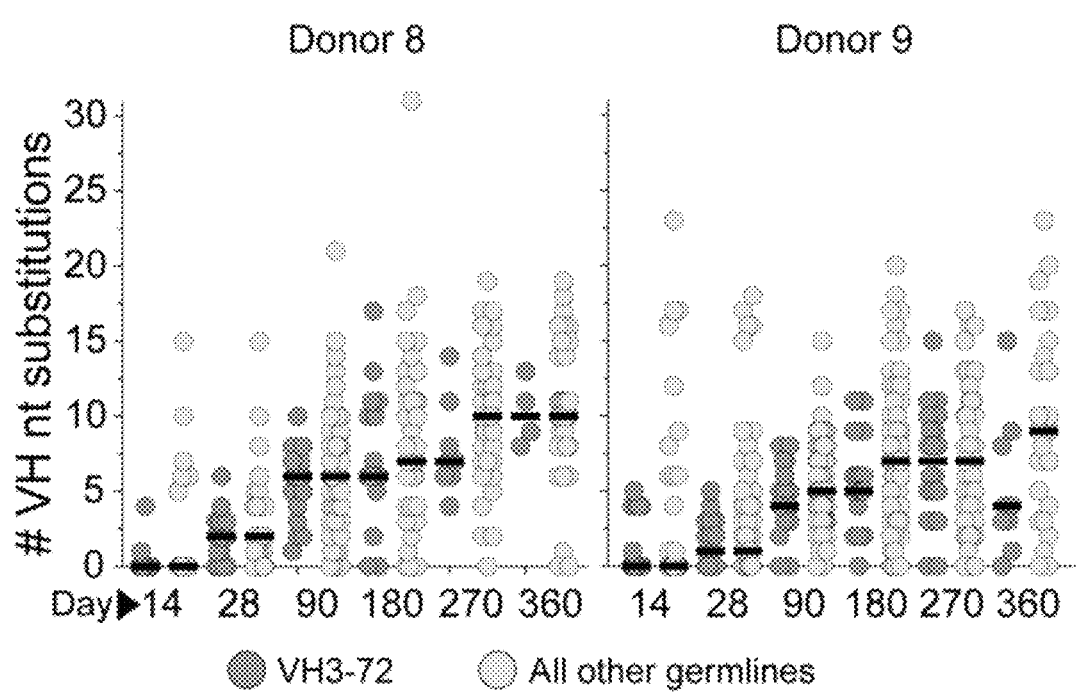
Figure 6E:
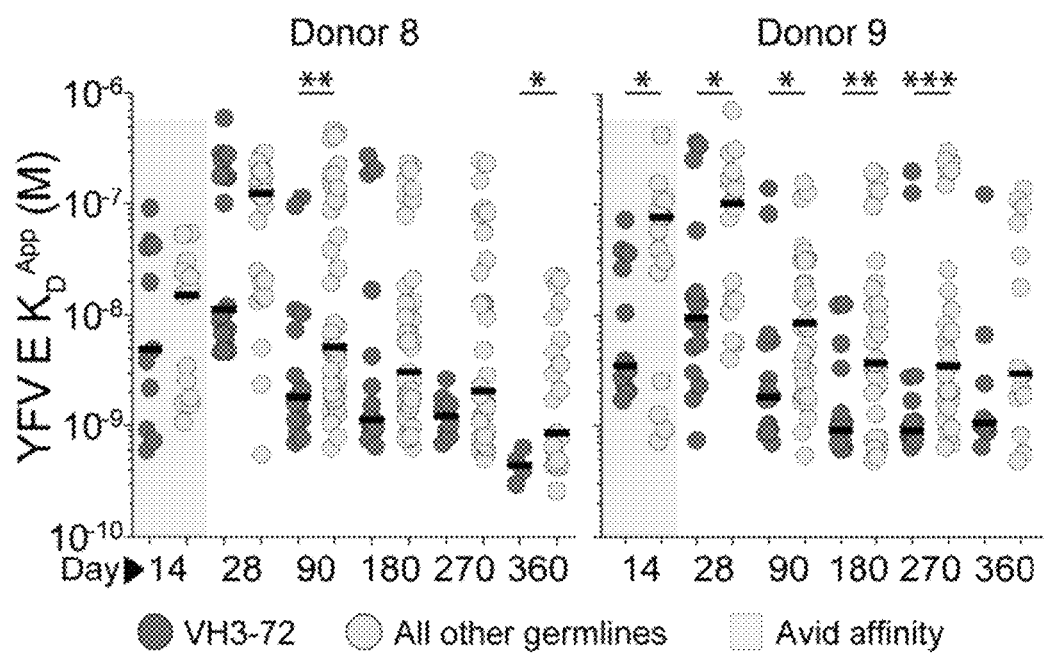

Germline gene usage of the isolated mAbs was analyzed. In both donors, mAbs utilizing the VH3-72 germline gene dominated the response at all time points (FIG. 6A). A large fraction of these mAbs also utilized one of five dominant light chain (LC) germline genes and displayed shorter-than-average heavy chain (HC) complementary determining region 3 (CDRH3) lengths, suggesting a shared mode of antigen recognition (FIG. 6B-C). The binding affinities of the mAbs utilizing VH3-72 were significantly higher than those observed for mAbs utilizing other VH germlines, despite containing similar levels of SHM (FIG. 6D-E). Table 1 summarizes germline usage and number of nucleotide substitutions for isolated mAbs.

Figure 7A:
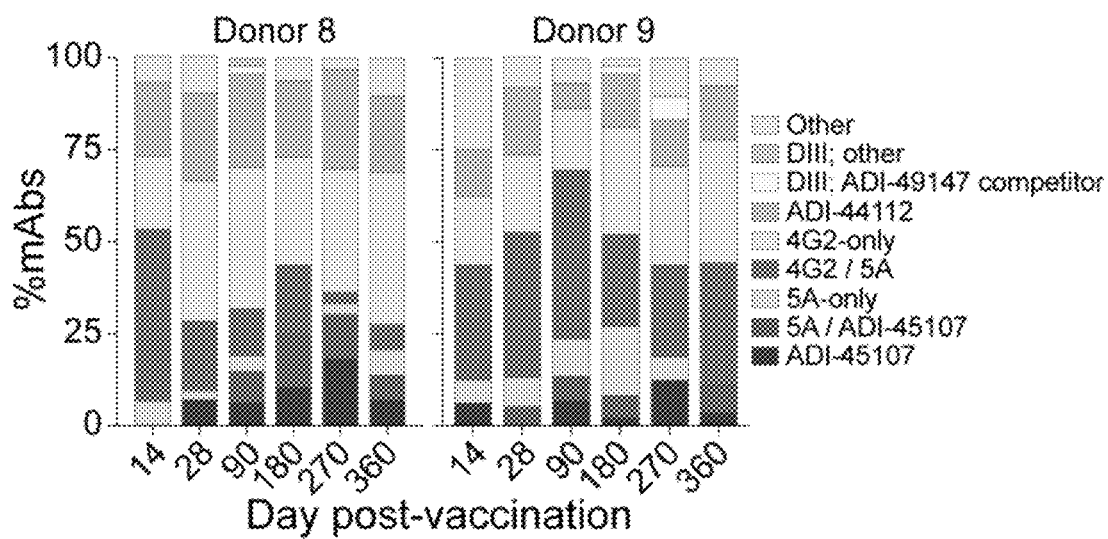
Figure 7B:
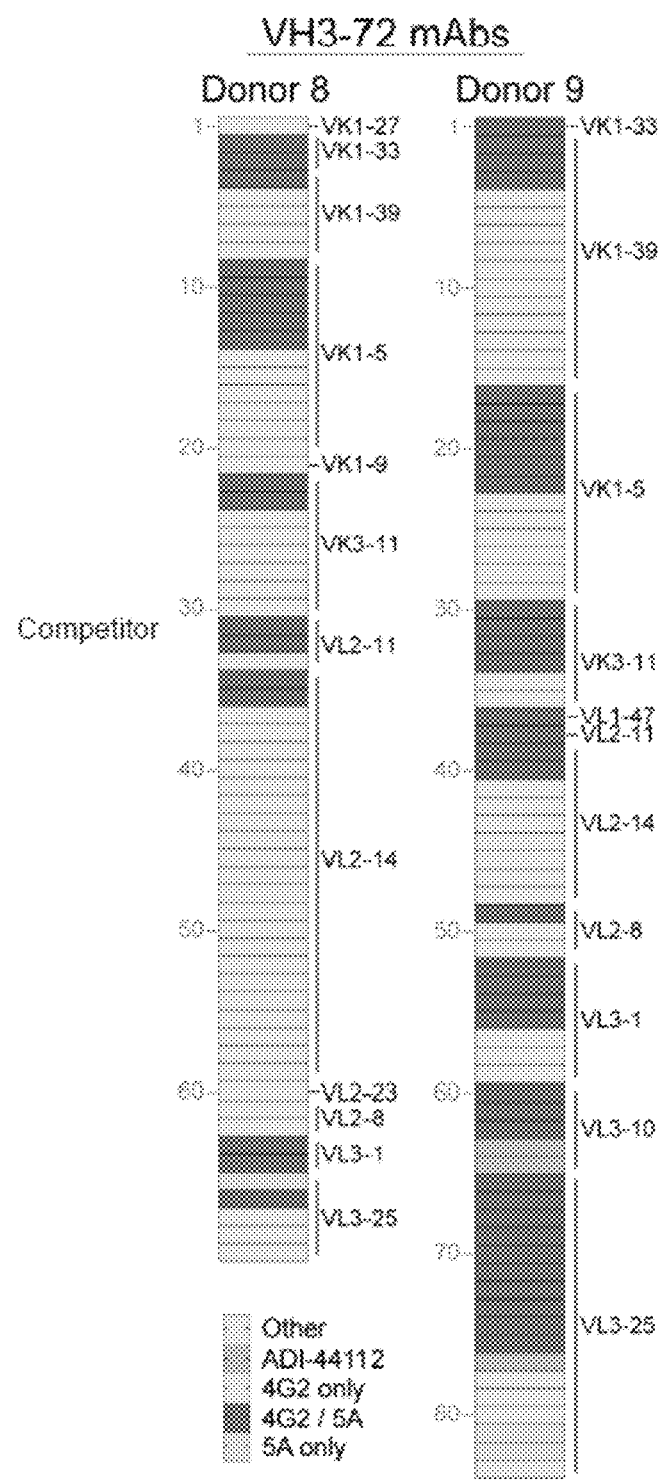
Figure 7C:
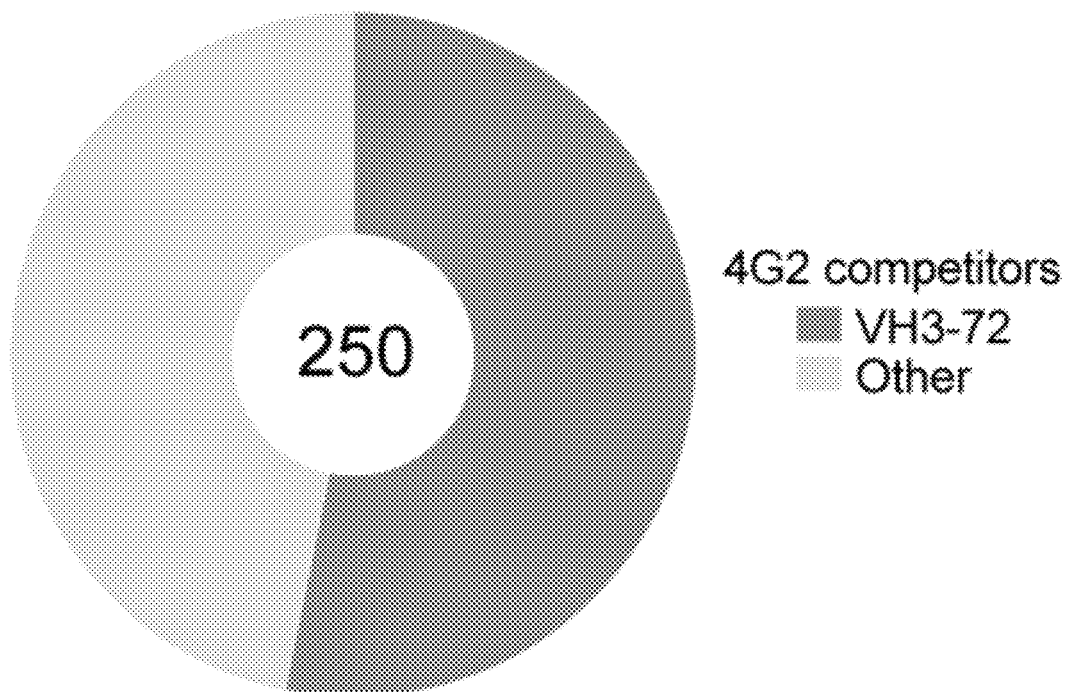
Figure 7D:
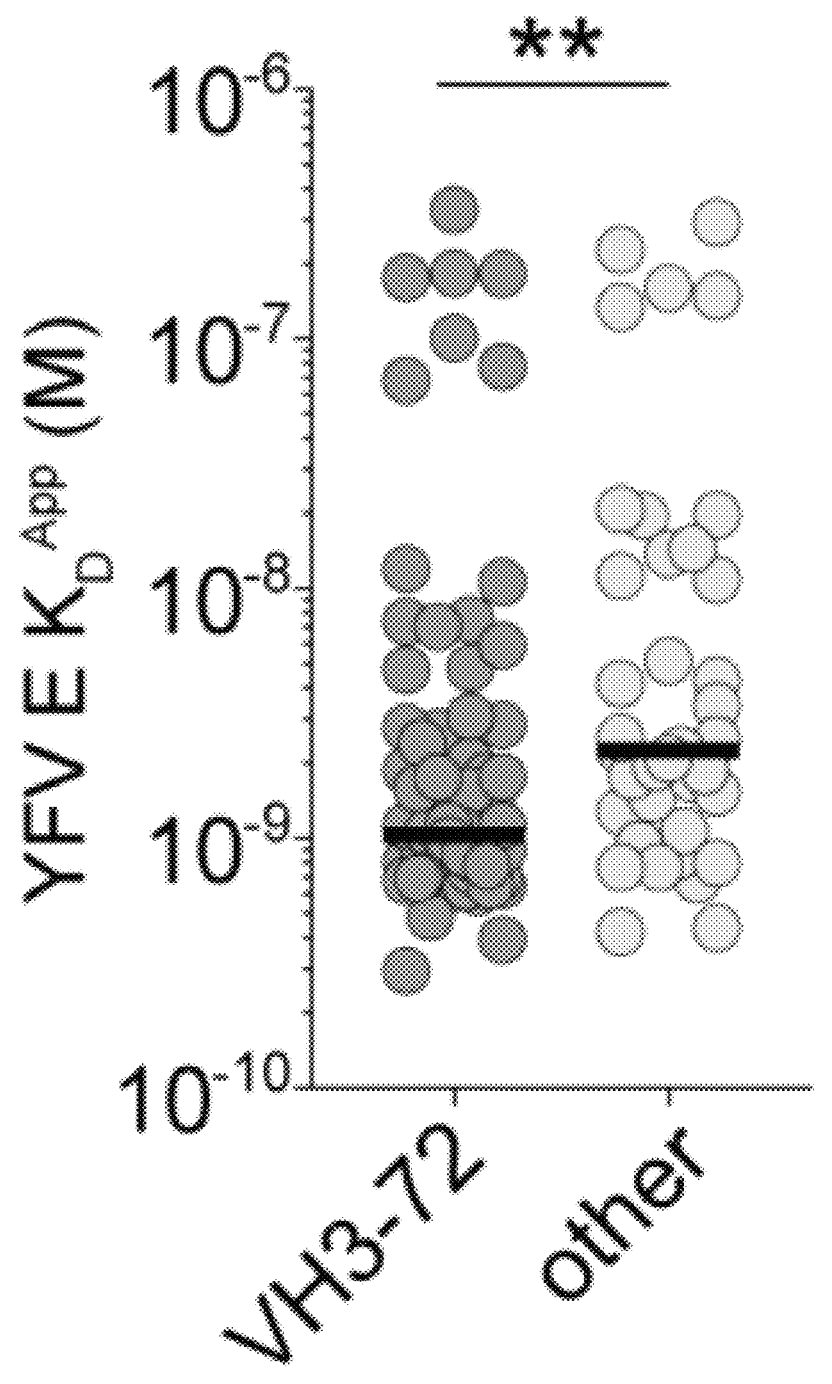

To explore the epitope coverage of the isolated mAbs, pairwise competition experiments were performed using the newly isolated mAbs and two well-characterized control mAbs, 4G2 and 5A, which recognize proximal but non-overlapping epitopes within DII of the YFV E monomer. 4G2 is a pan-flavivirus mAb that targets the FL, whereas 5A is a YFV E-specific mAb that binds to a FL-proximal epitope overlapping the proposed prM association region. Competition experiments were performed using high-throughput surface plasmon resonance (SPR) on a Carterra LSA instrument. Reactivity of the mAbs with a recombinant YFV-17D DIII protein by BLI was also evaluated. The majority of mAbs recognized one of eight distinct antigenic sites, which were defined based on reactivity with DIII and competition with 4G2, 5A, and three of the newly isolated mAbs (ADI-49147, ADI-44112, and ADI-45107) (FIG. 7A). A subset of mAbs competed with both 5A and ADI-45107, suggesting that these two antigenic sites are in close proximity. A small subset of mAbs (6 of 772) recognized epitopes within DIII. Five of the DIII-directed mAbs cross-competed, whereas the sixth, ADI-48945, may recognize a unique epitope. Over half of the mAbs from both donors competed with 4G2 and/or 5A, suggesting that the majority of the YFV E-specific response is mediated by Abs that target epitopes within or proximal to the FL on DII (FIG. 7A). Nearly all the mAbs that utilized the VH3-72 germline gene competed with 4G2 (FIG. 7B). Accordingly, analysis of the sequence features of the mAbs clustered by competition group revealed that over half of the mAbs that competed with 4G2 utilized the VH3-72 germline gene (FIG. 7C). The 4G2 competitor mAbs utilizing VH3-72 showed significantly higher affinities compared to those utilizing other $V_H$ germline genes (FIG. 7D). Although the proportion of mAbs targeting each antigenic site did not change dramatically over time, suppression of 4G2/5A competitor mAbs was observed at later timepoints in donor 8 (days 270 and 360). Furthermore, in both donors, mAbs that competed with both 5A and ADI-45107 did not emerge until day 28-90. Results suggest that the vast majority of the YFV E-specific response is directed against epitopes within or proximal to the FL on domain II, and there are only minor shifts in Ab immunodominance hierarchy during the maturation of the B cell response to YFV-17D.

Highly Potent Neutralizing Antibodies Recognize FL Proximal Epitopes

The relationship between antigenic site and neutralization potency was investigated. Over 90% of the mAbs that competed either with 5A only or both 5A and ADI-45107 showed neutralizing activity (FIG. 8A). The majority (78%) of highly potent neutralizing antibodies ($IC_{50}$<1 nM) in the panel belonged to these two competition groups (FIG. 8B-8C). Table 2 provides bin data for these antibodies. Analysis of the sequence features of these 5A-only or 5A/ADI-45107 competitor neutralizing antibodies revealed that nearly 40% utilized VH4-4/VL1-51 germline gene pairing and did not show evidence of a convergent CDRH3 sequence, suggesting a common mode of germline-encoded antigen recognition (FIG. 8D). In line with prior studies, most of the DIII-directed mAbs also showed highly potent neutralizing activity. In contrast to the 5A competitors and DIII-directed mAbs, only a minority of the mAbs belonging to other competition groups showed neutralizing activity. For example, only 12% and 20% of mAbs that competed with 4G2 only or both 4G2 and 5A, respectively, displayed neutralization $IC_{50}$s<100 nM. The results demonstrate that the nAb response to YFV-17D is primarily mediated by Abs that recognize FL proximal epitopes within DII of the YFV E protein.

A Subset of mAbs Display Cross-Reactivity with E Proteins from Other Flaviviruses The isolated mAbs were evaluated for binding reactivity to recombinant DENV-2, DENV-4, WNV, or ZIKV E proteins. In both donors, about 6% of YFV E-reactive mAbs showed cross-reactivity to at least one heterologous flavivirus E protein (FIG. 9A). The majority of these cross-reactive mAbs targeted the highly conserved FL epitope and bound to all five flavivirus E proteins with high apparent avid affinities ($K_D^{Apps}$<10 nM) (FIG. 9B-9C). Correspondingly, the small subset of mAbs that bound to epitopes outside of the FL generally displayed more limited cross-reactivity profiles and lower $K_D^{Apps}$ (FIG. 9C). Only 6 out of 50 cross-reactive mAbs showed neutralizing activity against YFV-17D, and only a single mAb, the DIII binder ADI-48905, showed detectable albeit weak neutralizing activity against ZIKV ($IC_{50}$~100 nM). None of the mAbs had measurable neutralization activity against the West Nile virus or Japanese encephalitis virus reporter viral particles. YFV-17D vaccination thus appears to induce a subset of Abs that display broad flavivirus binding activity, the majority of which target the highly conserved FL and show little to no cross-neutralizing activity.

Table 1 below provides the germline usage and amino acid sequence information of 152 anti-YFV antibodies as described herein. The sequences provided in Table 1 include the CDRH3 sequence (SEQ ID NOs. 1, 3, 5, 7, 9, 11, 13, 15, 17, 19, 21, 23, 27, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, and 302) and the CDRL3 sequence (SEQ ID NOs. 2, 4, 6, 8, 10, 12, 14, 16, 18, 20, 22, 24, 26, 29, 31 33 35 37 39 41 43 45 47 49 51 53 55 57 59 61 63 65 67 69 71 73 75 77 79 81 83 85 87 89 91 93 95 97 99 101 103 105 107 109 111 113 115 117 119 121 123 125 127 129 131 133 135 137 139 141 143 145 147 149 151 153 155 157 159 161 163 165 167 169 171 173 175 177 179 181 183 185 187 189 191 193 195 197 199 201 203 205 207 209 211 213 215 217 219 221 223 225 227 229 231 233 235 237 239 241 243 245 247 249 251 253 255 257 259 261 263 265 267 269 271 273 275 277 279 281 283 285 287 289 291 293 295 297 299 301, and 303) for each listed antibody.

Table 2 below provides affinity and neutralization data for the 152 anti-YFV antibodies set forth in Table 1.

Table 3 below provides partial amino acid sequences for the CDRs of the heavy and light chains of each of the 152 anti-YFV antibodies set forth in Table 1. CDRs are indicated in bold/underlined. Each CDR amino acid sequence is also listed separately in the sequence listing (CDRH1 and CDRH2 correspond to SEQ ID NOs.: 607-840; CDRL1 and CDRL2 correspond to SEQ ID NOs.: 841-1005).

TABLE 1

Germline usage and sequence information of anti-YFV antibodies

| Antibody Number | Name | VH germline gene usage | LC germline gene usage | CDRH3 sequence | CDRL3 sequence | Number of nucleotide substitutions in VH | Number of nucleotide substitutions in VL |
|---|---|---|---|---|---|---|---|
| 1 | ADI-49039 | VH4-38-2 | VL1-51 | ARNAPENYYGSGRESFDI (SEQ ID NO: 1) | GTWDSSLSAWV (SEQ ID NO: 2) | 7 | 5 |
| 2 | ADI-49147 | VH3-23 | VK3-15 | AKDHGGKYGWWYFDL (SEQ ID NO: 3) | QQYDNWPLT (SEQ ID NO: 4) | 8 | 4 |
| 3 | ADI-42229 | VH4-38-2 | VL1-51 | ARNAPENYYGSGRESFDI (SEQ ID NO: 5) | GTWDSSLSAWV (SEQ ID NO: 6) | 5 | 5 |
| 4 | ADI-45090 | VH3-33 | VL1-44 | ARDLEVGAEYLYYHYGMDV (SEQ ID NO: 7) | AAWDDSLNGWV (SEQ ID NO: 8) | 11 | 10 |

TABLE 1-continued Germline usage and sequence information of anti-YFV antibodies

| Antibody Number | Name | VH germline gene usage | LC germline gene usage | CDRH3 sequence | CDRL3 sequence | Number of nucleotide substitutions in VH | Number of nucleotide substitutions in VL |
|---|---|---|---|---|---|---|---|
| 5 | ADI-45097 | VH3-30 | VL1-51 | AKDSSTSWYQVVYHIDY (SEQ ID NO: 9) | ETWDSSLNAVV (SEQ ID NO: 10) | 7 | 6 |
| 6 | ADI-49133 | VH3-23 | VK1-39 | AKDLAVSTPRYWFDS (SEQ ID NO: 11) | QQSYSIPRIT (SEQ ID NO: 12) | 10 | 9 |
| 7 | ADI-49033 | VH3-23 | VK1-39 | AKDMAVSVHRGWFDD (SEQ ID NO: 13) | QQSYSPPMYT (SEQ ID NO: 14) | 14 | 9 |
| 8 | ADI-49044 | VH3-33 | VL1-44 | ARDLEVGAEYIYYYYGMDV (SEQ ID NO: 15) | AAWDDSRNGWV (SEQ ID NO: 16) | 10 | 9 |
| 9 | ADI-45083 | VH4-4 | VL1-51 | ARSHWRSPQSVTFDL (SEQ ID NO: 17) | GTWDTSSLSAGRV (SEQ ID NO: 18) | 16 | 5 |
| 10 | ADI-42225 | VH4-4 | VL1-51 | ARIAAGYSTSWYYFDY (SEQ ID NO: 19) | GTWDTSLSAGRV (SEQ ID NO: 20) | 5 | 3 |
| 11 | ADI-49139 | VH4-4 | VL1-51 | AKDMWAGTTTNWFGP (SEQ ID NO: 21) | GTWDTSLGVV (SEQ ID NO: 22) | 9 | 5 |
| 12 | ADI-48969 | VH3-11 | VL2-11 | AREFSSRPFDL (SEQ ID NO: 23) | CSYAGTYTSNYV (SEQ ID NO: 24) | 10 | 6 |
| 13 | ADI-48900 | VH4-4 | VL1-51 | ARVNPPQYSSGWYSVY (SEQ ID NO: 25) | GTWDNSLGAVV (SEQ ID NO: 26) | 7 | 3 |
| 14 | ADI-42232 | VH4-4 | N/A | ARVAWTSSSSCYYDY (SEQ ID NO: 27) | N/A | 5 | 0 |
| 15 | ADI-42786 | VH4-4 | VL1-51 | ARDGEGHYYRSGDNWFDR (SEQ ID NO: 28) | GTWDSSLSAVV (SEQ ID NO: 29) | 6 | 4 |
| 16 | ADI-42210 | VH4-4 | VL1-51 | ARAELSAWYYFDH (SEQ ID NO: 30) | GTWDTSLSAGRV (SEQ ID NO: 31) | 6 | 0 |
| 17 | ADI-50201 | VH3-11 | VK3-15 | ARVSPLDDGYGYTYYGMDV (SEQ ID NO: 32) | QQYNNWPPRT (SEQ ID NO: 33) | 10 | 2 |
| 18 | ADI-48895 | VH3-11 | VK1-12 | ARDWAELTTITNYFYP (SEQ ID NO: 34) | QQAKSFPPT (SEQ ID NO: 35) | 8 | 1 |
| 19 | ADI-42228 | VH3-9 | VL2-14 | AKAENRIGYCSAGSCYLTYFDY (SEQ ID NO: 36) | NSYTSSSTLV (SEQ ID NO: 37) | 4 | 4 |
| 20 | ADI-45113 | VH3-23 | VK3-15 | AKDPKYSSGWWAFDY (SEQ ID NO: 38) | QQYDDWPL (SEQ ID NO: 39) | 2 | 1 |
| 21 | ADI-42198 | VH4-4 | VL1-51 | ARVEWAYSSSWWLDY (SEQ ID NO: 40) | GTWDTSLSAGGV (SEQ ID NO: 41) | 4 | 3 |
| 22 | ADI-42190 | VH3-11 | VL2-14 | AKHTGDKPLVWAPSVYGLDV (SEQ ID NO: 42) | SSYTRRSTLV (SEQ ID NO: 43) | 9 | 7 |

TABLE 1-continued

Germline usage and sequence information of anti-YFV antibodies

| Antibody Number | Name | VH germline gene usage | LC germline gene usage | CDRH3 sequence | CDRL3 sequence | Number of nucleotide substitutions in VH | Number of nucleotide substitutions in VL |
|---|---|---|---|---|---|---|---|
| 23 | ADI-49154 | VH4-4 | VL1-51 | ARVSVSTSAWYADY (SEQ ID NO: 44) | GTWDTSLSTV (SEQ ID NO: 45) | 8 | 1 |
| 24 | ADI-49183 | VH3-11 | VL2-14 | ARELSSRIDY (SEQ ID NO: 46) | SSYPGTSALVI (SEQ ID NO: 47) | 16 | 5 |
| 25 | ADI-42201 | VH3-33 | VK1-39 | ARAQDGQQLVNYYGMDV (SEQ ID NO: 48) | QQSYSTPYT (SEQ ID NO: 49) | 8 | 4 |
| 26 | ADI-42144 | VH3-30 | VL1-40 | ARGGDYGDYESNNPAEYFQH (SEQ ID NO: 50) | QSYDSSLSGHV (SEQ ID NO: 51) | 1 | 0 |
| 27 | ADI-50219 | VH4-59 | VK3-11 | AGHREDPYGAYGAS (SEQ ID NO: 52) | QQRTNWPFT (SEQ ID NO: 53) | 15 | 4 |
| 28 | ADI-48897 | VH4-61 | VK3-11 | ASRKEVRGTEDYFDY (SEQ ID NO: 54) | HQRTNWPWT (SEQ ID NO: 55) | 12 | 2 |
| 29 | ADI-42194 | VH4-61 | VK3-11 | AKVEEDGYTNVVRDY (SEQ ID NO: 56) | LQRTNWPFT (SEQ ID NO: 57) | 6 | 4 |
| 30 | ADI-49189 | VH3-11 | VL2-14 | AREGTRGRMD (SEQ ID NO: 58) | SSYTSGTTLGV (SEQ ID NO: 59) | 9 | 4 |
| 31 | ADI-49188 | VH4-4 | VL1-51 | ARDSWSGPTRNWFDP (SEQ ID NO: 60) | GTWDSSLGGVI (SEQ ID NO: 61) | 14 | 8 |
| 32 | ADI-42188 | VH4-4 | VL1-51 | ARVVWEYSNAWCVDF (SEQ ID NO: 62) | ETWDSSLGVVV (SEQ ID NO: 63) | 3 | 0 |
| 33 | ADI-50026 | VH3-30 | VK1-33 | ARNTYYDRSGLIAY (SEQ ID NO: 64) | QQYDNLSRLT (SEQ ID NO: 65) | 7 | 3 |
| 34 | ADI-42809 | VH4-4 | VL1-51 | ARGPLKSYWYFDL (SEQ ID NO: 66) | GTWDTSLSAGRV (SEQ ID NO: 67) | 7 | 0 |
| 35 | ADI-46596 | VH4-4 | VL1-51 | ARYCSGATCYGSNGMDV (SEQ ID NO: 68) | GTWDFRLSAL (SEQ ID NO: 69) | 8 | 5 |
| 36 | ADI-50205 | VH3-30 | VL2-14 | AKDQCGGDCTADY (SEQ ID NO: 70) | SSYTSSGTPVV (SEQ ID NO: 71) | 6 | 3 |
| 37 | ADI-42830 | VH4-4 | VL1-51 | ASTLWGGPLSVASDY (SEQ ID NO: 72) | GTWDSSPSAGRV (SEQ ID NO: 73) | 8 | 4 |
| 38 | ADI-49186 | VH3-30 | VK4-1 | ARDYYASGDGYFDY (SEQ ID NO: 74) | QQYYSTPRT (SEQ ID NO: 75) | 17 | 8 |
| 39 | ADI-46591 | VH4-4 | VL1-51 | VRYCSSTSCYGLNGMDV (SEQ ID NO: 76) | GTWDTRLSAL (SEQ ID NO: 77) | 11 | 3 |
| 40 | ADI-48955 | VH3-11 | VL1-51 | ARDGSLVNAIDY (SEQ ID NO: 78) | GTWDTSLSAAWV (SEQ ID NO: 79) | 8 | 3 |

TABLE 1-continued

Germline usage and sequence information of anti-YFV antibodies

| Antibody Number | Name | VH germline gene usage | LC germline gene usage | CDRH3 sequence | CDRL3 sequence | Number of nucleotide substitutions in VH | Number of nucleotide substitutions in VL |
|---|---|---|---|---|---|---|---|
| 41 | ADI-42818 | VH4-4 | VL1-51 | ARVRWSGSTSWDLDY (SEQ ID NO: 80) | GTWDTSPSAGGV (SEQ ID NO: 81) | 9 | 2 |
| 42 | ADI-50531 | VH2-5 | VL2-14 | AHSPRRITMVRGVIITWGDGMDV (SEQ ID NO: 82) | SSYTSSSTLAV (SEQ ID NO: 83) | 0 | 1 |
| 43 | ADI-46586 | VH3-11 | VL1-51 | ARDGSMVNAIDY (SEQ ID NO: 84) | GTWDSSLSAAWV (SEQ ID NO: 85) | 6 | 2 |
| 44 | ADI-49138 | VH3-33 | VL2-14 | ARDAYASGDGGIDY (SEQ ID NO: 86) | SSYRSSGTPYV (SEQ ID NO: 87) | 6 | 3 |
| 45 | ADI-45075 | VH3-23 | VK1-33 | AKDLRGVGGWYYFDY (SEQ ID NO: 88) | QQYDNLPLT (SEQ ID NO: 89) | 2 | 2 |
| 46 | ADI-42831 | VH3-23 | VK1-5 | AKDQGVTTDWPSDY (SEQ ID NO: 90) | QHYETYSVR (SEQ ID NO: 91) | 20 | 13 |
| 47 | ADI-42230 | VH3-30-3 | VK1-27 | PRDGLPGANQYFFYYGMDV (SEQ ID NO: 92) | QKYNSAPLT (SEQ ID NO: 93) | 2 | 4 |
| 48 | ADI-42847 | VH4-61 | VK3-11 | VRVEEYVNNEEVRDY (SEQ ID NO: 94) | LQRTNWPFT (SEQ ID NO: 95) | 11 | 1 |
| 49 | ADI-42821 | VH3-23 | VK1-5 | ARDQGFTTDWPCDY (SEQ ID NO: 96) | QHYNSFSVK (SEQ ID NO: 97) | 15 | 10 |
| 50 | ADI-42849 | VH3-11 | VL3-21 | ARDSNFNSNLDY (SEQ ID NO: 98) | QVWDSSSDHPWV (SEQ ID NO: 99) | 3 | 2 |
| 51 | ADI-42151 | VH4-4 | VL1-51 | ARGPLKTYWYFDL (SEQ ID NO: 100) | GTWDTSLSAGRV (SEQ ID NO: 101) | 1 | 0 |
| 52 | ADI-46001 | VH3-11 | VL3-21 | ARDSNYFYGLDV (SEQ ID NO: 102) | QVWDTSIDHHWV (SEQ ID NO: 103) | 3 | 7 |
| 53 | ADI-45154 | VH3-30 | VL2-8 | AKDICSGDCGGDY (SEQ ID NO: 104) | SSYAGSNNWVV (SEQ ID NO: 105) | 3 | 1 |
| 54 | ADI-49161 | VH1-18 | VL2-14 | AREDDDYYSMDV (SEQ ID NO: 106) | SSYTTTSLVI (SEQ ID NO: 107) | 15 | 6 |
| 55 | ADI-42154 | VH3-7 | VK2-28 | ARDISCISTSCYGGYYYYGMDV (SEQ ID NO: 108) | MQALQTPPRT (SEQ ID NO: 109) | 1 | 0 |
| 56 | ADI-48916 | VH3-33 | VK1-17 | ARDYYASGDGSIDY (SEQ ID NO: 110) | LQHNSYPLT (SEQ ID NO: 111) | 8 | 2 |
| 57 | ADI-45085 | VH3-23 | VK1-5 | AKYYDSSGYYYFDY (SEQ ID NO: 112) | KQYNRNPYT (SEQ ID NO: 113) | 4 | 4 |
| 58 | ADI-42211 | VH3-30 | VK1-27 | AKGSVSVAGAEDY (SEQ ID NO: 114) | QKYNSAPQT (SEQ ID NO: 115) | | |

TABLE 1-continued

Germline usage and sequence information of anti-YFV antibodies

| Antibody Number | Name | VH germline gene usage | LC germline gene usage | CDRH3 sequence | CDRL3 sequence | Number of nucleotide substitutions in VH | Number of nucleotide substitutions in VL |
|---|---|---|---|---|---|---|---|
| 59 | ADI-4890 8 | VH3-9 | VK3-15 | AKGYDSSGYYWADY (SEQ ID NO: 116) | QQYNNWPPLT (SEQ ID NO: 117) | 10 | 6 |
| 60 | ADI-4891 3 | VH4-4 | VK4-1 | ARERGGYFTEPFDI (SEQ ID NO: 118) | QQYYRTPWT (SEQ ID NO: 119) | 9 | 3 |
| 61 | ADI-4514 0 | VH3-48 | VL1-51 | AATIFGVVSFDY (SEQ ID NO: 120) | GTWDSALGAAV (SEQ ID NO: 121) | 7 | 1 |
| 62 | ADI-5021 1 | VH3-23 | VK1-5 | AKYYDSSGYYYLDY (SEQ ID NO: 122) | QQYNRDPYT (SEQ ID NO: 123) | 9 | 4 |
| 63 | ADI-4219 9 | VH3-72 | VL3-25 | CRESGEGFDP (SEQ ID NO: 124) | QSADRSGSVI (SEQ ID NO: 125) | 5 | 11 |
| 64 | ADI-4223 1 | VH1-18 | VK3-11 | ARDQSHGTFGGVIDSTTLFYYYGMDV (SEQ ID NO: 126) | QQRSNWPS (SEQ ID NO: 127) | 6 | 0 |
| 65 | ADI-4516 4 | VH4-39 | VK1-39 | ARGYCSSTSCFYYYYGMDV (SEQ ID NO: 128) | QQSYSTPLT (SEQ ID NO: 129) | 0 | 0 |
| 66 | ADI-4223 3 | VH3-21 | VK3-20 | ARDHYFDSSGDYLSYYYNGMDV (SEQ ID NO: 130) | QQYGSSPRA (SEQ ID NO: 131) | 8 | 6 |
| 67 | ADI-4219 1 | VH3-72 | VK1-39 | ARVYGGPDDY (SEQ ID NO: 132) | QQSSITPPT (SEQ ID NO: 133) | 3 | 2 |
| 68 | ADI-4889 9 | VH3-23 | VK1-5 | AKDGVTTINGWFHFEY (SEQ ID NO: 134) | QQYNSFPFT (SEQ ID NO: 135) | 9 | 2 |
| 69 | ADI-4914 5 | VH3-72 | VK1-39 | TRITGDRYWYLDL (SEQ ID NO: 136) | QQTYSASGS (SEQ ID NO: 137) | 11 | 13 |
| 70 | ADI-4672 9 | VH4-61 | VK1-39 | ARGWFGYSNYGLYYYYGMDV (SEQ ID NO: 138) | QQSYSTPWT (SEQ ID NO: 139) | 1 | 0 |
| 71 | ADI-4672 2 | VH4-4 | VL1-51 | ARDFWSGSNWFDP (SEQ ID NO: 140) | GTWDNSLGVV (SEQ ID NO: 141) | 1 | 0 |
| 72 | ADI-4514 8 | VH3-9 | VK3-20 | AKDIGDSYGSGSYYLPYGAYYGMDV (SEQ ID NO: 142) | QQYGSSPG (SEQ ID NO: 143) | 0 | 2 |
| 73 | ADI-4916 8 | VH3-23 | VK1-5 | AKHYDSSGYYYEDY (SEQ ID NO: 144) | HQYKDFPWT (SEQ ID NO: 145) | 11 | 6 |
| 74 | ADI-4904 0 | VH3-72 | VK1-5 | ARVRDGEYDY (SEQ ID NO: 146) | QQYNSYSP (SEQ ID NO: 147) | 9 | 4 |
| 75 | ADI-4218 7 | VH3-21 | VK3-20 | ARDNSEVEDYGDYVLYHYYGMDV (SEQ ID NO: 148) | QQYGSSPF (SEQ ID NO: 149) | 4 | 3 |
| 76 | ADI-4956 1 | VH3-30 | VL2-14 | AKDQCGGDCTADY (SEQ ID NO: 150) | SSYTSSSTPVV (SEQ ID NO: 151) | 2 | 3 |

TABLE 1-continued

Germline usage and sequence information of anti-YFV antibodies

| Antibody Number | Name | VH germline gene usage | LC germline gene usage | CDRH3 sequence | CDRL3 sequence | Number of nucleotide substitutions in VH | Number of nucleotide substitutions in VL |
|---|---|---|---|---|---|---|---|
| 77 | ADI-42219 | VH3-30-3 | VL2-11 | ARGYTGYDGFDY (SEQ ID NO: 152) | CSYATNYGVV (SEQ ID NO: 153) | 8 | 2 |
| 78 | ADI-50535 | VH1-18 | VL6-57 | ARRPYYYGSRRPAGHMDV (SEQ ID NO: 154) | QSYDSSNVV (SEQ ID NO: 155) | 0 | 0 |
| 79 | ADI-45128 | VH4-30-4 | VL1-51 | GRDSDKNYFDY (SEQ ID NO: 156) | GAWDSSLSAHVV (SEQ ID NO: 157) | 8 | 2 |
| 80 | ADI-45136 | VH3-33 | VK1-5 | AKTYDSNAYYYLDY (SEQ ID NO: 158) | QQYNRYPYT (SEQ ID NO: 159) | 7 | 7 |
| 81 | ADI-42189 | VH3-30 | VK1-17 | ASLWFIVMTMSKNPETDY (SEQ ID NO: 160) | LQHHSYPWT (SEQ ID NO: 161) | 6 | 2 |
| 82 | ADI-45078 | VH3-23 | VK1-5 | AKYYDSSGYYYFDH (SEQ ID NO: 162) | QQYNRDPYT (SEQ ID NO: 163) | 15 | 11 |
| 83 | ADI-49162 | VH3-23 | VK1-5 | AKFYDSSGYYYFDY (SEQ ID NO: 164) | QQYNTYPYT (SEQ ID NO: 165) | 17 | 13 |
| 84 | ADI-42223 | VH3-72 | VK1-39 | VRLYGDYVAYFDY (SEQ ID NO: 166) | QQSYSTPWT (SEQ ID NO: 167) | 5 | 7 |
| 85 | ADI-48435 | VH1-18 | VL2-14 | ARRGTTVTRFGVIQYYYGMDV (SEQ ID NO: 168) | SSYTSSSTLV (SEQ ID NO: 169) | 0 | 1 |
| 86 | ADI-46742 | VH4-59 | VL3-21 | ARETANNWFDP (SEQ ID NO: 170) | QVWDNSSDRRV (SEQ ID NO: 171) | 16 | 8 |
| 87 | ADI-42787 | VH3-30-3 | VK3-15 | ARASMNIPRPPVHDY (SEQ ID NO: 172) | QQYNTWWT (SEQ ID NO: 173) | 9 | 3 |
| 88 | ADI-46718 | VH3-23 | VK1-39 | AKDRSQGDYGDYVADY (SEQ ID NO: 174) | QQSYSTPLT (SEQ ID NO: 175) | 0 | 0 |
| 89 | ADI-49141 | VH4-4 | VK3-15 | ARVQTSHSELWFGEFGAD (SEQ ID NO: 176) | QQYNTWPKT (SEQ ID NO: 177) | 3 | 1 |
| 90 | ADI-42213 | VH3-23 | VK3-20 | AKDGGYSTDWYFDL (SEQ ID NO: 178) | QQYGSSRRT (SEQ ID NO: 179) | 7 | 2 |
| 91 | ADI-42844 | VH3-30 | VK1-5 | AKGYDSNGYYYIDY (SEQ ID NO: 180) | QQYNRYPYT (SEQ ID NO: 181) | 5 | 1 |
| 92 | ADI-45161 | VH3-33 | VL2-14 | ARDVGYQLLQVYGMDV (SEQ ID NO: 182) | SSYTSSSTLDVV (SEQ ID NO: 183) | 0 | 0 |
| 93 | ADI-42192 | VH4-31 | VK3-15 | ARAEYDTSGYYQQRLPEYFQH (SEQ ID NO: 184) | QQYNSWPPIT (SEQ ID NO: 185) | 5 | 1 |
| 94 | ADI-48910 | VH3-23 | VK1-5 | AKYYDSSGYYYFHS (SEQ ID NO: 186) | QQYNRYPYT (SEQ ID NO: 187) | 13 | 7 |

TABLE 1-continued

Germline usage and sequence information of anti-YFV antibodies

| Antibody Number | Name | VH germline gene usage | LC germline gene usage | CDRH3 sequence | CDRL3 sequence | Number of nucleotide substitutions in VH | Number of nucleotide substitutions in VL |
|---|---|---|---|---|---|---|---|
| 95 | ADI-42193 | VH3-72 | VL1-47 | AREHGDYGLDY (SEQ ID NO: 188) | ATWDVSLSNDVL (SEQ ID NO: 189) | 8 | 4 |
| 96 | ADI-49590 | VH1-2 | VK3-20 | YVDYYYDSSGYYSPFDY (SEQ ID NO: 190) | QQYGSSPPIT (SEQ ID NO: 191) | 1 | 2 |
| 97 | ADI-45076 | VH3-72 | VK1-39 | ARVDGEEVALIY (SEQ ID NO: 192) | QQSSTTRWT (SEQ ID NO: 193) | 8 | 11 |
| 98 | ADI-48968 | VH3-72 | VK1-39 | VRVWGGEAARYDY (SEQ ID NO: 194) | QHASTTPWT (SEQ ID NO: 195) | 13 | 12 |
| 99 | ADI-42212 | VH3-72 | VL3-1 | SRHMGFGLDL (SEQ ID NO: 196) | QAWDTTTAGGV (SEQ ID NO: 197) | 3 | 6 |
| 100 | ADI-48462 | VH3-33 | VK3-20 | ARDYYGSGDGYFDY (SEQ ID NO: 198) | QQYGSSPRA (SEQ ID NO: 199) | 0 | 0 |
| 101 | ADI-45127 | VH2-26 | VL2-8 | ARIPVEYGTPRGSFDT (SEQ ID NO: 200) | SSYGGNNDLV (SEQ ID NO: 201) | 11 | 8 |
| 102 | ADI-42200 | VH3-30-3 | VK3-11 | AGGSPDY (SEQ ID NO: 202) | QQRSNWPYT (SEQ ID NO: 203) | 9 | 4 |
| 103 | ADI-50203 | VH3-30 | VK1-5 | ARAYDSRGYYYIEH (SEQ ID NO: 204) | QQYKTYWT (SEQ ID NO: 205) | 14 | 8 |
| 104 | ADI-42149 | VH1-18 | VL2-14 | AREIDSNYVFDY (SEQ ID NO: 206) | SSYTSSGTNI (SEQ ID NO: 207) | 2 | 0 |
| 105 | ADI-42181 | VH3-7 | VK3-15 | ARKLSYSSGWYYFDY (SEQ ID NO: 208) | QQYNNWPPLT (SEQ ID NO: 209) | 2 | 3 |
| 106 | ADI-45126 | VH3-72 | VL3-10 | VTTTVILFDY (SEQ ID NO: 210) | YSTDSSGLLGV (SEQ ID NO: 211) | 9 | 8 |
| 107 | ADI-45074 | VH4-34 | VK4-1 | ARGRLAWGLRGQKSPNFFAY (SEQ ID NO: 212) | QQFHSPPWT (SEQ ID NO: 213) | 7 | 5 |
| 108 | ADI-49041 | VH3-15 | VK1-5 | ATAGIFGVVIMKGFDH (SEQ ID NO: 214) | QQYNDYPWT (SEQ ID NO: 215) | 9 | 9 |
| 109 | ADI-42227 | VH1-69 | VK1-17 | ARETYYYGSGSVPVHD (SEQ ID NO: 216) | LQHNTYPWT (SEQ ID NO: 217) | 9 | 1 |
| 110 | ADI-50220 | VH3-30 | VK1-5 | ARGYDSSGYWGFGDN (SEQ ID NO: 218) | QQYYSYPYT (SEQ ID NO: 219) | 16 | 6 |
| 111 | ADI-42141 | VH3-72 | VL3-25 | ARVEGGAWGAFDI (SEQ ID NO: 220) | QSADRSGTVV (SEQ ID NO: 221) | 1 | 1 |
| 112 | ADI-42216 | VH2-26 | VL2-8 | ARLWFTEYPGAFDI (SEQ ID NO: 222) | SSYAGSNALV (SEQ ID NO: 223) | 5 | 4 |

TABLE 1-continued

Germline usage and sequence information of anti-YFV antibodies

| Antibody Number | Name | VH germline gene usage | LC germline gene usage | CDRH3 sequence | CDRL3 sequence | Number of nucleotide substitutions in VH | Number of nucleotide substitutions in VL |
|---|---|---|---|---|---|---|---|
| 113 | ADI-50534 | VH4-39 | VL6-57 | ARHSSGSYYLAGYYFDY (SEQ ID NO: 224) | QSYDSSNWV (SEQ ID NO: 225) | 0 | 1 |
| 114 | ADI-49140 | VH3-72 | VL3-25 | ARLTDSGYDD (SEQ ID NO: 226) | HSPDSHVV (SEQ ID NO: 227) | 6 | 3 |
| 115 | ADI-46741 | VH4-59 | VL3-21 | ARETCSGGSCYYRVGSAFDI (SEQ ID NO: 228) | QVWDSSSDHEV (SEQ ID NO: 229) | 0 | 1 |
| 116 | ADI-42195 | VH3-9 | VK1-33 | VKDYCSGGRCYSFDY (SEQ ID NO: 230) | QQWGT (SEQ ID NO: 231) | 6 | 4 |
| 117 | ADI-42172 | VH3-30 | VK1-5 | AKAYDSSAYYYLDY (SEQ ID NO: 232) | QQYNRYPYT (SEQ ID NO: 233) | 3 | 4 |
| 118 | ADI-42178 | VH3-30 | VK1-5 | AKAYDSRGYYYLDY (SEQ ID NO: 234) | QQYNRYSYT (SEQ ID NO: 235) | 3 | 6 |
| 119 | ADI-49032 | VH3-23 | VK1-5 | AKDLTHRLGSIFGKLTFDAFDI (SEQ ID NO: 236) | QQYNNFWT (SEQ ID NO: 237) | 23 | 4 |
| 120 | ADI-50197 | VH3-30 | VL1-40 | AKDLTPYFYDSGAFDH (SEQ ID NO: 238) | HSYDSNMSGSV (SEQ ID NO: 239) | 17 | 7 |
| 121 | ADI-48894 | VH3-72 | VK1-27 | ARVFGGPTDY (SEQ ID NO: 240) | QKYYSAPLIT (SEQ ID NO: 241) | 7 | 2 |
| 122 | ADI-42226 | VH3-72 | VL3-25 | ARVVNGLDV (SEQ ID NO: 242) | QSADSSVADSSVV (SEQ ID NO: 243) | 7 | 1 |
| 123 | ADI-49037 | VH3-30-3 | VK3-11 | ARGQPDY (SEQ ID NO: 244) | QQRSNWPYT (SEQ ID NO: 245) | 7 | 4 |
| 124 | ADI-46739 | VH4-4 | VL1-51 | AGKKWELLGFRFDP (SEQ ID NO: 246) | GTWDNSLGMVV (SEQ ID NO: 247) | 9 | 4 |
| 125 | ADI-42810 | VH1-3 | VL2-14 | ARQWLGHFDY (SEQ ID NO: 248) | SSYTSSSTYV (SEQ ID NO: 249) | 1 | 0 |
| 126 | ADI-49137 | VH3-72 | VK3-11 | ARVFSYYLDY (SEQ ID NO: 250) | QQPGNWPPAFT (SEQ ID NO: 251) | 11 | 3 |
| 127 | ADI-42817 | VH2-5 | VK3-15 | AHRHIAARLYRDDDVFDV (SEQ ID NO: 252) | QQYNNWIT (SEQ ID NO: 253) | 2 | 2 |
| 128 | ADI-50218 | VH1-8 | VK1D-12 | ARGLNTVTNSDY (SEQ ID NO: 254) | QQANSFPWT (SEQ ID NO: 255) | 0 | 0 |
| 129 | ADI-42126 | VH1-2 | VK2-28 | ASGLSPDFSVLDV (SEQ ID NO: 256) | MQALQTPYT (SEQ ID NO: 257) | 0 | 1 |
| 130 | ADI-42186 | VH6-1 | VL1-44 | AREGAGYYDSSGYYPLSYDAFDI (SEQ ID NO: 258) | AAWDDNLIGVV (SEQ ID NO: 259) | 3 | 4 |

TABLE 1-continued

Germline usage and sequence information of anti-YFV antibodies

| Antibody Number | Name | VH germline gene usage | LC germline gene usage | CDRH3 sequence | CDRL3 sequence | Number of nucleotide substitutions in VH | Number of nucleotide substitutions in VL |
|---|---|---|---|---|---|---|---|
| 131 | ADI-48890 | VH3-72 | VL2-8 | ARVRGSYWDY (SEQ ID NO: 260) | SSFAGSNNLYV (SEQ ID NO: 261) | 6 | 0 |
| 132 | ADI-42206 | VH3-72 | VL2-14 | GRDRGWLDI (SEQ ID NO: 262) | SSYTRSSTRV (SEQ ID NO: 263) | 2 | 3 |
| 133 | ADI-46724 | VH4-4 | VL1-51 | ARVIRDLRDYYDGSGYGPDAFDI (SEQ ID NO: 264) | ETWDSRLSVV (SEQ ID NO: 265) | 16 | 4 |
| 134 | ADI-50539 | VH4-4 | VL1-51 | ARARWEDGNYYYGMDV (SEQ ID NO: 266) | GTWDSSLSAVV (SEQ ID NO: 267) | 0 | 0 |
| 135 | ADI-45156 | VH3-23 | VK1-39 | AKDQSSGWPNYYYGMDV (SEQ ID NO: 268) | QQSYSTPWT (SEQ ID NO: 269) | 0 | 0 |
| 136 | ADI-50536 | VH7-4-1 | VK1-39 | VRGYCSSTSCYGGLYWFDP (SEQ ID NO: 270) | QQSYSTPRT (SEQ ID NO: 271) | 0 | 1 |
| 137 | ADI-42217 | VH3-30-3 | VL1-40 | ARHSGGYSSKDKPTEYFQH (SEQ ID NO: 272) | QSYDSSLSGVV (SEQ ID NO: 273) | 6 | 2 |
| 138 | ADI-48951 | VH4-4 | VK4-1 | ARDVGVAAVITGSVR (SEQ ID NO: 274) | QQFYTTPST (SEQ ID NO: 275) | 6 | 4 |
| 139 | ADI-50537 | VH7-4-1 | VK1-39 | ARGYCSSTSCYGGLYWFDP (SEQ ID NO: 276) | QQSYSTPRT (SEQ ID NO: 277) | 0 | 0 |
| 140 | ADI-46737 | VH3-30 | VK1-17 | ARDGAGDYIWGSYRHKGLHYYYGMDV (SEQ ID NO: 278) | LQHNSYPLT (SEQ ID NO: 279) | 0 | 0 |
| 141 | ADI-50538 | VH4-4 | VL6-57 | AKDPRTFYGVVMLLDDP (SEQ ID NO: 280) | QSYDSTTVV (SEQ ID NO: 281) | 9 | 7 |
| 142 | ADI-48950 | VH3-30 | VL2-8 | ARGFGELPGFDI (SEQ ID NO: 282) | SSYAGSNNFVV (SEQ ID NO: 283) | 15 | 4 |
| 143 | ADI-42114 | VH3-21 | VL1-51 | ARDSWGPFDY (SEQ ID NO: 284) | GTWDSSLSAKV (SEQ ID NO: 285) | 0 | 0 |
| 144 | ADI-49194 | VH3-33 | VK1-5 | AKTYDSRAYYYLDY (SEQ ID NO: 286) | QQYNRYPYT (SEQ ID NO: 287) | 8 | 7 |
| 145 | ADI-42124 | VH3-23 | VL2-11 | AKDLFYDFWTGITIDY (SEQ ID NO: 288) | CSYAGSYTFVL (SEQ ID NO: 289) | 4 | 0 |
| 146 | ADI-45123 | VH3-7 | VK1-39 | ARDGGTVSDGLDV (SEQ ID NO: 290) | QQTFSIWT (SEQ ID NO: 291) | 8 | 7 |
| 147 | ADI-50533 | VH4-4 | VL1-51 | ARVVWYSSSSHLFDY (SEQ ID NO: 292) | GTWDSSLSAGKV (SEQ ID NO: 293) | 0 | 0 |
| 148 | ADI-49205 | VH3-33 | VL2-8 | ARIKSDAFDL (SEQ ID NO: 294) | FSYAGSNNYV (SEQ ID NO: 295) | 10 | 6 |

TABLE 1-continued

Germline usage and sequence information of anti-YFV antibodies

| Antibody Number | Name | VH germline gene usage | LC germline gene usage | CDRH3 sequence | CDRL3 sequence | Number of nucleotide substitutions in VH | Number of nucleotide substitutions in VL |
|---|---|---|---|---|---|---|---|
| 149 | ADI-45151 | VH3-30 | VK2-24 | AKFPLRDGGSGEGFDY (SEQ ID NO: 296) | MQASQFPLT (SEQ ID NO: 297) | 17 | 3 |
| 150 | ADI-46728 | VH3-30-3 | VK1-33 | ARNTYYDRRRTFDY (SEQ ID NO: 298) | QQYDNLPPVT (SEQ ID NO: 299) | 0 | 0 |
| 151 | ADI-49030 | VH3-72 | VL3-1 | AGVGITGTTGIDY (SEQ ID NO: 300) | QAWDSSTDVV (SEQ ID NO: 301) | 0 | 0 |
| 152 | ADI-50200 | VH3-9 | VK1-27 | AKGAAAGPFPYFYYAMDV (SEQ ID NO: 302) | QKYQSAPPT (SEQ ID NO: 303) | 14 | 5 |

TABLE 2

Affinity and Neutralization data for anti-YFV antibodies

| Antibody Number | Name | Monovalent Binding (KD) | Neut (100 nM) Avg. % Neutralization | Neut (10 nM) Avg. % Neutralization | Epitope Binning Data | B Cell Classification |
|---|---|---|---|---|---|---|
| 1 | ADI-49039 | 4.15E-07 | 99.07 | 99.41 | 4G2 and 5A | Atypical IgM memory (IgM+ IgD− CD27− SHM+) |
| 2 | ADI-49147 | 3.73E-09 | 97.78 | 99.65 | DIII; ADI-49147 competitor | IgD memory (IgM− IgD+ SHM+) |
| 3 | ADI-42229 | 7.87E-09 | 99.64 | 99.76 | 4G2 and 5A | IgM-only (IgM+ IgD− CD27+) |
| 4 | ADI-45090 | 2.11E-09 | 99.56 | 98.83 | DIII; ADI-49147 competitor | swIg+ CD27+ |
| 5 | ADI-45097 | 1.62E-09 | 99.32 | 99.38 | Blocks 5A only | swIg+ CD27− |
| 6 | ADI-49133 | 6.91E-09 | 99.90 | 98.57 | Blocks 5A only | IgM+ IgD+ CD27+ |
| 7 | ADI-49033 | 1.80E-08 | 99.86 | 99.95 | 5A and ADI-45107 | Atypical IgM memory (IgM+ IgD+ CD27− SHM+) |
| 8 | ADI-49044 | 1.88E-09 | 99.93 | 99.68 | Other | swIg+ CD27− |
| 9 | ADI-45083 | 3.45E-09 | 99.69 | 99.59 | Blocks 5A only | swIg+ CD27− |
| 10 | ADI-42225 | 3.15E-08 | 99.69 | 99.76 | Blocks 5A only | swIg+ CD27+ |
| 11 | ADI-49139 | 3.45E-09 | 99.53 | 100.00 | 5A and ADI-45107 | swIg+ CD27+ |
| 12 | ADI-48969 | 5.86E-09 | 99.88 | 98.12 | 5A and ADI-45107 | IgG+ CD27− |
| 13 | ADI-48900 | 2.62E-08 | 99.70 | 99.94 | Blocks 5A only | Atypical IgM memory (IgM+ IgD+ CD27− SHM+) |
| 14 | ADI-42232 | 1.46E-08 | 99.77 | 99.85 | 5A and ADI-45107 | swIg+ CD27+ |
| 15 | ADI-42786 | 1.27E-08 | 92.79 | 89.16 | Blocks 5A only | swIg+ CD27+ |
| 16 | ADI-42210 | 1.87E-08 | 99.64 | 99.76 | 5A and ADI-45107 | swIg+ CD27+ |
| 17 | ADI-50201 | 1.31E-08 | 99.28 | 97.94 | 5A and ADI-45107 | Atypical IgM memory (IgM+ IgD+ CD27− SHM+) |
| 18 | ADI-48895 | 4.49E-09 | 99.71 | 99.78 | 5A and ADI-45107 | IgG+ CD27+ |
| 19 | ADI-42228 | 8.64E-09 | 97.69 | 69.43 | ADI-45107 | swIg+ CD27− |
| 20 | ADI-45113 | 2.53E-07 | 98.92 | 98.77 | DIII; ADI-49147 competitor | IgD memory (IgM− IgD+ SHM+) |
| 21 | ADI-42198 | 3.32E-08 | 99.71 | 99.77 | 5A and ADI-45107 | Atypical IgM memory (IgM+ IgD+ CD27− SHM+) |
| 22 | ADI-42190 | 1.31E-08 | 99.80 | 99.18 | Blocks 5A only | swIg+ CD27+ |

TABLE 2-continued

Affinity and Neutralization data for anti-YFV antibodies

| Antibody Number | Name | Monovalent Binding (KD) | Neut (100 nM) Avg. % Neutralization | Neut (10 nM) Avg. % Neutralization | Epitope Binning Data | B Cell Classification |
|---|---|---|---|---|---|---|
| 23 | ADI-49154 | 1.41E−07 | 98.78 | 98.26 | 5A and ADI-45107 | Atypical IgM memory (IgM+ IgD− CD27− SHM+) |
| 24 | ADI-49183 | 2.21E−09 | 99.90 | 99.86 | 5A and ADI-45107 | IgG+ CD27+ |
| 25 | ADI-42201 | 1.13E−07 | 99.33 | 98.70 | Blocks 5A only | IgM+ IgD+ CD27+ |
| 26 | ADI-42144 | 1.09E−08 | 5.24 | 16.76 | blocks 4G2 only | swIg+ CD27− |
| 27 | ADI-50219 | 8.59E−10 | 99.54 | 99.48 | Blocks 5A only | IgG+ CD27+ |
| 28 | ADI-48897 | 3.22E−09 | 96.74 | 98.45 | 5A and ADI-45107 | IgG+ CD27− |
| 29 | ADI-42194 | 5.44E−09 | 99.59 | 99.58 | Blocks 5A only | swIg+ CD27+ |
| 30 | ADI-49189 | 1.27E−08 | 99.84 | 98.09 | 5A and ADI-45107 | Atypical IgM memory (IgM+ IgD+ CD27− SHM+) |
| 31 | ADI-49188 | 9.54E−09 | 99.96 | 99.47 | 5A and ADI-45107 | IgG+ CD27+ |
| 32 | ADI-42188 | 3.71E−08 | 99.80 | 99.77 | 5A and ADI-45107 | IgM-only (IgM+ IgD− CD27+) |
| 33 | ADI-50026 | >1.0E−07 | 99.93 | 99.91 | Other | swIg+ CD27+ |
| 34 | ADI-42809 | 3.78E−09 | 94.44 | 95.50 | 5A and ADI-45107 | swIg+ CD27+ |
| 35 | ADI-46596 | 5.11E−09 | 96.03 | 99.34 | 5A and ADI-45107 | Atypical IgM memory (IgM+ IgD+ CD27− SHM+) |
| 36 | ADI-50205 | 1.88E−08 | 99.70 | 99.64 | Blocks 5A only | IgM+ IgD+ CD27+ |
| 37 | ADI-42830 | 3.48E−09 | 95.10 | 93.86 | Blocks 5A only | swIg+ CD27− |
| 38 | ADI-49186 | 1.23E−08 | 99.46 | 99.81 | Blocks 5A only | IgG+ CD27+ |
| 39 | ADI-46591 | 9.60E−09 | 98.23 | 97.22 | 5A and ADI-45107 | Atypical IgM memory (IgM+ IgD+ CD27− SHM+) |
| 40 | ADI-48955 | 2.05E−09 | 99.87 | 96.91 | 5A and ADI-45107 | IgG+ CD27+ |
| 41 | ADI-42818 | 2.41E−09 | 95.52 | 94.94 | Blocks 5A only | swIg+ CD27+ |
| 42 | ADI-50531 | >1.0E−07 | 98.70 | 98.22 | Other | n.d. |
| 43 | ADI-46586 | 2.16E−09 | 97.63 | 97.56 | 5A and ADI-45107 | IgG+ CD27+ |
| 44 | ADI-49138 | 1.75E−08 | 99.75 | 94.66 | Other | IgD memory (IgM− IgD+ SHM+) |
| 45 | ADI-45075 | 2.61E−08 | 99.36 | 98.41 | DIII; ADI-49147 competitor | Atypical IgM memory (IgM+ IgD+ CD27− SHM+) |
| 46 | ADI-42831 | 1.96E−08 | 90.78 | 93.35 | Blocks 5A only | IgD memory (IgM− IgD+ SHM+) |
| 47 | ADI-42230 | 1.99E−09 | 94.25 | 32.22 | Other | swIg+ CD27− |
| 48 | ADI-42847 | 3.21E−09 | 83.08 | 91.27 | Blocks 5A only | swIg+ CD27+ |
| 49 | ADI-42821 | 1.21E−08 | 93.76 | 90.48 | Blocks 5A only | swIg+ CD27+ |
| 50 | ADI-42849 | 1.98E−09 | 95.03 | 94.68 | 5A and ADI-45107 | swIg+ CD27− |
| 51 | ADI-42151 | 2.97E−07 | 94.29 | 71.97 | 5A and ADI-45107 | IgM+ IgD+ CD27+ |
| 52 | ADI-46001 | 6.17E−09 | 98.61 | 99.26 | 5A and ADI-45107 | IgG+ CD27− |
| 53 | ADI-45154 | >1.0E−07 | 97.85 | 96.42 | Blocks 5A only | IgM-only (IgM+ IgD− CD27+) |
| 54 | ADI-49161 | 1.81E−09 | 92.08 | 91.30 | Other | swIg+ CD27− |
| 55 | ADI-42154 | 1.64E−07 | 98.99 | 96.53 | Blocks 5A only | Atypical IgM memory (IgM+ IgD+ CD27− SHM+) |
| 56 | ADI-48916 | 3.93E−07 | 99.79 | 88.13 | Other | Atypical IgM memory (IgM+ IgD+ CD27− SHM+) |
| 57 | ADI-45085 | 1.52E−07 | 99.32 | 96.95 | Other | swIg+ CD27+ |
| 58 | ADI-42211 | 1.64E−09 | 99.73 | 92.83 | Other | IgM+ IgD+ CD27+ |
| 59 | ADI-48908 | 1.76E−09 | 99.80 | 74.90 | Blocks 5A only | IgG+ CD27+ |
| 60 | ADI-48913 | 1.86E−07 | 98.86 | 81.30 | Other | Atypical IgM memory (IgM+ IgD+ CD27− SHM+) |
| 61 | ADI-45140 | 4.60E−09 | 82.51 | 41.20 | ADI-44112 | swIg+ CD27+ |
| 62 | ADI-50211 | 2.08E−08 | 99.80 | 90.42 | 5A and ADI-45107 | IgG+ CD27+ |

TABLE 2-continued

Affinity and Neutralization data for anti-YFV antibodies

| Antibody Number | Name | Monovalent Binding (KD) | Neut (100 nM) Avg. % Neutralization | Neut (10 nM) Avg. % Neutralization | Epitope Binning Data | B Cell Classification |
|---|---|---|---|---|---|---|
| 63 | ADI-42199 | 7.00E−10 | 93.81 | 45.88 | 4G2 and 5A | swIg+ CD27+ |
| 64 | ADI-42231 | 4.21E−08 | 86.32 | 42.38 | Other | swIg+ CD27+ |
| 65 | ADI-45164 | >1.0E−07 | 92.56 | 90.63 | Other | n.d. |
| 66 | ADI-42233 | 2.98E−09 | 88.94 | 33.48 | 4G2 and 5A | swIg+ CD27+ |
| 67 | ADI-42191 | 2.13E−09 | 99.56 | 80.41 | blocks 4G2 only | swIg+ CD27+ |
| 68 | ADI-48899 | 4.34E−07 | 97.45 | 45.70 | Other | IgM+ IgD+ CD27+ |
| 69 | ADI-49145 | 1.05E−09 | 94.23 | 86.66 | blocks 4G2 only | swIg+ CD27− |
| 70 | ADI-46729 | >1.0E−07 | 97.92 | 90.19 | blocks 4G2 only | n.d. |
| 71 | ADI-46722 | >1.0E−07 | 94.16 | 89.67 | Blocks 5A only | n.d. |
| 72 | ADI-45148 | >1.0E−07 | 94.92 | 23.00 | Blocks 5A only | IgM-only (IgM+ IgD− CD27+) |
| 73 | ADI-49168 | 2.41E−08 | 99.78 | 94.55 | ADI-45107 | IgG+ CD27+ |
| 74 | ADI-49040 | 9.99E−10 | 97.00 | 47.80 | 4G2 and 5A | swIg+ CD27− |
| 75 | ADI-42187 | 4.01E−09 | 97.44 | 63.78 | 4G2 and 5A | swIg+ CD27+ |
| 76 | ADI-49561 | 2.42445E−07 | 98.78 | 76.85 | Blocks 5A only | IgM+ IgD+ CD27+ |
| 77 | ADI-42219 | 4.05E−09 | 99.59 | 89.06 | 4G2 and 5A | swIg+ CD27+ |
| 78 | ADI-50535 | >1.0E−07 | 97.31 | 70.22 | Other | n.d. |
| 79 | ADI-45128 | 3.54E−09 | 71.21 | 32.72 | Other | Atypical IgM memory (IgM+ IgD+ CD27− SHM+) |
| 80 | ADI-45136 | 1.68E−08 | 99.50 | 15.36 | Other | swIg+ CD27+ |
| 81 | ADI-42189 | 2.40E−09 | 96.78 | 71.86 | ADI-44112 | swIg+ CD27+ |
| 82 | ADI-45078 | 5.88E−09 | 98.28 | 46.04 | ADI-45107 | swIg+ CD27+ |
| 83 | ADI-49162 | 2.19E−09 | 99.64 | 41.35 | Other | swIg+ CD27+ |
| 84 | ADI-42223 | 1.04E−09 | 60.40 | 27.92 | blocks 4G2 only | swIg+ CD27+ |
| 85 | ADI-48435 | >1.0E−07 | 98.28 | 82.33 | Other | IgM+ IgD+ CD27+ |
| 86 | ADI-46742 | >1.0E−07 | 97.87 | 70.85 | ADI-44112 | n.d. |
| 87 | ADI-42787 | 4.50E−10 | 0 | 0 | ADI-44112 | swIg+ CD27− |
| 88 | ADI-46718 | >1.0E−07 | 91.16 | 48.14 | Other | n.d. |
| 89 | ADI-49141 | 1.87E−07 | 99.87 | 80.61 | Other | swIg+ CD27− |
| 90 | ADI-42213 | 1.52E−08 | 99.00 | 47.91 | 4G2 and 5A | swIg+ CD27+ |
| 91 | ADI-42844 | 1.37E−07 | 95.65 | 79.34 | Other | swIg+ CD27+ |
| 92 | ADI-45161 | >1.0E−07 | 90.85 | 20.97 | Other | n.d. |
| 93 | ADI-42192 | 2.04E−07 | 89.44 | 38.91 | Other | IgM+ IgD+ CD27+ |
| 94 | ADI-48910 | 2.42E−09 | 99.95 | 59.48 | Other | IgG+ CD27+ |
| 95 | ADI-42193 | 9.22E−10 | 95.83 | 55.55 | 4G2 and 5A | swIg+ CD27+ |
| 96 | ADI-49590 | 1.09E−07 | 97.28 | 39.45 | Other | IgD memory (IgD+ IgM− CD27− SHM+) |
| 97 | ADI-45076 | 8.82E−10 | 40.69 | 13.70 | blocks 4G2 only | swIg+ CD27+ |
| 98 | ADI-48968 | 9.63E−10 | 97.97 | 31.34 | blocks 4G2 only | IgG+ CD27+ |
| 99 | ADI-42212 | 8.84E−10 | 99.71 | 89.90 | 4G2 and 5A | swIg+ CD27+ |
| 100 | ADI-48462 | >1.0E−07 | 97.94 | 48.44 | Blocks 5A only | activated naïve (IgM+ IgD+ CD71+ /CD21loSHM−) |
| 101 | ADI-45127 | 6.69E−09 | 75.27 | 21.17 | 4G2 and 5A | swIg+ CD27− |
| 102 | ADI-42200 | 5.63E−09 | 86.80 | 30.37 | 4G2 and 5A | swIg+ CD27− |
| 103 | ADI-50203 | 2.24E−08 | 99.89 | 11.77 | Other | IgG+ CD27+ |
| 104 | ADI-42149 | 1.77E−07 | 88.08 | 65.95 | Other | swIg+ CD27− |
| 105 | ADI-42181 | 3.15E−08 | 82.16 | 7.59 | 4G2 and 5A | swIg+ CD27+ |
| 106 | ADI-45126 | 1.68E−09 | 86.51 | 35.29 | ADI-44112 | IgM-only (IgM+ IgD− CD27+) |
| 107 | ADI-45074 | 6.99E−10 | 49.44 | 15.50 | Other | swIg+ CD27+ |
| 108 | ADI-49041 | 9.97E−10 | 89.17 | 23.10 | ADI-44112 | swIg+ CD27− |
| 109 | ADI-42227 | 6.58E−10 | 96.46 | 49.47 | ADI-44112 | swIg+ CD27+ |
| 110 | ADI-50220 | 3.64E−09 | 99.84 | 49.33 | ADI-45107 | IgG+ CD27− |
| 111 | ADI-42141 | 1.75E−09 | 0 | 32.14 | blocks 4G2 only | swIg+ CD27− |
| 112 | ADI-42216 | 1.14E−08 | 94.45 | 46.85 | 4G2 and 5A | swIg+ CD27− |
| 113 | ADI-50534 | >1.0E−07 | 85.81 | 43.79 | Other | n.d. |
| 114 | ADI-49140 | 1.04E−09 | 98.41 | 2.59 | 4G2 and 5A | swIg+ CD27− |
| 115 | ADI-46741 | >1.0E−07 | 94.68 | 23.14 | ADI-44112 | n.d. |
| 116 | ADI-42195 | 1.86E−09 | 92.25 | 31.33 | Other | swIg+ CD27− |
| 117 | ADI-42172 | 1.29E−07 | 97.07 | 29.12 | Other | swIg+ CD27+ |
| 118 | ADI-42178 | 3.44E−08 | 99.40 | 41.04 | Other | swIg+ CD27− |
| 119 | ADI-49032 | 4.86E−10 | 96.71 | 29.73 | ADI-45107 | swIg+ CD27+ |
| 120 | ADI-50197 | >1.0E−07 | 70.54 | 12.24 | Other | IgG+ CD27− |
| 121 | ADI-48894 | 9.56E−08 | 97.88 | 59.39 | blocks 4G2 only | Atypical IgM memory (IgM+ IgD+ CD27− SHM+) |

TABLE 2-continued

Affinity and Neutralization data for anti-YFV antibodies

| Antibody Number | Name | Monovalent Binding (KD) | Neut (100 nM) Avg. % Neutralization | Neut (10 nM) Avg. % Neutralization | Epitope Binning Data | B Cell Classification |
|---|---|---|---|---|---|---|
| 122 | ADI-42226 | 8.43E−10 | 94.21 | 33.76 | Blocks 5A only | swIg+ CD27− |
| 123 | ADI-49037 | 3.53E−09 | 79.59 | 7.14 | 4G2 and 5A | swIg+ CD27+ |
| 124 | ADI-46739 | >1.0E−07 | 95.66 | 55.09 | Other | n.d. |
| 125 | ADI-42810 | >1.0E−07 | 0 | 0 | Other | Atypical IgM memory (IgM+ IgD+ CD27− SHM+) |
| 126 | ADI-49137 | 8.54E−10 | 46.64 | 50.93 | blocks 4G2 only | IgD memory (IgM− IgD+ SHM+) |
| 127 | ADI-42817 | 4.15E−09 | 72.58 | 34.36 | Other | swIg+ CD27+ |
| 128 | ADI-50218 | >1.0E−07 | 66.77 | 14.49 | Other | Naïve (IgM+ IgD+ CD71− CD21+ SHM−) |
| 129 | ADI-42126 | 3.31E−07 | 20.23 | 1.07 | Other | swIg+ CD27+ |
| 130 | ADI-42186 | 1.21E−09 | 84.73 | 43.51 | Other | swIg+ CD27− |
| 131 | ADI-48890 | >1.0E−07 | 84.12 | 0 | Other | n.d. |
| 132 | ADI-42206 | 1.73E−09 | 71.04 | 23.09 | 4G2 and 5A | swIg+ CD27+ |
| 133 | ADI-46724 | >1.0E−07 | 93.22 | 62.53 | 5A and ADI-45107 | n.d. |
| 134 | ADI-50539 | >1.0E−07 | 79.84 | 42.88 | Other | n.d. |
| 135 | ADI-45156 | >1.0E−07 | 54.57 | 2.90 | Other | n.d. |
| 136 | ADI-50536 | >1.0E−07 | 99.76 | 13.96 | Other | n.d. |
| 137 | ADI-42217 | 4.00E−09 | 50.24 | 3.33 | blocks 4G2 only | swIg+ CD27+ |
| 138 | ADI-48951 | 2.67E−09 | 78.84 | 41.95 | Other | Atypical IgM memory (IgM+ IgD+ CD27− SHM+) |
| 139 | ADI-50537 | >1.0E−07 | 90.56 | 13.47 | Other | n.d. |
| 140 | ADI-46737 | >1.0E−07 | 66.49 | 49.68 | Other | n.d. |
| 141 | ADI-50538 | >1.0E−07 | 74.32 | 19.58 | Other | n.d. |
| 142 | ADI-48950 | 1.53E−09 | 69.81 | 14.45 | blocks 4G2 only | IgD memory (IgD+ IgM− CD27− SHM+) |
| 143 | ADI-42114 | >1.0E−07 | 70.93 | 23.01 | ADI-45107 | n.d. |
| 144 | ADI-49194 | 2.34E−07 | 80.83 | 46.50 | Other | IgG+ CD27+ |
| 145 | ADI-42124 | 5.88E−09 | 63.14 | 62.65 | Other | IgM-only (IgM+ IgD− CD27+) |
| 146 | ADI-45123 | 2.10E−09 | 59.03 | 27.03 | ADI-45107 | swIg+ CD27+ |
| 147 | ADI-50533 | >1.0E−07 | 78.78 | 43.72 | Other | n.d. |
| 148 | ADI-49205 | 1.29E−08 | 90.74 | 44.01 | 5A and ADI-45107 | IgG+ CD27− |
| 149 | ADI-45151 | >1.0E−07 | 0 | 0 | blocks 4G2 only | swIg+ CD27+ |
| 150 | ADI-46728 | >1.0E−07 | 89.49 | 48.99 | Other | n.d. |
| 151 | ADI-49030 | 1.25E−07 | 63.26 | 4.97 | Other | Naïve |
| 152 | ADI-50200 | >1.0E−07 | 97.30 | 0 | 4G2 and 5A | IgM+ IgD+ CD27+ |

*NN—non-neutralizing;
n.d.—not determined;
Other—did not block any of the listed competition assay controls

TABLE 3

Informal Sequence Listing

| Antibody Number | SEQ ID NO: | Sequence | Clone # (ADI) | Descriptors |
|---|---|---|---|---|
| 1 | 304 | QVQLQESGPGLVKPSETLSLTCAVSGYSISSG FYWGWIRQPPGKGLEWIGSMYQSGITYYNP SLKSRVTISVDTSKSQFSLKLTSVTAADTAM YYCARNAPENYYGSGRESFDIWGQGTMVT VSS | ADI-49039 | Heavy chain variable region ("HC") amino acid sequence |
| 2 | 305 | QVQLQESGGDLVQPGGSLRLSCAASGFTFSN YAMNWVRQAPGKGLEWVSAINRGGDSTY YADSVKGRFTISRDNSKNTLYLQMNSLRAE DTAVYYCAKDHGGKYGWWYFDLWGRGT LVTVSS | ADI-49147 | Heavy chain variable region ("HC") amino acid sequence |
| 3 | 306 | QVQLQESGPGLVKPSETLSLTCAVSGYSISSG FYWGWIRQPPGKGLEWIGSMYHSGITYYNP SLKSRVTISVDTSKNQFSLKLTSVTAADTAM YYCARNAPENYYGSGRESFDIWGQGTTVT VSS | ADI-42229 | Heavy chain variable region ("HC") amino acid sequence |
| 4 | 307 | EVQLVESGGGLVQPGRPLRLSCAASGFAFSS YGMHWVRQAPGKGLEWVALIRFDGTIKY | ADI-45090 | Heavy chain variable region |

TABLE 3-continued

Informal Sequence Listing

| Antibody Number | SEQ ID NO: | Sequence | Clone # (ADI) | Descriptors |
|---|---|---|---|---|
| | | YADSVKGRFTISRDNAKNTLYLQMSSLRAE DTAVYYCARDLEVGAEYLYYHYGMDVWG QGTTVTVSS | | ("HC") amino acid sequence |
| 5 | 308 | EVQLVESGGGVVQPGRSLRLSCAASGFTFNS HGMHWVRQAPGKGLEWVAVISYDGTKKY FADSVKGRFTISRDNSKNTLYLQMSSLRADD TAVYYCAKDSSTSWYQVVYHIDYWGQGTL VTVSS | ADI-45097 | Heavy chain variable region ("HC") amino acid sequence |
| 6 | 309 | EVQLLESGGGLVQPGGSLRLSCAASGFTFRN YAMNWVRQTPGKGLEWVSGISGGGDSTNY ADSVKGRFTISRDNSRNTLYLQLNSLRAEDT AVYYCAKDLAVSTPRYWFDSWGQGTLVTV SS | ADI-49133 | Heavy chain variable region ("HC") amino acid sequence |
| 7 | 310 | EVQLVESGGGLVQPGGSLRLSCAASGLIFRN YAMSWVRQAPGKGLEWVSSFSGSGGSAYY ADSVKGRFTISRDNSKSTVYLQMNRLRVED TAVYYCAKDMAVSVHRGWFDDWGQGTLV TVSS | ADI-49033 | Heavy chain variable region ("HC") amino acid sequence |
| 8 | 311 | QVQLVESGGGVVQPGRSLRLSCAASGFAFSS YGMHWVRQAPGKGLEWVAGMRFDGTKIY YADSVKGRFTISRDNSKNTLYLQMNSLRAE DTAVYFCARDLEVGAEYIYYYYGMDVWG QGTTVTVSS | ADI-49044 | Heavy chain variable region ("HC") amino acid sequence |
| 9 | 312 | QVQLVESGPGLVKPSGTLSLTCAVSGGSISS DYWWSWVRQPPGKGLEYIGEIYHTGSTNY NPSLKSRVTVSLDRSKNVFSLTLRSVTAADT AVYYCARSHWRSPQSVTFDLWGQGTTVTV SS | ADI-45083 | Heavy chain variable region ("HC") amino acid sequence |
| 10 | 313 | QVQLQESGPGLVKPSGTLSLTCAVSGGSITSS NWWSWVRQPPGKGLEWIGDIYHSGSTSYN PSLKSRVTISVDKSKNHFSLKLTSVTAADTA VYYCARIAAGYSTSWYYFDYWGQGTLVTV SS | ADI-42225 | Heavy chain variable region ("HC") amino acid sequence |
| 11 | 314 | EVQLVETGSGLVRPSGTLSLTCAVSGDSISSN NWWSWVRQPPGKGLEWIGEIYHSGSTSYN PSLKSRVTISIDKSNNHFSLKLTSVTAADTAV YYCAKDMWAGTTTNWFGPWGQGTLVTVS S | ADI-49139 | Heavy chain variable region ("HC") amino acid sequence |
| 12 | 315 | QVTLKESGGALVKPAGSLTLSCAASGFTFG DYYMSWIRQAPGKGLEWISYISSSGSSIYYT DSVRGRFTISRDNARNSLYLQMNSLRVEDT AVYYCAREFSSRPFDLWGQGTLVTVSS | ADI-48969 | Heavy chain variable region ("HC") amino acid sequence |
| 13 | 316 | EVQLQESGPGLVKPSGTLSLTCAVSGGSISSS DWWSWVRQPPGKGLEWIGEIYHSGSTSYN PSVKSRVSISVDKSKNQFSLQLSSVTAADTAI YYCARVNPPQYSSGWYSVYWGQGLVTVS S | ADI-48900 | Heavy chain variable region ("HC") amino acid sequence |
| 14 | 317 | QVQLQQSGPGLVKPSGTLSLTCAVSGDSISSS HWWCWVRQPPGKGLEWIGEIYHSGSTSYN PSLKSRVTISVDKSKNQFSLKLSSVTAADTA VYFCARVAWTSSSSCYYDYWGQGLVTVS S | ADI-42232 | Heavy chain variable region ("HC") amino acid sequence |
| 15 | 318 | EVQLVESGPGLVKPSGTLSLTCAVSGGSISSS YWWSWVRQSPGKGLEWIGEVYHSGSTHY NPSLKSRVTISVDKSKNQFSLKLSSVTAADT AVYYCARDGEGHYYRSGDNWFDRWGQGT LVTVSS | ADI-42786 | Heavy chain variable region ("HC") amino acid sequence |
| 16 | 319 | EVQLLESGPGLVQPSGTLSLTCTASGGSISSS NWWSWVRQPPGKGLEWIGDIYHTGSTSYN PSLKSRVTISVDKSKNQFSLKLSSVTAADTA VYYCARAELSAWYYFDHWGQGTLVTVSS | ADI-42210 | Heavy chain variable region ("HC") amino acid sequence |
| 17 | 320 | QVQLVESGGGLVKPGGSLRLSCAASGFIFSD YYMNWIRQAPGKGLDWVSTISGSGKSIYYA | ADI-50201 | Heavy chain variable region |

TABLE 3-continued

Informal Sequence Listing

| Antibody Number | SEQ ID NO: | Sequence | Clone # (ADI) | Descriptors |
|---|---|---|---|---|
| | | DSVKGRFTISRDNAKNSLYLQMNSLSAEDT AVYYCARVSPLDDGYGYTYYGMDVWGQG TTVTVSS | | ("HC") amino acid sequence |
| 18 | 321 | EVQLLESGGGLVKPGGSLRLSCAASGFTFSD YYMSWIRQAPGKGLEWVSYITSSGNTKYY ADSVKGRFTISRDNAKNSLYLQISSLRAEDT AVYYCARDWAELTTITNYFYPWGQGTTVT VSS | ADI-48895 | Heavy chain variable region ("HC") amino acid sequence |
| 19 | 322 | EVQLLESGGGLVQPGRSLRLSCAASGFTFDD YAMHWVRQPPGKGLEWVSGISWNGGGIG YADSVKGRFTISRDNAKNSLYLQMNSLRAD DTALYYCAKAENRIGYCSAGSCYLTYFDY WGQGTLVTVSS | ADI-42228 | Heavy chain variable region ("HC") amino acid sequence |
| 20 | 323 | QVQLVQSGGGLVQPGGSLRLSCAASGFTFSS YAMSWVRQAPGKGLEWVSAISGSGGSTYY ADSVKGRFTISRDNSKNTLHLQMSSLRAEDT AVYYCAKDPKYSSGWWAFDYWGQGTLVT VSS | ADI-45113 | Heavy chain variable region ("HC") amino acid sequence |
| 21 | 324 | EVQLVESGPGLVKPSGTLSLTCAVSGGSISSN KWWSWVRQPPGKGLEWIGEIYHSGSTSYN PSLKSRVSISVDKSKNQFSLKLSSVTAADTA VYYCARVEWAYSSSWWLDYWGQGTLVTV SS | ADI-42198 | Heavy chain variable region ("HC") amino acid sequence |
| 22 | 325 | QVQLVESGGGLVKPGGSLRLSCAASGFTFSD DYMSWIRQAPGKGLEWVSYISGSGRAMYY ADSVQGRFTVSRDNAKNSLFLQMNNLRAED TAVYYCAKHTGDKPLVWAPSVYGLDVWG QGTTVTVSS | ADI-42190 | Heavy chain variable region ("HC") amino acid sequence |
| 23 | 326 | QVQLQESGPGLVKPSGTLSLTCAVSGSSITSS HWWSWVRQPPGKGLAWIGDIYHSGGTTY NPSLKSRVTISVDKSKNQFSLKLSSVTAADT AVYYCARVSVSTSAWYADYWGQGTLVTVS S | ADI-49154 | Heavy chain variable region ("HC") amino acid sequence |
| 24 | 327 | QVQLVESGGGLVKPGGSLRLSCVASGFTFN NYYMRWMRQAPGKGLEWVSQISSSGSIKD YADSVKGRFTVSRDNAKNSLYLQLNSLRAD DTAVYFCARELSSRIDYWGQGTLVTVSS | ADI-49183 | Heavy chain variable region ("HC") amino acid sequence |
| 25 | 328 | EVQLVESGGGVVQPGRSLRLSCVASGFTLRS YGMHWVRQVPGKGLEWVAVSWYDGSNK HYADSVKGRFSISRDNSKNTLYLQMNSLRA EDTAVYYCARAQDGQQLVNYYGMDVWG QGTTVTVSS | ADI-42201 | Heavy chain variable region ("HC") amino acid sequence |
| 26 | 329 | QVQLVESGGGVVQPGRSLRLSCAASGFTFSS YTMHWVRQAPGKGLEWVAVISYDGSNKY YADSVKGRFTISRDNSKNTLYLQMNSLRAE DTAVYYCARGGDYGDYESNNPAEYFQHW GQGTLVTVSS | ADI-42144 | Heavy chain variable region ("HC") amino acid sequence |
| 27 | 330 | QVQLQESGPGLVKPSETLSLTCTVSGDSISVS YWSWIRQFPGKGLEWIGYIYNSGNANYNPS LESRVTISIDTSKNRFSLRLSSVTAADTAVYY CAGHREDPYGAYGASWGQGTLVTVSS | ADI-50219 | Heavy chain variable region ("HC") amino acid sequence |
| 28 | 331 | EVQLLESGPGLVKPSETLSLTCTVSGGSLSSD SHFWGWIRQPPGKGLEWIGYIYYSGNANYN PSLQSRVTISLDKSKNQFSLRLTSVTAADTA VYYCASRKEVRGTEDYFDYWGQGTLVTVS S | ADI-48897 | Heavy chain variable region ("HC") amino acid sequence |
| 29 | 332 | EVQLQESGPGLVKPSETLSLTCTVSGGSVSS GSYYWSWIRQPPGKGLEWIGYIYDSGNTNY NPSLKSRVTISVDTSKRQFSLRLTSVTAADT AVYYCAKVEEDGYTNVVRDYWGQGTLVT VSS | ADI-42194 | Heavy chain variable region ("HC") amino acid sequence |
| 30 | 333 | EVQLVESGGGLVKPGGSLRLSCAASGFTFSD YYMSWIRQAPGKGLECIA**CISSSGSMIYYAD | ADI-49189 | Heavy chain variable region |

TABLE 3-continued

Informal Sequence Listing

| Antibody Number | SEQ ID NO: | Sequence | Clone # (ADI) | Descriptors |
|---|---|---|---|---|
| | | SVKGRFTISRDNAKNSLYLQLNSLRVEDTAV YYCAREGTRGRMDWGQGTLVTVSS | | ("HC") amino acid sequence |
| 31 | 334 | EVQLLESGPGLVRPSGTLSLTCAVSGGSISTT DWWSWVRQPPGKGLEWIGEINQSGSTSYSP SFKSRVSISVDKSKRQFSLKLTSVTAADTAV YYCARDSWSGPTRNWFDPWGRGTLVTVSS | ADI-49188 | Heavy chain variable region ("HC") amino acid sequence |
| 32 | 335 | EVQLLESGPGLVKPSGTLSLTCAVSGGSISSG NWWSWVRQPPGKGLEWIGEIYHSGSANYN PSLKSRVTISVDKSKNQFSLKLTSVTAADTA VYYCARVVWEYSNAWCVDFWGQTTVTV SS | ADI-42188 | Heavy chain variable region ("HC") amino acid sequence |
| 33 | 336 | EVQLLESGGGVVQPGRSLRLSCAASGFTFTT YAMHWVRQAPGKGLEWVAAVSYDGNNKY YADSVKGRFTISRDNSRNTLYLQMNSLRAE DTAVYFCARNTYYDRSGLIAYWGQGALVT VSS | ADI-50026 | Heavy chain variable region ("HC") amino acid sequence |
| 34 | 337 | QVQLVESGPGLVKPSGTLSLTCAVSGDSISST NWWSWVRQPPGKGLEYIGEIFHSGSTNYNP FLKSRVTISVDKSKNHFSLKLSSVTAADTAV YYCARGPLKSYWYFDLWGRGTLVTVSS | ADI-42809 | Heavy chain variable region ("HC") amino acid sequence |
| 35 | 338 | QVQLQESGPGLVKPSGTLSLTCAVSGGSISS NNWWSWVRQPPGKGLEWIGDTYHSGSPSY NPSLKSRVTISVDKSKNEFSLKLSSVTAADT AVYFCARYCSGATCYGSNGMDVWGQGTT VTVSS | ADI-46596 | Heavy chain variable region ("HC") amino acid sequence |
| 36 | 339 | QVQLQESGGGVVQPGRSLRLSCAASGFTFS NFGMHWVRQAPGKGLEWVAIISYDRSNKD YADSVKGRFTISRDNSKNTLYLQMNSLRAE DTAVYYCAKDQCGGDCTADYWGQGTLVT VSS | ADI-50205 | Heavy chain variable region ("HC") amino acid sequence |
| 37 | 340 | EVQLLESGPGLVRPSGTLSLTCAVSGASISSN HWWTWVRQPPGKGLEWIGEIYHSGSPTYN PSLKSRVTISVDKSKNQFSLKLNSVTAADTA VYYCASTLWGGPLSVASDYWGQGTLVTVS S | ADI-42830 | Heavy chain variable region ("HC") amino acid sequence |
| 38 | 341 | QVQLVESGGGVVQPGRSLRLSCAASGFTFS NSGMHWVRQAPGQGLEWVALISYTGETK YYSDSLKARFTISRDNSKNTLYLQMSSLSNE DTAVYYCARDYYASGDGYFDYWGQGTLV TVSS | ADI-49186 | Heavy chain variable region ("HC") amino acid sequence |
| 39 | 342 | QVQLQQWGPELVKPSGTLSLTCTVSGGSISSI SWWSWVRQSPGKGLEWIGEINHSGSTVYN PSLKSRVTISVDKSKKQFSLKLRSVTAADTA VYYCVRYCSSTSCYGLNGMDVWGQGTTV TVSS | ADI-46591 | Heavy chain variable region ("HC") amino acid sequence |
| 40 | 343 | QVQLVQSGGGLVNPGGSLRLSCAASGFTFT DYYMSWIRQAPGKGLEWVSYISSSGNTRYY ADSVKGRFTISRDNAKNSLSLQMNSLRPEDT AIYYCARDGSLVNAIDYWGQGTLVTVSS | ADI-48955 | Heavy chain variable region ("HC") amino acid sequence |
| 41 | 344 | EVQLVESGPGLVKPSGTLSLTCAVSGGSITG SNWWSWVRQPPGKGLEWIGEIYHTGSTSY NPSLKSRVTISVDNSKNHFSLRLTSVTAADT AVYYCARVRWSGSTSWDLDYWGQGTLVT VSS | ADI-42818 | Heavy chain variable region ("HC") amino acid sequence |
| 42 | 345 | EVTLKESGPTLVKPTQTLTLTCTFSGFSLSTS GVGVGWIRQPPGKALEWLALIYWDDDKRY SPSLKSRLTITKDTSKNQVVLTMTNMDPVDT ATYYCAHSPRRITMVRGVIITWGDGMDV WGQGTTVTVSS | ADI-50531 | Heavy chain variable region ("HC") amino acid sequence |
| 43 | 346 | EVQLVESGGGLVKPGGSLRLSCAASGFTFTD YYMSWIRQAPGKGLEWVSYITSSGNTKYY ADSVKGRFTISRDNAKNSLFLQMNSLRAEDT AVYFCARDGSMVNAIDYWGQGTLVTVSS | ADI-46586 | Heavy chain variable region ("HC") amino acid sequence |

TABLE 3-continued

Informal Sequence Listing

| Antibody Number | SEQ ID NO: | Sequence | Clone # (ADI) | Descriptors |
|---|---|---|---|---|
| 44 | 347 | QVQLVESGGGVVQPGRSLRLSCAASGFTFS NSGMHWVRQAPGKGLEWVSVIWYDESNK YYADSVKGRFTISRDNSKNTVYLQMNTLRA EDTAVYYCARDAYASGDGGIDYWGQGALV TVSS | ADI-49138 | Heavy chain variable region ("HC") amino acid sequence |
| 45 | 348 | EVQLLESGGGLVQPGGSLRLSCAASGFTFSS YAMSWVRQAPGKGLEWVSVISDSGGSTYY ADSVKGRFTISRDNSKNTLYLQMNSLRAED TAVYYCAKDLRGVGGWYYFDYWGQGTLV TVSS | ADI-45075 | Heavy chain variable region ("HC") amino acid sequence |
| 46 | 349 | EVQLVESGGGLVQPGGSLRLSCAASGFTFIN YAMTWVRQAPGKGLEWVSAISGNGDGTY YADSVKGRFTLSRDNAKNTIYLHMSALRDE DTALYYCAKDQGVTTDWPSDYWGQGTLV TVSS | ADI-42831 | Heavy chain variable region ("HC") amino acid sequence |
| 47 | 350 | QVQLVESGGGVVQPGRSLRLSCAASGFTFSS YAMHWVRQAPGKGLEWVAVISHDGSNKY YADSVKGRFTISRDNSKNTLYLQINSLRAED TAVYYCPRDGLPGANQYFFYYGMDVWGQ GTTVTVSS | ADI-42230 sequence | Heavy chain variable region ("HC") amino acid |
| 48 | 351 | EVQLLESGPRLVKPSETLSLTCTVSGGSVRG GSHYWSWIRQPPGKGLEWIGYVYDSGSTNY NPSLKSRVSISVDMSKKQFSLKLRSVTAADT AVYHCVRVEEYVNNEEVRDYWGQGTMVT VSS | ADI-42847 | Heavy chain variable region ("HC") amino acid sequence |
| 49 | 352 | EVQLLESGGGLVPPGGSLRLSCAASGFTFSN YAMSWVRQAPGKGLEWVSAISGSGDSTYY ADSVKGRFTLSRDTSKKMVYLHMSNLRDD DTAVYYCARDQGFTTDWPCDYWGQGTLV TVSS | ADI-42821 | Heavy chain variable region ("HC") amino acid sequence |
| 50 | 353 | QVQLVESGGGLVKPGGSLRLSCAASGFTFSD YYMSWIRQAPGKGLEWVSYITSSGNTMYY ADSVKGRFTISRDNAKNSLYLQMNSLRAED TAVYYCARDSNFNSNLDYWGQGTLVTVSS | ADI-42849 | Heavy chain variable region ("HC") amino acid sequence |
| 51 | 354 | QVQLQESGPGLVKPSGTLSLTCAVSGGSISSS NWWSWVRQPPGKGLEWIGEIYHSGSTTYN PSLKSRVTISVDKSKNQFSLKLSSVTAADTA VYYCARGPLKTYWYFDLWGRGTLVTVSS | ADI-42151 | Heavy chain variable region ("HC") amino acid sequence |
| 52 | 355 | EVQLVESGGGLVKPGGSLRLSCAASGFTFSD YYMSWIRQAPGKGLEWVSYISSSGNTIYYA DSVKGRFTISRDNAKNSLYLQLNSLRAGDTA VYYCARDSNYFYGLDVWGQGTTVTVSS | ADI-46001 | Heavy chain variable region ("HC") amino acid sequence |
| 53 | 356 | EVQLVESGGGVVQPGRSLRLSCAASGFTFSN YGMHWVRQAPGKGLEWVAVISYDGSNKY YADSVKGRFTISRDDSKNTLYLQVNSLRAED TAVYYCAKDICSGDCGGGDYWGQGTLVTV SS | ADI-45154 | Heavy chain variable region ("HC") amino acid sequence |
| 54 | 357 | QVQLVQSGAEVKKPGASVKVSCKASGYTFN TYAMTWVRQAPGQGLEWMGWISTYNGNT VFGQKFQGRVTLSDTDTSTSTAYMELRSLTS DDTAVYYCAREDDDYYSMDVWGQGTTVT VSS | ADI-49161 | Heavy chain variable region ("HC") amino acid sequence |
| 55 | 358 | EVQLVQSGGGLVQPGGSLRLSCAASGFTFST YWMSWVRQAPGKGLEWVANIKQDGSEKY YVDSVKGRFTISRDNAKNSLYLQMNSLRAE DTAVYYCARDISCISTSCYGGYYYYGMDV WGQGTTVTVSS | ADI-42154 | Heavy chain variable region ("HC") amino acid sequence |
| 56 | 359 | EVQLVESGGGVVQPGRSLRLSCAASGFTFSN SGMHWVRQAPGKGLEWVAVIWYDSRNQN YADSVKGRFTISRDNSKNTLFLQMNSLRAED TAVYYCARDYYASGDGSIDYWGQGTLVTV SS | ADI-48916 | Heavy chain variable region ("HC") amino acid sequence |

TABLE 3-continued

Informal Sequence Listing

| Antibody Number | SEQ ID NO: | Sequence | Clone # (ADI) | Descriptors |
|---|---|---|---|---|
| 57 | 360 | EVQLVESGGGLVQPGGSLRLSCAASGFTFSS YAMSWVRQAPGKGLEWVSTFSGRGGSTYY ADFVKGRFTISRDNSKNTLYLQMNSLRAED TAVYYCAKYYDSSGYYYFDYWGQGTLVTV SS | ADI-45085 | Heavy chain variable region ("HC") amino acid sequence |
| 58 | 361 | QVQLVESGGGVVQPGRSLRLSCGGSGFTFSS YGMHWVRQAPGKGLEWVAVISYDGSKKY SADSVKGRFTISRDNSKNTLYLQMNSLRAED TAVYYCAKGSVSVAGAEDYWGQGTLVTVS S | ADI-42211 | Heavy chain variable region ("HC") amino acid sequence |
| 59 | 362 | EVQLLESGGGLVQPGRSLRLSCAVSGFTFAE YAMHWVRQAPGKGLEWVSSISWNSGRIGY VDSVRGRFTISRDNAKNSLYLQMNSLRVED TAFYYCAKGYDSSGYYWADYWGQGTLVT VSS | ADI-48908 | Heavy chain variable region ("HC") amino acid sequence |
| 60 | 363 | EVQLLESGPGLVKPSETLSLTCTVSGGSISSY YWSWIRQPAGKGLELIGRIYTSGSGNYNPSL KRRVTMSVDTSKNQISLRLNSVTAADTAVY YCARERGGYFTEPFDIWGQGTMVTVSS | ADI-48913 | Heavy chain variable region ("HC") amino acid sequence |
| 61 | 364 | EVQLLESGGGLVHPGGSLRLSCAASGFTFSD YEMNWVRQAPGKGLEWVSHISSSGNIIYYA DSVKGRFTISRDNAKDSLYLQMNSLRAEDT AVYYCAATIFGVVSFDYWGQGTLVTVSS | ADI-45140 | Heavy chain variable region ("HC") amino acid sequence |
| 62 | 365 | EVQLVESGGGLVQPGGSLRLSCAASGFTFSA YAMSWVRQAPGRGLEWVSAISGSDRRIYY ADSVKGRFSISRDNSKNTLYLQMSSLRAEDT AVYYCAKYYDSSGYYYLDYWGQGTLVTVS S | ADI-50211 | Heavy chain variable region ("HC") amino acid sequence |
| 63 | 366 | EVQLVESGGGLVQPGGSLRLSCAASGFTFSD HYMAWVRQAPGKGLEWVGRIRNKPNSYT TEYAASVKGRFTISRHDSENSLYLQMNSLKT EDTAVYYCCRESGEGFDPWGQGTLVTVSS | ADI-42199 | Heavy chain variable region ("HC") amino acid sequence |
| 64 | 367 | QVQLVQSGAEVKKPGASVKVSCKASGYSFT TYGISWVRQAPGQGLEWMGWISGYSGDTN YAQKVQGRVTMTTDTSTSTAYMELRSLRSD DTAVYYCARDQSHGTFGGVIDSTTLFYYY GMDVWGQGTTVTVSS | ADI-42231 | Heavy chain variable region ("HC") amino acid sequence |
| 65 | 368 | EVQLQESGPGLVKPSETLSLTCTVSGGSISSS SYYWGWIRQPPGKGLEWIGSIYYSGSTYYN PSLKSRVTISVDTSKNQFSLKLSSVTAADTA VYYCARGYCSSTSCFYYYYGMDVWGQGT TVTVSS | ADI-45164 | Heavy chain variable region ("HC") amino acid sequence |
| 66 | 369 | EVQLVESGGGLVKPGGSLRLSCVASGFTFSR YSMNWVRQAPGKGLEWVSSISHSGRYIYY ADSEKGRFTISRDNAKNSLYLQMNSLRAED TAVYYCARDHYFDSSGDYLSYYYNGMDV WGQGTTVTVSS | ADI-42233 | Heavy chain variable region ("HC") amino acid sequence |
| 67 | 370 | EVQLVESGGGLVQPGGSLRLSCAASGFTFSD HYMDWVRQAPGKGLEWVGRTRNKPNSHT TEYAASVKGRFTISRDDSKNSLYLQMNSLQ TEDTAVYYCARVYGGPDDYWGQGTLVTVS S | ADI-42191 | Heavy chain variable region ("HC") amino acid sequence |
| 68 | 371 | EVQLVESGGGLVQPGGSLRLSCAASGFIYTN YAMYWVRQAPGKGLEWVSAISGSGGITYY ADSVKGRFTISRDNSKNTLYLQMNSLRAED KAVYYCAKDGVTTINGWFHFEYWGQGTL VTVSS | ADI-48899 | Heavy chain variable region ("HC") amino acid sequence |
| 69 | 372 | EVQLLESGGGLVQPGGSLRLSCAASGFIFSD YMDWVRQTPGKGPEWVGRITNRPNSYTT EYAASVKGRFTISRDDSTNSLFLHMNSLKTE DTAVYYCTRITGDRYWYLDLWGRGTLVTV SS | ADI-49145 | Heavy chain variable region ("HC") amino acid sequence |

TABLE 3-continued

Informal Sequence Listing

| Antibody Number | SEQ ID NO: | Sequence | Clone # (ADI) | Descriptors |
|---|---|---|---|---|
| 70 | 373 | EVQLVESGPGLVKPSQTLSLTCTVSGGSISSG SYYWSWIRQPAGKGLEWIGRIYTSGSTNYN PSLKSRVTMSVDTSKNQFSLKLSSVTAADTA VYYCARGWFGYSNYGLYYYYGMDVWGQ GTTVTVSS | ADI-46729 | Heavy chain variable region ("HC") amino acid sequence |
| 71 | 374 | EVQLVESGPGLVKPSGTLSLTCAVSGGSISSS NWWSWVRQPPGKGLEWIGEIYHSESTNYN PSLKSRVTISVDKSKNQFSLKLSSVTAADTA VYYCARDFWSGSNWFDPWGQGTLVTVSS | ADI-46722 | Heavy chain variable region ("HC") amino acid sequence |
| 72 | 375 | EVQLLESGGGLVQPGRSLRLSCAASGFTFDD YAMHWVRQAPGKGLEWVSGISWNSGSIGY ADSVKGRFTISRDNAKNSLYLQMNSLRAED TALYYCAKDIGDSYGSGSYYLPYGAYYGM DVWGQGTTVTVSS | ADI-45148 | Heavy chain variable region ("HC") amino acid sequence |
| 73 | 376 | EVQLLESGGGLVQPGGSLRLSCAASGFTFSS YAMSWVRQATGRGLEWVSSIRSSGGRTEY ADSVKGRFTISRDNSKNTLYLQMDSLRAED TALYYCAKHYDSSGYYYEDYWGQGTLVTV SS | ADI-49168 | Heavy chain variable region ("HC") amino acid sequence |
| 74 | 377 | EVQLVESGGALVHPGGSLGLSCAASGFTFSD HYMDWVRQAPGKGLEWVGRIRNKPNSYA TQYAASVKGRFTISRDDSKKSLYLQMNSLN TEDTAVYYCARVRDGEYDYWGQGTLVTVS S | ADI-49040 | Heavy chain variable region ("HC") amino acid sequence |
| 75 | 378 | EVQLLESGGGLVKPGGSLRLSCAASGFTFSS YSMNWVRQAPGKGLEWVSSISSRSSFMYY ADSVKGRFTISRDNAKNSLYLQMNSLRVED TAVYYCARDNSEVEDYGDYVLYHYYGMD VWGQGTTVTVSS | ADI-42187 | Heavy chain variable region ("HC") amino acid sequence |
| 76 | 379 | EVQLLESGGGVVQPGRSLRLSCVASGFTFSS YGMHWVRQAPGKGLEWVALISYDGSNKY YADSVKGRFTISRDNSKNTLYLQMNSLRAE DTAVYYCAKDQCGGDCTADYWGQGTLVT VSS | ADI-49561 | Heavy chain variable region ("HC") amino acid sequence |
| 77 | 380 | QVQLVESGGGVVQPGRSLRLSCAASGFTFSS LAMHWVRQAPGKGLEWVATISYDVSNKY YADSVKGRFTISRDNSKNTLFLQMNSLRPED TAVYYCARGYTGYDGFDYWGQGTLVTVSS | ADI-42219 | Heavy chain variable region ("HC") amino acid sequence |
| 78 | 381 | QVQLVQSGAEVKKPGASVKVSCKASGYTFT SYGISWVRQAPGQGLEWMGWISAYNGNTN YAQKLQGRVTMTTDTSTSTAYMELRSLRSD DTAVYYCARRPYYYGSRRPAGHMDVWGQ GTTVTVSS | ADI-50535 | Heavy chain variable region ("HC") amino acid sequence |
| 79 | 382 | QVQLQESGPGLVRPSQTLSLTCTVSGGAISS GDYYWSWVRQPPGKGLEWIGYIHYSGTTY NNPSLKSRVTIAVDTSKNQFSLKLSSVTAAD TAVYFCGRDSDKNYFDYWGQGTLVTVSS | ADI-45128 | Heavy chain variable region ("HC") amino acid sequence |
| 80 | 383 | EVQLVESGGGVVRPGRSLRLSCAASGFTFSS YGMHWVRQAPGKGLEWVAVIRFDGSNTV YADSVKGRFTISRDNSKNTLYLQMNSLRAE DTAVYYCAKTYDSNAYYYLDYWGQGTLVT VSS | ADI-45136 | Heavy chain variable region ("HC") amino acid sequence |
| 81 | 384 | EVQLVESGGGVVQPGWSLRLSCAVSGFTFS SYAMHWVRQAPGKGLEWVAVISYDGSYK WYADSVKGRFTISRDNSKNTVYLQMNSLRA EDTAVYYCASLWFIVMTMSKNPETDYWG QGTLVTVSS | ADI-42189 | Heavy chain variable region ("HC") amino acid sequence |
| 82 | 385 | EVQLVESGGGLIQPGGSLRLSCAASGFSFSSH AMTWVRQAPGKGLQWVSSIRGSDRTTNYA DSVKGRFTVSRDNSKNTLYLQMNSLRAEDT AIYYCAKYYDSSGYYYFDHWGQGTLVTVS S | ADI-45078 | Heavy chain variable region ("HC") amino acid sequence |

TABLE 3-continued

Informal Sequence Listing

| Antibody Number | SEQ ID NO: | Sequence | Clone # (ADI) | Descriptors |
|---|---|---|---|---|
| 83 | 386 | EVQLVESGGTFLQPGGSLRLSCVASGFTFGT HAMSWVRQAPGKGLEWVSTFSGSGGRTY YADSVKGRFTISRDNSKSTLYLEMSALRAED TAVYYCAKFYDSSGYYYFDYWGQGTLVTV SS | ADI-49162 | Heavy chain variable region ("HC") amino acid sequence |
| 84 | 387 | EVQLVESGGGLVQPGGSLRLSCAASGFTFSD YYMDWVRQAPGKGLEWVGGIRNKPNSYT TEYAASVKGRFTISRDDSKNSLFLQMNSLKT EDTAVYYCVRLYGDYVAYFDYWGQGTLVT VSS | ADI-42223 | Heavy chain variable region ("HC") amino acid sequence |
| 85 | 388 | QVQLVQSGAEVKKPGASVKVSCKASGYTFT SYGISWVRQAPGQGLEWMGWISAYNGNTN YAQKLQGRVTMTTDTSTSTAYMELRSLRSD DTAVYYCARRGTTVTRFGVIQYYYGMDV WGQGTTVTVSS | ADI-48435 | Heavy chain variable region ("HC") amino acid sequence |
| 86 | 389 | QVQLQESGPGLVKPSETLSLTCTVSGASIRSY LWSWIRQPPGKELEWLGSIYHSGSTKYNPS LKSRVTISADTSKNQFSLKLNSVTAADTAVF YCARETANNWFDPWGQGTLVTVSS | ADI-46742 | Heavy chain variable region ("HC") amino acid sequence |
| 87 | 390 | EVQLVESGGGVVQSGRSLRLSCAASGFTFSG NAMHWVRQAPGKGLEWVAVILYDGSNQY YADSVKGRFTISRDNSKNTLYLQMNSLRPA DTAVYYCARASMMPRPPVHDYWGQGTLV TVSS | ADI-42787 | Heavy chain variable region ("HC") amino acid sequence |
| 88 | 391 | EVQLLESGGGLVQPGGSLRLSCAASGFTFSS YAMSWVRQAPGKGLEWVSAISGSGGSTYY ADSVKGRFTISRDNSKNTLYLQMNSLRAED TAVYYCAKDRSQGDYGDYVADYWSQGTL VTVSS | ADI-46718 | Heavy chain variable region ("HC") amino acid sequence |
| 89 | 392 | EVQLQESGPGLVKPSGTLSLTCAVSGGSISSS NWWTWVRQPPGKGLEWIGEIYHSGSTNYN PSLESRVTMSVDKSKNQFSLKLSSVTAADTA VYYCARVQTSHSELWFGEFGADWGQGTL VTVSS | ADI-49141 | Heavy chain variable region ("HC") amino acid sequence |
| 90 | 393 | EVQLLESGGGLVQPGGSLRLSCAASGFTFTY YAMSWVRQAPGKGLEWVSGISGSGDSTYN ADSVKGRVTISRDNSKNTLYLQMNSLRAED TAVYYCAKDGGYSTDWYFDLWGRGTLVT VSS | ADI-42213 | Heavy chain variable region ("HC") amino acid sequence |
| 91 | 394 | QVQLVESGGGVVQPGRSLRLSCTASGFTFSS YGMHWVRQAPGKGPEWVAVISYDGSKKY FADSVKGRFTISRDNSKNTLYLQMNSLRAE DTAVYSCAKGYDSNGYYYIDYWGQGTPVT VSS | ADI-42844 | Heavy chain variable region ("HC") amino acid sequence |
| 92 | 395 | QVQLQESGGGVVQPGRSLRLSCAASGFTFSS YGMHWVRQAPGKGLEWVAVIWYDGSNKY YADSVKGRFTISRDNSKNTLYLQMNSLRAE DTAVYYCARDVGYQLLQVYGMDVWGQG TTVTVSS | ADI-45161 | Heavy chain variable region ("HC") amino acid sequence |
| 93 | 396 | EVQLLESGPGLVKPSQTLSLTCSVSGGSISSG GYYWTWIRQPPGKGLEWIGYIYYTGSTYYN PSLKSRVTISVDTSKNQFSLKLSSVTAADTA VYFCARAEYDTSGYYQQRLPEYFQHWGQ GTLVTVSS | ADI-42192 | Heavy chain variable region ("HC") amino acid sequence |
| 94 | 397 | EVQLVQSGGGLVQRGGSLRLSCAASGFTFSS YAMTWVRQAPGKGLEWVSDMNHSGDRTN YADSVRGRFTISRDNSKNTLYLQMNSLRAE DTAVYYCAKYYDSSGYYYFHSWGQGTLVT VSS | ADI-48910 | Heavy chain variable region ("HC") amino acid sequence |
| 95 | 398 | EVQLLESGGGLVQPGGSLRLSCAASGFIFSD HYMAWVRQAPGKGLEWVGRSRNRPNSYT TEYAASAKGRFTISRDDSKTSLYLQMNSLKT EDTAVYYCAREHGDYGLDYWGQGTLVTVS S | ADI-42193 | Heavy chain variable region ("HC") amino acid sequence |

TABLE 3-continued

Informal Sequence Listing

| Antibody Number | SEQ ID NO: | Sequence | Clone # (ADI) | Descriptors |
|---|---|---|---|---|
| 96 | 399 | QVQLVQSGAEVKKPGASVKVSCKASGYTFT GYYMHWVRQAPGQGLEWMGRINPNSGGT NYAQKFQGRVTMTRDTSISTAYMELSRLRS DDTAVYYCYVDYYYDSSGYYSPFDYWGQG TLVTVSS | ADI-49590 | Heavy chain variable region ("HC") amino acid sequence |
| 97 | 400 | EVQLVESGGGFVQPGGSLRLSCAASGFIFSD YYMDWVRQAPGKGLEWVGRIRNKPNSYT TEYAASVKGRFSISRDDLKNSLYLQMNSLK TEDTAEYYCARVDGEEVALIYWGQGALVT VSS | ADI-45076 | Heavy chain variable region ("HC") amino acid sequence |
| 98 | 401 | EVQLLESGGGLGQPGGSLRLSCVASKFTFSD HYMDWVRQAPGKGLEWVGRIRNKPNGYT TEYAASVKGRFIISRDDSKNSLYLQMKSLKI EDTAIYYCVRVWGGEAARYDYWGQGALV TVSS | ADI-48968 | Heavy chain variable region ("HC") amino acid sequence |
| 99 | 402 | EVQLVESGGGLVQPGGSLRLSCAASGFTFSD HYMDWVRQAPGKGLEWVGRSRNKPNSYIT EYAASVKGRFTISRDDSKNSLYLQMNSLKTE DTAVYYCSRHMGFGLDLWGQGTLVTVSS | ADI-42212 | Heavy chain variable region ("HC") amino acid sequence |
| 100 | 403 | QVQLVQSGGGVVQPGRSLRLSCAASGFTFSS YGMHWVRQAPGKGLEWVAVIWYDGSNKY YADSVKGRFTISRDNSKNTLYLQMNSLRAE DTAVYYCARDYYGSDGYFDYWGQGTTV TVSS | ADI-48462 | Heavy chain variable region ("HC") amino acid sequence |
| 101 | 404 | EVQLVESGPVLVKPTETLRLTCTVSGFSLSN TKLGVSWIRQPPGKALEWLAHIFSNAEKSS SKSLKSRLSISQDTSKSLVVLTMTNMDPVDT ATYFCARIPVEYGTPRGSFDTWGQGTTVTV SS | ADI-45127 | Heavy chain variable region ("HC") amino acid sequence |
| 102 | 405 | EVQLVESGGGVVQPGRSLRLSCAASGLTFST YTLHWVRQAPGKGLEWVAVISSDGGNKYY ADSVKGRFTISRDSSKNTLYLQMNSLRTEDT AVYYCAGGSPDYWGQGALVTVSS | ADI-42200 | Heavy chain variable region ("HC") amino acid sequence |
| 103 | 406 | EVQLVESGGGVVQPGRSLRLSCVPSGFTFSS YAMHWVRQAPGKGLEWVAMMSYDGGDK NYADSVKGRFTISRDNSKNTLYLQMRSLRA EDTAIYYCARAYDSRGYYYIEHWGQGTLVT VSS | ADI-50203 | Heavy chain variable region ("HC") amino acid sequence |
| 104 | 407 | QVQLVQSGAEVRKPGASVKVSCKASGYTFT SYGISWVRQAPGQGLEWMGWISTYNGNTN YAQKLQGRVTMTTDTSTSTAYMELRSLRSD DTAVYYCAREIDSNYVFDYWGQGTLVTVSS | ADI-42149 | Heavy chain variable region ("HC") amino acid sequence |
| 105 | 408 | EVQLVESGGGLVQPGGSLRLSCAASGFTFSN YWMNWVRQAPGKGLEWVANIKQDGSEKY YVDSVKGRFTISRDNAKNSLYLQMNSLRAE DTAVYYCARKLSYSSGWYYFDYWGQGTL VTVSS | ADI-42181 | Heavy chain variable region ("HC") amino acid sequence |
| 106 | 409 | EVQLVESGGGLVQPGGSLRLSCAASGFTFSD HYMDWVRQAPGKGLEWVGRSTNKPNSYT TTYAASVRGRFTISRDESKNSLYLQMNSLKS DDTAVYYCVTTTVILFDYWGQGTLVTVSS | ADI-45126 | Heavy chain variable region ("HC") amino acid sequence |
| 107 | 410 | QVQLQQWGAGLLKPSETLSLTCAVYGGSFS GYYWSWIRQPPGKGLEWIGEINHRGSTDYN PSLKSRVTMSVDTSKNQFSLRLSSVTAADTA LYYCARGRLAWGLRGQKSPNFFAYWGQG ATVTVSS | ADI-45074 | Heavy chain variable region ("HC") amino acid sequence |
| 108 | 411 | EVQLVESGGGLVKPGGSLRLSCAASGFTFSH AWMTWVRQAPGKGLEWVGRIKSETDGGT ANYAAPVKGRFTISRDDSKNTVYLQMVSLK TEDTAVYYCATAGIFGVVIMKGFDHWGQG TTVTVSS | ADI-49041 | Heavy chain variable region ("HC") amino acid sequence |
| 109 | 412 | EVQLLESGAEVKEPGSSVKVSCKPSGGTFSS YVISWVRQAPGQGLEWMGGIIPIFGTPNYA | ADI-42227 | Heavy chain variable region |

TABLE 3-continued

Informal Sequence Listing

| Antibody Number | SEQ ID NO: | Sequence | Clone # (ADI) | Descriptors |
|---|---|---|---|---|
| | | QKFQGRVTITADDSTSTAHMELSSLTSDDTA VYYCARETYYYGSGSVPVHDWGQGTLVTV SS | | ("HC") amino acid sequence |
| 110 | 413 | EVQLVESGGGVVQPGRSLRLSCAASGFIFSS NSMHWVRQAPGKGLKWVAIISNDGRNKFY ADAVKGRFTVSRDNSKNTLYLQMNSLRPED TAVYYCARGYDSSGYWGFGDNWGQGTLV TVSS | ADI-50220 | Heavy chain variable region ("HC") amino acid sequence |
| 111 | 414 | QVQLVQSGGGLVQPGGSLRLSCAASGFTFS DHYMDWVRQAPGKGLEWVGRTRNKANSY TTKYAASVKGRFTISRDDSKNSLYLQMNSL KTEDTAVYYCARVEGGAWGAFDIWGQGT TVTVSS | ADI-42141 | Heavy chain variable region ("HC") amino acid sequence |
| 112 | 415 | QVTLKESGPVLVKPTETLTLTCTVSGFSLSN TKMGVTWIRQPPGKALEWLAHIFSNDEKS CNTSLKSRLTISKDTSKSQVVLTMTNMDPV DTATYYCARLWFTEYPGAFDIWGQGTMVT VSS | ADI-42216 | Heavy chain variable region ("HC") amino acid sequence |
| 113 | 416 | EVQLQESGPGLVKPSETLSLTCTVSGGSISSS SYYWGWIRQPPGKGLEWIGSIYYSGSTYYN PSLKSRVTISVDTSKNQFSLKLSSVTAADTA VYYCARHSSGSYYLAGYYFDYWGQGTLVT VSS | ADI-50534 | Heavy chain variable region ("HC") amino acid sequence |
| 114 | 417 | EVQLVESGGGLVQPGGSLRLSCAASGFTFSD HYMDWVRQAPGRGLEWVGRSRNKVNSYT TDYAASVKGRFTISRDDSKNSLFLRMNSLKT EDTAVYYCARLTDSGYDDWGLGTLVTVSS | ADI-49140 | Heavy chain variable region ("HC") amino acid sequence |
| 115 | 418 | EVQLVESGPGLVKPSETLSLTCTVSGGSISSY YWSWIRQPPGKGLEWIGYIYYSGSTNYNPS LKSRVTISVDTSKNQFSLKLSSVTAADTAVY YCARETCSGGSCYYRVGSAFDIWGQGTTV TVSS | ADI-46741 | Heavy chain variable region ("HC") amino acid sequence |
| 116 | 419 | EVQLLESGGGMVQPGRSLRLSCAASGFTFD DYDMHWVRQGPGKGLEWVSGISWNSGGR GYADSVKGRFTISRDNAKNSLYLQMNSLRV EDTALYYCVKDYCSGGRCYSFDYWGQGTL VTVSS | ADI-42195 | Heavy chain variable region ("HC") amino acid sequence |
| 117 | 420 | QVQLVESGGGVVQPGRSLRLSCAASGFTFSS YGMHWVRQAPGKGLEWVAVMSYDGSNK YYADSLKGRFTISRDNSKNTLYLQMNSLRA EDTAVYFCAKAYDSSAYYYLDYWGQGTLV TVSS | ADI-42172 | Heavy chain variable region ("HC") amino acid sequence |
| 118 | 421 | EVQLVESGGGVIQPGRSLRLSCAASGFNFSS YGMHWVRQAPGKGLEWVAVISYDGSNKY YADSVKGRFTISRDNSKNTLYLQMNSLRAE DTAVHYCAKAYDSRGYYYLDYWGQGTLV TVSS | ADI-42178 | Heavy chain variable region ("HC") amino acid sequence |
| 119 | 422 | EVQLVQSGGGLVQPGGSLRLSCVGSGLTLSS SAMSWVRQAPGKGLECVSGITGSGSDSSYA ASVKGRFTISRDNSKNTVYLQMNSLRAEDT AVYYCAKDLTHRLGSIFGKLTFDAFDIWG PGTMVTVSS | ADI-49032 | Heavy chain variable region ("HC") amino acid sequence |
| 120 | 423 | EVQLVESGGGVVQPGRSLRLSCAASGFTFSS YGMHWVRQAPGKPEWVAVISEDGNKDH YVDSVKGRFSIYRDNSKTVFLRMTSLRAED TAVYYCAKDLTPYFYDSGAFDHWGQGTLV TVSS | ADI-50197 | Heavy chain variable region ("HC") amino acid sequence |
| 121 | 424 | EVQLVESGGGLVQPGGSLRLSCAVSGFTFSD HYMDWVRQAPGKGLEWVGRSRNKVNSYI TEYAASVKGRFSISRDDSKNSLYLQMNSLKI EDTAVYYCARVFGGPTDYWGQGTLVTVSS | ADI-48894 | Heavy chain variable region ("HC") amino acid sequence |
| 122 | 425 | EVQLLESGGGLVQPGGSLRLSCAASGFIFSD HYMDWVRQAPGKGLEWVG**RIRNKPNSYT | ADI-42226 | Heavy chain variable region |

TABLE 3-continued

Informal Sequence Listing

| Antibody Number | SEQ ID NO: | Sequence | Clone # (ADI) | Descriptors |
|---|---|---|---|---|
| | | TDYAAYVKGRFSISRDDSKNSLFLQMNSLK TEDTAVYYCARVVNGLDVWGQGTTVTVSS | | ("HC") amino acid sequence |
| 123 | 426 | EVQLVESGGGVVQPGRSLRLSCAASGFTLSS YVMHWVRQAPGKGLEWVAVISSDGTNKY YADSVKGRFTISRDSSKNTLYLQMNSLRPED SAVYYCARGQPDYWGQGTLVTVSS | ADI-49037 | Heavy chain variable region ("HC") amino acid sequence |
| 124 | 427 | EVQLVESGPGLVKPSGTLSLTCAVSGGSISSD NWWSWVRQAPGKGLEWIGEIYHTGSTSYN PSLKSRVTISLDKSKNHFSLKLNSLTAADTA VYYCAGKKWELLGFRFDPWGQGTLVTVSS | ADI-46739 | Heavy chain variable region ("HC") amino acid sequence |
| 125 | 428 | QVQLVESGAEEKKPGASVKVSCKASGYTFT SYAMHWVRQAPGQRLEWMGWINAGNGNT KYSQKFQGRVTITRDTSASTAYMELSSLRSE DTAVYYCARQWLGHFDYWGQGTLVTVSS | ADI-42810 | Heavy chain variable region ("HC") amino acid sequence |
| 126 | 429 | EVQLVESGGGLVQPGGSLRLSCAASGFIFSD HYMAWVRQAPGKGLEWVGHVGNKANTY TTEYAASVKGRFTISRDDSKKSLYLQMNRL KSEDTAVYYCARVFSYYLDYWGQGTPVTV SS | ADI-49137 | Heavy chain variable region ("HC") amino acid sequence |
| 127 | 430 | QVTLKESGPTLVKPTQTLTLTCTFSGFSLSTS GVGVGWTRQPPGKALEWLALIYWDDDKR YSPSLKSRLTITKDTSKNQVVLTMTKMDPV DTATYYCAHRHIAARLYRDDDVFDVWGQ GTMVTVSS | ADI-42817 | Heavy chain variable region ("HC") amino acid sequence |
| 128 | 431 | QVQLVQSGAEVKKPGASVKVSCKASGYTFT SYDINWVRQATGQGLEWMGWMNPNSGNT GYAQKFQGRVTMTRNTSISTAYMELSSLRS EDTAVYYCARGLNTVTNSDYWGQGTLVTV SS | ADI-50218 | Heavy chain variable region ("HC") amino acid sequence |
| 129 | 432 | QVQLVQSGAEVKKPGASVKVSCKASGYTFT GYYMHWVRQAPGQGLEWMGWINPNSGGT NYAQKFQGWVTMTRDTSISTAYMELSRLRS DDTAVYYCASGLSPDFSVLDVWGQGTTVT VSS | ADI-42126 | Heavy chain variable region ("HC") amino acid sequence |
| 130 | 433 | QVQLQQSGPGLVKPSQTLSLTCAISGDSVST NSAAWNWIRQSPSRGLEWLGRTYYRSKWY NDYALSVKSRITIKPDTSKNQFSLQLNSVTPE DTAVYYCAREGAGYYDSSGYYPLSYDAFD IWGRGTMVTVSS | ADI-42186 | Heavy chain variable region ("HC") amino acid sequence |
| 131 | 434 | EVQLVESGGGLVQPGGSLRLSCAASGFTFSD HYMDWVRQAPGKGLEWVGRARNRANSYT TEYAASVKGRFAASRDDSKNSLYLQMNSLK TEDTAVYYCARVRGSYWDYWGQGTLVTVS S | ADI-48890 | Heavy chain variable region ("HC") amino acid sequence |
| 132 | 435 | QVQLVQSGGGLVQPGGSLRLSCAASGFTFS DHYMDWVRQAPGKGLEWVGRIRNKVNSY TTEYAASVKGRFTISRDDSKNSLYLQMNSL KTEDTAVYYCGRDRGWLDIWGQGTMVTV SS | ADI-42206 | Heavy chain variable region ("HC") amino acid sequence |
| 133 | 436 | QVQLQESGPGLVEPSGTLSLTCVVTGDSISSR SWWSWVRQPPGKGLEWIGEIYHSGTTTYSP SLKSRVIISLDKSENHFSLKMTSVTAADTAV YYCARVIRDLRDYYDGSGYGPDAFDIWGQ GTTVTVSS | ADI-46724 | Heavy chain variable region ("HC") amino acid sequence |
| 134 | 437 | EVQLVESGPGLVKPSGTLSLTCAVSGGSISSS NWWSWVRQPPGKGLEWIGEIYHSGSTNYN PSLKSRVTISVDKSKNQFSLKLSSVTAADTA VYYCARARWEDGNYYYGMDVWGQGTTV TVSS | ADI-50539 | Heavy chain variable region ("HC") amino acid sequence |

TABLE 3-continued

Informal Sequence Listing

| Antibody Number | SEQ ID NO: | Sequence | Clone # (ADI) | Descriptors |
|---|---|---|---|---|
| 135 | 438 | EVQLVESGGGLVQPGGSLRLSCAASGFTFSSYAMSWVRQAPGKGLEWVSAISGSGGSTYYADSVKGRFTISRDNSKNTLYLQMNSLRAEDTAVYYCAKDQSSGWPNYYYGMDVWGQGTTVTVSS | ADI-45156 | Heavy chain variable region ("HC") amino acid sequence |
| 136 | 439 | QVQLVESGSELKKPGASVKVSCKASGYTFTSYAMNWVRQAPGQGLEWMGWINTNTGNPTYAQGFTGRFVFSLDTSVSTAYLQISSLKAEDTAVYYCVRGYCSSTSCYGGLYWFDPWGQGTLVTVSS | ADI-50536 | Heavy chain variable region ("HC") amino acid sequence |
| 137 | 440 | EVQLVESGGGVVQPGRSLRLSCADSGFTFSYSAIHWVRQAPGKGLEWVAVISYDGSNKYYADSVKGRFTISRDNSKNTLYLQMNSLRPEDTAVYYCARHSGGYSSKDKPTEYFQHWGQGTLVTVSS | ADI-42217 | Heavy chain variable region ("HC") amino acid sequence |
| 138 | 441 | EVQLLESGPGLVKPSGTLSLTCAVSGASISSNNWWSWVRQSPGKGLEWIGEIFHSGTTNYNPSLKSRVTISVDKSKNQFSLKLNSVTAADTAVYYCARDVGVAAVITGSVRWGQGTLVTVSS | ADI-48951 | Heavy chain variable region ("HC") amino acid sequence |
| 139 | 442 | QVQLVQSGSELKKPGASVKVSCKASGYTFTSYAMNWVRQAPGQGLEWMGWINTNTGNPTYAQGFTGRFVFSLDTSVSTAYLQISSLKAEDTAVYYCARGYCSSTSCYGGLYWFDPWGQGTLVTVSS | ADI-50537 | Heavy chain variable region ("HC") amino acid sequence |
| 140 | 443 | QVQLVQSGGGVVQPGRSLRLSCAASGFTFSSYAMHWVRQAPGKGLEWVAVISYDGSNKYYADSVKGRFTISRDNSKNTLYLQMNSLRAEDTAVYYCARDGAGDYIWGSYRHKGLHYYYGMDVWGQGTTVTVSS | ADI-46737 | Heavy chain variable region ("HC") amino acid sequence |
| 141 | 444 | EVQLVESGPGLVMPSGTLSLTCTVSGISISSSNWWSWVRQSPGKGLEWIGEVYHSGSTKYNPSLKSRVTISVDKSRNQFSLKLNSVTAADTAVYYCAKDPRTFYGVVMLLDDPWGQGTLVTVSS | ADI-50538 | Heavy chain variable region ("HC") amino acid sequence |
| 142 | 445 | EVQLVESGGGVVQPGRSLRLSCAVSGFTFSTSPLHWVRQAPGKGLEWVASSFVATDKYYADSVKGRFTVSRDNSKNTLYLQMNSLRPEDTAVYYCARGFGELPGFDIWGQGTMVTVSS | ADI-48950 | Heavy chain variable region ("HC") amino acid sequence |
| 143 | 446 | EVQLLESGGGLVKPGGSLRLSCAASGFTFSSYSMNWVRQAPGKGLEWVSSISSSSSYIYYADSVKGRFTISRDNAKNSLYLQMNSLRAEDTAVYYCARDSWGPFDYWGQGTLVTVSS | ADI-42114 | Heavy chain variable region ("HC") amino acid sequence |
| 144 | 447 | EVQLVESGGAVVQPGRSLRLSCAASGFTFSSYGMHWVRQAPGKGLESVAVIWYDGSNKNYADSVKGRFTISRDNSKNTLFLQMNSLRAEDSAMYYCAKTYDSRAYYYLDYWGQGTLVTVSS | ADI-49194 | Heavy chain variable region ("HC") amino acid sequence |
| 145 | 448 | EVQLLESGGGLVQPGGSLRLSCAASGFTFSSYAMSWVRQAPGKGLELVSAISSSGGSTYYADSVKGRFTISRDNSKNTLYLQMNSLRAEDTALYYCAKDLFYDFWTGITIDYWGQGTLVTVSS | ADI-42124 | Heavy chain variable region ("HC") amino acid sequence |
| 146 | 449 | EVQLLESGGGLVQPGGSLRLSCAASGFIFSNYWMSWVRQAPGKGLEWVANIKPDGSEKYYVESVRGRFTISRDNAKNSLYLQMNSLRAEDTAVFYCARDGGTVSDGLDVWGQGTTVTVSS | ADI-45123 | Heavy chain variable region ("HC") amino acid sequence |
| 147 | 450 | QVQLQESGPGLVKPSGTLSLTCAVSGGSISSSNWWSWVRQPPGKGLEWIGEIYHSGSTNYNPSLKSRVTISVDKSKNQFSLKLSSVTAADTAVYYCARVVWYSSSSHLFDYWGQGTLVTVSS | ADI-50533 | Heavy chain variable region ("HC") amino acid sequence |

TABLE 3-continued

Informal Sequence Listing

| Antibody Number | SEQ ID NO: | Sequence | Clone # (ADI) | Descriptors |
|---|---|---|---|---|
| 148 | 451 | EVQLVESGGGVVQTGRSLRLSCAASGFTFSISGMHWVRQAPGKGLEWVALIWYDGTKKYYADSVKGRFTISRDDFKNTVYLQMNSLRADDTAVYYCARIKSDAFDLWGQGTTVTVSS | ADI-49205 | Heavy chain variable region ("HC") amino acid sequence |
| 149 | 452 | EVQLLESGGGVVQPGKSLRLSCAASGFSFGDYGMHWVRQTPDKGLEWVAVILFDSKKFYADSVRGRFTISRDNSKNNLYLQMSSLRPEDTAVYYCAKFPLRDGGSGEGFDYWGQGTLVTVSS | ADI-45151 | Heavy chain variable region ("HC") amino acid sequence |
| 150 | 453 | EVQLVESGGGVVQPGRSLRLSCAASGFTFSSYAMHWVRQAPGKGLEWVAVISYDGSNKYYADSVKGRFTISRDNSKNTLYLQMNSLRAEDTAVYYCARNTYYDRRRTFDYWGQGTLVTVSS | ADI-46728 | Heavy chain variable region ("HC") amino acid sequence |
| 151 | 454 | QVQLVQSGGGLVQPGGSLRLSCAASGFTFSDHYMDWVRQAPGKGLEWVGRTRNKANSYTTEYAASVKGRFTISRDDSKNSLYLQMNSLKTEDTAVYYCAGVGITGTTGIDYWGQGTLVTVSS | ADI-49030 | Heavy chain variable region ("HC") amino acid sequence |
| 152 | 455 | EVQLLESGGDLVQPGRSLRLSCAASGFNLIDYAMHWVRQVPGKGLEWVSGISWNSRSIGYADSVKGRFTISRDNAKNSLYLQMDSLKHEDTALFYCAKGAAAGPFPYFYYAMDVWGQGTTVTVSS | ADI-50200 | Heavy chain variable region ("HC") amino acid sequence |
| 1 | 456 | QSVLTQPPSVSAAPGQKVTISCSGSSSNIGNNYVSWYQQLPGAAPKWYDNKKRPSGIPDRFSGSASGTSATMGITGLQTGDEADYYCGTWDSSLSAWVFGGGTKVTVL | ADI-49039 | Light chain variable region ("LC") amino acid sequence |
| 2 | 457 | DIRVTQSPATLSVSPGERATLSCRASQSVSSNLAWYQQKPGQAPRLLIYDASNRATGWVRFSGSGSGTDFTLTISSLQSEDFAVYYCQQYDNWPLTFGGGTKVEK | ADI-49147 | Light chain variable region ("LC") amino acid sequence |
| 3 | 458 | QSVVTQPPSVSAAPGQKVTISCSGSSSNIGNNYVSWYQQFPRTAPKLLIYDNKKRPSGIPDRFSGSASGTSATLGITGLQTGDEADYYCGTWDSSLSAWVFGGGTKVTVL | ADI-42229 | Light chain variable region ("LC") amino acid sequence |
| 4 | 459 | QPVLTQPPSASGTPGQRVTIFCSGSRSNIGTYTINWYQKLPGTAPKLLIYSNNRGPSGVPDRFSGSQSGTSASLAISGLQPEDEADYYCAAWDDSLNGWVFGGGTKVTVL | ADI-45090 | Light chain variable region ("LC") amino acid sequence |
| 5 | 460 | QSVVTQPPSVSAAPGQKVTISCSGSSSNIGNNYVAWYQQLPGRAPKLLIHDNKKRPSGIPDRFSGSASGTSATLGITGLQTGDEADYYCETWDSSLNAVVFGGGTKLTVL | ADI-45097 | Light chain variable region ("LC") amino acid sequence |
| 6 | 461 | DIQMTQSPSSLSASVGDRVTITCRASQTISVDLNWYQHKPGKAPKLLIFAASTLQSGVPSRFSGSGSGTDFTLTIRSLQPEDFATYYCQQSYSIPRITFGQGTRLEK | ADI-49133 | Light chain variable region ("LC") amino acid sequence |
| 7 | 462 | EIVMTQSPALSASVRDRVTITCRASQSIGSDLNWYQQRPGKAPMLLIYAATGLQSGVPSRFSGSGSGTDFTLTISNLQPEDFATYYCQQSYSPPMYTFGQGTKVDIK | ADI-49033 | Light chain variable region ("LC") amino acid sequence |
| 8 | 463 | QPVLTQPPSASGTPGQRVTISCSGSSSNIGTNTVSWYQQLPGTAPQLLVFSRTQRPSGVPDRFSGSKSGTSASLAISGLQSDDEADYYCAAWDDSRNGWVFGGGTKLTVL | ADI-49044 | Light chain variable region ("LC") amino acid sequence |
| 9 | 464 | QPVLTQPPSVSAAPGQKVTISCSGSNSNIGNYYVSWYQQFPGTAPKLLIYDNNKRPSGIPDRFSGSKSGTSATLAITGLQTGDEAHYYCGTWDTSLSAGRVFGGGTKLTVL | ADI-45083 | Light chain variable region ("LC") amino acid sequence |

TABLE 3-continued

Informal Sequence Listing

| Antibody Number | SEQ ID NO: | Sequence | Clone # (ADI) | Descriptors |
|---|---|---|---|---|
| 10 | 465 | QSALTQPPSVSAAPGQKVTISCSGSSSNIGNS YVSWYQQVPGTAPKLLIYDNNKRPSGIPDRF SGSKSGTSATLGITGLQAGDEADYYCGTWD TSLSAGRVFGRGTKLTVL | ADI-42225 | Light chain variable region ("LC") amino acid sequence |
| 11 | 466 | QSVLTQPPSVSAAPGQKVTISCSGSSSNIGYS HVSWYQQLPGTAPKVLIYDNDKRPSGIPDRF SGSKSGTSATLGITGLQTGDEADYYCGTWD TSLGVVFGGGTKLTVL | ADI-49139 | Light chain variable region ("LC") amino acid sequence |
| 12 | 467 | QSVLTQPRSVSGSPGQSVTISCTGTSSDVGA YNFVSWYQQHPGKAPKLMIYDVNKRPSGV PDRFSGSKSGNTASLTISGLQAEDEADYHCCSYAGTYTSNYVFGSGTKVTVL | ADI-48969 | Light chain variable region ("LC") amino acid sequence |
| 13 | 468 | QSVVTQPPSVSAAPGQKVTISCSGSSSNIGNN YVSWYQQLSETAPKLLIYDNNKRPSGIPNRF SGSKSGTSATLGITGLQTGDEADYYCGTWD NSLGAVVFGGGTKVTVL | ADI-48900 | Light chain variable region ("LC") amino acid sequence |
| 14 | N/A | N/A | ADI-42232 | Light chain variable region ("LC") amino acid sequence |
| 15 | 469 | QSVLTQPPSVSAAPGQKVTISCSGSSSNIGSN YVSWYQQFPGTAPKLLIYDNSKRPSGIPDRF SGSMSGTSATLGITGLQTGDEADYYCGTWD SSLSAVVFGGGTKVTVL | ADI-42786 | Light chain variable region ("LC") amino acid sequence |
| 16 | 470 | QSVLTQPPSVSAAPGQKVTISCSGSSSNIGNN YVSWYQQLPGTAPKWYDNNKRPSGIPDRF SGSKSGTSATLGITGLQTGDEADYYCGTWD TSLSAGRVFGGGTKLTVL | ADI-42210 | Light chain variable region ("LC") amino acid sequence |
| 17 | 471 | EIVLTQSPATLSVSPGERATLSCRASRSVSSN LAWYQQKPGQAPRLLIYGASTRATGIPARFT GSGSGTEFTLTISSLQSEDFAVYYCQQYNNW PPRTFGQGTKVDIK | ADI-50201 | Light chain variable region ("LC") amino acid sequence |
| 18 | 472 | DIQLTQSPSSVSASVGDRVTITCRASQGISSW LAWYQQKPGKAPKLLIFIAASSLQSGVPSRFS GSGSGTDFTLTISSLQPEDFATYYCQQAKSF PPTFGQGTRLEIK | ADI-48895 | Light chain variable region ("LC") amino acid sequence |
| 19 | 473 | QPVLTQPASVSGSPGQSITISCTGTSSDVGGY NYVSWYQQHPGKAPKLLIYDVSNRPSGVSN RFSGSKSANSASLTISGLQAEDEADYYCNSY TSSSTLVFGGGTKLTVL | ADI-42228 | Light chain variable region ("LC") amino acid sequence |
| 20 | 474 | EIVMTQSPATLSVSPGERATLSCRASQSVSSN LAWYQQKPGQAPRLLIYGASTRATGIPARFS GSGSGTEFTLTISSLQSEDFALYYCQQYDDW PLFGQGTRLEIK | ADI-45113 | Light chain variable region ("LC") amino acid sequence |
| 21 | 475 | QSVLTQPPSVSAAPGQKVTISCSGSSSNIGNN YVSWYQQLPGTAPKLLIYDNNKRPSGIPDRF SGSKSGTSATLGITGLQTGDEADYICGTWDT SLSAGGVFGGGTKLTVL | ADI-42198 | Light chain variable region ("LC") amino acid sequence |
| 22 | 476 | QSVLTQPASVSGSPGQSITISCTGTSSDIGAY NYVSWYQQHPGKAPKLMIYDVTNRPSGVS NRFSGSKSGSSASLTISGLQTEDEADYYCSSY TRRSTLVFGGGTKLTVL | ADI-42190 | Light chain variable region ("LC") amino acid sequence |
| 23 | 477 | QSVLTQPPSVSAAPGQKVTISCSGSSSNIGNN YVSWYQQLPGTAPKLLIYDNNKRPSGIPDRF SGSKSGTSATLGITGLQTGDEANYYCGTWD TSLSTVFGGGTKLTVL | ADI-49154 | Light chain variable region ("LC") amino acid sequence |
| 24 | 478 | QSALTQPASVSGSPGQSITISCTGTGSDVGG YNFVSWYQQHPGKAPKLMLYDVNNRPSGV SNRFSGSKSGNTASLTISGLQAEDEADYYCSS YPGTSALVIFGGGTRLTVL | ADI-49183 | Light chain variable region ("LC") amino acid sequence |

TABLE 3-continued

Informal Sequence Listing

| Antibody Number | SEQ ID NO: | Sequence | Clone # (ADI) | Descriptors |
|---|---|---|---|---|
| 25 | 479 | DIQMTQSPSSLSASVGDRVTITCRASQSISSY LNWYQQKPGEAPNLLIFAASILQSGVPSRFS GSGSGTDFTLTISSLQPEDFATYYCQQSYSTP YTFGQGTKVEIK | ADI-42201 | Light chain variable region ("LC") amino acid sequence |
| 26 | 480 | QSVLTQPPSVSGAPGQRVTISCTGSSSNIGAG YDVHWYQQLPGTAPKLLIYGNSNRPSGVPD RFSGSKSGTSASLAITGLQAEDEADYYCQSY DSSLSGHVVFGGGTKLTVL | ADI-42144 | Light chain variable region ("LC") amino acid sequence |
| 27 | 481 | EIVLTQSPATLSSSPGERATLSCRASQSVNSY LVWYQQKPGQAPRLLIYDASNRATGIPARFT GSGSGTDFTLTISSLEPEDFAVYYCQQRTNW PFTFGQGTKVDIK | ADI-50219 | Light chain variable region ("LC") amino acid sequence |
| 28 | 482 | EIVLTQSPATLSLSPGERATLSCRASQSVNRY LAWYQQKPGQAPRLLIYDASNRATGIPARFS GSGSGTDFTLTISSLEPEDFAVYYCHQRTNW PWTFGQGTKVEIK | ADI-48897 | Light chain variable region ("LC") amino acid sequence |
| 29 | 483 | EIVMTQSPATLSLSPGERATLSCRASQSVSNY LAWYQQKPGQAPRLLISDASSRATGIPARFR GSGSGTDFTLTISSLEPEDFAVYYCLQRTNW PFTFGPGTKVEIK | ADI-42194 | Light chain variable region ("LC") amino acid sequence |
| 30 | 484 | QSVLTQPASVSGSPGQSITISCTGTSSDIGGY NYVSWYQQHPGKVPKLVIYDVSNRPSGVSN RFSGSKSGNTASLTISGLQAEDEADYYCSSY TSGTTLGVFGTGTKLTVL | ADI-49189 | Light chain variable region ("LC") amino acid sequence |
| 31 | 485 | QSVVTQPPSVSAAPGQKVTISCSGRSSNIGNS DVSWYQQFPGRAPKLLIYDNDERPSGIPDRF SGSKSGTSATLDITGLQTGDEADYYCGTWD SSLGGVIFGGGTKVTVL | ADI-49188 | Light chain variable region ("LC") amino acid sequence |
| 32 | 486 | QSVLTQPPSVSAAPGQKVTISCSGSSSNIGNN YVSWYQQLPGTAPKLLIYDNNKRPSGIPDRF SGSKSGTSATLGITGLQTGDEADYYCETWD SSLGVVVFGGGTKLTVL | ADI-42188 | Light chain variable region ("LC") amino acid sequence |
| 33 | 487 | DIQVTQSPSSLSASVGDRVTITCQASQDISNY LNWYQHKPGRAPKLLIYDASNLERGVPSRF SGSGSGTDFTFTISSLQPEDIATYYCQQYDNL SRLTFGGGTKLEK | ADI-50026 | Light chain variable region ("LC") amino acid sequence |
| 34 | 488 | QSVLTQPPSVSAAPGQKVTISCSGSSSNIGNN YVSWYQQLPGTAPKLLIYDNNKRPSGIPDRF SGSKSGTSATLGITGLQTGDEADYYCGTWD TSLSAGRVFGGGTKLTVL | ADI-42809 | Light chain variable region ("LC") amino acid sequence |
| 35 | 489 | QSVLTQPPSMSAAPGQKVTISCSGSSSNIGNN YVSWYRQLPGTAPKLLIYDNDKRPSGIPDRF SGSKSGTTATLGITGLQTGDEAVYYCGTWD FRLSALFGGGTKLTVL | ADI-46596 | Light chain variable region ("LC") amino acid sequence |
| 36 | 490 | QSVLIQPASVSGSPGQSITISCTGTSSDVGGD KYVSWYQQHPGKAPKLVIYEVSNRPSGVSN RFSGSKSGNTASLTISGLQAEDEADYYCSSY TSSGTPVVCGGGTKVTVL | ADI-50205 | Light chain variable region ("LC") amino acid sequence |
| 37 | 491 | QSVLTQPPSVSAAPGQKVTISCSGSSSNIGNY YVSWYQQVPGTAPKLLIYDNNKRPSGIPDRF SGSKSGTSATLGITGLHTGDEAEYYCGTWD SSPSAGRVFGGGTKLTVL | ADI-42830 | Light chain variable region ("LC") amino acid sequence |
| 38 | 492 | DIVLTQSPDSLAVSLGERATINCKSSQSVLFG SNQKSCLAWYQQKPGQSPKLLIFIWASTRES GVPDRFSGSGSGTDFTLTISSLQAEDVAVYY CQQYYSTPRTFGQGTKVEIK | ADI-49186 | Light chain variable region ("LC") amino acid sequence |
| 39 | 493 | QSVLTQPPSVSAAPGQKVTISCSGSSSNIGSN FVSWYQQLPGTAPKLLIYDNNKRPSGIPDRF SGSKSGTSATLAITGLQTGDEADYYCGTWD TRLSALFGGGTKVTVL | ADI-46591 | Light chain variable region ("LC") amino acid sequence |

TABLE 3-continued

Informal Sequence Listing

| Antibody Number | SEQ ID NO: | Sequence | Clone # (ADI) | Descriptors |
|---|---|---|---|---|
| 40 | 494 | QSVLTQPPSVSAAPGQKVTISCSGSSSNFGN DYVSWYQQLPGTAPKWYDNDKRPSGIPDR FSGSKSGTSATLGITGLQTGDEADYYCGTW DTSLSAAWVFGGGTKVTVL | ADI-48955 | Light chain variable region ("LC") amino acid sequence |
| 41 | 495 | QSVVTQPPSVSAAPGQKVTISCSGSSSNIGNN YVSWYQQLPGTAPKLLIYDNNKRPSGIPDRF SGSTSGTSATLGITGLQTGDEAVYYCGTWD TSPSAGGVFGGGTKVTVL | ADI-42818 | Light chain variable region ("LC") amino acid sequence |
| 42 | 496 | QPVLTQPASVSGSPGQSITISCTGTSSDVGGY NYVSWYQQHPGKAPKLMIYDVSNRPSGVSN RFSGSKSGNTASLTISGLQAEDEADYYCSSY TSSSTLAVFGGGTKLTVL | ADI-50531 | Light chain variable region ("LC") amino acid sequence |
| 43 | 497 | QPVLTQPPSVSAAPGQKVTISCSGSSSNIGND YVSWYQQLPGTAPKLLIYDNNKRPSGIPDRF SGSKSGTSATLGITGLQTGDEGDYYCGTWD SSLSAAWVFGGGTKVTVL | ADI-46586 | Light chain variable region ("LC") amino acid sequence |
| 44 | 498 | QPVLTQSASVSGSPGQSITISCTGTSSDVGGY KYVSWYQQHPGKAPKLMIYEVSNRPSGVSI RFSGSKSGNTASLTISGLQAADEADYYCSSY RSSGTPYVFGTGTKVTVL | ADI-49138 | Light chain variable region ("LC") amino acid sequence |
| 45 | 499 | EIVLTQSPSSLSASVGDRVTITCQASQDISNF LNWYQQKPGKAPKLLIYDASSLETGVPSRFS GSGSGTDFTFTISSLQPEDIATYYCQQYDNLP LTFGGGTKLEIK | ADI-45075 | Light chain variable region ("LC") amino acid sequence |
| 46 | 500 | DIRLTQSPSTLSASVGDRVTVTCRASQNINT YLAWYQQIPGKAPRLLIYRASTLESGVPSRF SGSGSGTEFTLTINSLQPDDYATYYCQHYET YSVRFGQGTKVEIK | ADI-42831 | Light chain variable region ("LC") amino acid sequence |
| 47 | 501 | DIQVTQSPSSLSASVGDRVTITCRASQGISNY LAWYQQKPGKVPKLLIFAASTLRSGVPSRFR GSGSGTDFTLTISSLQPEDVATYYCQKYNSA PLTFGGGTKVEIK | ADI-42230 | Light chain variable region ("LC") amino acid sequence |
| 48 | 502 | DIVMTQTPATLSLSPGERATLSCRASQSVSSY LAWYQQKPGQAPRLLIYGASNRATGIPARFS GSGSGTDFTLTISSLEPEDFAVYYCLQRTNW PFTFGPGTKVEIK | ADI-42847 | Light chain variable region ("LC") amino acid sequence |
| 49 | 503 | DIVLTQSPSTLSASVGDRVTVTCRASQNINT YLAWYQQIPGKAPRLLIYRASSLESGVPSRF SGSGSGTEFTLTISSLQPDDFATYYCQHYNSF SVKFGQGTKVEIK | ADI-42821 | Light chain variable region ("LC") amino acid sequence |
| 50 | 504 | SYELTQPPSVSVAPGQTARITCGGHNVGSKS VHWYQQKPGQAPVLVVYDDSDRPSGIPERF SGSNSGNTATLTISRVEAGDEADYYCQVWD SSSDHPWVFGGGTKVTVL | ADI-42849 | Light chain variable region ("LC") amino acid sequence |
| 51 | 505 | QSVVTQPPSVSAAPGQKVTISCSGSSSNIGNN YVSWYQQLPGTAPKLLIYDNNKRPSGIPDRF SGSKSGTSATLGITGLQTGDEADYYCGTWD TSLSAGRVFGGGTKLTVL | ADI-42151 | Light chain variable region ("LC") amino acid sequence |
| 52 | 506 | QPVLTQPPSVSVAPGQTARITCGGNNIGSKS VHWYQQKPGQAPMLVIYSNSDRPSGIPERFS GSNSGITATLTISRVEAGDEADYHCQVWDTS IDHHWVFGGGTKLTVL | ADI-46001 | Light chain variable region ("LC") amino acid sequence |
| 53 | 507 | QSVLIQPPSASGSPGQSVTISCTGTSSDVGGY NYVSWYQQHPGKAPKLMIYEVSKRPSGVPD RFSGSKSGNTASLTVSGLQAEDGADYYCSSY AGSNNWVVFGGGTKLTVL | ADI-45154 | Light chain variable region ("LC") amino acid sequence |
| 54 | 508 | QPVLTQPASVSGSPGQSITISCTGTSTDVGGY NYVSWYQQYPGKAPKLIIYDVTNRPSGVSH RFSGSKSGNTASLTISGLQAEDEADYYCSSY TTTSLVIFGGGTKLTVL | ADI-49161 | Light chain variable region ("LC") amino acid sequence |

TABLE 3-continued

Informal Sequence Listing

| Antibody Number | SEQ ID NO: | Sequence | Clone # (ADI) | Descriptors |
|---|---|---|---|---|
| 55 | 509 | DIVMTQSPLSLPVTPGEPASISCRSSQSLLHS NGYNYLDWYLQKPGQSPQLLIYLGSNRASGVPDRFSGSGSGTDFTLKISRVEAEDVGVYYCMQALQTPPRTFGQGTRLEIK | ADI-42154 | Light chain variable region ("LC") amino acid sequence |
| 56 | 510 | DIQVTQSPSSLSASVGGRVTITCRASQGIRND LGWYQRKPGKAPKRLIYAASSLQSGVPSRFS GSGSGTEFTLTISSLQPEDFATYYCLQHNSYP LTFGGGTKVIAK | ADI-48916 | Light chain variable region ("LC") amino acid sequence |
| 57 | 511 | DIQLTQSPSTLSASVGDRVTITCRASQSISTW LAWYQQKPGKAPKLLIYRASSLESGVPSRFS ASGSGTEFTLSISSLQPDDFATYYCKQYNRN PYTFGQGTKVEIK | ADI-45085 | Light chain variable region ("LC") amino acid sequence |
| 58 | 512 | DIQMTQSPSSLSASVGDRVTITCRASQGISSY LAWFQQKPGKVPKLLIYAASTLQSGVPSRFS GSGSGTDFTLTISSLQPEDVATYYCQKYNSA PQTFGQGTKVDIK | ADI-42211 | Light chain variable region ("LC") amino acid sequence |
| 59 | 513 | EIVMTQSPATLSVSPGERATLSCRASQSVSFN LAWYQQKPGQAPRLLISRASTRAAGVPARF SGSGSGTEFTLTISSLQSEDFAVYYCQQYNN WPPLTFGGGTKLEIK | ADI-48908 | Light chain variable region ("LC") amino acid sequence |
| 60 | 514 | DIQMTQSPDSLTVSLGERATINCKSSQSVLYS SNNKNSLAWYQQKPGQPPKLLIYWASTRESGVPDRFSGSGSGTDFTLTISSLQAADVAVYYCQQYYRTPWTFGQGTKVEK | ADI-48913 | Light chain variable region ("LC") amino acid sequence |
| 61 | 515 | QSVLTQPPSVSAAPGQKVTISCSGSSSNIGNN YVSWYQQLPGTAPKVLIYDNNKRPSGIPDRF SGSKSGTSATLGITGLQTGDEADYYCGTWD SALGAAVFGGGTKLTVL | ADI-45140 | Light chain variable region ("LC") amino acid sequence |
| 62 | 516 | DIQLTQSPSTLSASVGDRVTITCRASQSVSSW LAWYQQKPGKAPRLLIYRASSLESGVPSRFS GSGSGTEFTLTISSLQPDDFAAYYCQQYNRD PYTFGQGTKVEIK | ADI-50211 | Light chain variable region ("LC") amino acid sequence |
| 63 | 517 | SYELTQLPSVSVSPGQTARVTCSGDAL-- QYVYWYQQKPGQAPVVVIYKDTERPSGIPE RFSGSSSGTTVTLTITGVQAEDEADYYCQSA DRSGSVIFGGGTKVTVL | ADI-42199 | Light chain variable region ("LC") amino acid sequence |
| 64 | 518 | DIVMTQSPATLSLSPGERATLSCRASQSVSSY LAWYQQKPGQAPRLLIYDASNRATGIPARFS GSGSGTDFTLTISSLEPEDFAVYYCQQRSNW PSFGQGTKLEIK | ADI-42231 | Light chain variable region ("LC") amino acid sequence |
| 65 | 519 | DIRLTQSPSSLSASVGDRVTITCRASQSISSYL NWYQQKPGKAPKLLIYAASSLQSGVPSRFSG SGSGTDFTLTISSLQPEDFATYYCQQSYSTPL TFGGGTKVEIK | ADI-45164 | Light chain variable region ("LC") amino acid sequence |
| 66 | 520 | ETTLTQSPGTLSLSPGERATLSCRASRSVSGN YLAWYQQKPGQAPRLLIYAASSRATGIPDRF SGGGSGTHFTLTISRLEPEDFAVYYCQQYGS SPRAFGQGTKVEIK | ADI-42233 | Light chain variable region ("LC") amino acid sequence |
| 67 | 521 | EIVMTQSPSSLSASVGDRVTITCRASQSIRSY LNWYQQKPGKAPKLLIYAASSLQSGVPLRFS GSGSGTDFTLTISSLQPEDFATYYCQQSSITP PTFGQGTKLEIK | ADI-42191 | Light chain variable region ("LC") amino acid sequence |
| 68 | 522 | DIQMTQSPSTLSASVGDRVTITCRASQSISSW LAWYQQKPGKAPKLLIYQASSLESGVPSRFS GSESGTEFTLTISSLQPDDFATYYCQQYNSFP FTFGPGTKVEIK | ADI-48899 | Light chain variable region ("LC") amino acid sequence |
| 69 | 523 | DIVLTQSPSSLSASVGDRVTITCRASQSINNY LNWYQQKPGKAPNLLIFGASTLQSGVPSRFT GSGSGTVFTLTISSLQRDDFVIYYCQQTYSAS GSFGQGTKVEIK | ADI-49145 | Light chain variable region ("LC") amino acid sequence |

TABLE 3-continued

Informal Sequence Listing

| Antibody Number | SEQ ID NO: | Sequence | Clone # (ADI) | Descriptors |
|---|---|---|---|---|
| 70 | 524 | DIQLTQSPSSLSASVGDRVTITCRASQSISSYLNWYQQKPGKAPKLLIYAASSLQSGVPSRFSGSGSGTDFTLTISSLQPEDFATYYCQQSYSTPWTFGQGTKVEIK | ADI-46729 | Light chain variable region ("LC") amino acid sequence |
| 71 | 525 | QSALIQPPSVSAAPGQKVTISCSGSSSNIGNNYVSWYQQLPGTAPKLLIYDNNKRPSGIPDRFSGSKSGTSATLGITGLQTGDEADYYCGTWDNSLGVVFGGGTQLTVL | ADI-46722 | Light chain variable region ("LC") amino acid sequence |
| 72 | 526 | EIVLTQSPGTLSLSPGERATLSCRASQSVSSSYLAWYQQKPGQAPRLLIYGASSRATGIPDRFSGSGSGTDFTLSINRLEPEDFAVYYCQQYGSSPGFGQGTKVEIK | ADI-45148 | Light chain variable region ("LC") amino acid sequence |
| 73 | 527 | DIVLTQSPSTLSASVGDRVTITCRASQSISDWLAWYQQKPGKAPGLLIYRASGLESGVPSRFSGSGSGTEFTLTISSLQPDDFATYYCHQYKDFPWTFGQGTKVDIK | ADI-49168 | Light chain variable region ("LC") amino acid sequence |
| 74 | 528 | DIQMTQSPSTLSASVGDRVTITCRASQSISTWLAWYQLKPGKAPKLLIYKASNLQSGVPSRFSGSGSGTEFTLTISSLQPDDFATYYCQQYNSYSPWGQGTKLEIK | ADI-49040 | Light chain variable region ("LC") amino acid sequence |
| 75 | 529 | EIVLTQSPGTLSLSPGERATLSCRASQSVSSRYLAWYRQKPGQAPRLLIYGASSRATGIPDRFSGSGSGTDFTLTISRLEPEDFAVYYCQQYGSSPFFGGGTKLEIK | ADI-42187 | Light chain variable region ("LC") amino acid sequence |
| 76 | 530 | QSVLTQPASVSGSPGQSITISCTGTSSDVGGDKYVSWYQQHPGKAPKPMIYEVSNRPSGVSNRFSGSKSGNTASLTISGLQAEDEADYYCSSYTSSSTPVVFGGGTKLTVL | ADI-49561 | Light chain variable region ("LC") amino acid sequence |
| 77 | 531 | QPVLTQPRSVSGSPGQSVTISCTGTSSDVGGYNYVSWYQQHPGKAPKLMISDVSKRPSGVPDRFSGSKSGNTASLTISGLQADDEADYYCCSYATNYGVVFGGGTKVTVL | ADI-42219 | Light chain variable region ("LC") amino acid sequence |
| 78 | 532 | NFMLTQPHSVSESPGKTVTISCTRSSGSIASNYVQWYQQRPGSSPTTVIYEDNQRPSGVPDRFSGSIDSSSNSASLTISGLKTEDEADYYCQSYDSSNVVFGGGTKVTVL | ADI-50535 | Light chain variable region ("LC") amino acid sequence |
| 79 | 533 | QSVLTQPPSVSAAPGQKVTISCSGSSSNIGNNDVSWYQQLPGRAPKWYDNNKRPSGIPDRFSGSKSGTSATLGITGLQTGDEADYYCGAWDSSLSAHVVFGGGTKVTVL | ADI-45128 | Light chain variable region ("LC") amino acid sequence |
| 80 | 534 | DIVMTQTPSTLSASVGDRVTVTCRASQSISDWLAWYQQKAGKAPKLLIYRASSLESGVPPRFSGSGSGTEFTLTISSLRPDDFATYYCQQYNRYPYTFGQGTKVDIK | ADI-45136 | Light chain variable region ("LC") amino acid sequence |
| 81 | 535 | DIQVTQSPSSLSASVGDRVTITCRASQGIRNDLAWYQQRPGKAPKRLIYAASSLQSGVPSRFSGSGSGTEFTLTISSLQPEDFATYYCLQHHSYPWTFGQGTKVEIK | ADI-42189 | Light chain variable region ("LC") amino acid sequence |
| 82 | 536 | DIRMTQSPSTLSASIGDRVTITCRASQSISDWLAWYLQKPGKAPSLLIYRASSLETGVPSRFSGRGSGTEFTLTISSLQPDDFGTYYCQQYNRDPYTFGQGTKVDIK | ADI-45078 | Light chain variable region ("LC") amino acid sequence |
| 83 | 537 | DIQLTQSPSTLSASVGDRVTVTCRASQNVGGWLAWYQQKPGKAPKLLIFQASRLENGVPSRFSANASGTEFTLTIGSLQPDDFATYYCQQYNTYPYTFGQGTKVDIK | ADI-49162 | Light chain variable region ("LC") amino acid sequence |
| 84 | 538 | DIQLTQSPSSLSASVGDRVTITCRASQSISQYLNWYQQKPGKAPKLLISPASSFQSGVPSRFSGSGSGTDFTLTITSLQPEDFATYYCQQSYSTPWTFGQGTKVDIK | ADI-42223 | Light chain variable region ("LC") amino acid sequence |

TABLE 3-continued

Informal Sequence Listing

| Antibody Number | SEQ ID NO: | Sequence | Clone # (ADI) | Descriptors |
|---|---|---|---|---|
| 85 | 539 | QSVLTQPASVSGSPGQSITISCTGTSSDVGGY NYVSWYQQHPGKAPKLMIYDVSNRPSGVSN RFSGSKSGNTASLTISGLQAEDEADYYCSSY TSSSTLVFGGGTQLTVL | ADI-48435 | Light chain variable region ("LC") amino acid sequence |
| 86 | 540 | SYELTQPPSVSVAPGQTARIICGGNYIGGKS VHWYQQKPGQAPVLVVYNDNDRPSGIPERF SGSNSGNTATLTISRVAAGDEADYYCQVWD NSSDRRVFGGGTKLTVL | ADI-46742 | Light chain variable region ("LC") amino acid sequence |
| 87 | 541 | DIRVTQSPATLSVSPGERATLSCRASQRVNS NLAWYQQKPGQAPRLLIYGASTRATGIPVR FSGSGSGTEFTLTISSLQSEDFAVYYCQQYNT WWTFGQGTKVEIK | ADI-42787 | Light chain variable region ("LC") amino acid sequence |
| 88 | 542 | DIQMTQSPSSLSASVGDRVTITCRASQSISSY LNWYQQKPGKAPKLLIYAASSLQSGVPSRFS GSGSGSGTDFTLTISSLQPEDFATYYCQQSYSTP LTFGGGTKVDIK | ADI-46718 | Light chain variable region ("LC") amino acid sequence |
| 89 | 543 | DIVMTQSPATLSVSPGERATLSCRASQSVSS NLAWYQQKPGQAPRLLIYGASTRATGIPAR FSGSGSGTEFTLTISSLQSEDFAVYSCQQYNT WPKTFGQGTKVEIK | ADI-49141 | Light chain variable region ("LC") amino acid sequence |
| 90 | 544 | EIVLTQSPGTLSLSPGERATLSCRASQSVSSSF LAWYQQKPGQAPRLLIYGASSRATGIPDRFS GSGSGTDFTLT1RRLEPEDFAVYYCQQYGSS RRTFGGGTKVEK | ADI-42213 | Light chain variable region ("LC") amino acid sequence |
| 91 | 545 | DIRVTQSPSTLSASVGDRVTITCRASQSISSW LAWYQQKPGKAPKLLIYRASSLESGVPSRFS GSGSGTEFTLTISSLQPDDFATYYCQQYNRY PYTFGQGTKVEK | ADI-42844 | Light chain variable region ("LC") amino acid sequence |
| 92 | 546 | QSALTQPASVSGSPGQSITISCTGTSSDVGGY NYVSWYQQHPGKAPKLMIYEVSNRPSGVSN RFSGSKSGNTASLTISGLQAEDEADYYCSSY TSSSTLDVVFGGGTKLTVL | ADI-45161 | Light chain variable region ("LC") amino acid sequence |
| 93 | 547 | EIVMTQSPATLSVSPGERATLSCRASQSVSSN LAWYQQKPGQAPRLLIYGASTRATSIPARFS GSGSGTEFTLTISSLQSEDFAVYYCQQYNSW PPITFGQGTRLEK | ADI-42192 | Light chain variable region ("LC") amino acid sequence |
| 94 | 548 | DIRLTQSPSTLSASVGDRVSITCRASQSISDW LAWYQQKPGKAPKLLIYRASGLETGVPSRF SGSGSGTEFTLTISSLQPDDFATYYCQQYNR YPYTFGQGTKVDIK | ADI-48910 | Light chain variable region ("LC") amino acid sequence |
| 95 | 549 | QPVLIQPPSASGTPGQRVTISCSGSSSNFGSN FVYWYQQLPGTAPKLLIYRVNQRPSGVPDR FSGSKSGTSASLAISGLRSEDEADYYCATWD VSLSNDVLFGGGTKLTVL | ADI-42193 | Light chain variable region ("LC") amino acid sequence |
| 96 | 550 | DIVLTQSPATLSLSPGERATLSCRASQSVSSS YLSWYQQKPGQAPRLLIYGASSRATGIPDRF SGSGSGTDFTLTISRLEPEDFAVYYCQQYGS SPPITFGGGTKVEIK | ADI-49590 | Light chain variable region ("LC") amino acid sequence |
| 97 | 551 | DIQMTQSPSSLSASVGDRVTITCRASQTITRY MNWYQQKPGEAPKLLIYATSSLQSGVPSRF SGSGSGTDFTLTITNLQPADFATYYCQQSST TRWTFGQGTKVDIK | ADI-45076 | Light chain variable region ("LC") amino acid sequence |
| 98 | 552 | DIRLTQSPSSLSASVGDRVTITCRASQDIRKF LNWYQQKLGKAPSLLIYGASSLQSGVPSRFS GSGSGTDFTLTISSLQPEDFAIYYCHASTTP WTFGQGTKVEIK | ADI-48968 | Light chain variable region ("LC") amino acid sequence |
| 99 | 553 | SYELTQPPSVSVSPGQTATITCSGDKLGYTY TCWYQQKPGQSPVLVIYQDTKRPSQPERFS GSNSGNTATLTITGTQAMDEADYYCQAWD TTTAGGVFGGGTKLTVL | ADI-42212 | Light chain variable region ("LC") amino acid sequence |

TABLE 3-continued

Informal Sequence Listing

| Antibody Number | SEQ ID NO: | Sequence | Clone # (ADI) | Descriptors |
|---|---|---|---|---|
| 100 | 554 | DIVLTQSPGTLSLSPGERATLSCRASQSVSSS YLAWYQQKPGQAPRLLIYGASSRATGIPDRF SGSGSGTDFTLTISRLEPEDFAVYYCQQYGS SPRAFGPGTKVEIK | ADI-48462 | Light chain variable region ("LC") amino acid sequence |
| 101 | 555 | QSVLTQPPSASGSPGQSVTISCAGTRSDVGG YNFVSWYQQHPGKAPKLLIYEVNKRPSGVP DRFSGSKSANTASLTVSGLQAEDEAEYFCSS YGGNNDLVFGGGTKVTVL | ADI-45127 | Light chain variable region ("LC") amino acid sequence |
| 102 | 556 | EIVMTQSPATLSLSPGERGTLSCRTSQSVSSF LAWYQQKPGQAPRLLMYDASNRATGIPARF SGSGSGTDFTLTISSLEPEDFAVYYCQQRSN WPYTFGQGTKVDIK | ADI-42200 | Light chain variable region ("LC") amino acid sequence |
| 103 | 557 | GIQLTQSPSTLSASVGDRVTITCRASQSVSD WLAWYQQKPGRAPNLLIYRASSLQSGVPSR FSGSGSGTEFTLTINSLQPDDFATYYCQQYK TYWTFGQGTKVEIK | ADI-50203 | Light chain variable region ("LC") amino acid sequence |
| 104 | 558 | QSVLTQPASVSGSPGQSITISCTGTSSDVGGY NYVSWYQQHPGKAPKLMIYEVSNRPSGVSN RFSGSKSGNTASLTISGLQAEDEADYYCSSY TSSGTNIFGTGTKLTVL | ADI-42149 | Light chain variable region ("LC") amino acid sequence |
| 105 | 559 | DIVMTQTPATLSVSPGERATLSCRASQSVSS NVAWYQQKPGQAPRLLIHGASTRATGIPAR FSGSGSGTEFTLTISSLQSEDFAVYYCQQYN NWPPLTFGGGTKLEIK | ADI-42181 | Light chain variable region ("LC") amino acid sequence |
| 106 | 560 | SYELTQPPSVSVSPGQTARITCSGDALPKKY VYWFQQKSGQAPVLVIYEDRRGPSGIPERFS GSTSGTMATLTIRGAQVEDEADYFCYSTDSS GLLGVFGGGTKLTVL | ADI-45126 | Light chain variable region ("LC") amino acid sequence |
| 107 | 561 | DIQMTQSPDSLAVSLGERATINCKSSQSVFY SSNSQNYLAWYQQKPGQPPKLLIYWASTRE SGVPDRFSGSGSATDFSLTISSLQAEDVAVYY CQQFHSPPWTFGQGTKLEIK | ADI-45074 | Light chain variable region ("LC") amino acid sequence |
| 108 | 562 | DIVMTQSPSTLSASVGDRVVITCRASQSISN WLAWYQQKSGKAPKLLIYKASRLESGVPST FSGSGSGTEFTLTISSLQADDFASYYCQQYN DYPWTFGQGTKVEK | ADI-49041 | Light chain variable region ("LC") amino acid sequence |
| 109 | 563 | EIVMTQSPSSLSASVGDRVTITCRASQGIRND LGWYQQKPGKAPKRLIYAASSLQSGVPSRF SGSGSGREFTLTISSLQPEDFATYYCLQHNT YPWTFGQGTKVEK | ADI-42227 | Light chain variable region ("LC") amino acid sequence |
| 110 | 564 | DIQVTQSPSTLSASVGDRVSITCRASQTISSW LAWYQQKPGKAPKLLMYKASNLQSGVPSR FTGSGSGTEFTLTISSLQPDDFATYYCQQYYS YPYTFGPGTKVDIK | ADI-50220 | Light chain variable region ("LC") amino acid sequence |
| 111 | 565 | SYVLTQPPSVSVSPGQTARITCSGDALPKQY GYWYQQKPGQAPVLVIYKDSERPSQPERFS GSSSGTTVTLTISGVQAEDEADYYCQSADRS GTVVFGGGTKLTVL | ADI-42141 | Light chain variable region ("LC") amino acid sequence |
| 112 | 566 | QAVVTQPPSASGSPGQSVTISCTGTSSDVGG YNYVSWYQQHPGKAPKLMVYEVTKRPSGV PDRFSGSKSGNAASLTVSGLQAEDEAEYYCS SYAGSNALVFSGGTKLTVL | ADI-42216 | Light chain variable region ("LC") amino acid sequence |
| 113 | 567 | NFMLTQPHSVSESPGKTVTISCTRSSGSIASN YVQWYQQRPGSAPTTVIYEDNQRPSGVPDR FSGSIDSSSNSASLTISGLKTEDEADYYCQSY DSSNWVFGGGTKLTVL | ADI-50534 | Light chain variable region ("LC") amino acid sequence |
| 114 | 568 | QPELTQPPSVSVSPGQTARITCSGDALSKQY AYWYQQKPGQAPVVVIYKDSERPSGIPERFS GSRSGTTVTLTISGVQAEDEADYYCHSPDSH VVFGGGTKLTVL | ADI-49140 | Light chain variable region ("LC") amino acid sequence |

TABLE 3-continued

Informal Sequence Listing

| Antibody Number | SEQ ID NO: | Sequence | Clone # (ADI) | Descriptors |
|---|---|---|---|---|
| 115 | 569 | SYELIQLPSASVAPGKTARITCGGNNIGSKSV HWYQQKPGQAPVLVVYDDSDRPSGIPERFS GSNSGNTATLTISRVEAGDEADYYCQVWDS SSDHEVFGGGTKLTVL | ADI-46741 | Light chain variable region ("LC") amino acid sequence |
| 116 | 570 | DIQMTQSPSSLSASVGDRVTITCQASQDISNY LNWYQQKPGKAPKLLIYDVSKLKTGVPPRF SGSGSGTDFTFTISSLQPEDIATYYCQQWGT FGQGTKVDIK | ADI-42195 | Light chain variable region ("LC") amino acid sequence |
| 117 | 571 | EIVLTQSPSTLSASVGDRVTITCRASQSISDW LAWYQQKPGKAPNLLIYRASSLESGVPSRFS GSGSGTEFTLTISSLQPDDFATYYCQQYNRY PYTFGQGTKVEIK | ADI-42172 | Light chain variable region ("LC") amino acid sequence |
| 118 | 572 | DIQLTQSPSTLSASVGDRVTITCRASQSISDW LAWFQQKPGKAPKLLIYRASGLETGVPSRFS GSGSGTEFTLTISSLQPDDFATYYCQQYNRY SYTFGQGTKVEIK | ADI-42178 | Light chain variable region ("LC") amino acid sequence |
| 119 | 573 | DIRLTQSPSTLSASVGDRVTITCRASQSISGW LAWYQQKPGKAPKLLIYKASILESGVPSRFS GSQSGTEFTLTISSLQPDDFATYYCQQYNNF WTFGQGTKLEIK | ADI-49032 | Light chain variable region ("LC") amino acid sequence |
| 120 | 574 | QSVLTQPPSVSGAPGQRVTISCTGNSSNIGA GYEVHWYQQLPGTAPKLLIYGNNNRPSGVP DRFSGSKSGASGSLAVTGLRAEDEADYYCH SYDSNMSGSVFGGGTKVTVL | ADI-50197 | Light chain variable region ("LC") amino acid sequence |
| 121 | 575 | EIVLTQSPSSLSASVGDRVTITCRASQGISNY LAWYQQKPGKAPKLLIYAASTLQSGVPSRF SGSGSGTDHLTISSLQPEDVATYYCQKYYSA PLITFGPGTKVEK | ADI-48894 | Light chain variable region ("LC") amino acid sequence |
| 122 | 576 | SYELTQPPSVSVSPGQTARITCSGDALPKQY AYWYQQKPGQAPVLVIYKDTERPSGIPERFS GSSSGTTVTLTISGVQAEDEADYYCQSADSS VADSSVVFGGGTKLTVL | ADI-42226 | Light chain variable region ("LC") amino acid sequence |
| 123 | 577 | EIVLTQSPATLSLSPGERATLSCRASQSVSNY FAWYQQKPGQAPRLLIYGASNRATGVPARF SGSGSGTDFTLTISSLEPEDFAVYYCQQRSN WPYTFGQGTKVEIK | ADI-49037 | Light chain variable region ("LC") amino acid sequence |
| 124 | 578 | NFMLTQPPSVSAAPGQKVTISCSGSNSNIGN NFVSWYQQLPGTAPKLLIYDNNERPSGIPDR FSGSKSVTSATLGITGLQTGDEADYYCGTW DNSLGMVVFGGGTKLTVL | ADI-46739 | Light chain variable region ("LC") amino acid sequence |
| 125 | 579 | QSALTQPASVSGSPGQSITISCTGTSSDVGGY NYVSWYQQHPGKAPKLMIYEVSNRPSGVSN RFSGSKSGNTASLTISGLQAEDEADYYCSSY TSSSTYVFGTGTKVTVL | ADI-42810 | Light chain variable region ("LC") amino acid sequence |
| 126 | 580 | EIVLTQSPGTLALSPGERATLSCRASQSVSSY LAWYQQKPGQAPRLLIYDSSNRATGIPARFS GSGSGTDFTLTISSLEPEDFAVYYCQQPGNW PPAFTFGGGTKLEK | ADI-49137 | Light chain variable region ("LC") amino acid sequence |
| 127 | 581 | DIVMTQSPATLSVSPGERATLSCRASQSVTS KLAWYQQKPGQAPRLLIYGASTRATGIPAR FSGSGSGTEFTLTISSLQSEDFAVYYCQQYN NWITFGQGTRLEIK | ADI-42817 | Light chain variable region ("LC") amino acid sequence |
| 128 | 582 | DIQLTQSPSSVSAVGDRVTITCRASQGISSW LAWYQQKPGKAPKLLIYAASSLQSGVPSRFS GSGSGTDFTLTISSLQPEDFATYYCQQANSFP WTFGQGTKVDIK | ADI-50218 | Light chain variable region ("LC") amino acid sequence |
| 129 | 583 | DIVMTQSPLSLPVTPGEPASISCRSSQSLLHS NGYNSLDWYLQKPGQSPQLLIYLGSNRASG VPDRFSGSGSGTDFTLKISRVEAEDVGVYYC MQALQTPYTFGQGTKLEK | ADI-42126 | Light chain variable region ("LC") amino acid sequence |

TABLE 3-continued

Informal Sequence Listing

| Antibody Number | SEQ ID NO: | Sequence | Clone # (ADI) | Descriptors |
|---|---|---|---|---|
| 130 | 584 | QPVLTQPPSASGTPGQRVTISCSGSSSNIGSN TVHWYQQLPGTAPKLLIYSNNQRPSGVPDR LSGSRSGTSASLAISGLQSEDEAEYYCAAWD DNLIGVVFGGGTKLTVL | ADI-42186 | Light chain variable region ("LC") amino acid sequence |
| 131 | 585 | QSALTQPPSASGSPGQSVTISCTGTSSDVGG YNYVSWYQQHPGKAPKLMIYEVSKRPSGVP DRFSGSKSGNTASLTVSGLQAEDEADYYCSS FAGSNNLYVFGTGTKVTVL | ADI-48890 | Light chain variable region ("LC") amino acid sequence |
| 132 | 586 | QSVLTQPASVSGSPGQSITISCTGTSSDVGGY NYVSWYQQHPGKAPKLMIYDVTNRPSGVS NRFSGSRSGNTASLTISGLQAEDEADYYCSS YTRSSTRVFGGGTKLTVL | ADI-42206 | Light chain variable region ("LC") amino acid sequence |
| 133 | 587 | QPVLTQPPSVSAAPGQKVTISCSGSSSNIGSN FVSWYQQFPGTAPKLLIYDDNKRPSGIPDRF SGSKSGTSATLGITGLQTGDEADYYCETWD SRLSVVFGGGTKLTVL | ADI-46724 | Light chain variable region ("LC") amino acid sequence |
| 134 | 588 | QPVLTQPPSVSAAPGQKVTISCSGSSSNIGNN YVSWYQQLPGTAPKLLIYDNNKRPSGIPDRF SGSKSGTSATLGITGLQTGDEADYYCGTWD SSLSAVVFGGGTKVTVL | ADI-50539 | Light chain variable region ("LC") amino acid sequence |
| 135 | 589 | DIQLTQSPSSLSASVGDRVTITCRASQSISSYL NWYQQKPGKAPKLLIYAASSLQSGVPSRFSG SGSGTDFTLTISSLQPEDFATYYCQQSYSTP WTFGQGTKVDIK | ADI-45156 | Light chain variable region ("LC") amino acid sequence |
| 136 | 590 | DIRVTQSPSSLSASVGDRVTITSRASQSISSYL NWYQQKPGKAPKLLIYAASSLQSGVPSRFSG SGSGTDFTLTISSLQPEDFATYYCQQSYSTPR TFGGGTKVDIK | ADI-50536 | Light chain variable region ("LC") amino acid sequence |
| 137 | 591 | QSVLTQPPSVSGAPGQRVTISCTGSSSDIGAG YDVHWYQQLPGTAPKLLIYGNTNRPSGVPD RFSGSKSGTSASLAITGLQAEDEADYYCQSY DSSLSGVVFGGGTKLTVL | ADI-42217 | Light chain variable region ("LC") amino acid sequence |
| 138 | 592 | DIVLTQSPDSLAVSLGERAAINCKSSQSVFFS SDNKNYLAWYQQKPGQPPKLLIYWASTRES GVPDRFSGSGSGTDFTLTISSLQAEDVAVYY CQQFYTTPSTFGQGTKVEIK | ADI-48951 | Light chain variable region ("LC") amino acid sequence |
| 139 | 593 | DIQLTQSPSSLSASVGDRVTITCRASQSISSYL NWYQQKPGKAPKLLIYAASSLQSGVPSRFSG SGSGTDFTLTISSLQPEDFATYYCQQSYSTPR TFGGGTKVEIK | ADI-50537 | Light chain variable region ("LC") amino acid sequence |
| 140 | 594 | DIQLTQSPSSLSASVGDRVTITCRASQGIRND LGWYQQKPGKAPKRLIYAASSLQSGVPSRF SGSGSGTEFTLTISSLQPEDFATYYCLQHNSY PLTFGGGTKVEIK | ADI-46737 | Light chain variable region ("LC") amino acid sequence |
| 141 | 595 | NFMLTQPHSVSESPGNTVTISCTRSSGSIAST YVQWYQQRPGSAPSTVIYEDNQRPPGVPAR FSGSIDSSSNSASLTISGLETEDEADYYCQSY DSTTVVFGGGTKVTVL | ADI-50538 | Light chain variable region ("LC") amino acid sequence |
| 142 | 596 | SYVLTQPPSASGSPGQSVTISCTGTSSDFGGY NYVSWYQQHPGKAPKLMVYEVAKRPSGVP DRFSGSKSGNTASLTVSGLQAEDEADYYCSS YAGSNNFVVFGGGTKLTVL | ADI-48950 | Light chain variable region ("LC") amino acid sequence |
| 143 | 597 | QSVLTQPPSVSAAPGQKVTISCSGSSSNIGNN YVSWYQQLPGTAPKLLIYDNNKRPSGIPDRF SGSKSGTSATLGITGLQTGDEADYYCGTWD SSLSAKVFGGGTKLTVL | ADI-42114 | Light chain variable region ("LC") amino acid sequence |
| 144 | 598 | ETTLTQSPSTLSTSVGDRVTITCRASQSISSW LAWYQQKPGKAPKLLIYRASSLETEVPSRFS GSGSGTDFTLTISRLQPDDFATYFCQQYNRY PYTFGQGTKLEK | ADI-49194 | Light chain variable region ("LC") amino acid sequence |

TABLE 3-continued

Informal Sequence Listing

| Antibody Number | SEQ ID NO: | Sequence | Clone # (ADI) | Descriptors |
|---|---|---|---|---|
| 145 | 599 | QPVLTQPRSVSGSPGQSVTISCTGTSSDVGG YNYVSWYQQHPGKAPKLMIYDVSKRPSGV PDRFSGSKSGNTASLTISGLQAEDEADYYCC SYAGSYTFVLFGGGTKLTVL | ADI-42124 | Light chain variable region ("LC") amino acid sequence |
| 146 | 600 | DIRVTQSPSSLSASVGDRVTISCRASESISIYL NWYQQKPGKAPNLLIYAASSLQRGVPSRFS GSGSGTDFTLTITSLQAEDFATYYCQQTFSI WTFGQGTKVEIK | ADI-45123 | Light chain variable region ("LC") amino acid sequence |
| 147 | 601 | QPVLTQPPSVSAAPGQKVTISCSGSSSNIGNN YVSWYQQLPGTAPKLLIYDNNKRPSGIPDRF SGSKSGTSATLGITGLQTGDEADYYCGTWD SSLSAGKVFGGGTKLTVL | ADI-50533 | Light chain variable region ("LC") amino acid sequence |
| 148 | 602 | QSALTQPPSASGSPGQSVTISCTGTSSDVGGF NYVSWYQQHPGRAPKLVIYEVNRRPSGVPD RFSGSKSGYTASLTVSGLQAEDEADYYCFSY AGSNNYVFGTGTKVTVL | ADI-49205 | Light chain variable region ("LC") amino acid sequence |
| 149 | 603 | DIVMTQTPLSSPVTLGQPASISCRSSQSLVHS DGNTYLSWLQQRPGQPPRFLIYKISNRFSGV PDRFSGGGAGTDFTLKISRVEAEDVGVYYC MQASQFPLTFGGGTKVEIK | ADI-45151 | Light chain variable region ("LC") amino acid sequence |
| 150 | 604 | EIVMTQSPSSLSASVGDRVTITCQASQDISNY LNWYQQKPGKAPKLLIYDASNLETGVPSRF SGSGSGTDFTFTISSLQPEDIATYYCQQYDNL PPVTFGQGTRLEIK | ADI-46728 | Light chain variable region ("LC") amino acid sequence |
| 151 | 605 | QPVLTQPPSVSVSPGQTASITCSGDKLGDKY ACWYQQKPGQSPVLVIYQDSKRPSQPERFS GSNSGNTATLTISGTQAMDEADYYCQAWDS STDVVFGGGTKVTVL | ADI-49030 | Light chain variable region ("LC") amino acid sequence |
| 152 | 606 | DIQVTQSPSSLSASVGDRVTITCRASQGISNN LAWYQQKPGIFPKLLIYAASTLQSGVPSRFS GSGSGTDFILTISSLQPEDVATYYCQKYQSA PPTFGGGTKLE1K | ADI-50200 | Light chain variable region ("LC") amino acid sequence |

Materials and Methods

Study Design

Study subjects aged 30 and 31 years of age were vaccinated with the YFV-17D Stamaril vaccine. Heparinized blood (50-100 cc) was obtained from subjects before vaccination and on days 10, 14, 28, 90, 180, 270, and 360 following vaccination. Samples were processed in the Immune Monitoring and Flow Cytometry core laboratory at the Geisel School of Medicine at Dartmouth to obtain plasma and to isolate peripheral blood-derived B cells. Isolated cells and plasma were stored frozen in aliquots at −80° C.

Cells: Huh 7.5.1 cells (received from Dr. Jan Carette; originally from Dr. Frank Chisari) were passaged every 3 to 4 days using 0.05% Trypsin/EDTA solution (Gibco) and maintained in Dulbecco's Modified Eagle Medium (DMEM high glucose, Gibco) supplemented with 10% heat-inactivated fetal bovine serum (FBS, Atlanta Biologicals), 1% Penicillin/Streptomycin (P/S, Gibco), 1% Gluta-MAX (Gibco) and 25 mM HEPES (Gibco). Vero African grivet monkey kidney cells (obtained from ATCC) were passaged every 3 to 4 days using 0.05% Trypsin/EDTA solution (Gibco) and maintained in Dulbecco's Modified Eagle Medium (DMEM high glucose, Gibco) supplemented with 2% heat-inactivated fetal bovine serum (FBS, Atlanta Biologicals), 1% Penicillin/Streptomycin (P/S, Gibco), 1% Gluta-MAX (Gibco) and 25 mM HEPES (Gibco).

Yellow Fever virus 17D generation: YFV-17D was obtained from BEI Resources (cat #NR-115). 15 cm plates with Huh 7.5.1 in a confluency of 80% were infected with 90 μL of passage 2 stock of YFV-17D supernatant in 3 mL of infection media (DMEM low glucose (Gibco), 7% FBS, 1% Pen-Strep, 1% Gluta-MAX (Gibco), 25 mM HEPES (Gibco)) for 1 hour at 37 C and 5% CO2. After 3 days the supernatant was harvested and centrifuged twice at 4,000 rpm for 15 min at 4° C. to remove cell debris. The YFV-17D viral stock for neutralization assays was generated by ultracentrifugation of the pre-cleared supernatant at 28,000 rpm using a SW28 rotor (Beckman Coulter) in a Beckman Coulter Optima LE-80K ultracentrifuge for 4 hours through a 2 mL 30% (v/v) D-sucrose/PBS cushion. The pellet was allowed to resuspend overnight on ice in 300 ul PBS and afterwards aliquoted and frozen at −80 C.

Zika virus generation: The Zika virus strain MR 766 was obtained from ATCC (ATCC® VR-84™). For neutralization assay 15 cm plates with Vero cells in a confluency of 80% were infected with 90 μL of passage 1 stock of Zika supernatant in 3 mL of infection media (DMEM low glucose (Gibco), 2% FBS, 1% Pen-Strep, 1% Gluta-MAX (Gibco), 25 mM HEPES (Gibco)) for 1 hour at 37 C and 5% CO2. After 3 days the supernatant was harvested and centrifuged twice at 4,000 rpm for 15 min at 4° C. to remove cell debris.

Antigens and Antibodies

Production of recombinant YFV antigens: The coding region for the entire prM and soluble E (sE) region of the YFV Asibi Strain (Uniprot ID: Q6DV88, residues 122-678 of the genome polyprotein) was cloned into pMT-puro, an insect expression vector encoding a C-terminal double strep tag. Expression construct design was based on previously published structures of flavivirus antigens61, 62, 63. The YFV prM/E construct was used to generate an inducible, stable *Drosophila* S2 line. Protein expression was induced with addition of copper sulfate and allowed to proceed for 5-7 days. Recombinant protein was affinity-purified from the culture supernatant with a StrepTrap HP column (GE Healthcare). An additional purification step was carried out using size-exclusion chromatography step using an S200Increase column (GE Healthcare). The final protein preparations were stored in phosphate-buffered saline pH 7.4 supplemented with an additional 150 mM NaCl. Small aliquots were stored at −70° C. until use. The additional flavivirus antigens used int his study—DENV-2 E, DENV-4 E, WNV E and ZIKV E were expressed and purified essentially as described for YFV sE.

Flavivirus NS1 protein antigens: The NS1 proteins from dengue virus (serotypes 1-4), JEV, TBEV, WNV, YFV were purchased from Native Antigen Company (Cat #FLAVX4-NS1-100 and DENVX4-NS1-100) and the ZIKV NS1 was purchased from Meridian Life Science (Cat #R01636). The positive control antibodies reactive to the above NS1 proteins were obtained from Native Antigen Company: anti-DENV NS1 (Cat #AbDENVNS1-DA034), anti-ZIKV NS1 antibody (Cat #AbZIKVNS1-B4-100). The anti-YFV NS1 protein antibody was purchased from Meridain Life Sciences (Cat #C01906M). The anti-WNV NS1 antibody (Cat #HM484-X0632) and anti-TBEV NS1 antibody (Cat #HM477-X1462) were purchased from East Coast Bio. Flavivirus cross-reactive serum was used to detect the JEV NS1 protein.

YFV-17D DIII protein: The DIII region (aa 293-397) of YFV-17D E protein (Uniprot ID: P03314) was produced in *Drosophila* S2 cells using a modified pT350 vector (Felix Rey, Institut Pasteur, France). Protein expression was induced by CdCl2 and the supernatant was harvested 5-7 days post-induction. Recombinant protein was purified using a Strep-Tactin column (IBA) and size-exclusion chromatography using a S200Increase column (GE Healthcare) and 10 mMTris pH8/150 mM NaCl buffer.

Single B-Cell Sorting

For plasmablast sorting, PBMCs were stained using anti-human CD38 (PE), CD27 (BV421), CD20 (PE-Cy7), CD3 (PerCP-Cy5.5), CD8 (PerCP-Cy5.5), CD14 (PerCP-Cy5.5) and CD16 (PerCP-Cy5.5). Plasmablasts were defined as CD19+CD3−CD20−/loCD27highCD38high cells. For MBC sorting, B cells were purified using a MACS B cell isolation kit (Miltenyi Biotec; cat #130-091-151) and subsequently stained using anti-human CD19 (PE-Cy7), CD20 (PE-Cy7), CD3 (PerCP-Cy5.5), CD8 (PerCP-Cy5.5), CD14 (PerCP-Cy5.5), CD16 (PerCP-Cy5.5), IgD (BV421), IgM (AF-488), CD27 (BV510), CD21 (BV605), CD71 (APC-Cy7 and a mixture of dual-labeled (APC and PE) YFV E tetramers (25 nM each). Tetramers were prepared fresh for each experiment, and B cells that showed reactivity to the YFV E tetramers were single cell sorted. Single cells were sorted using a BD FACS Aria II (BD Biosciences) into 96-well PCR plates (BioRAD) containing 20 uL/well of lysis buffer [5 uL of 5× first strand cDNA buffer (Invitrogen), 0.625 uL of NP-40 (New England Biolabs), 0.25 uL RNaseOUT (Invitrogen), 1.25 uL dithiothreitol (Invitrogen), and 12.6 uL dH2O]. Plates were immediately stored at −80° C. Flow cytometry data were analyzed using FlowJo software.

Amplification and Cloning of Antibody Variable Genes

Antibody variable genes (IgH, IgK, and IgL) were amplified by reverse transcription PCR and nested PCRs using cocktails of IgG- and IgM-specific primers, as described previously (Tiller et al, J Immunol 2008). The primers used in the second round of PCR contained 40 base pairs of 5' and 3' homology to the digested expression vectors, which allowed for cloning by homologous recombination into *S. cerevisiae*. The lithium acetate method for chemical transformation was used to clone the PCR products into *S. cerevisiae* (Gietz and Schiestl, Nat Protoc 2007). 10 uL of unpurified heavy chain and light chain PCR product and 200 ng of the digested expression vectors were used per transformation reaction. Following transformation, individual yeast colonies were picked for sequencing and characterization.

Expression and Purification of IgGs and Fab Fragments

IgGs were expressed in *S. cerevisiae* cultures grown in 24-well plates, as described previously (Bornholdt et al, Science 2016b). After 6 days, the cultures were harvested by centrifugation and IgGs were purified by protein A-affinity chromatography. The bound antibodies were eluted with 200 mM acetic acid/50 mM NaCl (pH 3.5) into ⅛th volume 2 M Hepes (pH 8.0), and buffer-exchanged into PBS (pH 7.0).

The two YFV E-reactive control mAbs, 5A and 4G2, were produced in the human IgG1 constant region. The publicly available variable region sequences of the two control antibodies, 4G2 and 5A, were synthesized as gBlock fragments (IDT) with homologous overhangs for recombinational cloning into *S. cerevisiae*. Subsequent production was carried out as described above.

Fab fragments were generated by digesting the IgGs with papain for 2 h at 30° C. The digestion was terminated by the addition of iodoacetamide, and the Fab and Fc mixtures were passed over Protein A agarose to remove Fc fragments and undigested IgG. The flowthrough of the Protein A resin was then passed over CaptureSelect™ IgG-CH1 affinity resin (ThermoFischer Scientific), and eluted with 200 mM acetic acid/50 mM NaCl pH 3.5 into ⅛th volume 2M Hepes pH 8.0. Fab fragments then were buffer-exchanged into PBS pH 7.0.

Kinetics of Binding Measurements

Surface Plasmon Resonance Kinetic Measurements (SPR) of IgG binding: A Biacore 8K system, docked with a CAP sensor chip, sample compartment was set to 10° C., flow cell temperature to 25° C., and the data collection rate to 10 Hz. HBS-EP+ (10 mM HEPES pH 7.3, 150 mM NaCl, 3 mM EDTA, 0.05% Surfactant P20) was used as the running buffer. In each cycle, biotin CAPture reagent (GE Healthcare) diluted 1:20 in running buffer was injected over flow cells 1 and 2 for 600 s, at a flow rate of 5 uL/min, followed by a 900 s capture (1 uL/min) of biotinylated YFV E antigen (25 nM in HBS-EP+) over flow cell 2 to reach a minimum capture level of 400 RU. The antibodies (36-288 nM in HBS-EP+) were then injected over flow cells 1 and 2 for 300 s (30 uL/min), the dissociation monitored for 300 s (30 uL/min), and the surface regenerated at the oligonucleotide level with 6M Guanidine-HCl in 0.25 M NaOH for 120 s (10 uL/min). A minimum of two blank (HBS-EP+) injections also were run under identical conditions as described above and used to assess and subtract system artifacts. The data were aligned, double referenced, and fit to bivalent analyte binding model using Biacore 8K Evaluation Software, version 1.0.

Surface Plasmon Resonance Kinetic Measurements (SPR) of Fab binding: A Biacore 8K system, docked with a CAP sensor chip, sample compartment was set to 10° C., flow cell temperature to 25° C., and the data collection rate to 10 Hz. HBS-EP+(10 mM HEPES pH 7.3, 150 mM NaCl, 3 mM EDTA, 0.05% Surfactant P20) was used as the running buffer. In each cycle, biotin CAPture reagent (GE Healthcare) diluted 1:20 in running buffer was injected over flow cells 1 and 2 for 600 s, at a flow rate of 1 uL/min, followed by a 900 s capture (1 uL/min) of biotinylated YFV E protein (15 nM in HBS-EP+) over flow cell 2 to reach a minimum capture level of 275 RU. The Fabs (A5: 27-1 nM in HBS-EP+; 4G2: 4-0.125 nM in HBS-EP+) were then injected over flow cells 1 and 2 for 300 s (30 uL/min), the dissociation monitored for 1200 s (30 uL/min), and the surface regenerated at the oligonucleotide level with 6M Guanidine-HCl in 0.25 M NaOH for 185 s (10 uL/min). A minimum of two blank (HBS-EP+) injections also were run under identical conditions as described above and used to assess and subtract system artifacts. The data were aligned, double referenced, and fit to a 1:1 binding model using Biacore 8K Evaluation Software, version 1.0.

Bio-Layer Interferometry Kinetic Measurements (BLI): For monovalent apparent $K_D$ determination, IgG binding to recombinant YFV E antigen was measured by biolayer interferometry (BLI) using a ForteBio Octet HTX instrument (Molecular Devices). The IgGs were captured (1.5 nm) to anti-human IgG capture (AHC) biosensors Molecular Devices) and allowed to stand in PBSF (PBS with 0.1% w/v BSA) for a minimum of 30 min. After a short (60 s) baseline step in PBSF, the IgG-loaded biosensor tips were exposed (180 s, 1000 rpm of orbital shaking) to YFV E antigen (100 nM in PBSF) and then dipped (180 s, 1000 rpm of orbital shaking) into PBSF to measure any dissociation of the antigen from the biosensor tip surface. Data for which binding responses were >0.1 nm were aligned, inter-step corrected (to the association step) and fit to a 1:1 binding model using the ForteBio Data Analysis Software, version 11.1.

For bivalent apparent KD determination, IgG binding to recombinant biotinylated YFV E antigen was measured by biolayer interferometry (BLI) using a ForteBio Octet HTX instrument (Molecular Devices). Recombinant biotinylated YFV E was immobilized on streptavidin biosensors (Molecular Devices) and allowed to stand in PBSF (PBS with 0.1% w/v BSA) for a minimum of 30 min. After a short (60 s) baseline step in PBSF, the antigen-loaded biosensor tips were exposed (180 s, 1000 rpm of orbital shaking) to the IgGs (100 nM in PBSF) and then dipped (180 s, 1000 rpm of orbital shaking) into PBSF to measure any dissociation of the IgGs from the biosensor tip surface. Data for which binding responses were >0.1 nm were aligned, interstep corrected (to the association step) and fit to a 1:1 binding model using the ForteBio Data Analysis Software, version 11.1.

High Throughput Antibody Epitope Assignment

Bio-Layer Interferometry (BLI) Epitope Binning: For epitope binning, control antibodies A5 and 4G2 (produced as human IgG1 chimeras) were captured on anti-human IgG capture biosensors (0.9 nm) (Molecular Devices) and the biosensors were then blocked by exposing them to adalimumab (0.5 mg/mL; 20 min, 350 rpm of orbital shaking). After a short (60 s) baseline step in PBSF, a cross-interaction check was performed between the sample IgGs and the loaded biosensors (180 s, 1000 rpm of orbital shaking). No cross-interaction was observed for this panel of IgGs. The loaded biosensors were then subjected to a second short (60 s) baseline step in PBSF, followed by an association step in 100 nM recombinant YFV E monomer (180 s, 1000 rpm of orbital shaking). Finally, the binning step was performed in 100 nM sample IgGs in PBS with 0.1% BSA (PBSF) (180 s, 1000 rpm of orbital shaking). Data were analyzed using the FortéBio Data Analysis Software, version 11.1. Sample IgGs with a binning response lower than 0.1 nm were determined to compete with the control antibody. Sample IgGs with a binning response greater than 0.1 nm were determined to be non-competitors to the control antibody.

High-Throughput Epitope Binning Using Carterra LSA (SPR)

Binding kinetics and affinities. The kinetic rate and affinity constants for Yellow Fever antigen (supplied by Adimab as purified recombinant monomer, MW of 45 kDa) binding to a library of 770+ ADI mAbs (supplied as purified human IgG) were determined at a temperature of 25° C. in a "Capture Kinetics" assay format using Carterra's high throughput surface plasmon resonance (SPR) biosensor platform equipped with HC-30M chip type. To prepare the surfaces for this experiment, the chip was coated as a "lawn" with a capture reagent, namely goat anti-human-IgG Fc polyclonal cross-adsorbed to serum proteins from multiple other species (Southern Biotech, cat #2014-01) using standard amine coupling in a run buffer of 10 mM Hepes pH 7.4, 150 mM NaCl, 3 mM EDTA, 0.05% Tween20 (HBSET). Briefly, this involved priming the single flow cell (SFC) with HBSET run buffer, injecting a freshly prepared activation solution of 1:1:1 v/v/v 0.1 M N-hydroxysulfosuccinimide (Sulfo-NHS, Pierce)+0.4 M 1-ethyl-3-(3-dimethylamino-propyl)carbodiimide hydrochloride) (EDC, Pierce)+0.1 M MES pH 5.5 (Carterra) for 10 min, coupling 50 μg/ml goat anti-human-IgG Fc diluted into 10 mM sodium acetate pH 4.3 for 15 min, and quenching excess reactive esters with 1 M ethanolamine pH 8.5 for 7 min. This resulted in mean final coupled levels of 6256 RU±4% variance (as judged by the 384 reaction spots). The 96-channel printhead (96PH) was then primed in run buffer and used to capture the ADI mAbs as ligands, which were diluted to 2 μg/ml in run buffer and batch-printed 96 at a time onto discrete spots. Four serial docks of the 96PH were used to address all 4 print block locations, thus generating a 384-ligand array. The 96PH was returned to water for cleaning and the SFC was docked over the printed array and primed with the assay run buffer of HBSET+0.5 g/l BSA. Analyte samples of Yellow Fever Monomer antigen were prepared as an 8 membered 4 fold dilution series spanning nominal concentrations of 0.02-367 nM and injected in the SFC in ascending concentration after several buffer (blank) injections. Association and dissociation times were 5 min and 20 min respectively. Data were analyzed in Carterra's Kinetic Software as follows. The binding data on the reaction spots were double referenced by subtracting the responses from local reference spots (representing naked capture reagent) and then subtracting the responses from a buffer blank analyte 66. Double-referenced data were fit globally to a simple Langmuir model allowing each spot its own association rate constant (ka), dissociation rate constant (kd), and Rmax value. The equilibrium dissociation (affinity) constant (KD) was computed from the ratio of the kinetic rate constants, KD=kd/ka).

Epitope binning experiments: Carterra's LSA was used to perform epitope binning assays in a classical sandwich assay format67 using 6 benchmark mAbs (ADI-49582, ADI-44112, ADI-45107, ADI-49147, 4G2, and 5A) as analyte to probe the epitope diversity of the 770+ ADI library as ligands. An HCX-30M (pre-activated) chip type was used and experiments were performed at 25° C. The SFC and 96PH were primed in run buffer of 25 mM Mes pH5.5+ 0.01% Tween20. The ADI mAbs were diluted to 2 μg/ml in 10 mM sodium acetate pH 4.5 (coupling buffer) and coupled via the 96PH using 7 min contact time at each print block location. After 4 serial docks of the 96PH to build up a 384-ligand array, the SFC was docked over the entire surface to quench excess reactive esters by injecting ethanolamine pH8.5 for 7 min. Final coupled levels of each mAb ranged from 1000-4000 RU per spot. The 96PH was returned to water for cleaning and the SFC was primed in an assay run buffer of HBSET+0.5 g/l BSA. Each binding cycle involved a co-inject style of sample delivery whereby the antigen (50 nM Yellow Fever Monomer) and antibody analyte (20 ug/ml mAb or buffer) samples were injected back-to-back, with minimal dissociation time between them over the 384-ligand array. Typical association times were 3 or 5 min and surfaces were regenerated with 75 mM phosphoric acid after each binding cycle. The binding data were analyzed in Carterra's Epitope Software.

Micro-Titer Neutralization Assays

Monoclonal antibodies were serially diluted in DMEM high glucose medium (Gibco) containing 10% heat-inactivated FBS (Gibco), 1% Gluta-MAX Gibco), 1% P/S (Gibco) and 25 mM HEPES (Gibco) and incubated at room temperature with YFV-17D or ZIKV for 1 hour. YFV-17D or ZIKV was diluted to achieve 60% endpoint infection. The antibody-virus mixture was added in triplicates to 96-well plates (Costar 3595) containing 5×10^3 Huh 7.5.1 cell monolayers seeded the day before. Cells were incubated for 2 days at 37° C. and 5% $CO_2$. Cells were then fixed with 4% paraformaldehyde (Sigma) for 10 minutes and were washed afterwards with a Tris buffer (50 mM Tris, 150 mM NaCl (all Fisher Scientific), pH 7.6, three times. Fixed cells were incubated with a pan-flavivirus mouse mAb 4G2 (ATCC) at 2 µg/ml in Tris buffer containing 3% nonfat dry milk powder (BioRad), 0.5% Triton X-100 (MP Biomedicals), and 0.05% Tween 20 (Fisher Scientific) for one hour at room temperature (RT). Afterwards, cells were washed three times and incubated with the secondary antibody conjugated to Alexa Fluor 488 goat anti-mouse (Invitrogen) at 1:500 dilution for one hour at RT. Cells were washed again and nuclei were stained with Hoechst-33342 (Invitrogen) in a 1:2,000 dilution in PBS. Viral infectivity was measured by automated enumeration of Alexa Fluor 488-positive cells from captured images using Cytation-5 automated fluorescence microscope (BioTek) and analyzed using the Gen5 data analysis software (BioTek). The half maximal inhibitory concentration (IC50) of the mAbs was calculated using a nonlinear regression analysis with GraphPad Prism software. Viral neutralization data were subjected to nonlinear regression analysis to extract the half maximal inhibitory concentration (IC50) values (4-parameter, variable slope sigmoidal dose-response equation; GraphPad Prism).

Neutralization of donor plasma samples was carried out exactly as described above for purified IgGs. Serial dilutions of plasma were pre-incubated with YFV-17D infectious stock for 1 hour before adding to cell monolayers.

Purified total human IgG from non-immunized donors was used as negative control in purified IgG neutralization assays against YFV-17D and ZIKV (Cat #AB 2337042, Jackson Immuno Research).

FRNT Assay

Virus-specific mAbs were screened as previously described. Briefly, all purified mAbs were serially diluted in 199 medium (Thermo Scientific) containing 5% heat-inactivated fetal bovine serum (FBS) (Gibco-Invitrogen) and incubated at 37° C. with YFV-17DD. After 1 hr incubation, the Ab-virus mixture was added in duplicate to 96-well plates containing 80% confluent monolayers of Vero E6 cells. Plates were incubated for 1.5 h at 37° C. Wells were then overlaid with 1% methylcellulose in supplemented OptiMEM GlutaMAX media (Invitrogen) with 5% heat-inactivated FBS (Gibco-Invitrogen) and 1% amphotericin B and incubated at 37° C., 5% $CO_2$ for 72 hours. Cells were then fixed and permeabilized with Perm/Wash buffer (BD Biosciences) for 30 min. After permeabilization, cells were washed with phosphate-buffered saline (PBS) and incubated with 1:2000 dilution of anti-flavivirus antibody (MAB10216, EMD Millipore) in Perm/Wash buffer for 2 hours. After incubation, cells were washed with PBS and incubated with anti-mouse horseradish peroxidase (HRP)-conjugated secondary antibody (115035146, Jackson ImmunoResearch Laboratories) for 2 hrs. Plates were washed and developed with peroxidase substrate (KPL). The half maximal inhibitory concentration (IC50) of the mAbs was calculated using a nonlinear regression analysis with GraphPad Prism software.

Serum and Purified IgG ELISAs

For NS1 and E binding ELISAs, 96-well plates (Corning; Cat #3690) were coated with 5 µg/ml of NS1 or E protein diluted in PBS and incubated overnight at 4° C. Wells were washed and then blocked with 5% non-fat dried milk (NFDM) in PBS for 1 hour at 37° C. Wells were washed 3 times with PBS and serial dilutions of human plasm in 5% NFDM-PBS were added and incubated for 1 hour at 37° C. Plates were then washed 3 times with PBS and secondary cross-adsorbed anti-human IgG-HRP (Thermo Fisher Scientific; cat #31413) or anti-human-IgM (Sigma Aldrich; cat #AP114P) detection antibodies were added at 1:8000 dilution in 5% NFDM-PBS for 1 hour at 37° C. After washing 3 times with PBS detection reagent was added per manufacturer recommendations (Thermo Scientific; Cat #34029) and absorbance was measures at 450 nM wavelength using a Spectramax microplate Reader (Molecular Devices).

For virus binding ELISAs, 96-well ELISA plates were coated with 5 ug/ml of 4G2 (Millipore MAB10216) diluted in PBS and incubated for 2 hours at 37° C. After washing 3 times with PBS, whole YFV-17D viral particles diluted in PBS pH 7.4 and incubated overnight at 4° C. Plates were then washed 3 times with PBS and blocked with 5% NFDM-PBS for 1 hour at 37° C. After removal of the blocking solution, test antibodies diluted in 5% NFDM-PBS were allowed to bind for 1 hour at 37° C. Plates were then washed 3 times with PBS and secondary cross-adsorbed anti-human IgG-HRP (Thermo Fisher Scientific; cat #31413) or anti-human-IgM (Sigma Aldrich; cat #AP114P) detection antibodies were added at 1:8000 dilution in 5% NFDM-PBS for 1 hour at 37° C. After washing 3 times with PBS detection reagent was added per manufacturer recommendations (Thermo Scientific; Cat # 34029) and absorbance was measures at 450 nM wavelength using a Spectramax microplate Reader (Molecular Devices).

Binding of purified IgGs to viral particles was performed as described above. IgGs were diluted in 5% NFDM-PBS and tested at 100 nM concentration for single point reactivity test of plasmablast- and MBC-derived day 14 antibodies.

All references, patents, and patent publications cited herein are hereby incorporated by reference in their entireties for all that is taught therein.

What is claimed is:

1. An isolated antibody or antigen-binding fragment thereof that specifically binds to a Yellow Fever Virus (YFV) protein, the antibody or antigen-binding fragment thereof comprising:
   a) a heavy chain variable region comprising the amino acid sequence of SEQ ID NO: 307 and a light chain variable region comprising the amino acid sequence of SEQ ID NO: 459;
   b) a heavy chain variable region comprising the amino acid sequence of SEQ ID NO: 308 and a light chain variable region comprising the amino acid sequence of SEQ ID NO: 460;
   c) a heavy chain variable region comprising the amino acid sequence of SEQ ID NO: 311 and a light chain variable region comprising the amino acid sequence of SEQ ID NO: 463;
   d) a heavy chain variable region comprising the amino acid sequence of SEQ ID NO: 320 and a light chain variable region comprising the amino acid sequence of SEQ ID NO: 471; or
   e) a heavy chain variable region comprising the amino acid sequence of SEQ ID NO: 341 and a light chain variable region comprising the amino acid sequence of SEQ ID NO: 492.

2. The isolated antibody or antigen-binding fragment of claim 1, wherein the antibody or antigen-binding fragment thereof comprises a heavy chain variable region comprising the amino acid sequence of SEQ ID NO: 307 and a light chain variable region comprising the amino acid sequence of SEQ ID NO: 459.

3. The isolated antibody or antigen-binding fragment of claim 1, wherein the antibody or antigen-binding fragment thereof comprises a heavy chain variable region comprising the amino acid sequence of SEQ ID NO: 308 and a light chain variable region comprising the amino acid sequence of SEQ ID NO: 460.

4. The isolated antibody or antigen-binding fragment of claim 1, wherein the antibody or antigen-binding fragment thereof comprises a heavy chain variable region comprising the amino acid sequence of SEQ ID NO: 311 and a light chain variable region comprising the amino acid sequence of SEQ ID NO: 463.

5. The isolated antibody or antigen-binding fragment of claim 1, wherein the antibody or antigen-binding fragment thereof comprises a heavy chain variable region comprising the amino acid sequence of SEQ ID NO: 320 and a light chain variable region comprising the amino acid sequence of SEQ ID NO: 471.

6. The isolated antibody or antigen-binding fragment of claim 1, wherein the antibody or antigen-binding fragment thereof comprises a heavy chain variable region comprising the amino acid sequence of SEQ ID NO: 341 and a light chain variable region comprising the amino acid sequence of SEQ ID NO: 492.

7. The isolated antibody or antigen-binding fragment thereof of claim 1, wherein;
   a) the isolated antibody or antigen-binding fragment thereof displays neutralization activity toward YFV in vitro;
   b) the isolated antibody or antigen-binding fragment thereof displays an in vitro neutralization potency (IC50) of between about 0.5 microgram/milliliter (µg/ml) to about 5 µg/ml; between about 0.05 µg/ml to about 0.5 µg/ml; or less than about 0.05 mg/ml; and/or
   c) the isolated antibody or antigen-binding fragment thereof binds to an envelope protein of YFV.

8. The isolated antibody or antigen-binding fragment thereof of claim 7, wherein the isolated antibody or antigen-binding fragment thereof displays an in vitro neutralization potency (IC50) toward YFV of between about 0.5 microgram/milliliter (µg/ml) to about 5 µg/ml.

9. The isolated antibody or antigen-binding fragment thereof of claim 7, wherein the isolated antibody or antigen-binding fragment thereof displays an in vitro neutralization potency (IC50) toward YFV of between about 0.05 µg/ml to about 0.5 µg/ml.

10. The isolated antibody or antigen-binding fragment thereof of claim 7, wherein the isolated antibody or antigen-binding fragment thereof displays an in vitro neutralization potency (IC50) toward YFV of less than about 0.05 mg/ml.

11. The isolated antibody or antigen-binding fragment thereof of claim 1, wherein the antibody or antigen-binding fragment thereof displays an equilibrium dissociation constant of between about $1\times10^6$ M about $1\times10^{10}$ M.

12. The isolated antibody or antigen-binding fragment thereof of claim 7, wherein the antibody or antigen-binding fragment thereof comprises at least two characteristics a), b) and/or c).

13. The isolated antibody or antigen-binding fragment thereof of claim 7, wherein the antibody or antigen-binding fragment thereof comprises characteristics a), b) and c).

14. A pharmaceutical composition comprising: one or more isolated antibodies or antigen-binding fragments thereof according to claim 1, and a pharmaceutically acceptable carrier and/or excipient.

* * * * *

SEQUENCE LISTING

<160> NUMBER OF SEQ ID NOS: 1014

<210> SEQ ID NO 1
<211> LENGTH: 18
<212> TYPE: PRT
<213> ORGANISM: Artificial sequence
<220> FEATURE:
<223> OTHER INFORMATION: Synthetic polypeptide

<400> SEQUENCE: 1

Ala Arg Asn Ala Pro Glu Asn Tyr Tyr Gly Ser Gly Arg Glu Ser Phe
1               5                   10                  15

Asp Ile

<210> SEQ ID NO 2
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 2

Gly Thr Trp Asp Ser Ser Leu Ser Ala Trp Val
1               5                   10

<210> SEQ ID NO 3
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 3

Ala Lys Asp His Gly Gly Lys Tyr Gly Trp Trp Tyr Phe Asp Leu
1               5                   10                  15

<210> SEQ ID NO 4
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 4

Gln Gln Tyr Asp Asn Trp Pro Leu Thr
1               5

<210> SEQ ID NO 5
<211> LENGTH: 18
<212> TYPE: PRT
<213> ORGANISM: Artificial sequence
<220> FEATURE:
<223> OTHER INFORMATION: Synthetic polypeptide

<400> SEQUENCE: 5

Ala Arg Asn Ala Pro Glu Asn Tyr Tyr Gly Ser Gly Arg Glu Ser Phe
1               5                   10                  15

Asp Ile

<210> SEQ ID NO 6
<211> LENGTH: 11
<212> TYPE: PRT
<213> ORGANISM: Artificial sequence
<220> FEATURE:
<223> OTHER INFORMATION: Synthetic polypeptide

```
<400> SEQUENCE: 6

Gly Thr Trp Asp Ser Ser Leu Ser Ala Trp Val
1               5                   10

<210> SEQ ID NO 7
<211> LENGTH: 19
<212> TYPE: PRT
<213> ORGANISM: Artificial sequence
<220> FEATURE:
<223> OTHER INFORMATION: Synthetic polypeptide

<400> SEQUENCE: 7

Ala Arg Asp Leu Glu Val Gly Ala Glu Tyr Leu Tyr Tyr His Tyr Gly
1               5                   10                  15

Met Asp Val

<210> SEQ ID NO 8
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 8

Ala Ala Trp Asp Asp Ser Leu Asn Gly Trp Val
1               5                   10

<210> SEQ ID NO 9
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 9

Ala Lys Asp Ser Ser Thr Ser Trp Tyr Gln Val Val Tyr His Ile Asp
1               5                   10                  15

Tyr

<210> SEQ ID NO 10
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 10

Glu Thr Trp Asp Ser Ser Leu Asn Ala Val Val
1               5                   10

<210> SEQ ID NO 11
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 11

Ala Lys Asp Leu Ala Val Ser Thr Pro Arg Tyr Trp Phe Asp Ser
1               5                   10                  15

<210> SEQ ID NO 12
<211> LENGTH: 10
<212> TYPE: PRT
<213> ORGANISM: Artificial sequence
```

```
<220> FEATURE:
<223> OTHER INFORMATION: Synthetic polypeptide

<400> SEQUENCE: 12

Gln Gln Ser Tyr Ser Ile Pro Arg Ile Thr
1               5                   10

<210> SEQ ID NO 13
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 13

Ala Lys Asp Met Ala Val Ser Val His Arg Gly Trp Phe Asp Asp
1               5                   10                  15

<210> SEQ ID NO 14
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 14

Gln Gln Ser Tyr Ser Pro Pro Met Tyr Thr
1               5                   10

<210> SEQ ID NO 15
<211> LENGTH: 19
<212> TYPE: PRT
<213> ORGANISM: Artificial sequence
<220> FEATURE:
<223> OTHER INFORMATION: Synthetic polypeptide

<400> SEQUENCE: 15

Ala Arg Asp Leu Glu Val Gly Ala Glu Tyr Ile Tyr Tyr Tyr Gly
1               5                   10                  15

Met Asp Val

<210> SEQ ID NO 16
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 16

Ala Ala Trp Asp Asp Ser Arg Asn Gly Trp Val
1               5                   10

<210> SEQ ID NO 17
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 17

Ala Arg Ser His Trp Arg Ser Pro Gln Ser Val Thr Phe Asp Leu
1               5                   10                  15

<210> SEQ ID NO 18
<211> LENGTH: 13
<212> TYPE: PRT
```

<213> ORGANISM: Artificial sequence
<220> FEATURE:
<223> OTHER INFORMATION: Synthetic polypeptide

<400> SEQUENCE: 18

Gly Thr Trp Asp Thr Ser Ser Leu Ser Ala Gly Arg Val
1               5                   10

<210> SEQ ID NO 19
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 19

Ala Arg Ile Ala Ala Gly Tyr Ser Thr Ser Trp Tyr Tyr Phe Asp Tyr
1               5                   10                  15

<210> SEQ ID NO 20
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 20

Gly Thr Trp Asp Thr Ser Leu Ser Ala Gly Arg Val
1               5                   10

<210> SEQ ID NO 21
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 21

Ala Lys Asp Met Trp Ala Gly Thr Thr Thr Asn Trp Phe Gly Pro
1               5                   10                  15

<210> SEQ ID NO 22
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 22

Gly Thr Trp Asp Thr Ser Leu Gly Val Val
1               5                   10

<210> SEQ ID NO 23
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 23

Ala Arg Glu Phe Ser Ser Arg Pro Phe Asp Leu
1               5                   10

<210> SEQ ID NO 24
<211> LENGTH: 12
<212> TYPE: PRT
<213> ORGANISM: Artificial sequence

```
<220> FEATURE:
<223> OTHER INFORMATION: Synthetic polypeptide

<400> SEQUENCE: 24

Cys Ser Tyr Ala Gly Thr Tyr Thr Ser Asn Tyr Val
1               5                   10

<210> SEQ ID NO 25
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 25

Ala Arg Val Asn Pro Pro Gln Tyr Ser Ser Gly Trp Tyr Ser Val Tyr
1               5                   10                  15

<210> SEQ ID NO 26
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 26

Gly Thr Trp Asp Asn Ser Leu Gly Ala Val Val
1               5                   10

<210> SEQ ID NO 27
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 27

Ala Arg Val Ala Trp Thr Ser Ser Ser Cys Tyr Tyr Asp Tyr
1               5                   10                  15

<210> SEQ ID NO 28
<211> LENGTH: 18
<212> TYPE: PRT
<213> ORGANISM: Artificial sequence
<220> FEATURE:
<223> OTHER INFORMATION: Synthetic polypeptide

<400> SEQUENCE: 28

Ala Arg Asp Gly Glu Gly His Tyr Tyr Arg Ser Gly Asp Asn Trp Phe
1               5                   10                  15

Asp Arg

<210> SEQ ID NO 29
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 29

Gly Thr Trp Asp Ser Ser Leu Ser Ala Val Val
1               5                   10

<210> SEQ ID NO 30
<211> LENGTH: 13
<212> TYPE: PRT
```

```
<213> ORGANISM: Artificial sequence
<220> FEATURE:
<223> OTHER INFORMATION: Synthetic polypeptide

<400> SEQUENCE: 30

Ala Arg Ala Glu Leu Ser Ala Trp Tyr Tyr Phe Asp His
1               5                   10

<210> SEQ ID NO 31
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 31

Gly Thr Trp Asp Thr Ser Leu Ser Ala Gly Arg Val
1               5                   10

<210> SEQ ID NO 32
<211> LENGTH: 19
<212> TYPE: PRT
<213> ORGANISM: Artificial sequence
<220> FEATURE:
<223> OTHER INFORMATION: Synthetic polypeptide

<400> SEQUENCE: 32

Ala Arg Val Ser Pro Leu Asp Asp Gly Tyr Gly Tyr Thr Tyr Tyr Gly
1               5                   10                  15

Met Asp Val

<210> SEQ ID NO 33
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 33

Gln Gln Tyr Asn Asn Trp Pro Pro Arg Thr
1               5                   10

<210> SEQ ID NO 34
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 34

Ala Arg Asp Trp Ala Glu Leu Thr Thr Ile Thr Asn Tyr Phe Tyr Pro
1               5                   10                  15

<210> SEQ ID NO 35
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 35

Gln Gln Ala Lys Ser Phe Pro Pro Thr
1               5

<210> SEQ ID NO 36
<211> LENGTH: 22
```

```
<212> TYPE: PRT
<213> ORGANISM: Artificial sequence
<220> FEATURE:
<223> OTHER INFORMATION: Synthetic polypeptide

<400> SEQUENCE: 36

Ala Lys Ala Glu Asn Arg Ile Gly Tyr Cys Ser Ala Gly Ser Cys Tyr
1               5                   10                  15

Leu Thr Tyr Phe Asp Tyr
            20

<210> SEQ ID NO 37
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 37

Asn Ser Tyr Thr Ser Ser Ser Thr Leu Val
1               5                   10

<210> SEQ ID NO 38
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 38

Ala Lys Asp Pro Lys Tyr Ser Ser Gly Trp Trp Ala Phe Asp Tyr
1               5                   10                  15

<210> SEQ ID NO 39
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 39

Gln Gln Tyr Asp Asp Trp Pro Leu
1               5

<210> SEQ ID NO 40
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 40

Ala Arg Val Glu Trp Ala Tyr Ser Ser Ser Trp Trp Leu Asp Tyr
1               5                   10                  15

<210> SEQ ID NO 41
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 41

Gly Thr Trp Asp Thr Ser Leu Ser Ala Gly Gly Val
1               5                   10
```

```
<210> SEQ ID NO 42
<211> LENGTH: 20
<212> TYPE: PRT
<213> ORGANISM: Artificial sequence
<220> FEATURE:
<223> OTHER INFORMATION: Synthetic polypeptide

<400> SEQUENCE: 42

Ala Lys His Thr Gly Asp Lys Pro Leu Val Trp Ala Pro Ser Val Tyr
1               5                   10                  15

Gly Leu Asp Val
            20

<210> SEQ ID NO 43
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 43

Ser Ser Tyr Thr Arg Arg Ser Thr Leu Val
1               5                   10

<210> SEQ ID NO 44
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 44

Ala Arg Val Ser Val Ser Thr Ser Ala Trp Tyr Ala Asp Tyr
1               5                   10

<210> SEQ ID NO 45
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 45

Gly Thr Trp Asp Thr Ser Leu Ser Thr Val
1               5                   10

<210> SEQ ID NO 46
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 46

Ala Arg Glu Leu Ser Ser Arg Ile Asp Tyr
1               5                   10

<210> SEQ ID NO 47
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 47

Ser Ser Tyr Pro Gly Thr Ser Ala Leu Val Ile
1               5                   10
```

<210> SEQ ID NO 48
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 48

Ala Arg Ala Gln Asp Gly Gln Gln Leu Val Asn Tyr Tyr Gly Met Asp
1               5                   10                  15

Val

<210> SEQ ID NO 49
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 49

Gln Gln Ser Tyr Ser Thr Pro Tyr Thr
1               5

<210> SEQ ID NO 50
<211> LENGTH: 20
<212> TYPE: PRT
<213> ORGANISM: Artificial sequence
<220> FEATURE:
<223> OTHER INFORMATION: Synthetic polypeptide

<400> SEQUENCE: 50

Ala Arg Gly Gly Asp Tyr Gly Asp Tyr Glu Ser Asn Asn Pro Ala Glu
1               5                   10                  15

Tyr Phe Gln His
            20

<210> SEQ ID NO 51
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 51

Gln Ser Tyr Asp Ser Ser Leu Ser Gly His Val Val
1               5                   10

<210> SEQ ID NO 52
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 52

Ala Gly His Arg Glu Asp Pro Tyr Gly Ala Tyr Gly Ala Ser
1               5                   10

<210> SEQ ID NO 53
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 53

Gln Gln Arg Thr Asn Trp Pro Phe Thr
1               5

<210> SEQ ID NO 54
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 54

Ala Ser Arg Lys Glu Val Arg Gly Thr Glu Asp Tyr Phe Asp Tyr
1               5                   10                  15

<210> SEQ ID NO 55
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 55

His Gln Arg Thr Asn Trp Pro Trp Thr
1               5

<210> SEQ ID NO 56
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 56

Ala Lys Val Glu Glu Asp Gly Tyr Thr Asn Val Val Arg Asp Tyr
1               5                   10                  15

<210> SEQ ID NO 57
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 57

Leu Gln Arg Thr Asn Trp Pro Phe Thr
1               5

<210> SEQ ID NO 58
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 58

Ala Arg Glu Gly Thr Arg Gly Arg Met Asp
1               5                   10

<210> SEQ ID NO 59
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 59

```
Ser Ser Tyr Thr Ser Gly Thr Thr Leu Gly Val
1               5                   10
```

<210> SEQ ID NO 60
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 60

```
Ala Arg Asp Ser Trp Ser Gly Pro Thr Arg Asn Trp Phe Asp Pro
1               5                   10                  15
```

<210> SEQ ID NO 61
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 61

```
Gly Thr Trp Asp Ser Ser Leu Gly Gly Val Ile
1               5                   10
```

<210> SEQ ID NO 62
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 62

```
Ala Arg Val Val Trp Glu Tyr Ser Asn Ala Trp Cys Val Asp Phe
1               5                   10                  15
```

<210> SEQ ID NO 63
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 63

```
Glu Thr Trp Asp Ser Ser Leu Gly Val Val Val
1               5                   10
```

<210> SEQ ID NO 64
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 64

```
Ala Arg Asn Thr Tyr Tyr Asp Arg Ser Gly Leu Ile Ala Tyr
1               5                   10
```

<210> SEQ ID NO 65
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 65

Gln Gln Tyr Asp Asn Leu Ser Arg Leu Thr
1               5                   10

<210> SEQ ID NO 66
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 66

Ala Arg Gly Pro Leu Lys Ser Tyr Trp Tyr Phe Asp Leu
1               5                   10

<210> SEQ ID NO 67
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 67

Gly Thr Trp Asp Thr Ser Leu Ser Ala Gly Arg Val
1               5                   10

<210> SEQ ID NO 68
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 68

Ala Arg Tyr Cys Ser Gly Ala Thr Cys Tyr Gly Ser Asn Gly Met Asp
1               5                   10                  15

Val

<210> SEQ ID NO 69
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 69

Gly Thr Trp Asp Phe Arg Leu Ser Ala Leu
1               5                   10

<210> SEQ ID NO 70
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 70

Ala Lys Asp Gln Cys Gly Gly Asp Cys Thr Ala Asp Tyr
1               5                   10

<210> SEQ ID NO 71
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 71

```
Ser Ser Tyr Thr Ser Ser Gly Thr Pro Val Val
1               5                   10

<210> SEQ ID NO 72
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 72

Ala Ser Thr Leu Trp Gly Gly Pro Leu Ser Val Ala Ser Asp Tyr
1               5                   10                  15

<210> SEQ ID NO 73
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 73

Gly Thr Trp Asp Ser Ser Pro Ser Ala Gly Arg Val
1               5                   10

<210> SEQ ID NO 74
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 74

Ala Arg Asp Tyr Tyr Ala Ser Gly Asp Gly Tyr Phe Asp Tyr
1               5                   10

<210> SEQ ID NO 75
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 75

Gln Gln Tyr Tyr Ser Thr Pro Arg Thr
1               5

<210> SEQ ID NO 76
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 76

Val Arg Tyr Cys Ser Ser Thr Ser Cys Tyr Gly Leu Asn Gly Met Asp
1               5                   10                  15

Val

<210> SEQ ID NO 77
<211> LENGTH: 10
<212> TYPE: PRT
<213> ORGANISM: Artificial sequence
<220> FEATURE:
<223> OTHER INFORMATION: Synthetic polypeptide
```

```
<400> SEQUENCE: 77

Gly Thr Trp Asp Thr Arg Leu Ser Ala Leu
1               5                   10

<210> SEQ ID NO 78
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 78

Ala Arg Asp Gly Ser Leu Val Asn Ala Ile Asp Tyr
1               5                   10

<210> SEQ ID NO 79
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 79

Gly Thr Trp Asp Thr Ser Leu Ser Ala Ala Trp Val
1               5                   10

<210> SEQ ID NO 80
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 80

Ala Arg Val Arg Trp Ser Gly Ser Thr Ser Trp Asp Leu Asp Tyr
1               5                   10                  15

<210> SEQ ID NO 81
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 81

Gly Thr Trp Asp Thr Ser Pro Ser Ala Gly Gly Val
1               5                   10

<210> SEQ ID NO 82
<211> LENGTH: 23
<212> TYPE: PRT
<213> ORGANISM: Artificial sequence
<220> FEATURE:
<223> OTHER INFORMATION: Synthetic polypeptide

<400> SEQUENCE: 82

Ala His Ser Pro Arg Arg Ile Thr Met Val Arg Gly Val Ile Ile Thr
1               5                   10                  15

Trp Gly Asp Gly Met Asp Val
            20

<210> SEQ ID NO 83
<211> LENGTH: 11
<212> TYPE: PRT
<213> ORGANISM: Artificial sequence
<220> FEATURE:
```

<223> OTHER INFORMATION: Synthetic polypeptide

<400> SEQUENCE: 83

Ser Ser Tyr Thr Ser Ser Ser Thr Leu Ala Val
1               5                   10

<210> SEQ ID NO 84
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 84

Ala Arg Asp Gly Ser Met Val Asn Ala Ile Asp Tyr
1               5                   10

<210> SEQ ID NO 85
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 85

Gly Thr Trp Asp Ser Ser Leu Ser Ala Ala Trp Val
1               5                   10

<210> SEQ ID NO 86
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 86

Ala Arg Asp Ala Tyr Ala Ser Gly Asp Gly Gly Ile Asp Tyr
1               5                   10

<210> SEQ ID NO 87
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 87

Ser Ser Tyr Arg Ser Ser Gly Thr Pro Tyr Val
1               5                   10

<210> SEQ ID NO 88
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 88

Ala Lys Asp Leu Arg Gly Val Gly Gly Trp Tyr Tyr Phe Asp Tyr
1               5                   10                  15

<210> SEQ ID NO 89
<211> LENGTH: 9
<212> TYPE: PRT
<213> ORGANISM: Artificial sequence
<220> FEATURE:
<223> OTHER INFORMATION: Synthetic polypeptide

```
<400> SEQUENCE: 89

Gln Gln Tyr Asp Asn Leu Pro Leu Thr
1               5

<210> SEQ ID NO 90
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 90

Ala Lys Asp Gln Gly Val Thr Thr Asp Trp Pro Ser Asp Tyr
1               5                   10

<210> SEQ ID NO 91
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 91

Gln His Tyr Glu Thr Tyr Ser Val Arg
1               5

<210> SEQ ID NO 92
<211> LENGTH: 19
<212> TYPE: PRT
<213> ORGANISM: Artificial sequence
<220> FEATURE:
<223> OTHER INFORMATION: Synthetic polypeptide

<400> SEQUENCE: 92

Pro Arg Asp Gly Leu Pro Gly Ala Asn Gln Tyr Phe Phe Tyr Tyr Gly
1               5                   10                  15

Met Asp Val

<210> SEQ ID NO 93
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 93

Gln Lys Tyr Asn Ser Ala Pro Leu Thr
1               5

<210> SEQ ID NO 94
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 94

Val Arg Val Glu Glu Tyr Val Asn Asn Glu Glu Val Arg Asp Tyr
1               5                   10                  15

<210> SEQ ID NO 95
<211> LENGTH: 9
<212> TYPE: PRT
<213> ORGANISM: Artificial sequence
<220> FEATURE:
```

<223> OTHER INFORMATION: Synthetic polypeptide

<400> SEQUENCE: 95

Leu Gln Arg Thr Asn Trp Pro Phe Thr
1               5

<210> SEQ ID NO 96
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 96

Ala Arg Asp Gln Gly Phe Thr Thr Asp Trp Pro Cys Asp Tyr
1               5                   10

<210> SEQ ID NO 97
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 97

Gln His Tyr Asn Ser Phe Ser Val Lys
1               5

<210> SEQ ID NO 98
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 98

Ala Arg Asp Ser Asn Phe Asn Ser Asn Leu Asp Tyr
1               5                   10

<210> SEQ ID NO 99
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 99

Gln Val Trp Asp Ser Ser Ser Asp His Pro Trp Val
1               5                   10

<210> SEQ ID NO 100
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 100

Ala Arg Gly Pro Leu Lys Thr Tyr Trp Tyr Phe Asp Leu
1               5                   10

<210> SEQ ID NO 101
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 101

Gly Thr Trp Asp Thr Ser Leu Ser Ala Gly Arg Val
1               5                   10

<210> SEQ ID NO 102
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 102

Ala Arg Asp Ser Asn Tyr Phe Tyr Gly Leu Asp Val
1               5                   10

<210> SEQ ID NO 103
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 103

Gln Val Trp Asp Thr Ser Ile Asp His His Trp Val
1               5                   10

<210> SEQ ID NO 104
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 104

Ala Lys Asp Ile Cys Ser Gly Asp Cys Gly Gly Gly Asp Tyr
1               5                   10

<210> SEQ ID NO 105
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 105

Ser Ser Tyr Ala Gly Ser Asn Asn Trp Val Val
1               5                   10

<210> SEQ ID NO 106
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 106

Ala Arg Glu Asp Asp Asp Tyr Tyr Ser Met Asp Val
1               5                   10

<210> SEQ ID NO 107
<211> LENGTH: 10
<212> TYPE: PRT
<213> ORGANISM: Artificial sequence
<220> FEATURE:
<223> OTHER INFORMATION: Synthetic polypeptide

```
<400> SEQUENCE: 107

Ser Ser Tyr Thr Thr Thr Ser Leu Val Ile
1               5                   10

<210> SEQ ID NO 108
<211> LENGTH: 22
<212> TYPE: PRT
<213> ORGANISM: Artificial sequence
<220> FEATURE:
<223> OTHER INFORMATION: Synthetic polypeptide

<400> SEQUENCE: 108

Ala Arg Asp Ile Ser Cys Ile Ser Thr Ser Cys Tyr Gly Gly Tyr Tyr
1               5                   10                  15

Tyr Tyr Gly Met Asp Val
            20

<210> SEQ ID NO 109
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 109

Met Gln Ala Leu Gln Thr Pro Pro Arg Thr
1               5                   10

<210> SEQ ID NO 110
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 110

Ala Arg Asp Tyr Tyr Ala Ser Gly Asp Gly Ser Ile Asp Tyr
1               5                   10

<210> SEQ ID NO 111
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 111

Leu Gln His Asn Ser Tyr Pro Leu Thr
1               5

<210> SEQ ID NO 112
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 112

Ala Lys Tyr Tyr Asp Ser Ser Gly Tyr Tyr Tyr Phe Asp Tyr
1               5                   10

<210> SEQ ID NO 113
<211> LENGTH: 9
<212> TYPE: PRT
<213> ORGANISM: Artificial sequence
<220> FEATURE:
```

```
<223> OTHER INFORMATION: Synthetic polypeptide

<400> SEQUENCE: 113

Lys Gln Tyr Asn Arg Asn Pro Tyr Thr
1               5

<210> SEQ ID NO 114
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 114

Ala Lys Gly Ser Val Ser Val Ala Gly Ala Glu Asp Tyr
1               5                   10

<210> SEQ ID NO 115
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 115

Gln Lys Tyr Asn Ser Ala Pro Gln Thr
1               5

<210> SEQ ID NO 116
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 116

Ala Lys Gly Tyr Asp Ser Ser Gly Tyr Tyr Trp Ala Asp Tyr
1               5                   10

<210> SEQ ID NO 117
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 117

Gln Gln Tyr Asn Asn Trp Pro Pro Leu Thr
1               5                   10

<210> SEQ ID NO 118
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 118

Ala Arg Glu Arg Gly Gly Tyr Phe Thr Glu Pro Phe Asp Ile
1               5                   10

<210> SEQ ID NO 119
<211> LENGTH: 9
<212> TYPE: PRT
<213> ORGANISM: Artificial sequence
<220> FEATURE:
<223> OTHER INFORMATION: Synthetic polypeptide
```

```
<400> SEQUENCE: 119

Gln Gln Tyr Tyr Arg Thr Pro Trp Thr
1               5

<210> SEQ ID NO 120
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 120

Ala Ala Thr Ile Phe Gly Val Val Ser Phe Asp Tyr
1               5                   10

<210> SEQ ID NO 121
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 121

Gly Thr Trp Asp Ser Ala Leu Gly Ala Ala Val
1               5                   10

<210> SEQ ID NO 122
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 122

Ala Lys Tyr Tyr Asp Ser Ser Gly Tyr Tyr Tyr Leu Asp Tyr
1               5                   10

<210> SEQ ID NO 123
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 123

Gln Gln Tyr Asn Arg Asp Pro Tyr Thr
1               5

<210> SEQ ID NO 124
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 124

Cys Arg Glu Ser Gly Glu Gly Phe Asp Pro
1               5                   10

<210> SEQ ID NO 125
<211> LENGTH: 10
<212> TYPE: PRT
<213> ORGANISM: Artificial sequence
<220> FEATURE:
<223> OTHER INFORMATION: Synthetic polypeptide
```

```
<400> SEQUENCE: 125

Gln Ser Ala Asp Arg Ser Gly Ser Val Ile
1               5                   10

<210> SEQ ID NO 126
<211> LENGTH: 26
<212> TYPE: PRT
<213> ORGANISM: Artificial sequence
<220> FEATURE:
<223> OTHER INFORMATION: Synthetic polypeptide

<400> SEQUENCE: 126

Ala Arg Asp Gln Ser His Gly Thr Phe Gly Gly Val Ile Asp Ser Thr
1               5                   10                  15

Thr Leu Phe Tyr Tyr Tyr Gly Met Asp Val
            20                  25

<210> SEQ ID NO 127
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 127

Gln Gln Arg Ser Asn Trp Pro Ser
1               5

<210> SEQ ID NO 128
<211> LENGTH: 19
<212> TYPE: PRT
<213> ORGANISM: Artificial sequence
<220> FEATURE:
<223> OTHER INFORMATION: Synthetic polypeptide

<400> SEQUENCE: 128

Ala Arg Gly Tyr Cys Ser Ser Thr Ser Cys Phe Tyr Tyr Tyr Gly
1               5                   10                  15

Met Asp Val

<210> SEQ ID NO 129
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 129

Gln Gln Ser Tyr Ser Thr Pro Leu Thr
1               5

<210> SEQ ID NO 130
<211> LENGTH: 22
<212> TYPE: PRT
<213> ORGANISM: Artificial sequence
<220> FEATURE:
<223> OTHER INFORMATION: Synthetic polypeptide

<400> SEQUENCE: 130

Ala Arg Asp His Tyr Phe Asp Ser Ser Gly Asp Tyr Leu Ser Tyr Tyr
1               5                   10                  15

Tyr Asn Gly Met Asp Val
            20
```

```
<210> SEQ ID NO 131
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 131

Gln Gln Tyr Gly Ser Ser Pro Arg Ala
1               5

<210> SEQ ID NO 132
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 132

Ala Arg Val Tyr Gly Gly Pro Asp Asp Tyr
1               5                   10

<210> SEQ ID NO 133
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 133

Gln Gln Ser Ser Ile Thr Pro Pro Thr
1               5

<210> SEQ ID NO 134
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 134

Ala Lys Asp Gly Val Thr Thr Ile Asn Gly Trp Phe His Phe Glu Tyr
1               5                   10                  15

<210> SEQ ID NO 135
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 135

Gln Gln Tyr Asn Ser Phe Pro Phe Thr
1               5

<210> SEQ ID NO 136
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 136

Thr Arg Ile Thr Gly Asp Arg Tyr Trp Tyr Leu Asp Leu
1               5                   10

<210> SEQ ID NO 137
```

```
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 137

Gln Gln Thr Tyr Ser Ala Ser Gly Ser
1               5

<210> SEQ ID NO 138
<211> LENGTH: 20
<212> TYPE: PRT
<213> ORGANISM: Artificial sequence
<220> FEATURE:
<223> OTHER INFORMATION: Synthetic polypeptide

<400> SEQUENCE: 138

Ala Arg Gly Trp Phe Gly Tyr Ser Asn Tyr Gly Leu Tyr Tyr Tyr Tyr
1               5                   10                  15

Gly Met Asp Val
            20

<210> SEQ ID NO 139
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 139

Gln Gln Ser Tyr Ser Thr Pro Trp Thr
1               5

<210> SEQ ID NO 140
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 140

Ala Arg Asp Phe Trp Ser Gly Ser Asn Trp Phe Asp Pro
1               5                   10

<210> SEQ ID NO 141
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 141

Gly Thr Trp Asp Asn Ser Leu Gly Val Val
1               5                   10

<210> SEQ ID NO 142
<211> LENGTH: 25
<212> TYPE: PRT
<213> ORGANISM: Artificial sequence
<220> FEATURE:
<223> OTHER INFORMATION: Synthetic polypeptide

<400> SEQUENCE: 142

Ala Lys Asp Ile Gly Asp Ser Tyr Gly Ser Gly Ser Tyr Tyr Leu Pro
1               5                   10                  15
```

Tyr Gly Ala Tyr Tyr Gly Met Asp Val
                20                  25

<210> SEQ ID NO 143
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 143

Gln Gln Tyr Gly Ser Ser Pro Gly
1               5

<210> SEQ ID NO 144
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 144

Ala Lys His Tyr Asp Ser Ser Gly Tyr Tyr Tyr Glu Asp Tyr
1               5                   10

<210> SEQ ID NO 145
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 145

His Gln Tyr Lys Asp Phe Pro Trp Thr
1               5

<210> SEQ ID NO 146
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 146

Ala Arg Val Arg Asp Gly Glu Tyr Asp Tyr
1               5                   10

<210> SEQ ID NO 147
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 147

Gln Gln Tyr Asn Ser Tyr Ser Pro
1               5

<210> SEQ ID NO 148
<211> LENGTH: 23
<212> TYPE: PRT
<213> ORGANISM: Artificial sequence
<220> FEATURE:
<223> OTHER INFORMATION: Synthetic polypeptide

<400> SEQUENCE: 148

Ala Arg Asp Asn Ser Glu Val Glu Asp Tyr Gly Asp Tyr Val Leu Tyr

```
1               5                   10                  15

His Tyr Tyr Gly Met Asp Val
            20

<210> SEQ ID NO 149
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 149

Gln Gln Tyr Gly Ser Ser Pro Phe
1               5

<210> SEQ ID NO 150
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 150

Ala Lys Asp Gln Cys Gly Gly Asp Cys Thr Ala Asp Tyr
1               5                   10

<210> SEQ ID NO 151
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 151

Ser Ser Tyr Thr Ser Ser Ser Thr Pro Val Val
1               5                   10

<210> SEQ ID NO 152
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 152

Ala Arg Gly Tyr Thr Gly Tyr Asp Gly Phe Asp Tyr
1               5                   10

<210> SEQ ID NO 153
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 153

Cys Ser Tyr Ala Thr Asn Tyr Gly Val Val
1               5                   10

<210> SEQ ID NO 154
<211> LENGTH: 18
<212> TYPE: PRT
<213> ORGANISM: Artificial sequence
<220> FEATURE:
<223> OTHER INFORMATION: Synthetic polypeptide

<400> SEQUENCE: 154
```

```
Ala Arg Arg Pro Tyr Tyr Gly Ser Arg Arg Pro Ala Gly His Met
1               5                   10                  15

Asp Val

<210> SEQ ID NO 155
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 155

Gln Ser Tyr Asp Ser Ser Asn Val Val
1               5

<210> SEQ ID NO 156
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 156

Gly Arg Asp Ser Asp Lys Asn Tyr Phe Asp Tyr
1               5                   10

<210> SEQ ID NO 157
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 157

Gly Ala Trp Asp Ser Ser Leu Ser Ala His Val Val
1               5                   10

<210> SEQ ID NO 158
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 158

Ala Lys Thr Tyr Asp Ser Asn Ala Tyr Tyr Tyr Leu Asp Tyr
1               5                   10

<210> SEQ ID NO 159
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 159

Gln Gln Tyr Asn Arg Tyr Pro Tyr Thr
1               5

<210> SEQ ID NO 160
<211> LENGTH: 18
<212> TYPE: PRT
<213> ORGANISM: Artificial sequence
<220> FEATURE:
<223> OTHER INFORMATION: Synthetic polypeptide
```

```
<400> SEQUENCE: 160

Ala Ser Leu Trp Phe Ile Val Met Thr Met Ser Lys Asn Pro Glu Thr
1               5                   10                  15

Asp Tyr

<210> SEQ ID NO 161
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 161

Leu Gln His His Ser Tyr Pro Trp Thr
1               5

<210> SEQ ID NO 162
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 162

Ala Lys Tyr Tyr Asp Ser Ser Gly Tyr Tyr Phe Asp His
1               5                   10

<210> SEQ ID NO 163
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 163

Gln Gln Tyr Asn Arg Asp Pro Tyr Thr
1               5

<210> SEQ ID NO 164
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 164

Ala Lys Phe Tyr Asp Ser Ser Gly Tyr Tyr Phe Asp Tyr
1               5                   10

<210> SEQ ID NO 165
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 165

Gln Gln Tyr Asn Thr Tyr Pro Tyr Thr
1               5

<210> SEQ ID NO 166
<211> LENGTH: 13
<212> TYPE: PRT
<213> ORGANISM: Artificial sequence
<220> FEATURE:
<223> OTHER INFORMATION: Synthetic polypeptide
```

```
<400> SEQUENCE: 166

Val Arg Leu Tyr Gly Asp Tyr Val Ala Tyr Phe Asp Tyr
1               5                   10

<210> SEQ ID NO 167
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 167

Gln Gln Ser Tyr Ser Thr Pro Trp Thr
1               5

<210> SEQ ID NO 168
<211> LENGTH: 21
<212> TYPE: PRT
<213> ORGANISM: Artificial sequence
<220> FEATURE:
<223> OTHER INFORMATION: Synthetic polypeptide

<400> SEQUENCE: 168

Ala Arg Arg Gly Thr Thr Val Thr Arg Phe Gly Val Ile Gln Tyr Tyr
1               5                   10                  15

Tyr Gly Met Asp Val
            20

<210> SEQ ID NO 169
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 169

Ser Ser Tyr Thr Ser Ser Ser Thr Leu Val
1               5                   10

<210> SEQ ID NO 170
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 170

Ala Arg Glu Thr Ala Asn Asn Trp Phe Asp Pro
1               5                   10

<210> SEQ ID NO 171
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 171

Gln Val Trp Asp Asn Ser Ser Asp Arg Arg Val
1               5                   10

<210> SEQ ID NO 172
<211> LENGTH: 14
<212> TYPE: PRT
<213> ORGANISM: Artificial sequence
```

```
<220> FEATURE:
<223> OTHER INFORMATION: Synthetic polypeptide

<400> SEQUENCE: 172

Ala Arg Ala Ser Met Met Pro Arg Pro Pro Val His Asp Tyr
1               5                   10

<210> SEQ ID NO 173
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 173

Gln Gln Tyr Asn Thr Trp Trp Thr
1               5

<210> SEQ ID NO 174
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 174

Ala Lys Asp Arg Ser Gln Gly Asp Tyr Gly Asp Tyr Val Ala Asp Tyr
1               5                   10                  15

<210> SEQ ID NO 175
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 175

Gln Gln Ser Tyr Ser Thr Pro Leu Thr
1               5

<210> SEQ ID NO 176
<211> LENGTH: 18
<212> TYPE: PRT
<213> ORGANISM: Artificial sequence
<220> FEATURE:
<223> OTHER INFORMATION: Synthetic polypeptide

<400> SEQUENCE: 176

Ala Arg Val Gln Thr Ser His Ser Glu Leu Trp Phe Gly Glu Phe Gly
1               5                   10                  15

Ala Asp

<210> SEQ ID NO 177
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 177

Gln Gln Tyr Asn Thr Trp Pro Lys Thr
1               5

<210> SEQ ID NO 178
<211> LENGTH: 14
<212> TYPE: PRT
```

```
<213> ORGANISM: Artificial sequence
<220> FEATURE:
<223> OTHER INFORMATION: Synthetic polypeptide

<400> SEQUENCE: 178

Ala Lys Asp Gly Gly Tyr Ser Thr Asp Trp Tyr Phe Asp Leu
1               5                   10

<210> SEQ ID NO 179
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 179

Gln Gln Tyr Gly Ser Ser Arg Arg Thr
1               5

<210> SEQ ID NO 180
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 180

Ala Lys Gly Tyr Asp Ser Asn Gly Tyr Tyr Tyr Ile Asp Tyr
1               5                   10

<210> SEQ ID NO 181
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 181

Gln Gln Tyr Asn Arg Tyr Pro Tyr Thr
1               5

<210> SEQ ID NO 182
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 182

Ala Arg Asp Val Gly Tyr Gln Leu Leu Gln Val Tyr Gly Met Asp Val
1               5                   10                  15

<210> SEQ ID NO 183
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 183

Ser Ser Tyr Thr Ser Ser Ser Thr Leu Asp Val Val
1               5                   10

<210> SEQ ID NO 184
<211> LENGTH: 21
<212> TYPE: PRT
<213> ORGANISM: Artificial sequence
```

<220> FEATURE:
<223> OTHER INFORMATION: Synthetic polypeptide

<400> SEQUENCE: 184

Ala Arg Ala Glu Tyr Asp Thr Ser Gly Tyr Tyr Gln Gln Arg Leu Pro
1               5                   10                  15

Glu Tyr Phe Gln His
            20

<210> SEQ ID NO 185
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 185

Gln Gln Tyr Asn Ser Trp Pro Pro Ile Thr
1               5                   10

<210> SEQ ID NO 186
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 186

Ala Lys Tyr Tyr Asp Ser Ser Gly Tyr Tyr Tyr Phe His Ser
1               5                   10

<210> SEQ ID NO 187
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 187

Gln Gln Tyr Asn Arg Tyr Pro Tyr Thr
1               5

<210> SEQ ID NO 188
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 188

Ala Arg Glu His Gly Asp Tyr Gly Leu Asp Tyr
1               5                   10

<210> SEQ ID NO 189
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 189

Ala Thr Trp Asp Val Ser Leu Ser Asn Asp Val Leu
1               5                   10

<210> SEQ ID NO 190
<211> LENGTH: 17

<212> TYPE: PRT
<213> ORGANISM: Artificial sequence
<220> FEATURE:
<223> OTHER INFORMATION: Synthetic polypeptide

<400> SEQUENCE: 190

Tyr Val Asp Tyr Tyr Asp Ser Ser Gly Tyr Ser Pro Phe Asp
1               5                   10                  15
Tyr

<210> SEQ ID NO 191
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 191

Gln Gln Tyr Gly Ser Ser Pro Pro Ile Thr
1               5                   10

<210> SEQ ID NO 192
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 192

Ala Arg Val Asp Gly Glu Glu Val Ala Leu Ile Tyr
1               5                   10

<210> SEQ ID NO 193
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 193

Gln Gln Ser Ser Thr Thr Arg Trp Thr
1               5

<210> SEQ ID NO 194
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 194

Val Arg Val Trp Gly Gly Glu Ala Ala Arg Tyr Asp Tyr
1               5                   10

<210> SEQ ID NO 195
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 195

Gln His Ala Ser Thr Thr Pro Trp Thr
1               5

<210> SEQ ID NO 196

```
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 196

Ser Arg His Met Gly Phe Gly Leu Asp Leu
1               5                   10

<210> SEQ ID NO 197
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 197

Gln Ala Trp Asp Thr Thr Thr Ala Gly Gly Val
1               5                   10

<210> SEQ ID NO 198
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 198

Ala Arg Asp Tyr Tyr Gly Ser Gly Asp Gly Tyr Phe Asp Tyr
1               5                   10

<210> SEQ ID NO 199
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 199

Gln Gln Tyr Gly Ser Ser Pro Arg Ala
1               5

<210> SEQ ID NO 200
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 200

Ala Arg Ile Pro Val Glu Tyr Gly Thr Pro Arg Gly Ser Phe Asp Thr
1               5                   10                  15

<210> SEQ ID NO 201
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 201

Ser Ser Tyr Gly Gly Asn Asn Asp Leu Val
1               5                   10

<210> SEQ ID NO 202
<211> LENGTH: 7
```

```
<212> TYPE: PRT
<213> ORGANISM: Artificial sequence
<220> FEATURE:
<223> OTHER INFORMATION: Synthetic polypeptide

<400> SEQUENCE: 202

Ala Gly Gly Ser Pro Asp Tyr
1               5

<210> SEQ ID NO 203
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 203

Gln Gln Arg Ser Asn Trp Pro Tyr Thr
1               5

<210> SEQ ID NO 204
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 204

Ala Arg Ala Tyr Asp Ser Arg Gly Tyr Tyr Tyr Ile Glu His
1               5                   10

<210> SEQ ID NO 205
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 205

Gln Gln Tyr Lys Thr Tyr Trp Thr
1               5

<210> SEQ ID NO 206
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 206

Ala Arg Glu Ile Asp Ser Asn Tyr Val Phe Asp Tyr
1               5                   10

<210> SEQ ID NO 207
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 207

Ser Ser Tyr Thr Ser Ser Gly Thr Asn Ile
1               5                   10

<210> SEQ ID NO 208
<211> LENGTH: 15
<212> TYPE: PRT
```

```
<213> ORGANISM: Artificial sequence
<220> FEATURE:
<223> OTHER INFORMATION: Synthetic polypeptide

<400> SEQUENCE: 208

Ala Arg Lys Leu Ser Tyr Ser Ser Gly Trp Tyr Tyr Phe Asp Tyr
1               5                   10                  15

<210> SEQ ID NO 209
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 209

Gln Gln Tyr Asn Asn Trp Pro Pro Leu Thr
1               5                   10

<210> SEQ ID NO 210
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 210

Val Thr Thr Thr Val Ile Leu Phe Asp Tyr
1               5                   10

<210> SEQ ID NO 211
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 211

Tyr Ser Thr Asp Ser Ser Gly Leu Leu Gly Val
1               5                   10

<210> SEQ ID NO 212
<211> LENGTH: 20
<212> TYPE: PRT
<213> ORGANISM: Artificial sequence
<220> FEATURE:
<223> OTHER INFORMATION: Synthetic polypeptide

<400> SEQUENCE: 212

Ala Arg Gly Arg Leu Ala Trp Gly Leu Arg Gly Gln Lys Ser Pro Asn
1               5                   10                  15

Phe Phe Ala Tyr
            20

<210> SEQ ID NO 213
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 213

Gln Gln Phe His Ser Pro Pro Trp Thr
1               5

<210> SEQ ID NO 214
```

```
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 214

Ala Thr Ala Gly Ile Phe Gly Val Val Ile Met Lys Gly Phe Asp His
1               5                   10                  15

<210> SEQ ID NO 215
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 215

Gln Gln Tyr Asn Asp Tyr Pro Trp Thr
1               5

<210> SEQ ID NO 216
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 216

Ala Arg Glu Thr Tyr Tyr Tyr Gly Ser Gly Ser Val Pro Val His Asp
1               5                   10                  15

<210> SEQ ID NO 217
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 217

Leu Gln His Asn Thr Tyr Pro Trp Thr
1               5

<210> SEQ ID NO 218
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 218

Ala Arg Gly Tyr Asp Ser Ser Gly Tyr Trp Gly Phe Gly Asp Asn
1               5                   10                  15

<210> SEQ ID NO 219
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 219

Gln Gln Tyr Tyr Ser Tyr Pro Tyr Thr
1               5

<210> SEQ ID NO 220
<211> LENGTH: 13
```

<212> TYPE: PRT
<213> ORGANISM: Artificial sequence
<220> FEATURE:
<223> OTHER INFORMATION: Synthetic polypeptide

<400> SEQUENCE: 220

Ala Arg Val Glu Gly Gly Ala Trp Gly Ala Phe Asp Ile
1               5                   10

<210> SEQ ID NO 221
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 221

Gln Ser Ala Asp Arg Ser Gly Thr Val Val
1               5                   10

<210> SEQ ID NO 222
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 222

Ala Arg Leu Trp Phe Thr Glu Tyr Pro Gly Ala Phe Asp Ile
1               5                   10

<210> SEQ ID NO 223
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 223

Ser Ser Tyr Ala Gly Ser Asn Ala Leu Val
1               5                   10

<210> SEQ ID NO 224
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 224

Ala Arg His Ser Ser Gly Ser Tyr Tyr Leu Ala Gly Tyr Tyr Phe Asp
1               5                   10                  15
Tyr

<210> SEQ ID NO 225
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 225

Gln Ser Tyr Asp Ser Ser Asn Trp Val
1               5

<210> SEQ ID NO 226

```
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 226

Ala Arg Leu Thr Asp Ser Gly Tyr Asp Asp
1               5                   10

<210> SEQ ID NO 227
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 227

His Ser Pro Asp Ser His Val Val
1               5

<210> SEQ ID NO 228
<211> LENGTH: 20
<212> TYPE: PRT
<213> ORGANISM: Artificial sequence
<220> FEATURE:
<223> OTHER INFORMATION: Synthetic polypeptide

<400> SEQUENCE: 228

Ala Arg Glu Thr Cys Ser Gly Gly Ser Cys Tyr Tyr Arg Val Gly Ser
1               5                   10                  15

Ala Phe Asp Ile
            20

<210> SEQ ID NO 229
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 229

Gln Val Trp Asp Ser Ser Ser Asp His Glu Val
1               5                   10

<210> SEQ ID NO 230
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 230

Val Lys Asp Tyr Cys Ser Gly Gly Arg Cys Tyr Ser Phe Asp Tyr
1               5                   10                  15

<210> SEQ ID NO 231
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 231

Gln Gln Trp Gly Thr
1               5
```

<210> SEQ ID NO 232
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 232

Ala Lys Ala Tyr Asp Ser Ser Ala Tyr Tyr Tyr Leu Asp Tyr
1               5                   10

<210> SEQ ID NO 233
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 233

Gln Gln Tyr Asn Arg Tyr Pro Tyr Thr
1               5

<210> SEQ ID NO 234
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 234

Ala Lys Ala Tyr Asp Ser Arg Gly Tyr Tyr Tyr Leu Asp Tyr
1               5                   10

<210> SEQ ID NO 235
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 235

Gln Gln Tyr Asn Arg Tyr Ser Tyr Thr
1               5

<210> SEQ ID NO 236
<211> LENGTH: 22
<212> TYPE: PRT
<213> ORGANISM: Artificial sequence
<220> FEATURE:
<223> OTHER INFORMATION: Synthetic polypeptide

<400> SEQUENCE: 236

Ala Lys Asp Leu Thr His Arg Leu Gly Ser Ile Phe Gly Lys Leu Thr
1               5                   10                  15

Phe Asp Ala Phe Asp Ile
            20

<210> SEQ ID NO 237
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 237

Gln Gln Tyr Asn Asn Phe Trp Thr

```
1               5

<210> SEQ ID NO 238
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 238

Ala Lys Asp Leu Thr Pro Tyr Phe Tyr Asp Ser Gly Ala Phe Asp His
1               5                   10                  15

<210> SEQ ID NO 239
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 239

His Ser Tyr Asp Ser Asn Met Ser Gly Ser Val
1               5                   10

<210> SEQ ID NO 240
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 240

Ala Arg Val Phe Gly Gly Pro Thr Asp Tyr
1               5                   10

<210> SEQ ID NO 241
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 241

Gln Lys Tyr Tyr Ser Ala Pro Leu Ile Thr
1               5                   10

<210> SEQ ID NO 242
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 242

Ala Arg Val Val Asn Gly Leu Asp Val
1               5

<210> SEQ ID NO 243
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 243

Gln Ser Ala Asp Ser Ser Val Ala Asp Ser Ser Val Val
1               5                   10
```

<210> SEQ ID NO 244
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 244

Ala Arg Gly Gln Pro Asp Tyr
1               5

<210> SEQ ID NO 245
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 245

Gln Gln Arg Ser Asn Trp Pro Tyr Thr
1               5

<210> SEQ ID NO 246
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 246

Ala Gly Lys Lys Trp Glu Leu Leu Gly Phe Arg Phe Asp Pro
1               5                   10

<210> SEQ ID NO 247
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 247

Gly Thr Trp Asp Asn Ser Leu Gly Met Val Val
1               5                   10

<210> SEQ ID NO 248
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 248

Ala Arg Gln Trp Leu Gly His Phe Asp Tyr
1               5                   10

<210> SEQ ID NO 249
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 249

Ser Ser Tyr Thr Ser Ser Ser Thr Tyr Val
1               5                   10

```
<210> SEQ ID NO 250
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 250

Ala Arg Val Phe Ser Tyr Tyr Leu Asp Tyr
1               5                   10

<210> SEQ ID NO 251
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 251

Gln Gln Pro Gly Asn Trp Pro Pro Ala Phe Thr
1               5                   10

<210> SEQ ID NO 252
<211> LENGTH: 18
<212> TYPE: PRT
<213> ORGANISM: Artificial sequence
<220> FEATURE:
<223> OTHER INFORMATION: Synthetic polypeptide

<400> SEQUENCE: 252

Ala His Arg His Ile Ala Ala Arg Leu Tyr Arg Asp Asp Asp Val Phe
1               5                   10                  15

Asp Val

<210> SEQ ID NO 253
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 253

Gln Gln Tyr Asn Asn Trp Ile Thr
1               5

<210> SEQ ID NO 254
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 254

Ala Arg Gly Leu Asn Thr Val Thr Asn Ser Asp Tyr
1               5                   10

<210> SEQ ID NO 255
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 255

Gln Gln Ala Asn Ser Phe Pro Trp Thr
1               5
```

<210> SEQ ID NO 256
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 256

Ala Ser Gly Leu Ser Pro Asp Phe Ser Val Leu Asp Val
1               5                   10

<210> SEQ ID NO 257
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 257

Met Gln Ala Leu Gln Thr Pro Tyr Thr
1               5

<210> SEQ ID NO 258
<211> LENGTH: 23
<212> TYPE: PRT
<213> ORGANISM: Artificial sequence
<220> FEATURE:
<223> OTHER INFORMATION: Synthetic polypeptide

<400> SEQUENCE: 258

Ala Arg Glu Gly Ala Gly Tyr Tyr Asp Ser Ser Gly Tyr Tyr Pro Leu
1               5                   10                  15

Ser Tyr Asp Ala Phe Asp Ile
            20

<210> SEQ ID NO 259
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 259

Ala Ala Trp Asp Asp Asn Leu Ile Gly Val Val
1               5                   10

<210> SEQ ID NO 260
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 260

Ala Arg Val Arg Gly Ser Tyr Trp Asp Tyr
1               5                   10

<210> SEQ ID NO 261
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 261

Ser Ser Phe Ala Gly Ser Asn Asn Leu Tyr Val
1               5                   10

<210> SEQ ID NO 262
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 262

Gly Arg Asp Arg Gly Trp Leu Asp Ile
1               5

<210> SEQ ID NO 263
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 263

Ser Ser Tyr Thr Arg Ser Ser Thr Arg Val
1               5                   10

<210> SEQ ID NO 264
<211> LENGTH: 23
<212> TYPE: PRT
<213> ORGANISM: Artificial sequence
<220> FEATURE:
<223> OTHER INFORMATION: Synthetic polypeptide

<400> SEQUENCE: 264

Ala Arg Val Ile Arg Asp Leu Arg Asp Tyr Tyr Asp Gly Ser Gly Tyr
1               5                   10                  15

Gly Pro Asp Ala Phe Asp Ile
            20

<210> SEQ ID NO 265
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 265

Glu Thr Trp Asp Ser Arg Leu Ser Val Val
1               5                   10

<210> SEQ ID NO 266
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 266

Ala Arg Ala Arg Trp Glu Asp Gly Asn Tyr Tyr Tyr Gly Met Asp Val
1               5                   10                  15

<210> SEQ ID NO 267
<211> LENGTH: 11
<212> TYPE: PRT
<213> ORGANISM: Artificial sequence
<220> FEATURE:
<223> OTHER INFORMATION: Synthetic polypeptide

```
<400> SEQUENCE: 267

Gly Thr Trp Asp Ser Ser Leu Ser Ala Val Val
1               5                   10

<210> SEQ ID NO 268
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 268

Ala Lys Asp Gln Ser Ser Gly Trp Pro Asn Tyr Tyr Tyr Gly Met Asp
1               5                   10                  15

Val

<210> SEQ ID NO 269
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 269

Gln Gln Ser Tyr Ser Thr Pro Trp Thr
1               5

<210> SEQ ID NO 270
<211> LENGTH: 19
<212> TYPE: PRT
<213> ORGANISM: Artificial sequence
<220> FEATURE:
<223> OTHER INFORMATION: Synthetic polypeptide

<400> SEQUENCE: 270

Val Arg Gly Tyr Cys Ser Ser Thr Ser Cys Tyr Gly Gly Leu Tyr Trp
1               5                   10                  15

Phe Asp Pro

<210> SEQ ID NO 271
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 271

Gln Gln Ser Tyr Ser Thr Pro Arg Thr
1               5

<210> SEQ ID NO 272
<211> LENGTH: 19
<212> TYPE: PRT
<213> ORGANISM: Artificial sequence
<220> FEATURE:
<223> OTHER INFORMATION: Synthetic polypeptide

<400> SEQUENCE: 272

Ala Arg His Ser Gly Gly Tyr Ser Ser Lys Asp Lys Pro Thr Glu Tyr
1               5                   10                  15

Phe Gln His

<210> SEQ ID NO 273
<211> LENGTH: 11
```

```
<212> TYPE: PRT
<213> ORGANISM: Artificial sequence
<220> FEATURE:
<223> OTHER INFORMATION: Synthetic polypeptide

<400> SEQUENCE: 273

Gln Ser Tyr Asp Ser Ser Leu Ser Gly Val Val
1               5                   10

<210> SEQ ID NO 274
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 274

Ala Arg Asp Val Gly Val Ala Ala Val Ile Thr Gly Ser Val Arg
1               5                   10                  15

<210> SEQ ID NO 275
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 275

Gln Gln Phe Tyr Thr Thr Pro Ser Thr
1               5

<210> SEQ ID NO 276
<211> LENGTH: 19
<212> TYPE: PRT
<213> ORGANISM: Artificial sequence
<220> FEATURE:
<223> OTHER INFORMATION: Synthetic polypeptide

<400> SEQUENCE: 276

Ala Arg Gly Tyr Cys Ser Ser Thr Ser Cys Tyr Gly Gly Leu Tyr Trp
1               5                   10                  15

Phe Asp Pro

<210> SEQ ID NO 277
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 277

Gln Gln Ser Tyr Ser Thr Pro Arg Thr
1               5

<210> SEQ ID NO 278
<211> LENGTH: 26
<212> TYPE: PRT
<213> ORGANISM: Artificial sequence
<220> FEATURE:
<223> OTHER INFORMATION: Synthetic polypeptide

<400> SEQUENCE: 278

Ala Arg Asp Gly Ala Gly Asp Tyr Ile Trp Gly Ser Tyr Arg His Lys
1               5                   10                  15

Gly Leu His Tyr Tyr Tyr Gly Met Asp Val
                20                  25
```

<210> SEQ ID NO 279
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 279

Leu Gln His Asn Ser Tyr Pro Leu Thr
1               5

<210> SEQ ID NO 280
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 280

Ala Lys Asp Pro Arg Thr Phe Tyr Gly Val Val Met Leu Leu Asp Asp
1               5                   10                  15

Pro

<210> SEQ ID NO 281
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 281

Gln Ser Tyr Asp Ser Thr Thr Val Val
1               5

<210> SEQ ID NO 282
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 282

Ala Arg Gly Phe Gly Glu Leu Pro Gly Phe Asp Ile
1               5                   10

<210> SEQ ID NO 283
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 283

Ser Ser Tyr Ala Gly Ser Asn Asn Phe Val Val
1               5                   10

<210> SEQ ID NO 284
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 284

Ala Arg Asp Ser Trp Gly Pro Phe Asp Tyr

```
1               5                   10
```

<210> SEQ ID NO 285
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 285

```
Gly Thr Trp Asp Ser Ser Leu Ser Ala Lys Val
1               5                   10
```

<210> SEQ ID NO 286
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 286

```
Ala Lys Thr Tyr Asp Ser Arg Ala Tyr Tyr Tyr Leu Asp Tyr
1               5                   10
```

<210> SEQ ID NO 287
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 287

```
Gln Gln Tyr Asn Arg Tyr Pro Tyr Thr
1               5
```

<210> SEQ ID NO 288
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 288

```
Ala Lys Asp Leu Phe Tyr Asp Phe Trp Thr Gly Ile Thr Ile Asp Tyr
1               5                   10                  15
```

<210> SEQ ID NO 289
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 289

```
Cys Ser Tyr Ala Gly Ser Tyr Thr Phe Val Leu
1               5                   10
```

<210> SEQ ID NO 290
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 290

```
Ala Arg Asp Gly Gly Thr Val Ser Asp Gly Leu Asp Val
1               5                   10
```

<210> SEQ ID NO 291
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 291

Gln Gln Thr Phe Ser Ile Trp Thr
1               5

<210> SEQ ID NO 292
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 292

Ala Arg Val Val Trp Tyr Ser Ser Ser His Leu Phe Asp Tyr
1               5                   10                  15

<210> SEQ ID NO 293
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 293

Gly Thr Trp Asp Ser Ser Leu Ser Ala Gly Lys Val
1               5                   10

<210> SEQ ID NO 294
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 294

Ala Arg Ile Lys Ser Asp Ala Phe Asp Leu
1               5                   10

<210> SEQ ID NO 295
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 295

Phe Ser Tyr Ala Gly Ser Asn Asn Tyr Val
1               5                   10

<210> SEQ ID NO 296
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 296

Ala Lys Phe Pro Leu Arg Asp Gly Gly Ser Gly Glu Gly Phe Asp Tyr
1               5                   10                  15

<210> SEQ ID NO 297
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 297

Met Gln Ala Ser Gln Phe Pro Leu Thr
1               5

<210> SEQ ID NO 298
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 298

Ala Arg Asn Thr Tyr Tyr Asp Arg Arg Arg Thr Phe Asp Tyr
1               5                   10

<210> SEQ ID NO 299
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 299

Gln Gln Tyr Asp Asn Leu Pro Pro Val Thr
1               5                   10

<210> SEQ ID NO 300
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 300

Ala Gly Val Gly Ile Thr Gly Thr Thr Gly Ile Asp Tyr
1               5                   10

<210> SEQ ID NO 301
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 301

Gln Ala Trp Asp Ser Ser Thr Asp Val Val
1               5                   10

<210> SEQ ID NO 302
<211> LENGTH: 18
<212> TYPE: PRT
<213> ORGANISM: Artificial sequence
<220> FEATURE:
<223> OTHER INFORMATION: Synthetic polypeptide

<400> SEQUENCE: 302

Ala Lys Gly Ala Ala Ala Gly Pro Phe Pro Tyr Phe Tyr Tyr Ala Met
1               5                   10                  15

Asp Val

<210> SEQ ID NO 303
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 303

Gln Lys Tyr Gln Ser Ala Pro Pro Thr
1               5

<210> SEQ ID NO 304
<211> LENGTH: 125
<212> TYPE: PRT
<213> ORGANISM: Artificial sequence
<220> FEATURE:
<223> OTHER INFORMATION: Synthetic polypeptide

<400> SEQUENCE: 304

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
            20                  25                  30

Phe Tyr Trp Gly Trp Ile Arg Gln Pro Pro Gly Lys Gly Leu Glu Trp
        35                  40                  45

Ile Gly Ser Met Tyr Gln Ser Gly Ile Thr Tyr Tyr Asn Pro Ser Leu
    50                  55                  60

Lys Ser Arg Val Thr Ile Ser Val Asp Thr Ser Lys Ser Gln Phe Ser
65                  70                  75                  80

Leu Lys Leu Thr Ser Val Thr Ala Ala Asp Thr Ala Met Tyr Tyr Cys
                85                  90                  95

Ala Arg Asn Ala Pro Glu Asn Tyr Tyr Gly Ser Gly Arg Glu Ser Phe
            100                 105                 110

Asp Ile Trp Gly Gln Gly Thr Met Val Thr Val Ser Ser
        115                 120                 125

<210> SEQ ID NO 305
<211> LENGTH: 122
<212> TYPE: PRT
<213> ORGANISM: Artificial sequence
<220> FEATURE:
<223> OTHER INFORMATION: Synthetic polypeptide

<400> SEQUENCE: 305

Gln Val Gln Leu Gln Glu Ser Gly Gly Asp Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Asn Trp Val Arg Gln Ala Pro Gly Lys Gly Leu Glu Trp Val
        35                  40                  45

Ser Ala Ile Asn Arg Gly Gly Asp Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp His Gly Gly Lys Tyr Gly Trp Trp Tyr Phe Asp Leu Trp
            100                 105                 110

```
Gly Arg Gly Thr Leu Val Thr Val Ser Ser
        115                 120
```

```
<210> SEQ ID NO 306
<211> LENGTH: 125
<212> TYPE: PRT
<213> ORGANISM: Artificial sequence
<220> FEATURE:
<223> OTHER INFORMATION: Synthetic polypeptide

<400> SEQUENCE: 306

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
            20                  25                  30

Phe Tyr Trp Gly Trp Ile Arg Gln Pro Pro Gly Lys Gly Leu Glu Trp
        35                  40                  45

Ile Gly Ser Met Tyr His Ser Gly Ile Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Thr Ser Val Thr Ala Ala Asp Thr Ala Met Tyr Tyr Cys
                85                  90                  95

Ala Arg Asn Ala Pro Glu Asn Tyr Tyr Gly Ser Gly Arg Glu Ser Phe
            100                 105                 110

Asp Ile Trp Gly Gln Gly Thr Thr Val Thr Val Ser Ser
        115                 120                 125
```

```
<210> SEQ ID NO 307
<211> LENGTH: 126
<212> TYPE: PRT
<213> ORGANISM: Artificial sequence
<220> FEATURE:
<223> OTHER INFORMATION: Synthetic polypeptide

<400> SEQUENCE: 307

Glu Val Gln Leu Val Glu Ser Gly Gly Gly Leu Val Gln Pro Gly Arg
1               5                   10                  15

Pro Leu Arg Leu Ser Cys Ala Ala Ser Gly Phe Ala Phe Ser Ser Tyr
            20                  25                  30

Gly Met His Trp Val Arg Gln Ala Pro Gly Lys Gly Leu Glu Trp Val
        35                  40                  45

Ala Leu Ile Arg Phe Asp Gly Thr Ile Lys Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ala Glu Asp Thr Ala Val Tyr Tyr Cys
                85                  90                  95

Ala Arg Asp Leu Glu Val Gly Ala Glu Tyr Leu Tyr Tyr His Tyr Gly
            100                 105                 110

Met Asp Val Trp Gly Gln Gly Thr Thr Val Thr Val Ser Ser
        115                 120                 125
```

```
<210> SEQ ID NO 308
<211> LENGTH: 124
<212> TYPE: PRT
<213> ORGANISM: Artificial sequence
<220> FEATURE:
<223> OTHER INFORMATION: Synthetic polypeptide
```

-continued

<400> SEQUENCE: 308

Glu Val Gln Leu Val Glu Ser Gly Gly Val Val Gln Pro Gly Arg
1               5                   10                  15

Ser Leu Arg Leu Ser Cys Ala Ala Ser Gly Phe Thr Phe Asn Ser His
            20                  25                  30

Gly Met His Trp Val Arg Gln Ala Pro Gly Lys Gly Leu Glu Trp Val
        35                  40                  45

Ala Val Ile Ser Tyr Asp Gly Thr Lys Lys Tyr Phe Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Ser Ser Leu Arg Ala Asp Asp Thr Ala Val Tyr Tyr Cys
                85                  90                  95

Ala Lys Asp Ser Ser Thr Ser Trp Tyr Gln Val Val Tyr His Ile Asp
            100                 105                 110

Tyr Trp Gly Gln Gly Thr Leu Val Thr Val Ser Ser
        115                 120

<210> SEQ ID NO 309
<211> LENGTH: 122
<212> TYPE: PRT
<213> ORGANISM: Artificial sequence
<220> FEATURE:
<223> OTHER INFORMATION: Synthetic polypeptide

<400> SEQUENCE: 309

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Asn Tyr
            20                  25                  30

Ala Met Asn Trp Val Arg Gln Thr Pro Gly Lys Gly Leu Glu Trp Val
        35                  40                  45

Ser Gly Ile Ser Gly Gly Gly Asp Ser Thr Asn Tyr Ala Asp Ser Val
    50                  55                  60

Lys Gly Arg Phe Thr Ile Ser Arg Asp Asn Ser Arg Asn Thr Leu Tyr
65                  70                  75                  80

Leu Gln Leu Asn Ser Leu Arg Ala Glu Asp Thr Ala Val Tyr Tyr Cys
                85                  90                  95

Ala Lys Asp Leu Ala Val Ser Thr Pro Arg Tyr Trp Phe Asp Ser Trp
            100                 105                 110

Gly Gln Gly Thr Leu Val Thr Val Ser Ser
        115                 120

<210> SEQ ID NO 310
<211> LENGTH: 122
<212> TYPE: PRT
<213> ORGANISM: Artificial sequence
<220> FEATURE:
<223> OTHER INFORMATION: Synthetic polypeptide

<400> SEQUENCE: 310

Glu Val Gln Leu Val Glu Ser Gly Gly Gly Leu Val Gln Pro Gly Gly
1               5                   10                  15

Ser Leu Arg Leu Ser Cys Ala Ala Ser Gly Leu Ile Phe Arg Asn Tyr
            20                  25                  30

Ala Met Ser Trp Val Arg Gln Ala Pro Gly Lys Gly Leu Glu Trp Val
        35                  40                  45

```
Ser Ser Phe Ser Gly Ser Gly Gly Ser Ala Tyr Tyr Ala Asp Ser Val
    50                  55                  60

Lys Gly Arg Phe Thr Ile Ser Arg Asp Asn Ser Lys Ser Thr Val Tyr
 65                  70                  75                  80

Leu Gln Met Asn Arg Leu Arg Val Glu Asp Thr Ala Val Tyr Tyr Cys
                 85                  90                  95

Ala Lys Asp Met Ala Val Ser Val His Arg Gly Trp Phe Asp Asp Trp
                100                 105                 110

Gly Gln Gly Thr Leu Val Thr Val Ser Ser
            115                 120
```

<210> SEQ ID NO 311
<211> LENGTH: 126
<212> TYPE: PRT
<213> ORGANISM: Artificial sequence
<220> FEATURE:
<223> OTHER INFORMATION: Synthetic polypeptide

<400> SEQUENCE: 311

```
Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Ala Phe Ser Ser Tyr
                 20                  25                  30

Gly Met His Trp Val Arg Gln Ala Pro Gly Lys Gly Leu Glu Trp Val
             35                  40                  45

Ala Gly Met Arg Phe Asp Gly Thr Lys Ile Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Phe Cys
                 85                  90                  95

Ala Arg Asp Leu Glu Val Gly Ala Glu Tyr Ile Tyr Tyr Tyr Tyr Gly
                100                 105                 110

Met Asp Val Trp Gly Gln Gly Thr Thr Val Thr Val Ser Ser
            115                 120                 125
```

<210> SEQ ID NO 312
<211> LENGTH: 122
<212> TYPE: PRT
<213> ORGANISM: Artificial sequence
<220> FEATURE:
<223> OTHER INFORMATION: Synthetic polypeptide

<400> SEQUENCE: 312

```
Gln Val Gln Leu Val Glu Ser Gly Pro Gly Leu Val Lys Pro Ser Gly
  1               5                  10                  15

Thr Leu Ser Leu Thr Cys Ala Val Ser Gly Gly Ser Ile Ser Ser Asp
                 20                  25                  30

Tyr Trp Trp Ser Trp Val Arg Gln Pro Pro Gly Lys Gly Leu Glu Tyr
             35                  40                  45

Ile Gly Glu Ile Tyr His Thr Gly Ser Thr Asn Tyr Asn Pro Ser Leu
    50                  55                  60

Lys Ser Arg Val Thr Val Ser Leu Asp Arg Ser Lys Asn Val Phe Ser
 65                  70                  75                  80

Leu Thr Leu Arg Ser Val Thr Ala Ala Asp Thr Ala Val Tyr Tyr Cys
                 85                  90                  95

Ala Arg Ser His Trp Arg Ser Pro Gln Ser Val Thr Phe Asp Leu Trp
                100                 105                 110
```

```
Gly Gln Gly Thr Thr Val Thr Val Ser Ser
        115                 120
```

<210> SEQ ID NO 313
<211> LENGTH: 123
<212> TYPE: PRT
<213> ORGANISM: Artificial sequence
<220> FEATURE:
<223> OTHER INFORMATION: Synthetic polypeptide

<400> SEQUENCE: 313

```
Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Thr Ser Ser
            20                  25                  30

Asn Trp Trp Ser Trp Val Arg Gln Pro Pro Gly Lys Gly Leu Glu Trp
        35                  40                  45

Ile Gly Asp Ile Tyr His Ser Gly Ser Thr Ser Tyr Asn Pro Ser Leu
    50                  55                  60

Lys Ser Arg Val Thr Ile Ser Val Asp Lys Ser Lys Asn His Phe Ser
65                  70                  75                  80

Leu Lys Leu Thr Ser Val Thr Ala Ala Asp Thr Ala Val Tyr Tyr Cys
                85                  90                  95

Ala Arg Ile Ala Ala Gly Tyr Ser Thr Ser Trp Tyr Tyr Phe Asp Tyr
            100                 105                 110

Trp Gly Gln Gly Thr Leu Val Thr Val Ser Ser
        115                 120
```

<210> SEQ ID NO 314
<211> LENGTH: 122
<212> TYPE: PRT
<213> ORGANISM: Artificial sequence
<220> FEATURE:
<223> OTHER INFORMATION: Synthetic polypeptide

<400> SEQUENCE: 314

```
Glu Val Gln Leu Val Glu Thr Gly Ser Gly Leu Val Arg Pro Ser Gly
1               5                   10                  15

Thr Leu Ser Leu Thr Cys Ala Val Ser Gly Asp Ser Ile Ser Ser Asn
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Tyr Asn Pro Ser Leu
    50                  55                  60

Lys Ser Arg Val Thr Ile Ser Ile Asp Lys Ser Asn Asn His Phe Ser
65                  70                  75                  80

Leu Lys Leu Thr Ser Val Thr Ala Ala Asp Thr Ala Val Tyr Tyr Cys
                85                  90                  95

Ala Lys Asp Met Trp Ala Gly Thr Thr Thr Asn Trp Phe Gly Pro Trp
            100                 105                 110

Gly Gln Gly Thr Leu Val Thr Val Ser Ser
        115                 120
```

<210> SEQ ID NO 315
<211> LENGTH: 118
<212> TYPE: PRT
<213> ORGANISM: Artificial sequence
<220> FEATURE:
<223> OTHER INFORMATION: Synthetic polypeptide

<400> SEQUENCE: 315

Gln Val Thr Leu Lys Glu Ser Gly Gly Ala Leu Val Lys Pro Ala Gly
1               5                   10                  15

Ser Leu Thr Leu Ser Cys Ala Ala Ser Gly Phe Thr Phe Gly Asp Tyr
            20                  25                  30

Tyr Met Ser Trp Ile Arg Gln Ala Pro Gly Lys Gly Leu Glu Trp Ile
        35                  40                  45

Ser Tyr Ile Ser Ser Gly Ser Ser Ile Tyr Tyr Thr Asp Ser Val
    50                  55                  60

Arg Gly Arg Phe Thr Ile Ser Arg Asp Asn Ala Arg Asn Ser Leu Tyr
65                  70                  75                  80

Leu Gln Met Asn Ser Leu Arg Val Glu Asp Thr Ala Val Tyr Tyr Cys
                85                  90                  95

Ala Arg Glu Phe Ser Ser Arg Pro Phe Asp Leu Trp Gly Gln Gly Thr
            100                 105                 110

Leu Val Thr Val Ser Ser
            115

<210> SEQ ID NO 316
<211> LENGTH: 123
<212> TYPE: PRT
<213> ORGANISM: Artificial sequence
<220> FEATURE:
<223> OTHER INFORMATION: Synthetic polypeptide

<400> SEQUENCE: 316

Glu Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asp Trp Trp Ser Trp Val Arg Gln Pro Pro Gly Lys Gly Leu Glu Trp
        35                  40                  45

Ile Gly Glu Ile Tyr His Ser Gly Ser Thr Ser Tyr Asn Pro Ser Val
    50                  55                  60

Lys Ser Arg Val Ser Ile Ser Val Asp Lys Ser Lys Asn Gln Phe Ser
65                  70                  75                  80

Leu Gln Leu Ser Ser Val Thr Ala Ala Asp Thr Ala Ile Tyr Tyr Cys
                85                  90                  95

Ala Arg Val Asn Pro Pro Gln Tyr Ser Ser Gly Trp Tyr Ser Val Tyr
            100                 105                 110

Trp Gly Gln Gly Thr Leu Val Thr Val Ser Ser
        115                 120

<210> SEQ ID NO 317
<211> LENGTH: 122
<212> TYPE: PRT
<213> ORGANISM: Artificial sequence
<220> FEATURE:
<223> OTHER INFORMATION: Synthetic polypeptide

<400> SEQUENCE: 317

Gln Val Gln Leu Gln Gln Ser Gly Pro Gly Leu Val Lys Pro Ser Gly
1               5                   10                  15

Thr Leu Ser Leu Thr Cys Ala Val Ser Gly Asp Ser Ile Ser Ser Ser
            20                  25                  30

His Trp Trp Cys Trp Val Arg Gln Pro Pro Gly Lys Gly Leu Glu Trp
        35                  40                  45

Ile Gly Glu Ile Tyr His Ser Gly Ser Thr Ser Tyr Asn Pro Ser Leu
            50                  55                  60

Lys Ser Arg Val Thr Ile Ser Val Asp Lys Ser Lys Asn Gln Phe Ser
 65                  70                  75                  80

Leu Lys Leu Ser Ser Val Thr Ala Ala Asp Thr Ala Val Tyr Phe Cys
                85                  90                  95

Ala Arg Val Ala Trp Thr Ser Ser Ser Cys Tyr Tyr Asp Tyr Trp
            100                 105                 110

Gly Gln Gly Thr Leu Val Thr Val Ser Ser
            115                 120

<210> SEQ ID NO 318
<211> LENGTH: 125
<212> TYPE: PRT
<213> ORGANISM: Artificial sequence
<220> FEATURE:
<223> OTHER INFORMATION: Synthetic polypeptide

<400> SEQUENCE: 318

Glu Val Gln Leu Val Glu Ser Gly Pro Gly Leu Val Lys Pro Ser Gly
 1               5                  10                  15

Thr Leu Ser Leu Thr Cys Ala Val Ser Gly Gly Ser Ile Ser Ser Ser
                20                  25                  30

Tyr Trp Trp Ser Trp Val Arg Gln Ser Pro Gly Lys Gly Leu Glu Trp
            35                  40                  45

Ile Gly Glu Val Tyr His Ser Gly Ser Thr His Tyr Asn Pro Ser Leu
            50                  55                  60

Lys Ser Arg Val Thr Ile Ser Val Asp Lys Ser Lys Asn Gln Phe Ser
 65                  70                  75                  80

Leu Lys Leu Thr Ser Val Thr Ala Ala Asp Thr Ala Val Tyr Tyr Cys
                85                  90                  95

Ala Arg Asp Gly Glu Gly His Tyr Tyr Arg Ser Gly Asp Asn Trp Phe
            100                 105                 110

Asp Arg Trp Gly Gln Gly Thr Leu Val Thr Val Ser Ser
            115                 120                 125

<210> SEQ ID NO 319
<211> LENGTH: 120
<212> TYPE: PRT
<213> ORGANISM: Artificial sequence
<220> FEATURE:
<223> OTHER INFORMATION: Synthetic polypeptide

<400> SEQUENCE: 319

Glu Val Gln Leu Leu Glu Ser Gly Pro Gly Leu Val Gln Pro Ser Gly
 1               5                  10                  15

Thr Leu Ser Leu Thr Cys Thr Ala Ser Gly Gly Ser Ile Ser Ser Ser
                20                  25                  30

Asn Trp Trp Ser Trp Val Arg Gln Pro Pro Gly Lys Gly Leu Glu Trp
            35                  40                  45

Ile Gly Asp Ile Tyr His Thr Gly Ser Thr Ser Tyr Asn Pro Ser Leu
            50                  55                  60

Lys Ser Arg Val Thr Ile Ser Val Asp Lys Ser Lys Asn Gln Phe Ser
 65                  70                  75                  80

Leu Lys Leu Ser Ser Val Thr Ala Ala Asp Thr Ala Val Tyr Tyr Cys
                85                  90                  95

Ala Arg Ala Glu Leu Ser Ala Trp Tyr Tyr Phe Asp His Trp Gly Gln

```
                100             105             110

Gly Thr Leu Val Thr Val Ser Ser
        115             120

<210> SEQ ID NO 320
<211> LENGTH: 126
<212> TYPE: PRT
<213> ORGANISM: Artificial sequence
<220> FEATURE:
<223> OTHER INFORMATION: Synthetic polypeptide

<400> SEQUENCE: 320

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Ile Phe Ser Asp Tyr
            20                  25                  30

Tyr Met Asn Trp Ile Arg Gln Ala Pro Gly Lys Gly Leu Asp Trp Val
        35                  40                  45

Ser Thr Ile Ser Gly Ser Gly Lys Ser Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Ser Ala Glu Asp Thr Ala Val Tyr Tyr Cys
                85                  90                  95

Ala Arg Val Ser Pro Leu Asp Asp Gly Tyr Gly Tyr Thr Tyr Tyr Gly
            100                 105                 110

Met Asp Val Trp Gly Gln Gly Thr Thr Val Thr Val Ser Ser
        115                 120                 125

<210> SEQ ID NO 321
<211> LENGTH: 123
<212> TYPE: PRT
<213> ORGANISM: Artificial sequence
<220> FEATURE:
<223> OTHER INFORMATION: Synthetic polypeptide

<400> SEQUENCE: 321

Glu Val Gln Leu Leu Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Thr Ser Ser Gly Asn Thr Lys Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Ile Ser Ser Leu Arg Ala Glu Asp Thr Ala Val Tyr Tyr Cys
                85                  90                  95

Ala Arg Asp Trp Ala Glu Leu Thr Thr Ile Thr Asn Tyr Phe Tyr Pro
            100                 105                 110

Trp Gly Gln Gly Thr Thr Val Thr Val Ser Ser
        115                 120

<210> SEQ ID NO 322
<211> LENGTH: 129
<212> TYPE: PRT
<213> ORGANISM: Artificial sequence
<220> FEATURE:
```

<223> OTHER INFORMATION: Synthetic polypeptide

<400> SEQUENCE: 322

```
Glu Val Gln Leu Leu Glu Ser Gly Gly Gly Leu Val Gln Pro Gly Arg
1               5                   10                  15
Ser Leu Arg Leu Ser Cys Ala Ala Ser Gly Phe Thr Phe Asp Asp Tyr
            20                  25                  30
Ala Met His Trp Val Arg Gln Pro Pro Gly Lys Gly Leu Glu Trp Val
        35                  40                  45
Ser Gly Ile Ser Trp Asn Gly Gly Ile Gly Tyr Ala Asp Ser Val
    50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Asp Asp Thr Ala Leu Tyr Tyr Cys
                85                  90                  95
Ala Lys Ala Glu Asn Arg Ile Gly Tyr Cys Ser Ala Gly Ser Cys Tyr
            100                 105                 110
Leu Thr Tyr Phe Asp Tyr Trp Gly Gln Gly Thr Leu Val Thr Val Ser
            115                 120                 125
Ser
```

<210> SEQ ID NO 323
<211> LENGTH: 122
<212> TYPE: PRT
<213> ORGANISM: Artificial sequence
<220> FEATURE:
<223> OTHER INFORMATION: Synthetic polypeptide

<400> SEQUENCE: 323

```
Gln Val Gln Leu Val Gln Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Ala Met Ser Trp Val Arg Gln Ala Pro Gly Lys Gly Leu Glu Trp Val
        35                  40                  45
Ser Ala Ile Ser Gly Ser Gly Gly Ser Thr Tyr Tyr Ala Asp Ser Val
    50                  55                  60
Lys Gly Arg Phe Thr Ile Ser Arg Asp Asn Ser Lys Asn Thr Leu His
65                  70                  75                  80
Leu Gln Met Ser Ser Leu Arg Ala Glu Asp Thr Ala Val Tyr Tyr Cys
                85                  90                  95
Ala Lys Asp Pro Lys Tyr Ser Ser Gly Trp Trp Ala Phe Asp Tyr Trp
            100                 105                 110
Gly Gln Gly Thr Leu Val Thr Val Ser Ser
            115                 120
```

<210> SEQ ID NO 324
<211> LENGTH: 122
<212> TYPE: PRT
<213> ORGANISM: Artificial sequence
<220> FEATURE:
<223> OTHER INFORMATION: Synthetic polypeptide

<400> SEQUENCE: 324

```
Glu Val Gln Leu Val Glu Ser Gly Pro Gly Leu Val Lys Pro Ser Gly
1               5                   10                  15
Thr Leu Ser Leu Thr Cys Ala Val Ser Gly Gly Ser Ile Ser Ser Asn
            20                  25                  30
```

```
Lys Trp Trp Ser Trp Val Arg Gln Pro Pro Gly Lys Gly Leu Glu Trp
        35                  40                  45

Ile Gly Glu Ile Tyr His Ser Gly Ser Thr Ser Tyr Asn Pro Ser Leu
 50                  55                  60

Lys Ser Arg Val Ser Ile Ser Val Asp Lys Ser Lys Asn Gln Phe Ser
65                   70                  75                  80

Leu Lys Leu Ser Ser Val Thr Ala Ala Asp Thr Ala Val Tyr Tyr Cys
                85                  90                  95

Ala Arg Val Glu Trp Ala Tyr Ser Ser Ser Trp Trp Leu Asp Tyr Trp
                100                 105                 110

Gly Gln Gly Thr Leu Val Thr Val Ser Ser
            115                 120

<210> SEQ ID NO 325
<211> LENGTH: 127
<212> TYPE: PRT
<213> ORGANISM: Artificial sequence
<220> FEATURE:
<223> OTHER INFORMATION: Synthetic polypeptide

<400> SEQUENCE: 325

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Asp
                20                  25                  30

Tyr Met Ser Trp Ile Arg Gln Ala Pro Gly Lys Gly Leu Glu Trp Val
            35                  40                  45

Ser Tyr Ile Ser Gly Ser Gly Arg Ala Met Tyr Tyr Ala Asp Ser Val
 50                 55                  60

Gln Gly Arg Phe Thr Val Ser Arg Asp Asn Ala Lys Asn Ser Leu Phe
65                  70                  75                  80

Leu Gln Met Asn Asn Leu Arg Ala Glu Asp Thr Ala Val Tyr Tyr Cys
                85                  90                  95

Ala Lys His Thr Gly Asp Lys Pro Leu Val Trp Ala Pro Ser Val Tyr
                100                 105                 110

Gly Leu Asp Val Trp Gly Gln Gly Thr Thr Val Thr Val Ser Ser
            115                 120                 125

<210> SEQ ID NO 326
<211> LENGTH: 121
<212> TYPE: PRT
<213> ORGANISM: Artificial sequence
<220> FEATURE:
<223> OTHER INFORMATION: Synthetic polypeptide

<400> SEQUENCE: 326

Gln Val Gln Leu Gln Glu Ser Gly Pro Gly Leu Val Lys Pro Ser Gly
1               5                   10                  15

Thr Leu Ser Leu Thr Cys Ala Val Ser Gly Ser Ser Ile Thr Ser Ser
                20                  25                  30

His Trp Trp Ser Trp Val Arg Gln Pro Pro Gly Lys Gly Leu Ala Trp
            35                  40                  45

Ile Gly Asp Ile Tyr His Ser Gly Gly Thr Thr Tyr Asn Pro Ser Leu
 50                 55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
```

```
                85                  90                  95
Ala Arg Val Ser Val Ser Thr Ser Ala Trp Tyr Ala Asp Tyr Trp Gly
                100                 105                 110

Gln Gly Thr Leu Val Thr Val Ser Ser
        115                 120

<210> SEQ ID NO 327
<211> LENGTH: 117
<212> TYPE: PRT
<213> ORGANISM: Artificial sequence
<220> FEATURE:
<223> OTHER INFORMATION: Synthetic polypeptide

<400> SEQUENCE: 327

Gln Val Gln Leu Val Glu Ser Gly Gly Gly Leu Val Lys Pro Gly Gly
1               5                   10                  15

Ser Leu Arg Leu Ser Cys Val Ala Ser Gly Phe Thr Phe Asn Asn Tyr
                20                  25                  30

Tyr Met Arg Trp Met Arg Gln Ala Pro Gly Lys Gly Leu Glu Trp Val
            35                  40                  45

Ser Gln Ile Ser Ser Ser Gly Ser Ile Lys Asp Tyr Ala Asp Ser Val
    50                  55                  60

Lys Gly Arg Phe Thr Val Ser Arg Asp Asn Ala Lys Asn Ser Leu Tyr
65                  70                  75                  80

Leu Gln Leu Asn Ser Leu Arg Ala Asp Asp Thr Ala Val Tyr Phe Cys
                85                  90                  95

Ala Arg Glu Leu Ser Ser Arg Ile Asp Tyr Trp Gly Gln Gly Thr Leu
                100                 105                 110

Val Thr Val Ser Ser
        115

<210> SEQ ID NO 328
<211> LENGTH: 124
<212> TYPE: PRT
<213> ORGANISM: Artificial sequence
<220> FEATURE:
<223> OTHER INFORMATION: Synthetic polypeptide

<400> SEQUENCE: 328

Glu Val Gln Leu Val Glu Ser Gly Gly Gly Val Val Gln Pro Gly Arg
1               5                   10                  15

Ser Leu Arg Leu Ser Cys Val Ala Ser Gly Phe Thr Leu Arg Ser Tyr
                20                  25                  30

Gly Met His Trp Val Arg Gln Val Pro Gly Lys Gly Leu Glu Trp Val
            35                  40                  45

Ala Val Ser Trp Tyr Asp Gly Ser Asn Lys His Tyr Ala Asp Ser Val
    50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Gln Asp Gly Gln Gln Leu Val Asn Tyr Tyr Gly Met Asp
                100                 105                 110

Val Trp Gly Gln Gly Thr Thr Val Thr Val Ser Ser
        115                 120

<210> SEQ ID NO 329
<211> LENGTH: 127
```

```
<212> TYPE: PRT
<213> ORGANISM: Artificial sequence
<220> FEATURE:
<223> OTHER INFORMATION: Synthetic polypeptide

<400> SEQUENCE: 329

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Thr Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Tyr Gly Asp Tyr Glu Ser Asn Asn Pro Ala Glu
            100                 105                 110

Tyr Phe Gln His Trp Gly Gln Gly Thr Leu Val Thr Val Ser Ser
        115                 120                 125

<210> SEQ ID NO 330
<211> LENGTH: 120
<212> TYPE: PRT
<213> ORGANISM: Artificial sequence
<220> FEATURE:
<223> OTHER INFORMATION: Synthetic polypeptide

<400> SEQUENCE: 330

Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Ser Val Ser
            20                  25                  30

Tyr Trp Ser Trp Ile Arg Gln Phe Pro Gly Lys Gly Leu Glu Trp Ile
        35                  40                  45

Gly Tyr Ile Tyr Asn Ser Gly Asn Ala Asn Tyr Asn Pro Ser Leu Glu
    50                  55                  60

Ser Arg Val Thr Ile Ser Ile Asp Thr Ser Lys Asn Arg Phe Ser Leu
65                  70                  75                  80

Arg Leu Ser Ser Val Thr Ala Ala Asp Thr Ala Val Tyr Tyr Cys Ala
                85                  90                  95

Gly His Arg Glu Asp Pro Tyr Gly Ala Tyr Gly Ala Ser Trp Gly Gln
            100                 105                 110

Gly Thr Leu Val Thr Val Ser Ser
        115                 120

<210> SEQ ID NO 331
<211> LENGTH: 123
<212> TYPE: PRT
<213> ORGANISM: Artificial sequence
<220> FEATURE:
<223> OTHER INFORMATION: Synthetic polypeptide

<400> SEQUENCE: 331

Glu Val Gln Leu Leu Glu Ser Gly Pro Gly Leu Val Lys Pro Ser Glu
1               5                   10                  15

Thr Leu Ser Leu Thr Cys Thr Val Ser Gly Gly Ser Leu Ser Ser Asp
```

```
                    20                  25                  30

Ser His Phe Trp Gly Trp Ile Arg Gln Pro Pro Gly Lys Gly Leu Glu
        35                  40                  45

Trp Ile Gly Tyr Ile Tyr Tyr Ser Gly Asn Ala Asn Tyr Asn Pro Ser
    50                  55                  60

Leu Gln Ser Arg Val Thr Ile Ser Leu Asp Lys Ser Lys Asn Gln Phe
65                  70                  75                  80

Ser Leu Arg Leu Thr Ser Val Thr Ala Ala Asp Thr Ala Val Tyr Tyr
                85                  90                  95

Cys Ala Ser Arg Lys Glu Val Arg Gly Thr Glu Asp Tyr Phe Asp Tyr
            100                 105                 110

Trp Gly Gln Gly Thr Leu Val Thr Val Ser Ser
        115                 120

<210> SEQ ID NO 332
<211> LENGTH: 123
<212> TYPE: PRT
<213> ORGANISM: Artificial sequence
<220> FEATURE:
<223> OTHER INFORMATION: Synthetic polypeptide

<400> SEQUENCE: 332

Glu Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
                20                  25                  30

Ser Tyr Tyr Trp Ser Trp Ile Arg Gln Pro Pro Gly Lys Gly Leu Glu
        35                  40                  45

Trp Ile Gly Tyr Ile Tyr Asp Ser Gly Asn Thr Asn Tyr Asn Pro Ser
    50                  55                  60

Leu Lys Ser Arg Val Thr Ile Ser Val Asp Thr Ser Lys Arg Gln Phe
65                  70                  75                  80

Ser Leu Arg Leu Thr Ser Val Thr Ala Ala Asp Thr Ala Val Tyr Tyr
                85                  90                  95

Cys Ala Lys Val Glu Glu Asp Gly Tyr Thr Asn Val Val Arg Asp Tyr
            100                 105                 110

Trp Gly Gln Gly Thr Leu Val Thr Val Ser Ser
        115                 120

<210> SEQ ID NO 333
<211> LENGTH: 117
<212> TYPE: PRT
<213> ORGANISM: Artificial sequence
<220> FEATURE:
<223> OTHER INFORMATION: Synthetic polypeptide

<400> SEQUENCE: 333

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
                20                  25                  30

Tyr Met Ser Trp Ile Arg Gln Ala Pro Gly Lys Gly Leu Glu Cys Ile
        35                  40                  45

Ala Cys Ile Ser Ser Ser Gly Ser Met Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80
```

Leu Gln Leu Asn Ser Leu Arg Val Glu Asp Thr Ala Val Tyr Tyr Cys
                85                  90                  95

Ala Arg Glu Gly Thr Arg Gly Arg Met Asp Trp Gly Gln Gly Thr Leu
            100                 105                 110

Val Thr Val Ser Ser
        115

<210> SEQ ID NO 334
<211> LENGTH: 122
<212> TYPE: PRT
<213> ORGANISM: Artificial sequence
<220> FEATURE:
<223> OTHER INFORMATION: Synthetic polypeptide

<400> SEQUENCE: 334

Glu Val Gln Leu Leu Glu Ser Gly Pro Gly Leu Val Arg Pro Ser Gly
1               5                   10                  15

Thr Leu Ser Leu Thr Cys Ala Val Ser Gly Gly Ser Ile Ser Thr Thr
            20                  25                  30

Asp Trp Trp Ser Trp Val Arg Gln Pro Pro Gly Lys Gly Leu Glu Trp
        35                  40                  45

Ile Gly Glu Ile Asn Gln Ser Gly Ser Thr Ser Tyr Ser Pro Ser Phe
    50                  55                  60

Lys Ser Arg Val Ser Ile Ser Val Asp Lys Ser Lys Arg Gln Phe Ser
65                  70                  75                  80

Leu Lys Leu Thr Ser Val Thr Ala Ala Asp Thr Ala Val Tyr Tyr Cys
                85                  90                  95

Ala Arg Asp Ser Trp Ser Gly Pro Thr Arg Asn Trp Phe Asp Pro Trp
            100                 105                 110

Gly Arg Gly Thr Leu Val Thr Val Ser Ser
        115                 120

<210> SEQ ID NO 335
<211> LENGTH: 122
<212> TYPE: PRT
<213> ORGANISM: Artificial sequence
<220> FEATURE:
<223> OTHER INFORMATION: Synthetic polypeptide

<400> SEQUENCE: 335

Glu Val Gln Leu Leu Glu Ser Gly Pro Gly Leu Val Lys Pro Ser Gly
1               5                   10                  15

Thr Leu Ser Leu Thr Cys Ala Val Ser Gly Gly Ser Ile Ser Ser Gly
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Ala Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Thr Ser Val Thr Ala Ala Asp Thr Ala Val Tyr Tyr Cys
                85                  90                  95

Ala Arg Val Val Trp Glu Tyr Ser Asn Ala Trp Cys Val Asp Phe Trp
            100                 105                 110

Gly Gln Gly Thr Thr Val Thr Val Ser Ser
        115                 120

<210> SEQ ID NO 336

<211> LENGTH: 121
<212> TYPE: PRT
<213> ORGANISM: Artificial sequence
<220> FEATURE:
<223> OTHER INFORMATION: Synthetic polypeptide

<400> SEQUENCE: 336

Glu Val Gln Leu Leu Glu Ser Gly Gly Val Val Gln Pro Gly Arg
1               5                   10                  15

Ser Leu Arg Leu Ser Cys Ala Ala Ser Gly Phe Thr Phe Thr Thr Tyr
            20                  25                  30

Ala Met His Trp Val Arg Gln Ala Pro Gly Lys Gly Leu Glu Trp Val
        35                  40                  45

Ala Ala Val Ser Tyr Asp Gly Asn Asn Lys Tyr Tyr Ala Asp Ser Val
    50                  55                  60

Lys Gly Arg Phe Thr Ile Ser Arg Asp Asn Ser Arg Asn Thr Leu Tyr
65                  70                  75                  80

Leu Gln Met Asn Ser Leu Arg Ala Glu Asp Thr Ala Val Tyr Phe Cys
                85                  90                  95

Ala Arg Asn Thr Tyr Tyr Asp Arg Ser Gly Leu Ile Ala Tyr Trp Gly
            100                 105                 110

Gln Gly Ala Leu Val Thr Val Ser Ser
        115                 120

<210> SEQ ID NO 337
<211> LENGTH: 120
<212> TYPE: PRT
<213> ORGANISM: Artificial sequence
<220> FEATURE:
<223> OTHER INFORMATION: Synthetic polypeptide

<400> SEQUENCE: 337

Gln Val Gln Leu Val Glu Ser Gly Pro Gly Leu Val Lys Pro Ser Gly
1               5                   10                  15

Thr Leu Ser Leu Thr Cys Ala Val Ser Gly Asp Ser Ile Ser Ser Thr
            20                  25                  30

Asn Trp Trp Ser Trp Val Arg Gln Pro Pro Gly Lys Gly Leu Glu Tyr
        35                  40                  45

Ile Gly Glu Ile Phe His Ser Gly Ser Thr Asn Tyr Asn Pro Phe Leu
    50                  55                  60

Lys Ser Arg Val Thr Ile Ser Val Asp Lys Ser Lys Asn His Phe Ser
65                  70                  75                  80

Leu Lys Leu Ser Ser Val Thr Ala Ala Asp Thr Ala Val Tyr Tyr Cys
                85                  90                  95

Ala Arg Gly Pro Leu Lys Ser Tyr Trp Tyr Phe Asp Leu Trp Gly Arg
            100                 105                 110

Gly Thr Leu Val Thr Val Ser Ser
        115                 120

<210> SEQ ID NO 338
<211> LENGTH: 124
<212> TYPE: PRT
<213> ORGANISM: Artificial sequence
<220> FEATURE:
<223> OTHER INFORMATION: Synthetic polypeptide

<400> SEQUENCE: 338

Gln Val Gln Leu Gln Glu Ser Gly Pro Gly Leu Val Lys Pro Ser Gly
1               5                   10                  15

Thr Leu Ser Leu Thr Cys Ala Val Ser Gly Ser Ile Ser Ser Asn
            20                  25                  30

Asn Trp Trp Ser Trp Val Arg Gln Pro Pro Lys Gly Leu Glu Trp
            35                  40                  45

Ile Gly Asp Thr Tyr His Ser Gly Ser Pro Ser Tyr Asn Pro Ser Leu
        50                  55                  60

Lys Ser Arg Val Thr Ile Ser Val Asp Lys Ser Lys Asn Glu Phe Ser
65                  70                  75                  80

Leu Lys Leu Ser Ser Val Thr Ala Ala Asp Thr Ala Val Tyr Phe Cys
                85                  90                  95

Ala Arg Tyr Cys Ser Gly Ala Thr Cys Tyr Gly Ser Asn Gly Met Asp
            100                 105                 110

Val Trp Gly Gln Gly Thr Thr Val Thr Val Ser Ser
        115                 120

<210> SEQ ID NO 339
<211> LENGTH: 120
<212> TYPE: PRT
<213> ORGANISM: Artificial sequence
<220> FEATURE:
<223> OTHER INFORMATION: Synthetic polypeptide

<400> SEQUENCE: 339

Gln Val Gln Leu Gln Glu Ser Gly Gly Gly Val Val Gln Pro Gly Arg
1               5                   10                  15

Ser Leu Arg Leu Ser Cys Ala Ala Ser Gly Phe Thr Phe Ser Asn Phe
            20                  25                  30

Gly Met His Trp Val Arg Gln Ala Pro Gly Lys Gly Leu Glu Trp Val
            35                  40                  45

Ala Ile Ile Ser Tyr Asp Arg Ser Asn Lys Asp Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Gln Cys Gly Gly Asp Cys Thr Ala Asp Tyr Trp Gly Gln
            100                 105                 110

Gly Thr Leu Val Thr Val Ser Ser
        115                 120

<210> SEQ ID NO 340
<211> LENGTH: 122
<212> TYPE: PRT
<213> ORGANISM: Artificial sequence
<220> FEATURE:
<223> OTHER INFORMATION: Synthetic polypeptide

<400> SEQUENCE: 340

Glu Val Gln Leu Leu Glu Ser Gly Pro Gly Leu Val Arg Pro Ser Gly
1               5                   10                  15

Thr Leu Ser Leu Thr Cys Ala Val Ser Gly Ala Ser Ile Ser Ser Asn
            20                  25                  30

His Trp Trp Thr Trp Val Arg Gln Pro Pro Gly Lys Gly Leu Glu Trp
            35                  40                  45

Ile Gly Glu Ile Tyr His Ser Gly Ser Pro Thr Tyr Asn Pro Ser Leu
        50                  55                  60

Lys Ser Arg Val Thr Ile Ser Val Asp Lys Ser Lys Asn Gln Phe Ser
65                  70                  75                  80

```
Leu Lys Leu Asn Ser Val Thr Ala Ala Asp Thr Ala Val Tyr Tyr Cys
                85                  90                  95

Ala Ser Thr Leu Trp Gly Gly Pro Leu Ser Val Ala Ser Asp Tyr Trp
            100                 105                 110

Gly Gln Gly Thr Leu Val Thr Val Ser Ser
        115                 120
```

<210> SEQ ID NO 341
<211> LENGTH: 121
<212> TYPE: PRT
<213> ORGANISM: Artificial sequence
<220> FEATURE:
<223> OTHER INFORMATION: Synthetic polypeptide

<400> SEQUENCE: 341

```
Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Asn Ser
                20                  25                  30

Gly Met His Trp Val Arg Gln Ala Pro Gly Gln Gly Leu Glu Trp Val
            35                  40                  45

Ala Leu Ile Ser Tyr Thr Gly Glu Thr Lys Tyr Tyr Ser Asp Ser Leu
50                  55                  60

Lys Ala Arg Phe Thr Ile Ser Arg Asp Asn Ser Lys Asn Thr Leu Tyr
65                  70                  75                  80

Leu Gln Met Ser Ser Leu Ser Asn Glu Asp Thr Ala Val Tyr Tyr Cys
                85                  90                  95

Ala Arg Asp Tyr Tyr Ala Ser Gly Asp Gly Tyr Phe Asp Tyr Trp Gly
            100                 105                 110

Gln Gly Thr Leu Val Thr Val Ser Ser
        115                 120
```

<210> SEQ ID NO 342
<211> LENGTH: 124
<212> TYPE: PRT
<213> ORGANISM: Artificial sequence
<220> FEATURE:
<223> OTHER INFORMATION: Synthetic polypeptide

<400> SEQUENCE: 342

```
Gln Val Gln Leu Gln Gln Trp Gly Pro Glu Leu Val Lys Pro Ser Gly
1               5                   10                  15

Thr Leu Ser Leu Thr Cys Thr Val Ser Gly Gly Ser Ile Ser Ser Ile
                20                  25                  30

Ser Trp Trp Ser Trp Val Arg Gln Ser Pro Gly Lys Gly Leu Glu Trp
            35                  40                  45

Ile Gly Glu Ile Asn His Ser Gly Ser Thr Val Tyr Asn Pro Ser Leu
50                  55                  60

Lys Ser Arg Val Thr Ile Ser Val Asp Lys Ser Lys Lys Gln Phe Ser
65                  70                  75                  80

Leu Lys Leu Arg Ser Val Thr Ala Ala Asp Thr Ala Val Tyr Tyr Cys
                85                  90                  95

Val Arg Tyr Cys Ser Ser Thr Ser Cys Tyr Gly Leu Asn Gly Met Asp
            100                 105                 110

Val Trp Gly Gln Gly Thr Thr Val Thr Val Ser Ser
        115                 120
```

```
<210> SEQ ID NO 343
<211> LENGTH: 119
<212> TYPE: PRT
<213> ORGANISM: Artificial sequence
<220> FEATURE:
<223> OTHER INFORMATION: Synthetic polypeptide

<400> SEQUENCE: 343

Gln Val Gln Leu Val Gln Ser Gly Gly Gly Leu Val Asn Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Asn Thr Arg Tyr Tyr Ala Asp Ser Val
    50                  55                  60

Lys Gly Arg Phe Thr Ile Ser Arg Asp Asn Ala Lys Asn Ser Leu Ser
65                  70                  75                  80

Leu Gln Met Asn Ser Leu Arg Pro Glu Asp Thr Ala Ile Tyr Tyr Cys
                85                  90                  95

Ala Arg Asp Gly Ser Leu Val Asn Ala Ile Asp Tyr Trp Gly Gln Gly
            100                 105                 110

Thr Leu Val Thr Val Ser Ser
        115

<210> SEQ ID NO 344
<211> LENGTH: 122
<212> TYPE: PRT
<213> ORGANISM: Artificial sequence
<220> FEATURE:
<223> OTHER INFORMATION: Synthetic polypeptide

<400> SEQUENCE: 344

Glu Val Gln Leu Val Glu Ser Gly Pro Gly Leu Val Lys Pro Ser Gly
1               5                   10                  15

Thr Leu Ser Leu Thr Cys Ala Val Ser Gly Gly Ser Ile Thr Gly Ser
            20                  25                  30

Asn Trp Trp Ser Trp Val Arg Gln Pro Pro Gly Lys Gly Leu Glu Trp
        35                  40                  45

Ile Gly Glu Ile Tyr His Thr Gly Ser Thr Ser Tyr Asn Pro Ser Leu
    50                  55                  60

Lys Ser Arg Val Thr Ile Ser Val Asp Asn Ser Lys Asn His Phe Ser
65                  70                  75                  80

Leu Arg Leu Thr Ser Val Thr Ala Ala Asp Thr Ala Val Tyr Tyr Cys
                85                  90                  95

Ala Arg Val Arg Trp Ser Gly Ser Thr Ser Trp Asp Leu Asp Tyr Trp
            100                 105                 110

Gly Gln Gly Thr Leu Val Thr Val Ser Ser
        115                 120

<210> SEQ ID NO 345
<211> LENGTH: 131
<212> TYPE: PRT
<213> ORGANISM: Artificial sequence
<220> FEATURE:
<223> OTHER INFORMATION: Synthetic polypeptide

<400> SEQUENCE: 345

Glu Val Thr Leu Lys Glu Ser Gly Pro Thr Leu Val Lys Pro Thr Gln
1               5                   10                  15
```

-continued

```
Thr Leu Thr Leu Thr Cys Thr Phe Ser Gly Phe Ser Leu Ser Thr Ser
             20                  25                  30

Gly Val Gly Val Gly Trp Ile Arg Gln Pro Pro Gly Lys Ala Leu Glu
         35                  40                  45

Trp Leu Ala Leu Ile Tyr Trp Asp Asp Asp Lys Arg Tyr Ser Pro Ser
 50                  55                  60

Leu Lys Ser Arg Leu Thr Ile Thr Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95

Cys Ala His Ser Pro Arg Arg Ile Thr Met Val Arg Gly Val Ile Ile
                100                 105                 110

Thr Trp Gly Asp Gly Met Asp Val Trp Gly Gln Gly Thr Thr Val Thr
            115                 120                 125

Val Ser Ser
    130

<210> SEQ ID NO 346
<211> LENGTH: 119
<212> TYPE: PRT
<213> ORGANISM: Artificial sequence
<220> FEATURE:
<223> OTHER INFORMATION: Synthetic polypeptide

<400> SEQUENCE: 346

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Thr Asp Tyr
             20                  25                  30

Tyr Met Ser Trp Ile Arg Gln Ala Pro Gly Lys Gly Leu Glu Trp Val
         35                  40                  45

Ser Tyr Ile Thr Ser Ser Gly Asn Thr Lys Tyr Tyr Ala Asp Ser Val
 50                  55                  60

Lys Gly Arg Phe Thr Ile Ser Arg Asp Asn Ala Lys Asn Ser Leu Phe
 65                  70                  75                  80

Leu Gln Met Asn Ser Leu Arg Ala Glu Asp Thr Ala Val Tyr Phe Cys
                 85                  90                  95

Ala Arg Asp Gly Ser Met Val Asn Ala Ile Asp Tyr Trp Gly Gln Gly
                100                 105                 110

Thr Leu Val Thr Val Ser Ser
        115

<210> SEQ ID NO 347
<211> LENGTH: 121
<212> TYPE: PRT
<213> ORGANISM: Artificial sequence
<220> FEATURE:
<223> OTHER INFORMATION: Synthetic polypeptide

<400> SEQUENCE: 347

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Asn Ser
             20                  25                  30

Gly Met His Trp Val Arg Gln Ala Pro Gly Lys Gly Leu Glu Trp Val
         35                  40                  45

Ser Val Ile Trp Tyr Asp Glu Ser Asn Lys Tyr Tyr Ala Asp Ser Val
```

```
                    50                  55                  60
Lys Gly Arg Phe Thr Ile Ser Arg Asp Asn Ser Lys Asn Thr Val Tyr
 65                  70                  75                  80

Leu Gln Met Asn Thr Leu Arg Ala Glu Asp Thr Ala Val Tyr Tyr Cys
                 85                  90                  95

Ala Arg Asp Ala Tyr Ala Ser Gly Asp Gly Ile Asp Tyr Trp Gly
            100                 105                 110

Gln Gly Ala Leu Val Thr Val Ser Ser
        115                 120

<210> SEQ ID NO 348
<211> LENGTH: 122
<212> TYPE: PRT
<213> ORGANISM: Artificial sequence
<220> FEATURE:
<223> OTHER INFORMATION: Synthetic polypeptide

<400> SEQUENCE: 348

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Val Ile Ser Asp Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Leu Arg Gly Val Gly Gly Trp Tyr Tyr Phe Asp Tyr Trp
            100                 105                 110

Gly Gln Gly Thr Leu Val Thr Val Ser Ser
        115                 120

<210> SEQ ID NO 349
<211> LENGTH: 121
<212> TYPE: PRT
<213> ORGANISM: Artificial sequence
<220> FEATURE:
<223> OTHER INFORMATION: Synthetic polypeptide

<400> SEQUENCE: 349

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ile Asn Tyr
                20                  25                  30

Ala Met Thr Trp Val Arg Gln Ala Pro Gly Lys Gly Leu Glu Trp Val
            35                  40                  45

Ser Ala Ile Ser Gly Asn Gly Asp Gly Thr Tyr Tyr Ala Asp Ser Val
        50                  55                  60

Lys Gly Arg Phe Thr Leu Ser Arg Asp Asn Ala Lys Asn Thr Ile Tyr
 65                  70                  75                  80

Leu His Met Ser Ala Leu Arg Asp Glu Asp Thr Ala Leu Tyr Tyr Cys
                 85                  90                  95

Ala Lys Asp Gln Gly Val Thr Thr Asp Trp Pro Ser Tyr Trp Gly
            100                 105                 110
```

```
Gln Gly Thr Leu Val Thr Val Ser Ser
        115                 120
```

<210> SEQ ID NO 350
<211> LENGTH: 126
<212> TYPE: PRT
<213> ORGANISM: Artificial sequence
<220> FEATURE:
<223> OTHER INFORMATION: Synthetic polypeptide

<400> SEQUENCE: 350

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser His Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Ile Asn Ser Leu Arg Ala Glu Asp Thr Ala Val Tyr Tyr Cys
                85                  90                  95

Pro Arg Asp Gly Leu Pro Gly Ala Asn Gln Tyr Phe Phe Tyr Tyr Gly
            100                 105                 110

Met Asp Val Trp Gly Gln Gly Thr Thr Val Thr Val Ser Ser
        115                 120                 125
```

<210> SEQ ID NO 351
<211> LENGTH: 123
<212> TYPE: PRT
<213> ORGANISM: Artificial sequence
<220> FEATURE:
<223> OTHER INFORMATION: Synthetic polypeptide

<400> SEQUENCE: 351

```
Glu Val Gln Leu Leu Glu Ser Gly Pro Arg Leu Val Lys Pro Ser Glu
1               5                   10                  15

Thr Leu Ser Leu Thr Cys Thr Val Ser Gly Gly Ser Val Arg Gly Gly
            20                  25                  30

Ser His Tyr Trp Ser Trp Ile Arg Gln Pro Pro Gly Lys Gly Leu Glu
        35                  40                  45

Trp Ile Gly Tyr Val Tyr Asp Ser Gly Ser Thr Asn Tyr Asn Pro Ser
    50                  55                  60

Leu Lys Ser Arg Val Ser Ile Ser Val Asp Met Ser Lys Lys Gln Phe
65                  70                  75                  80

Ser Leu Lys Leu Arg Ser Val Thr Ala Ala Asp Thr Ala Val Tyr His
                85                  90                  95

Cys Val Arg Val Glu Glu Tyr Val Asn Asn Glu Glu Val Arg Asp Tyr
            100                 105                 110

Trp Gly Gln Gly Thr Met Val Thr Val Ser Ser
        115                 120
```

<210> SEQ ID NO 352
<211> LENGTH: 121
<212> TYPE: PRT
<213> ORGANISM: Artificial sequence
<220> FEATURE:
<223> OTHER INFORMATION: Synthetic polypeptide -continued

```
<400> SEQUENCE: 352

Glu Val Gln Leu Leu Glu Ser Gly Gly Gly Leu Val Pro Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Asp Ser Thr Tyr Tyr Ala Asp Ser Val
    50                  55                  60

Lys Gly Arg Phe Thr Leu Ser Arg Asp Thr Ser Lys Lys Met Val Tyr
65                  70                  75                  80

Leu His Met Ser Asn Leu Arg Asp Asp Thr Ala Val Tyr Tyr Cys
                85                  90                  95

Ala Arg Asp Gln Gly Phe Thr Thr Asp Trp Pro Cys Asp Tyr Trp Gly
            100                 105                 110

Gln Gly Thr Leu Val Thr Val Ser Ser
        115                 120

<210> SEQ ID NO 353
<211> LENGTH: 119
<212> TYPE: PRT
<213> ORGANISM: Artificial sequence
<220> FEATURE:
<223> OTHER INFORMATION: Synthetic polypeptide

<400> SEQUENCE: 353

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Thr Ser Ser Gly Asn Thr Met Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Asn Phe Asn Ser Asn Leu Asp Tyr Trp Gly Gln Gly
            100                 105                 110

Thr Leu Val Thr Val Ser Ser
        115

<210> SEQ ID NO 354
<211> LENGTH: 120
<212> TYPE: PRT
<213> ORGANISM: Artificial sequence
<220> FEATURE:
<223> OTHER INFORMATION: Synthetic polypeptide

<400> SEQUENCE: 354

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45
```

```
Ile Gly Glu Ile Tyr His Ser Gly Ser Thr Thr Tyr Asn Pro Ser Leu
        50                  55                  60

Lys Ser Arg Val Thr Ile Ser Val Asp Lys Ser Lys Asn Gln Phe Ser
 65                  70                  75                  80

Leu Lys Leu Ser Ser Val Thr Ala Ala Asp Thr Ala Val Tyr Tyr Cys
                85                  90                  95

Ala Arg Gly Pro Leu Lys Thr Tyr Trp Tyr Phe Asp Leu Trp Gly Arg
                100                 105                 110

Gly Thr Leu Val Thr Val Ser Ser
                115                 120

<210> SEQ ID NO 355
<211> LENGTH: 119
<212> TYPE: PRT
<213> ORGANISM: Artificial sequence
<220> FEATURE:
<223> OTHER INFORMATION: Synthetic polypeptide

<400> SEQUENCE: 355

Glu Val Gln Leu Val Glu Ser Gly Gly Gly Leu Val Lys Pro Gly Gly
 1               5                   10                  15

Ser Leu Arg Leu Ser Cys Ala Ala Ser Gly Phe Thr Phe Ser Asp Tyr
                20                  25                  30

Tyr Met Ser Trp Ile Arg Gln Ala Pro Gly Lys Gly Leu Glu Trp Val
            35                  40                  45

Ser Tyr Ile Ser Ser Ser Gly Asn Thr Ile Tyr Tyr Ala Asp Ser Val
        50                  55                  60

Lys Gly Arg Phe Thr Ile Ser Arg Asp Asn Ala Lys Asn Ser Leu Tyr
 65                  70                  75                  80

Leu Gln Leu Asn Ser Leu Arg Ala Gly Asp Thr Ala Val Tyr Tyr Cys
                85                  90                  95

Ala Arg Asp Ser Asn Tyr Phe Tyr Gly Leu Asp Val Trp Gly Gln Gly
                100                 105                 110

Thr Thr Val Thr Val Ser Ser
                115

<210> SEQ ID NO 356
<211> LENGTH: 121
<212> TYPE: PRT
<213> ORGANISM: Artificial sequence
<220> FEATURE:
<223> OTHER INFORMATION: Synthetic polypeptide

<400> SEQUENCE: 356

Glu Val Gln Leu Val Glu Ser Gly Gly Gly Val Val Gln Pro Gly Arg
 1               5                   10                  15

Ser Leu Arg Leu Ser Cys Ala Ala Ser Gly Phe Thr Phe Ser Asn Tyr
                20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asp Ser Lys Asn Thr Leu Tyr
 65                  70                  75                  80

Leu Gln Val Asn Ser Leu Arg Ala Glu Asp Thr Ala Val Tyr Tyr Cys
                85                  90                  95

Ala Lys Asp Ile Cys Ser Gly Asp Cys Gly Gly Gly Asp Tyr Trp Gly
                100                 105                 110
```

```
<210> SEQ ID NO 357
<211> LENGTH: 119
<212> TYPE: PRT
<213> ORGANISM: Artificial sequence
<220> FEATURE:
<223> OTHER INFORMATION: Synthetic polypeptide

<400> SEQUENCE: 357

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Asn Thr Tyr
            20                  25                  30

Ala Met Thr Trp Val Arg Gln Ala Pro Gly Gln Gly Leu Glu Trp Met
        35                  40                  45

Gly Trp Ile Ser Thr Tyr Asn Gly Asn Thr Val Phe Gly Gln Lys Phe
    50                  55                  60

Gln Gly Arg Val Thr Leu Ser Thr Asp Thr Ser Thr Ser Thr Ala Tyr
65                  70                  75                  80

Met Glu Leu Arg Ser Leu Thr Ser Asp Asp Thr Ala Val Tyr Tyr Cys
                85                  90                  95

Ala Arg Glu Asp Asp Asp Tyr Tyr Ser Met Asp Val Trp Gly Gln Gly
            100                 105                 110

Thr Thr Val Thr Val Ser Ser
        115
```

(Note: position 115 shows "Gln Gly Thr Leu Val Thr Val Ser Ser" from previous sequence at top of page)

Preceding fragment from prior sequence:
```
Gln Gly Thr Leu Val Thr Val Ser Ser
        115                 120
```

```
<210> SEQ ID NO 358
<211> LENGTH: 129
<212> TYPE: PRT
<213> ORGANISM: Artificial sequence
<220> FEATURE:
<223> OTHER INFORMATION: Synthetic polypeptide

<400> SEQUENCE: 358

Glu Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ile Ser Cys Ile Ser Thr Ser Cys Tyr Gly Gly Tyr Tyr
            100                 105                 110

Tyr Tyr Gly Met Asp Val Trp Gly Gln Gly Thr Thr Val Thr Val Ser
        115                 120                 125

Ser

<210> SEQ ID NO 359
<211> LENGTH: 121
<212> TYPE: PRT
<213> ORGANISM: Artificial sequence
```

<220> FEATURE:
<223> OTHER INFORMATION: Synthetic polypeptide

<400> SEQUENCE: 359

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Ser Arg Asn Gln Asn Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Arg Asp Tyr Tyr Ala Ser Gly Asp Gly Ser Ile Asp Tyr Trp Gly
            100                 105                 110

Gln Gly Thr Leu Val Thr Val Ser Ser
        115                 120

<210> SEQ ID NO 360
<211> LENGTH: 121
<212> TYPE: PRT
<213> ORGANISM: Artificial sequence
<220> FEATURE:
<223> OTHER INFORMATION: Synthetic polypeptide

<400> SEQUENCE: 360

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Thr Phe Ser Gly Arg Gly Gly Ser Thr Tyr Tyr Ala Asp Phe Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Tyr Tyr Asp Ser Ser Gly Tyr Tyr Tyr Phe Asp Tyr Trp Gly
            100                 105                 110

Gln Gly Thr Leu Val Thr Val Ser Ser
        115                 120

<210> SEQ ID NO 361
<211> LENGTH: 120
<212> TYPE: PRT
<213> ORGANISM: Artificial sequence
<220> FEATURE:
<223> OTHER INFORMATION: Synthetic polypeptide

<400> SEQUENCE: 361

Gln Val Gln Leu Val Glu Ser Gly Gly Gly Val Val Gln Pro Gly Arg
1               5                   10                  15

Ser Leu Arg Leu Ser Cys Gly Gly Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Val Ile Ser Tyr Asp Gly Ser Lys Lys Tyr Ser Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gly Ser Val Ser Val Ala Gly Ala Asp Tyr Trp Gly Gln
            100                 105                 110

Gly Thr Leu Val Thr Val Ser Ser
            115                 120

<210> SEQ ID NO 362
<211> LENGTH: 121
<212> TYPE: PRT
<213> ORGANISM: Artificial sequence
<220> FEATURE:
<223> OTHER INFORMATION: Synthetic polypeptide

<400> SEQUENCE: 362

Glu Val Gln Leu Leu Glu Ser Gly Gly Gly Leu Val Gln Pro Gly Arg
 1               5                  10                  15

Ser Leu Arg Leu Ser Cys Ala Val Ser Gly Phe Thr Phe Ala Glu Tyr
                20                  25                  30

Ala Met His Trp Val Arg Gln Ala Pro Gly Lys Gly Leu Glu Trp Val
            35                  40                  45

Ser Ser Ile Ser Trp Asn Ser Gly Arg Ile Gly Tyr Val Asp Ser Val
 50                  55                  60

Arg Gly Arg Phe Thr Ile Ser Arg Asp Asn Ala Lys Asn Ser Leu Tyr
 65                  70                  75                  80

Leu Gln Met Asn Ser Leu Arg Val Glu Asp Thr Ala Phe Tyr Tyr Cys
                 85                  90                  95

Ala Lys Gly Tyr Asp Ser Ser Gly Tyr Tyr Trp Ala Asp Tyr Trp Gly
            100                 105                 110

Gln Gly Thr Leu Val Thr Val Ser Ser
            115                 120

<210> SEQ ID NO 363
<211> LENGTH: 120
<212> TYPE: PRT
<213> ORGANISM: Artificial sequence
<220> FEATURE:
<223> OTHER INFORMATION: Synthetic polypeptide

<400> SEQUENCE: 363

Glu Val Gln Leu Leu Glu Ser Gly Pro Gly Leu Val Lys Pro Ser Glu
 1               5                  10                  15

Thr Leu Ser Leu Thr Cys Thr Val Ser Gly Gly Ser Ile Ser Ser Tyr
                20                  25                  30

Tyr Trp Ser Trp Ile Arg Gln Pro Ala Gly Lys Gly Leu Glu Leu Ile
            35                  40                  45

Gly Arg Ile Tyr Thr Ser Gly Ser Gly Asn Tyr Asn Pro Ser Leu Lys
 50                  55                  60

Arg Arg Val Thr Met Ser Val Asp Thr Ser Lys Asn Gln Ile Ser Leu
 65                  70                  75                  80

Arg Leu Asn Ser Val Thr Ala Ala Asp Thr Ala Val Tyr Tyr Cys Ala
                 85                  90                  95

Arg Glu Arg Gly Gly Tyr Phe Thr Glu Pro Phe Asp Ile Trp Gly Gln
            100                 105                 110

Gly Thr Met Val Thr Val Ser Ser
        115                 120

<210> SEQ ID NO 364
<211> LENGTH: 119
<212> TYPE: PRT
<213> ORGANISM: Artificial sequence
<220> FEATURE:
<223> OTHER INFORMATION: Synthetic polypeptide

<400> SEQUENCE: 364

Glu Val Gln Leu Leu Glu Ser Gly Gly Gly Leu Val His Pro Gly Gly
1               5                   10                  15

Ser Leu Arg Leu Ser Cys Ala Ala Ser Gly Phe Thr Phe Ser Asp Tyr
            20                  25                  30

Glu Met Asn Trp Val Arg Gln Ala Pro Gly Lys Gly Leu Glu Trp Val
        35                  40                  45

Ser His Ile Ser Ser Ser Gly Asn Ile Ile Tyr Tyr Ala Asp Ser Val
    50                  55                  60

Lys Gly Arg Phe Thr Ile Ser Arg Asp Asn Ala Lys Asp Ser Leu Tyr
65                  70                  75                  80

Leu Gln Met Asn Ser Leu Arg Ala Glu Asp Thr Ala Val Tyr Tyr Cys
                85                  90                  95

Ala Ala Thr Ile Phe Gly Val Val Ser Phe Asp Tyr Trp Gly Gln Gly
            100                 105                 110

Thr Leu Val Thr Val Ser Ser
        115

<210> SEQ ID NO 365
<211> LENGTH: 121
<212> TYPE: PRT
<213> ORGANISM: Artificial sequence
<220> FEATURE:
<223> OTHER INFORMATION: Synthetic polypeptide

<400> SEQUENCE: 365

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
            20                  25                  30

Ala Met Ser Trp Val Arg Gln Ala Pro Gly Arg Gly Leu Glu Trp Val
        35                  40                  45

Ser Ala Ile Ser Gly Ser Asp Arg Arg Ile Tyr Tyr Ala Asp Ser Val
    50                  55                  60

Lys Gly Arg Phe Ser Ile Ser Arg Asp Asn Ser Lys Asn Thr Leu Tyr
65                  70                  75                  80

Leu Gln Met Ser Ser Leu Arg Ala Glu Asp Thr Ala Val Tyr Tyr Cys
                85                  90                  95

Ala Lys Tyr Tyr Asp Ser Ser Gly Tyr Tyr Tyr Leu Asp Tyr Trp Gly
            100                 105                 110

Gln Gly Thr Leu Val Thr Val Ser Ser
        115                 120

<210> SEQ ID NO 366
<211> LENGTH: 119
<212> TYPE: PRT

```
<213> ORGANISM: Artificial sequence
<220> FEATURE:
<223> OTHER INFORMATION: Synthetic polypeptide

<400> SEQUENCE: 366

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp His
            20                  25                  30

Tyr Met Ala Trp Val Arg Gln Ala Pro Gly Lys Gly Leu Glu Trp Val
        35                  40                  45

Gly Arg Ile Arg Asn Lys Pro Asn Ser Tyr Thr Thr Glu Tyr Ala Ala
50                  55                  60

Ser Val Lys Gly Arg Phe Thr Ile Ser Arg His Asp Ser Glu Asn Ser
65                  70                  75                  80

Leu Tyr Leu Gln Met Asn Ser Leu Lys Thr Glu Asp Thr Ala Val Tyr
                85                  90                  95

Tyr Cys Cys Arg Glu Ser Gly Gly Phe Asp Pro Trp Gly Gln Gly
            100                 105                 110

Thr Leu Val Thr Val Ser Ser
        115

<210> SEQ ID NO 367
<211> LENGTH: 133
<212> TYPE: PRT
<213> ORGANISM: Artificial sequence
<220> FEATURE:
<223> OTHER INFORMATION: Synthetic polypeptide

<400> SEQUENCE: 367

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Thr Tyr
            20                  25                  30

Gly Ile Ser Trp Val Arg Gln Ala Pro Gly Gln Gly Leu Glu Trp Met
        35                  40                  45

Gly Trp Ile Ser Gly Tyr Ser Gly Asp Thr Asn Tyr Ala Gln Lys Val
50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Gln Ser His Gly Thr Phe Gly Gly Val Ile Asp Ser Thr
            100                 105                 110

Thr Leu Phe Tyr Tyr Gly Met Asp Val Trp Gly Gln Gly Thr Thr
        115                 120                 125

Val Thr Val Ser Ser
    130

<210> SEQ ID NO 368
<211> LENGTH: 127
<212> TYPE: PRT
<213> ORGANISM: Artificial sequence
<220> FEATURE:
<223> OTHER INFORMATION: Synthetic polypeptide

<400> SEQUENCE: 368

Glu Val Gln Leu Gln Glu Ser Gly Pro Gly Leu Val Lys Pro Ser Glu
1               5                   10                  15
```

```
Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
            35                  40                  45

Trp Ile Gly Ser Ile Tyr Tyr Ser Gly Ser Thr Tyr Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                85                  90                  95

Cys Ala Arg Gly Tyr Cys Ser Ser Thr Ser Cys Phe Tyr Tyr Tyr Tyr
                100                 105                 110

Gly Met Asp Val Trp Gly Gln Gly Thr Thr Val Thr Val Ser Ser
                115                 120                 125
```

<210> SEQ ID NO 369
<211> LENGTH: 129
<212> TYPE: PRT
<213> ORGANISM: Artificial sequence
<220> FEATURE:
<223> OTHER INFORMATION: Synthetic polypeptide

<400> SEQUENCE: 369

```
Glu Val Gln Leu Val Glu Ser Gly Gly Gly Leu Val Lys Pro Gly Gly
 1               5                  10                  15

Ser Leu Arg Leu Ser Cys Val Ala Ser Gly Phe Thr Phe Ser Arg Tyr
                20                  25                  30

Ser Met Asn Trp Val Arg Gln Ala Pro Gly Lys Gly Leu Glu Trp Val
                35                  40                  45

Ser Ser Ile Ser His Ser Gly Arg Tyr Ile Tyr Tyr Ala Asp Ser Glu
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg Asp His Tyr Phe Asp Ser Ser Gly Asp Tyr Leu Ser Tyr Tyr
                100                 105                 110

Tyr Asn Gly Met Asp Val Trp Gly Gln Gly Thr Thr Val Thr Val Ser
                115                 120                 125

Ser
```

<210> SEQ ID NO 370
<211> LENGTH: 119
<212> TYPE: PRT
<213> ORGANISM: Artificial sequence
<220> FEATURE:
<223> OTHER INFORMATION: Synthetic polypeptide

<400> SEQUENCE: 370

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asp His
                20                  25                  30

Tyr Met Asp Trp Val Arg Gln Ala Pro Gly Lys Gly Leu Glu Trp Val
                35                  40                  45

Gly Arg Thr Arg Asn Lys Pro Asn Ser His Thr Thr Glu Tyr Ala Ala
 50                  55                  60
```

Ser Val Lys Gly Arg Phe Thr Ile Ser Arg Asp Asp Ser Lys Asn Ser
65                  70                  75                  80

Leu Tyr Leu Gln Met Asn Ser Leu Gln Thr Glu Asp Thr Ala Val Tyr
                85                  90                  95

Tyr Cys Ala Arg Val Tyr Gly Gly Pro Asp Asp Tyr Trp Gly Gln Gly
            100                 105                 110

Thr Leu Val Thr Val Ser Ser
        115

<210> SEQ ID NO 371
<211> LENGTH: 123
<212> TYPE: PRT
<213> ORGANISM: Artificial sequence
<220> FEATURE:
<223> OTHER INFORMATION: Synthetic polypeptide

<400> SEQUENCE: 371

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Tyr Thr Asn Tyr
            20                  25                  30

Ala Met Tyr Trp Val Arg Gln Ala Pro Gly Lys Gly Leu Glu Trp Val
        35                  40                  45

Ser Ala Ile Ser Gly Ser Gly Gly Ile Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Lys Ala Val Tyr Tyr Cys
                85                  90                  95

Ala Lys Asp Gly Val Thr Thr Ile Asn Gly Trp Phe His Phe Glu Tyr
            100                 105                 110

Trp Gly Gln Gly Thr Leu Val Thr Val Ser Ser
        115                 120

<210> SEQ ID NO 372
<211> LENGTH: 122
<212> TYPE: PRT
<213> ORGANISM: Artificial sequence
<220> FEATURE:
<223> OTHER INFORMATION: Synthetic polypeptide

<400> SEQUENCE: 372

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ile Phe Ser Asp Tyr
            20                  25                  30

Tyr Met Asp Trp Val Arg Gln Thr Pro Gly Lys Gly Pro Glu Trp Val
        35                  40                  45

Gly Arg Ile Thr Asn Arg Pro Asn Ser Tyr Thr Thr Glu Tyr Ala Ala
    50                  55                  60

Ser Val Lys Gly Arg Phe Thr Ile Ser Arg Asp Asp Ser Thr Asn Ser
65                  70                  75                  80

Leu Phe Leu His Met Asn Ser Leu Lys Thr Glu Asp Thr Ala Val Tyr
                85                  90                  95

Tyr Cys Thr Arg Ile Thr Gly Asp Arg Tyr Trp Tyr Leu Asp Leu Trp
            100                 105                 110

Gly Arg Gly Thr Leu Val Thr Val Ser Ser 115          120

<210> SEQ ID NO 373
<211> LENGTH: 128
<212> TYPE: PRT
<213> ORGANISM: Artificial sequence
<220> FEATURE:
<223> OTHER INFORMATION: Synthetic polypeptide

<400> SEQUENCE: 373

Glu Val Gln Leu Val Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Ser Tyr Tyr Trp Ser Trp Ile Arg Gln Pro Ala Gly Lys Gly Leu Glu
        35                  40                  45

Trp Ile Gly Arg Ile Tyr Thr Ser Gly Ser Thr Asn Tyr Asn Pro Ser
    50                  55                  60

Leu Lys Ser Arg Val Thr Met Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Trp Phe Gly Tyr Ser Asn Tyr Gly Leu Tyr Tyr Tyr
            100                 105                 110

Tyr Gly Met Asp Val Trp Gly Gln Gly Thr Thr Val Thr Val Ser Ser
        115                 120                 125

<210> SEQ ID NO 374
<211> LENGTH: 120
<212> TYPE: PRT
<213> ORGANISM: Artificial sequence
<220> FEATURE:
<223> OTHER INFORMATION: Synthetic polypeptide

<400> SEQUENCE: 374

Glu Val Gln Leu Val Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Glu Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Asp Phe Trp Ser Gly Ser Asn Trp Phe Asp Pro Trp Gly Gln
            100                 105                 110

Gly Thr Leu Val Thr Val Ser Ser
        115                 120

<210> SEQ ID NO 375
<211> LENGTH: 132
<212> TYPE: PRT
<213> ORGANISM: Artificial sequence
<220> FEATURE:
<223> OTHER INFORMATION: Synthetic polypeptide

<400> SEQUENCE: 375

Glu Val Gln Leu Leu Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
            85                  90                  95

Ala Lys Asp Ile Gly Asp Ser Tyr Gly Ser Gly Ser Tyr Tyr Leu Pro
            100                 105                 110

Tyr Gly Ala Tyr Tyr Gly Met Asp Val Trp Gly Gln Gly Thr Thr Val
        115                 120                 125

Thr Val Ser Ser
        130

<210> SEQ ID NO 376
<211> LENGTH: 121
<212> TYPE: PRT
<213> ORGANISM: Artificial sequence
<220> FEATURE:
<223> OTHER INFORMATION: Synthetic polypeptide

<400> SEQUENCE: 376

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Thr Gly Arg Gly Leu Glu Trp Val
        35                  40                  45

Ser Ser Ile Arg Ser Ser Gly Gly Arg Thr Glu Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asp Ser Leu Arg Ala Glu Asp Thr Ala Leu Tyr Tyr Cys
            85                  90                  95

Ala Lys His Tyr Asp Ser Ser Gly Tyr Tyr Tyr Glu Asp Tyr Trp Gly
            100                 105                 110

Gln Gly Thr Leu Val Thr Val Ser Ser
        115                 120

<210> SEQ ID NO 377
<211> LENGTH: 119
<212> TYPE: PRT
<213> ORGANISM: Artificial sequence
<220> FEATURE:
<223> OTHER INFORMATION: Synthetic polypeptide

<400> SEQUENCE: 377

Glu Val Gln Leu Val Glu Ser Gly Gly Ala Leu Val His Pro Gly Gly
1               5                   10                  15

Ser Leu Gly Leu Ser Cys Ala Ala Ser Gly Phe Thr Phe Ser Asp His
            20                  25                  30

Tyr Met Asp Trp Val Arg Gln Ala Pro Gly Lys Gly Leu Glu Trp Val 35                  40                  45
Gly Arg Ile Arg Asn Lys Pro Asn Ser Tyr Ala Thr Gln Tyr Ala Ala
        50                  55                  60

Ser Val Lys Gly Arg Phe Thr Ile Ser Arg Asp Asp Ser Lys Lys Ser
65                  70                  75                  80

Leu Tyr Leu Gln Met Asn Ser Leu Asn Thr Glu Asp Thr Ala Val Tyr
                85                  90                  95

Tyr Cys Ala Arg Val Arg Asp Gly Glu Tyr Asp Tyr Trp Gly Gln Gly
            100                 105                 110

Thr Leu Val Thr Val Ser Ser
        115

<210> SEQ ID NO 378
<211> LENGTH: 130
<212> TYPE: PRT
<213> ORGANISM: Artificial sequence
<220> FEATURE:
<223> OTHER INFORMATION: Synthetic polypeptide

<400> SEQUENCE: 378

Glu Val Gln Leu Leu Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Arg Ser Ser Phe Met Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Val Glu Asp Thr Ala Val Tyr Tyr Cys
                85                  90                  95

Ala Arg Asp Asn Ser Glu Val Glu Asp Tyr Gly Asp Tyr Val Leu Tyr
            100                 105                 110

His Tyr Tyr Gly Met Asp Val Trp Gly Gln Gly Thr Thr Val Thr Val
        115                 120                 125

Ser Ser
    130

<210> SEQ ID NO 379
<211> LENGTH: 120
<212> TYPE: PRT
<213> ORGANISM: Artificial sequence
<220> FEATURE:
<223> OTHER INFORMATION: Synthetic polypeptide

<400> SEQUENCE: 379

Glu Val Gln Leu Leu Glu Ser Gly Gly Gly Val Val Gln Pro Gly Arg
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Leu Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

```
Leu Gln Met Asn Ser Leu Arg Ala Glu Asp Thr Ala Val Tyr Tyr Cys
                85                  90                  95

Ala Lys Asp Gln Cys Gly Gly Asp Cys Thr Ala Asp Tyr Trp Gly Gln
            100                 105                 110

Gly Thr Leu Val Thr Val Ser Ser
        115                 120
```

<210> SEQ ID NO 380
<211> LENGTH: 119
<212> TYPE: PRT
<213> ORGANISM: Artificial sequence
<220> FEATURE:
<223> OTHER INFORMATION: Synthetic polypeptide

<400> SEQUENCE: 380

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Leu
            20                  25                  30

Ala Met His Trp Val Arg Gln Ala Pro Gly Lys Gly Leu Glu Trp Val
        35                  40                  45

Ala Thr Ile Ser Tyr Asp Val Ser Asn Lys Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Pro Glu Asp Thr Ala Val Tyr Tyr Cys
                85                  90                  95

Ala Arg Gly Tyr Thr Gly Tyr Asp Gly Phe Asp Tyr Trp Gly Gln Gly
            100                 105                 110

Thr Leu Val Thr Val Ser Ser
        115
```

<210> SEQ ID NO 381
<211> LENGTH: 125
<212> TYPE: PRT
<213> ORGANISM: Artificial sequence
<220> FEATURE:
<223> OTHER INFORMATION: Synthetic polypeptide

<400> SEQUENCE: 381

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Arg Pro Tyr Tyr Tyr Gly Ser Arg Arg Pro Ala Gly His Met
            100                 105                 110

Asp Val Trp Gly Gln Gly Thr Thr Val Thr Val Ser Ser
        115                 120                 125
```

<210> SEQ ID NO 382

<211> LENGTH: 119
<212> TYPE: PRT
<213> ORGANISM: Artificial sequence
<220> FEATURE:
<223> OTHER INFORMATION: Synthetic polypeptide

<400> SEQUENCE: 382

Gln Val Gln Leu Gln Glu Ser Gly Pro Gly Leu Val Arg Pro Ser Gln
1               5                   10                  15

Thr Leu Ser Leu Thr Cys Thr Val Ser Gly Gly Ala Ile Ser Ser Gly
            20                  25                  30

Asp Tyr Tyr Trp Ser Trp Val Arg Gln Pro Pro Gly Lys Gly Leu Glu
        35                  40                  45

Trp Ile Gly Tyr Ile His Tyr Ser Gly Thr Thr Tyr Asn Asn Pro Ser
    50                  55                  60

Leu Lys Ser Arg Val Thr Ile Ala Val Asp Thr Ser Lys Asn Gln Phe
65                  70                  75                  80

Ser Leu Lys Leu Ser Ser Val Thr Ala Ala Asp Thr Ala Val Tyr Phe
                85                  90                  95

Cys Gly Arg Asp Ser Asp Lys Asn Tyr Phe Asp Tyr Trp Gly Gln Gly
            100                 105                 110

Thr Leu Val Thr Val Ser Ser
        115

<210> SEQ ID NO 383
<211> LENGTH: 121
<212> TYPE: PRT
<213> ORGANISM: Artificial sequence
<220> FEATURE:
<223> OTHER INFORMATION: Synthetic polypeptide

<400> SEQUENCE: 383

Glu Val Gln Leu Val Glu Ser Gly Gly Gly Val Val Arg Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Arg Phe Asp Gly Ser Asn Thr Val Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Thr Tyr Asp Ser Asn Ala Tyr Tyr Tyr Leu Asp Tyr Trp Gly
            100                 105                 110

Gln Gly Thr Leu Val Thr Val Ser Ser
        115                 120

<210> SEQ ID NO 384
<211> LENGTH: 125
<212> TYPE: PRT
<213> ORGANISM: Artificial sequence
<220> FEATURE:
<223> OTHER INFORMATION: Synthetic polypeptide

<400> SEQUENCE: 384

Glu Val Gln Leu Val Glu Ser Gly Gly Gly Val Val Gln Pro Gly Trp
1               5                   10                  15

-continued

```
Ser Leu Arg Leu Ser Cys Ala Val Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Tyr Lys Trp Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Ser Leu Trp Phe Ile Val Met Thr Met Ser Lys Asn Pro Glu Thr
            100                 105                 110

Asp Tyr Trp Gly Gln Gly Thr Leu Val Thr Val Ser Ser
        115                 120                 125

<210> SEQ ID NO 385
<211> LENGTH: 121
<212> TYPE: PRT
<213> ORGANISM: Artificial sequence
<220> FEATURE:
<223> OTHER INFORMATION: Synthetic polypeptide

<400> SEQUENCE: 385

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Ser Phe Ser Ser His
            20                  25                  30

Ala Met Thr Trp Val Arg Gln Ala Pro Gly Lys Gly Leu Gln Trp Val
        35                  40                  45

Ser Ser Ile Arg Gly Ser Asp Arg Thr Thr Asn Tyr Ala Asp Ser Val
    50                  55                  60

Lys Gly Arg Phe Thr Val Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Lys Tyr Tyr Asp Ser Ser Gly Tyr Tyr Tyr Phe Asp His Trp Gly
            100                 105                 110

Gln Gly Thr Leu Val Thr Val Ser Ser
        115                 120

<210> SEQ ID NO 386
<211> LENGTH: 121
<212> TYPE: PRT
<213> ORGANISM: Artificial sequence
<220> FEATURE:
<223> OTHER INFORMATION: Synthetic polypeptide

<400> SEQUENCE: 386

Glu Val Gln Leu Val Glu Ser Gly Gly Thr Phe Leu Gln Pro Gly Gly
1               5                   10                  15

Ser Leu Arg Leu Ser Cys Val Ala Ser Gly Phe Thr Phe Gly Thr His
            20                  25                  30

Ala Met Ser Trp Val Arg Gln Ala Pro Gly Lys Gly Leu Glu Trp Val
        35                  40                  45

Ser Thr Phe Ser Gly Ser Gly Gly Arg Thr Tyr Tyr Ala Asp Ser Val
    50                  55                  60

Lys Gly Arg Phe Thr Ile Ser Arg Asp Asn Ser Lys Ser Thr Leu Tyr
65                  70                  75                  80
```

```
Leu Glu Met Ser Ala Leu Arg Ala Glu Asp Thr Ala Val Tyr Tyr Cys
                85                  90                  95

Ala Lys Phe Tyr Asp Ser Ser Gly Tyr Tyr Phe Asp Tyr Trp Gly
            100                 105                 110

Gln Gly Thr Leu Val Thr Val Ser Ser
        115                 120

<210> SEQ ID NO 387
<211> LENGTH: 122
<212> TYPE: PRT
<213> ORGANISM: Artificial sequence
<220> FEATURE:
<223> OTHER INFORMATION: Synthetic polypeptide

<400> SEQUENCE: 387

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Asp Trp Val Arg Gln Ala Pro Gly Lys Gly Leu Glu Trp Val
        35                  40                  45

Gly Gly Ile Arg Asn Lys Pro Asn Ser Tyr Thr Thr Glu Tyr Ala Ala
    50                  55                  60

Ser Val Lys Gly Arg Phe Thr Ile Ser Arg Asp Asp Ser Lys Asn Ser
65                  70                  75                  80

Leu Phe Leu Gln Met Asn Ser Leu Lys Thr Glu Asp Thr Ala Val Tyr
                85                  90                  95

Tyr Cys Val Arg Leu Tyr Gly Asp Tyr Val Ala Tyr Phe Asp Tyr Trp
            100                 105                 110

Gly Gln Gly Thr Leu Val Thr Val Ser Ser
        115                 120

<210> SEQ ID NO 388
<211> LENGTH: 128
<212> TYPE: PRT
<213> ORGANISM: Artificial sequence
<220> FEATURE:
<223> OTHER INFORMATION: Synthetic polypeptide

<400> SEQUENCE: 388

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Arg Gly Thr Thr Val Thr Arg Phe Gly Val Ile Gln Tyr Tyr
            100                 105                 110

Tyr Gly Met Asp Val Trp Gly Gln Gly Thr Thr Val Thr Val Ser Ser
        115                 120                 125
```

```
<210> SEQ ID NO 389
<211> LENGTH: 117
<212> TYPE: PRT
<213> ORGANISM: Artificial sequence
<220> FEATURE:
<223> OTHER INFORMATION: Synthetic polypeptide

<400> SEQUENCE: 389

Gln Val Gln Leu Gln Glu Ser Gly Pro Gly Leu Val Lys Pro Ser Glu
1               5                   10                  15

Thr Leu Ser Leu Thr Cys Thr Val Ser Gly Ala Ser Ile Arg Ser Tyr
            20                  25                  30

Leu Trp Ser Trp Ile Arg Gln Pro Pro Gly Lys Glu Leu Glu Trp Leu
        35                  40                  45

Gly Ser Ile Tyr His Ser Gly Ser Thr Lys Tyr Asn Pro Ser Leu Lys
    50                  55                  60

Ser Arg Val Thr Ile Ser Ala Asp Thr Ser Lys Asn Gln Phe Ser Leu
65                  70                  75                  80

Lys Leu Asn Ser Val Thr Ala Ala Asp Thr Ala Val Tyr Phe Cys Ala
                85                  90                  95

Arg Glu Thr Ala Asn Asn Trp Phe Asp Pro Trp Gly Gln Gly Thr Leu
            100                 105                 110

Val Thr Val Ser Ser
        115

<210> SEQ ID NO 390
<211> LENGTH: 121
<212> TYPE: PRT
<213> ORGANISM: Artificial sequence
<220> FEATURE:
<223> OTHER INFORMATION: Synthetic polypeptide

<400> SEQUENCE: 390

Glu Val Gln Leu Val Glu Ser Gly Gly Gly Val Val Gln Ser Gly Arg
1               5                   10                  15

Ser Leu Arg Leu Ser Cys Ala Ala Ser Gly Phe Thr Phe Ser Gly Asn
            20                  25                  30

Ala Met His Trp Val Arg Gln Ala Pro Gly Lys Gly Leu Glu Trp Val
        35                  40                  45

Ala Val Ile Leu Tyr Asp Gly Ser Asn Gln Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Ala Asp Thr Ala Val Tyr Tyr Cys
                85                  90                  95

Ala Arg Ala Ser Met Met Pro Arg Pro Pro Val His Asp Tyr Trp Gly
            100                 105                 110

Gln Gly Thr Leu Val Thr Val Ser Ser
        115                 120

<210> SEQ ID NO 391
<211> LENGTH: 123
<212> TYPE: PRT
<213> ORGANISM: Artificial sequence
<220> FEATURE:
<223> OTHER INFORMATION: Synthetic polypeptide

<400> SEQUENCE: 391

Glu Val Gln Leu Leu Glu Ser Gly Gly Gly Leu Val Gln Pro Gly Gly
1               5                   10                  15
```

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Ser Gln Gly Asp Tyr Gly Asp Tyr Val Ala Asp Tyr
            100                 105                 110

Trp Ser Gln Gly Thr Leu Val Thr Val Ser Ser
        115                 120

<210> SEQ ID NO 392
<211> LENGTH: 125
<212> TYPE: PRT
<213> ORGANISM: Artificial sequence
<220> FEATURE:
<223> OTHER INFORMATION: Synthetic polypeptide

<400> SEQUENCE: 392

Glu Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
                20                  25                  30

Asn Trp Trp Thr Trp Val Arg Gln Pro Pro Gly Lys Gly Leu Glu Trp
            35                  40                  45

Ile Gly Glu Ile Tyr His Ser Gly Ser Thr Asn Tyr Asn Pro Ser Leu
        50                  55                  60

Glu Ser Arg Val Thr Met Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Val Gln Thr Ser His Ser Glu Leu Trp Phe Gly Glu Phe Gly
            100                 105                 110

Ala Asp Trp Gly Gln Gly Thr Leu Val Thr Val Ser Ser
        115                 120                 125

<210> SEQ ID NO 393
<211> LENGTH: 121
<212> TYPE: PRT
<213> ORGANISM: Artificial sequence
<220> FEATURE:
<223> OTHER INFORMATION: Synthetic polypeptide

<400> SEQUENCE: 393

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Tyr Tyr
                20                  25                  30

Ala Met Ser Trp Val Arg Gln Ala Pro Gly Lys Gly Leu Glu Trp Val
            35                  40                  45

Ser Gly Ile Ser Gly Ser Gly Asp Ser Thr Tyr Asn Ala Asp Ser Val
        50                  55                  60

Lys Gly Arg Val Thr Ile Ser Arg Asp Asn Ser Lys Asn Thr Leu Tyr

```
              65                  70                  75                  80
Leu Gln Met Asn Ser Leu Arg Ala Glu Asp Thr Ala Val Tyr Tyr Cys
                    85                  90                  95

Ala Lys Asp Gly Gly Tyr Ser Thr Asp Trp Tyr Phe Asp Leu Trp Gly
                100                 105                 110

Arg Gly Thr Leu Val Thr Val Ser Ser
            115                 120
```

<210> SEQ ID NO 394
<211> LENGTH: 121
<212> TYPE: PRT
<213> ORGANISM: Artificial sequence
<220> FEATURE:
<223> OTHER INFORMATION: Synthetic polypeptide

<400> SEQUENCE: 394

```
Gln Val Gln Leu Val Glu Ser Gly Gly Gly Val Val Gln Pro Gly Arg
1               5                   10                  15

Ser Leu Arg Leu Ser Cys Thr Ala Ser Gly Phe Thr Phe Ser Ser Tyr
                20                  25                  30

Gly Met His Trp Val Arg Gln Ala Pro Gly Lys Gly Pro Glu Trp Val
            35                  40                  45

Ala Val Ile Ser Tyr Asp Gly Ser Lys Lys Tyr Phe Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Ser Cys
                    85                  90                  95

Ala Lys Gly Tyr Asp Ser Asn Gly Tyr Tyr Tyr Ile Asp Tyr Trp Gly
                100                 105                 110

Gln Gly Thr Pro Val Thr Val Ser Ser
            115                 120
```

<210> SEQ ID NO 395
<211> LENGTH: 123
<212> TYPE: PRT
<213> ORGANISM: Artificial sequence
<220> FEATURE:
<223> OTHER INFORMATION: Synthetic polypeptide

<400> SEQUENCE: 395

```
Gln Val Gln Leu Gln Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                    85                  90                  95

Ala Arg Asp Val Gly Tyr Gln Leu Leu Gln Val Tyr Gly Met Asp Val
                100                 105                 110

Trp Gly Gln Gly Thr Thr Val Thr Val Ser Ser
            115                 120
```

<210> SEQ ID NO 396
<211> LENGTH: 129
<212> TYPE: PRT
<213> ORGANISM: Artificial sequence
<220> FEATURE:
<223> OTHER INFORMATION: Synthetic polypeptide

<400> SEQUENCE: 396

Glu Val Gln Leu Leu Glu Ser Gly Pro Gly Leu Val Lys Pro Ser Gln
1               5                   10                  15

Thr Leu Ser Leu Thr Cys Ser Val Ser Gly Gly Ser Ile Ser Ser Gly
            20                  25                  30

Gly Tyr Tyr Trp Thr Trp Ile Arg Gln Pro Pro Gly Lys Gly Leu Glu
        35                  40                  45

Trp Ile Gly Tyr Ile Tyr Tyr Thr Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Phe
                85                  90                  95

Cys Ala Arg Ala Glu Tyr Asp Thr Ser Gly Tyr Tyr Gln Gln Arg Leu
            100                 105                 110

Pro Glu Tyr Phe Gln His Trp Gly Gln Gly Thr Leu Val Thr Val Ser
        115                 120                 125

Ser

<210> SEQ ID NO 397
<211> LENGTH: 121
<212> TYPE: PRT
<213> ORGANISM: Artificial sequence
<220> FEATURE:
<223> OTHER INFORMATION: Synthetic polypeptide

<400> SEQUENCE: 397

Glu Val Gln Leu Val Gln Ser Gly Gly Gly Leu Val Gln Arg Gly Gly
1               5                   10                  15

Ser Leu Arg Leu Ser Cys Ala Ala Ser Gly Phe Thr Phe Ser Ser Tyr
            20                  25                  30

Ala Met Thr Trp Val Arg Gln Ala Pro Gly Lys Gly Leu Glu Trp Val
        35                  40                  45

Ser Asp Met Asn His Ser Gly Asp Arg Thr Asn Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Tyr Tyr Asp Ser Ser Gly Tyr Tyr Tyr Phe His Ser Trp Gly
            100                 105                 110

Gln Gly Thr Leu Val Thr Val Ser Ser
        115                 120

<210> SEQ ID NO 398
<211> LENGTH: 120
<212> TYPE: PRT
<213> ORGANISM: Artificial sequence
<220> FEATURE:
<223> OTHER INFORMATION: Synthetic polypeptide

<400> SEQUENCE: 398

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ile Phe Ser Asp His
            20                  25                  30

Tyr Met Ala Trp Val Arg Gln Ala Pro Gly Lys Gly Leu Glu Trp Val
        35                  40                  45

Gly Arg Ser Arg Asn Arg Pro Asn Ser Tyr Thr Thr Glu Tyr Ala Ala
    50                  55                  60

Ser Ala Lys Gly Arg Phe Thr Ile Ser Arg Asp Asp Ser Lys Thr Ser
65                  70                  75                  80

Leu Tyr Leu Gln Met Asn Ser Leu Lys Thr Glu Asp Thr Ala Val Tyr
                85                  90                  95

Tyr Cys Ala Arg Glu His Gly Asp Tyr Gly Leu Asp Tyr Trp Gly Gln
            100                 105                 110

Gly Thr Leu Val Thr Val Ser Ser
            115                 120

<210> SEQ ID NO 399
<211> LENGTH: 124
<212> TYPE: PRT
<213> ORGANISM: Artificial sequence
<220> FEATURE:
<223> OTHER INFORMATION: Synthetic polypeptide

<400> SEQUENCE: 399

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Arg Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Tyr Val Asp Tyr Tyr Asp Ser Ser Gly Tyr Tyr Ser Pro Phe Asp
            100                 105                 110

Tyr Trp Gly Gln Gly Thr Leu Val Thr Val Ser Ser
        115                 120

<210> SEQ ID NO 400
<211> LENGTH: 121
<212> TYPE: PRT
<213> ORGANISM: Artificial sequence
<220> FEATURE:
<223> OTHER INFORMATION: Synthetic polypeptide

<400> SEQUENCE: 400

Glu Val Gln Leu Val Glu Ser Gly Gly Gly Phe Val Gln Pro Gly Gly
1               5                   10                  15

Ser Leu Arg Leu Ser Cys Ala Ala Ser Gly Phe Ile Phe Ser Asp Tyr
            20                  25                  30

Tyr Met Asp Trp Val Arg Gln Ala Pro Gly Lys Gly Leu Glu Trp Val
        35                  40                  45

Gly Arg Ile Arg Asn Lys Pro Asn Ser Tyr Thr Thr Glu Tyr Ala Ala

```
                    50                  55                  60

Ser Val Lys Gly Arg Phe Ser Ile Ser Arg Asp Asp Leu Lys Asn Ser
 65                  70                  75                  80

Leu Tyr Leu Gln Met Asn Ser Leu Lys Thr Glu Asp Thr Ala Glu Tyr
                     85                  90                  95

Tyr Cys Ala Arg Val Asp Gly Glu Glu Val Ala Leu Ile Tyr Trp Gly
                100                 105                 110

Gln Gly Ala Leu Val Thr Val Ser Ser
            115                 120

<210> SEQ ID NO 401
<211> LENGTH: 122
<212> TYPE: PRT
<213> ORGANISM: Artificial sequence
<220> FEATURE:
<223> OTHER INFORMATION: Synthetic polypeptide

<400> SEQUENCE: 401

Glu Val Gln Leu Leu Glu Ser Gly Gly Gly Leu Gly Gln Pro Gly Gly
  1               5                  10                  15

Ser Leu Arg Leu Ser Cys Val Ala Ser Lys Phe Thr Phe Ser Asp His
                 20                  25                  30

Tyr Met Asp Trp Val Arg Gln Ala Pro Gly Lys Gly Leu Glu Trp Val
             35                  40                  45

Gly Arg Ile Arg Asn Lys Pro Asn Gly Tyr Thr Thr Glu Tyr Ala Ala
 50                  55                  60

Ser Val Lys Gly Arg Phe Ile Ile Ser Arg Asp Asp Ser Lys Asn Ser
 65                  70                  75                  80

Leu Tyr Leu Gln Met Lys Ser Leu Lys Ile Glu Asp Thr Ala Ile Tyr
                     85                  90                  95

Tyr Cys Val Arg Val Trp Gly Gly Glu Ala Ala Arg Tyr Asp Tyr Trp
                100                 105                 110

Gly Gln Gly Ala Leu Val Thr Val Ser Ser
            115                 120

<210> SEQ ID NO 402
<211> LENGTH: 119
<212> TYPE: PRT
<213> ORGANISM: Artificial sequence
<220> FEATURE:
<223> OTHER INFORMATION: Synthetic polypeptide

<400> SEQUENCE: 402

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Asp His
                 20                  25                  30

Tyr Met Asp Trp Val Arg Gln Ala Pro Gly Lys Gly Leu Glu Trp Val
             35                  40                  45

Gly Arg Ser Arg Asn Lys Pro Asn Ser Tyr Ile Thr Glu Tyr Ala Ala
 50                  55                  60

Ser Val Lys Gly Arg Phe Thr Ile Ser Arg Asp Asp Ser Lys Asn Ser
 65                  70                  75                  80

Leu Tyr Leu Gln Met Asn Ser Leu Lys Thr Glu Asp Thr Ala Val Tyr
                     85                  90                  95

Tyr Cys Ser Arg His Met Gly Phe Gly Leu Asp Leu Trp Gly Gln Gly
                100                 105                 110
```

```
Thr Leu Val Thr Val Ser Ser
        115
```

<210> SEQ ID NO 403
<211> LENGTH: 121
<212> TYPE: PRT
<213> ORGANISM: Artificial sequence
<220> FEATURE:
<223> OTHER INFORMATION: Synthetic polypeptide

<400> SEQUENCE: 403

```
Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Tyr Gly Ser Gly Asp Gly Tyr Phe Asp Tyr Trp Gly
            100                 105                 110

Gln Gly Thr Thr Val Thr Val Ser Ser
        115                 120
```

<210> SEQ ID NO 404
<211> LENGTH: 124
<212> TYPE: PRT
<213> ORGANISM: Artificial sequence
<220> FEATURE:
<223> OTHER INFORMATION: Synthetic polypeptide

<400> SEQUENCE: 404

```
Glu Val Gln Leu Val Glu Ser Gly Pro Val Leu Val Lys Pro Thr Glu
1               5                   10                  15

Thr Leu Arg Leu Thr Cys Thr Val Ser Gly Phe Ser Leu Ser Asn Thr
            20                  25                  30

Lys Leu Gly Val Ser Trp Ile Arg Gln Pro Pro Gly Lys Ala Leu Glu
        35                  40                  45

Trp Leu Ala His Ile Phe Ser Asn Ala Glu Lys Ser Ser Ser Lys Ser
    50                  55                  60

Leu Lys Ser Arg Leu Ser Ile Ser Gln Asp Thr Ser Lys Ser Leu Val
65                  70                  75                  80

Val Leu Thr Met Thr Asn Met Asp Pro Val Asp Thr Ala Thr Tyr Phe
                85                  90                  95

Cys Ala Arg Ile Pro Val Glu Tyr Gly Thr Pro Arg Gly Ser Phe Asp
            100                 105                 110

Thr Trp Gly Gln Gly Thr Thr Val Thr Val Ser Ser
        115                 120
```

<210> SEQ ID NO 405
<211> LENGTH: 114
<212> TYPE: PRT
<213> ORGANISM: Artificial sequence
<220> FEATURE:
<223> OTHER INFORMATION: Synthetic polypeptide -continued

<400> SEQUENCE: 405

Glu Val Gln Leu Val Glu Ser Gly Gly Gly Val Val Gln Pro Gly Arg
1               5                   10                  15

Ser Leu Arg Leu Ser Cys Ala Ala Ser Gly Leu Thr Phe Ser Thr Tyr
            20                  25                  30

Thr Leu His Trp Val Arg Gln Ala Pro Gly Lys Gly Leu Glu Trp Val
        35                  40                  45

Ala Val Ile Ser Ser Asp Gly Gly Asn Lys Tyr Tyr Ala Asp Ser Val
    50                  55                  60

Lys Gly Arg Phe Thr Ile Ser Arg Asp Ser Ser Lys Asn Thr Leu Tyr
65                  70                  75                  80

Leu Gln Met Asn Ser Leu Arg Thr Glu Asp Thr Ala Val Tyr Tyr Cys
                85                  90                  95

Ala Gly Gly Ser Pro Asp Tyr Trp Gly Gln Gly Ala Leu Val Thr Val
            100                 105                 110

Ser Ser

<210> SEQ ID NO 406
<211> LENGTH: 121
<212> TYPE: PRT
<213> ORGANISM: Artificial sequence
<220> FEATURE:
<223> OTHER INFORMATION: Synthetic polypeptide

<400> SEQUENCE: 406

Glu Val Gln Leu Val Glu Ser Gly Gly Gly Val Val Gln Pro Gly Arg
1               5                   10                  15

Ser Leu Arg Leu Ser Cys Val Pro Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Met Met Ser Tyr Asp Gly Asp Lys Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Arg Ser Leu Arg Ala Glu Asp Thr Ala Ile Tyr Tyr Cys
                85                  90                  95

Ala Arg Ala Tyr Asp Ser Arg Gly Tyr Tyr Tyr Ile Glu His Trp Gly
            100                 105                 110

Gln Gly Thr Leu Val Thr Val Ser Ser
        115                 120

<210> SEQ ID NO 407
<211> LENGTH: 119
<212> TYPE: PRT
<213> ORGANISM: Artificial sequence
<220> FEATURE:
<223> OTHER INFORMATION: Synthetic polypeptide

<400> SEQUENCE: 407

Gln Val Gln Leu Val Gln Ser Gly Ala Glu Val Arg Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Thr Tyr Asn Gly Asn Thr Asn Tyr Ala Gln Lys Leu

```
                50                  55                  60
Gln Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Glu Ile Asp Ser Asn Tyr Val Phe Asp Tyr Trp Gly Gln Gly
                100                 105                 110

Thr Leu Val Thr Val Ser Ser
            115

<210> SEQ ID NO 408
<211> LENGTH: 122
<212> TYPE: PRT
<213> ORGANISM: Artificial sequence
<220> FEATURE:
<223> OTHER INFORMATION: Synthetic polypeptide

<400> SEQUENCE: 408

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Asn Tyr
                 20                  25                  30

Trp Met Asn Trp Val Arg Gln Ala Pro Gly Lys Gly Leu Glu Trp Val
             35                  40                  45

Ala Asn Ile Lys Gln Asp Gly Ser Glu Lys Tyr Tyr Val Asp Ser Val
         50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Lys Leu Ser Tyr Ser Ser Gly Trp Tyr Tyr Phe Asp Tyr Trp
                100                 105                 110

Gly Gln Gly Thr Leu Val Thr Val Ser Ser
            115                 120

<210> SEQ ID NO 409
<211> LENGTH: 119
<212> TYPE: PRT
<213> ORGANISM: Artificial sequence
<220> FEATURE:
<223> OTHER INFORMATION: Synthetic polypeptide

<400> SEQUENCE: 409

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Asp His
                 20                  25                  30

Tyr Met Asp Trp Val Arg Gln Ala Pro Gly Lys Gly Leu Glu Trp Val
             35                  40                  45

Gly Arg Ser Thr Asn Lys Pro Asn Ser Tyr Thr Thr Tyr Ala Ala
         50                  55                  60

Ser Val Arg Gly Arg Phe Thr Ile Ser Arg Asp Glu Ser Lys Asn Ser
 65                  70                  75                  80

Leu Tyr Leu Gln Met Asn Ser Leu Lys Ser Asp Asp Thr Ala Val Tyr
                 85                  90                  95

Tyr Cys Val Thr Thr Val Ile Leu Phe Asp Tyr Trp Gly Gln Gly
                100                 105                 110
```

```
Thr Leu Val Thr Val Ser Ser
        115

<210> SEQ ID NO 410
<211> LENGTH: 126
<212> TYPE: PRT
<213> ORGANISM: Artificial sequence
<220> FEATURE:
<223> OTHER INFORMATION: Synthetic polypeptide

<400> SEQUENCE: 410

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Arg Gly Ser Thr Asp Tyr Asn Pro Ser Leu Lys
    50                  55                  60

Ser Arg Val Thr Met Ser Val Asp Thr Ser Lys Asn Gln Phe Ser Leu
65                  70                  75                  80

Arg Leu Ser Ser Val Thr Ala Ala Asp Thr Ala Leu Tyr Tyr Cys Ala
                85                  90                  95

Arg Gly Arg Leu Ala Trp Gly Leu Arg Gly Gln Lys Ser Pro Asn Phe
            100                 105                 110

Phe Ala Tyr Trp Gly Gln Gly Ala Thr Val Thr Val Ser Ser
        115                 120                 125

<210> SEQ ID NO 411
<211> LENGTH: 125
<212> TYPE: PRT
<213> ORGANISM: Artificial sequence
<220> FEATURE:
<223> OTHER INFORMATION: Synthetic polypeptide

<400> SEQUENCE: 411

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser His Ala
            20                  25                  30

Trp Met Thr Trp Val Arg Gln Ala Pro Gly Lys Gly Leu Glu Trp Val
        35                  40                  45

Gly Arg Ile Lys Ser Glu Thr Asp Gly Gly Thr Ala Asn Tyr Ala Ala
    50                  55                  60

Pro Val Lys Gly Arg Phe Thr Ile Ser Arg Asp Asp Ser Lys Asn Thr
65                  70                  75                  80

Val Tyr Leu Gln Met Val Ser Leu Lys Thr Glu Asp Thr Ala Val Tyr
                85                  90                  95

Tyr Cys Ala Thr Ala Gly Ile Phe Gly Val Val Ile Met Lys Gly Phe
            100                 105                 110

Asp His Trp Gly Gln Gly Thr Thr Val Thr Val Ser Ser
        115                 120                 125

<210> SEQ ID NO 412
<211> LENGTH: 123
<212> TYPE: PRT
<213> ORGANISM: Artificial sequence
<220> FEATURE:
<223> OTHER INFORMATION: Synthetic polypeptide
```

<400> SEQUENCE: 412

Glu Val Gln Leu Leu Glu Ser Gly Ala Glu Val Lys Glu Pro Gly Ser
1               5                   10                  15

Ser Val Lys Val Ser Cys Lys Pro Ser Gly Gly Thr Phe Ser Ser Tyr
            20                  25                  30

Val Ile Ser Trp Val Arg Gln Ala Pro Gly Gln Gly Leu Glu Trp Met
        35                  40                  45

Gly Gly Ile Ile Pro Ile Phe Gly Thr Pro Asn Tyr Ala Gln Lys Phe
    50                  55                  60

Gln Gly Arg Val Thr Ile Thr Ala Asp Asp Ser Thr Ser Thr Ala His
65                  70                  75                  80

Met Glu Leu Ser Ser Leu Thr Ser Asp Asp Thr Ala Val Tyr Tyr Cys
                85                  90                  95

Ala Arg Glu Thr Tyr Tyr Tyr Gly Ser Gly Ser Val Pro Val His Asp
            100                 105                 110

Trp Gly Gln Gly Thr Leu Val Thr Val Ser Ser
        115                 120

<210> SEQ ID NO 413
<211> LENGTH: 122
<212> TYPE: PRT
<213> ORGANISM: Artificial sequence
<220> FEATURE:
<223> OTHER INFORMATION: Synthetic polypeptide

<400> SEQUENCE: 413

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Ile Phe Ser Ser Asn
            20                  25                  30

Ser Met His Trp Val Arg Gln Ala Pro Gly Lys Gly Leu Lys Trp Val
        35                  40                  45

Ala Ile Ile Ser Asn Asp Gly Arg Asn Lys Phe Tyr Ala Asp Ala Val
    50                  55                  60

Lys Gly Arg Phe Thr Val Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Arg Gly Tyr Asp Ser Ser Gly Tyr Trp Gly Phe Asp Asn Trp
            100                 105                 110

Gly Gln Gly Thr Leu Val Thr Val Ser Ser
        115                 120

<210> SEQ ID NO 414
<211> LENGTH: 122
<212> TYPE: PRT
<213> ORGANISM: Artificial sequence
<220> FEATURE:
<223> OTHER INFORMATION: Synthetic polypeptide

<400> SEQUENCE: 414

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Asp His
            20                  25                  30

Tyr Met Asp Trp Val Arg Gln Ala Pro Gly Lys Gly Leu Glu Trp Val
        35                  40                  45

```
Gly Arg Thr Arg Asn Lys Ala Asn Ser Tyr Thr Thr Lys Tyr Ala Ala
    50                  55                  60

Ser Val Lys Gly Arg Phe Thr Ile Ser Arg Asp Asp Ser Lys Asn Ser
 65                 70                  75                  80

Leu Tyr Leu Gln Met Asn Ser Leu Lys Thr Glu Asp Thr Ala Val Tyr
                85                  90                  95

Tyr Cys Ala Arg Val Glu Gly Gly Ala Trp Gly Ala Phe Asp Ile Trp
            100                 105                 110

Gly Gln Gly Thr Thr Val Thr Val Ser Ser
            115                 120

<210> SEQ ID NO 415
<211> LENGTH: 122
<212> TYPE: PRT
<213> ORGANISM: Artificial sequence
<220> FEATURE:
<223> OTHER INFORMATION: Synthetic polypeptide

<400> SEQUENCE: 415

Gln Val Thr Leu Lys Glu Ser Gly Pro Val Leu Val Lys Pro Thr Glu
 1               5                  10                  15

Thr Leu Thr Leu Thr Cys Thr Val Ser Gly Phe Ser Leu Ser Asn Thr
                20                  25                  30

Lys Met Gly Val Thr Trp Ile Arg Gln Pro Pro Gly Lys Ala Leu Glu
            35                  40                  45

Trp Leu Ala His Ile Phe Ser Asn Asp Glu Lys Ser Cys Asn Thr Ser
 50                 55                  60

Leu Lys Ser Arg Leu Thr Ile Ser Lys Asp Thr Ser Lys Ser Gln Val
 65                 70                  75                  80

Val Leu Thr Met Thr Asn Met Asp Pro Val Asp Thr Ala Thr Tyr Tyr
                85                  90                  95

Cys Ala Arg Leu Trp Phe Thr Glu Tyr Pro Gly Ala Phe Asp Ile Trp
            100                 105                 110

Gly Gln Gly Thr Met Val Thr Val Ser Ser
            115                 120

<210> SEQ ID NO 416
<211> LENGTH: 125
<212> TYPE: PRT
<213> ORGANISM: Artificial sequence
<220> FEATURE:
<223> OTHER INFORMATION: Synthetic polypeptide

<400> SEQUENCE: 416

Glu Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Ser Ser
                20                  25                  30

Ser Tyr Tyr Trp Gly Trp Ile Arg Gln Pro Pro Gly Lys Gly Leu Glu
            35                  40                  45

Trp Ile Gly Ser Ile Tyr Tyr Ser Gly Ser Thr Tyr Tyr Asn Pro Ser
 50                 55                  60

Leu Lys Ser Arg Val Thr Ile Ser Val Asp Thr Ser Lys Asn Gln Phe
 65                 70                  75                  80

Ser Leu Lys Leu Ser Ser Val Thr Ala Ala Asp Thr Ala Val Tyr Tyr
                85                  90                  95

Cys Ala Arg His Ser Ser Gly Ser Tyr Tyr Leu Ala Gly Tyr Tyr Phe
            100                 105                 110
```

```
Asp Tyr Trp Gly Gln Gly Thr Leu Val Thr Val Ser Ser
        115                 120                 125
```

<210> SEQ ID NO 417
<211> LENGTH: 119
<212> TYPE: PRT
<213> ORGANISM: Artificial sequence
<220> FEATURE:
<223> OTHER INFORMATION: Synthetic polypeptide

<400> SEQUENCE: 417

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp His
            20                  25                  30

Tyr Met Asp Trp Val Arg Gln Ala Pro Gly Arg Gly Leu Glu Trp Val
        35                  40                  45

Gly Arg Ser Arg Asn Lys Val Asn Ser Tyr Thr Thr Asp Tyr Ala Ala
    50                  55                  60

Ser Val Lys Gly Arg Phe Thr Ile Ser Arg Asp Asp Ser Lys Asn Ser
65                  70                  75                  80

Leu Phe Leu Arg Met Asn Ser Leu Lys Thr Glu Asp Thr Ala Val Tyr
                85                  90                  95

Tyr Cys Ala Arg Leu Thr Asp Ser Gly Tyr Asp Asp Trp Gly Leu Gly
            100                 105                 110

Thr Leu Val Thr Val Ser Ser
        115
```

<210> SEQ ID NO 418
<211> LENGTH: 126
<212> TYPE: PRT
<213> ORGANISM: Artificial sequence
<220> FEATURE:
<223> OTHER INFORMATION: Synthetic polypeptide

<400> SEQUENCE: 418

```
Glu Val Gln Leu Val Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Thr Cys Ser Gly Gly Ser Cys Tyr Tyr Arg Val Gly Ser Ala
            100                 105                 110

Phe Asp Ile Trp Gly Gln Gly Thr Thr Val Thr Val Ser Ser
        115                 120                 125
```

<210> SEQ ID NO 419
<211> LENGTH: 122
<212> TYPE: PRT
<213> ORGANISM: Artificial sequence
<220> FEATURE:
<223> OTHER INFORMATION: Synthetic polypeptide

<400> SEQUENCE: 419

Glu Val Gln Leu Leu Glu Ser Gly Gly Met Val Gln Pro Gly Arg
1               5                   10                  15

Ser Leu Arg Leu Ser Cys Ala Ala Ser Gly Phe Thr Phe Asp Asp Tyr
            20                  25                  30

Asp Met His Trp Val Arg Gln Gly Pro Gly Lys Gly Leu Glu Trp Val
        35                  40                  45

Ser Gly Ile Ser Trp Asn Ser Gly Arg Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Val Glu Asp Thr Ala Leu Tyr Tyr Cys
                85                  90                  95

Val Lys Asp Tyr Cys Ser Gly Arg Cys Tyr Ser Phe Asp Tyr Trp
            100                 105                 110

Gly Gln Gly Thr Leu Val Thr Val Ser Ser
        115                 120

<210> SEQ ID NO 420
<211> LENGTH: 121
<212> TYPE: PRT
<213> ORGANISM: Artificial sequence
<220> FEATURE:
<223> OTHER INFORMATION: Synthetic polypeptide

<400> SEQUENCE: 420

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Met Ser Tyr Asp Gly Ser Asn Lys Tyr Tyr Ala Asp Ser Leu
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Lys Ala Tyr Asp Ser Ser Ala Tyr Tyr Tyr Leu Asp Tyr Trp Gly
            100                 105                 110

Gln Gly Thr Leu Val Thr Val Ser Ser
        115                 120

<210> SEQ ID NO 421
<211> LENGTH: 121
<212> TYPE: PRT
<213> ORGANISM: Artificial sequence
<220> FEATURE:
<223> OTHER INFORMATION: Synthetic polypeptide

<400> SEQUENCE: 421

Glu Val Gln Leu Val Glu Ser Gly Gly Gly Val Ile Gln Pro Gly Arg
1               5                   10                  15

Ser Leu Arg Leu Ser Cys Ala Ala Ser Gly Phe Asn Phe Ser Ser Tyr
            20                  25                  30

Gly Met His Trp Val Arg Gln Ala Pro Gly Lys Gly Leu Glu Trp Val
        35                  40                  45

```
Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val His Tyr Cys
                85                  90                  95

Ala Lys Ala Tyr Asp Ser Arg Gly Tyr Tyr Tyr Leu Asp Tyr Trp Gly
            100                 105                 110

Gln Gly Thr Leu Val Thr Val Ser Ser
            115                 120
```

<210> SEQ ID NO 422
<211> LENGTH: 129
<212> TYPE: PRT
<213> ORGANISM: Artificial sequence
<220> FEATURE:
<223> OTHER INFORMATION: Synthetic polypeptide

<400> SEQUENCE: 422

```
Glu Val Gln Leu Val Gln Ser Gly Gly Gly Leu Val Gln Pro Gly Gly
 1               5                  10                  15

Ser Leu Arg Leu Ser Cys Val Gly Ser Gly Leu Thr Leu Ser Ser Ser
            20                  25                  30

Ala Met Ser Trp Val Arg Gln Ala Pro Gly Lys Gly Leu Glu Cys Val
        35                  40                  45

Ser Gly Ile Thr Gly Ser Gly Ser Asp Ser Ser Tyr Ala Ala Ser Val
    50                  55                  60

Lys Gly Arg Phe Thr Ile Ser Arg Asp Asn Ser Lys Asn Thr Val Tyr
 65                  70                  75                  80

Leu Gln Met Asn Ser Leu Arg Ala Glu Asp Thr Ala Val Tyr Tyr Cys
                85                  90                  95

Ala Lys Asp Leu Thr His Arg Leu Gly Ser Ile Phe Gly Lys Leu Thr
            100                 105                 110

Phe Asp Ala Phe Asp Ile Trp Gly Pro Gly Thr Met Val Thr Val Ser
        115                 120                 125

Ser
```

<210> SEQ ID NO 423
<211> LENGTH: 123
<212> TYPE: PRT
<213> ORGANISM: Artificial sequence
<220> FEATURE:
<223> OTHER INFORMATION: Synthetic polypeptide

<400> SEQUENCE: 423

```
Glu Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Pro Glu Trp Val
        35                  40                  45

Ala Val Ile Ser Glu Asp Gly Asn Lys Asp His Tyr Val Asp Ser Val
    50                  55                  60

Lys Gly Arg Phe Ser Ile Tyr Arg Asp Asn Ser Lys Ser Thr Val Phe
 65                  70                  75                  80

Leu Arg Met Thr Ser Leu Arg Ala Glu Asp Thr Ala Val Tyr Tyr Cys
                85                  90                  95
```

```
Ala Lys Asp Leu Thr Pro Tyr Phe Tyr Asp Ser Gly Ala Phe Asp His
            100                 105                 110

Trp Gly Gln Gly Thr Leu Val Thr Val Ser Ser
        115                 120
```

<210> SEQ ID NO 424
<211> LENGTH: 119
<212> TYPE: PRT
<213> ORGANISM: Artificial sequence
<220> FEATURE:
<223> OTHER INFORMATION: Synthetic polypeptide

<400> SEQUENCE: 424

```
Glu Val Gln Leu Val Glu Ser Gly Gly Gly Leu Val Gln Pro Gly Gly
1               5                   10                  15

Ser Leu Arg Leu Ser Cys Ala Val Ser Gly Phe Thr Phe Ser Asp His
            20                  25                  30

Tyr Met Asp Trp Val Arg Gln Ala Pro Gly Lys Gly Leu Glu Trp Val
        35                  40                  45

Gly Arg Ser Arg Asn Lys Val Asn Ser Tyr Ile Thr Glu Tyr Ala Ala
    50                  55                  60

Ser Val Lys Gly Arg Phe Ser Ile Ser Arg Asp Asp Ser Lys Asn Ser
65                  70                  75                  80

Leu Tyr Leu Gln Met Asn Ser Leu Lys Ile Glu Asp Thr Ala Val Tyr
                85                  90                  95

Tyr Cys Ala Arg Val Phe Gly Gly Pro Thr Asp Tyr Trp Gly Gln Gly
            100                 105                 110

Thr Leu Val Thr Val Ser Ser
        115
```

<210> SEQ ID NO 425
<211> LENGTH: 118
<212> TYPE: PRT
<213> ORGANISM: Artificial sequence
<220> FEATURE:
<223> OTHER INFORMATION: Synthetic polypeptide

<400> SEQUENCE: 425

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ile Phe Ser Asp His
            20                  25                  30

Tyr Met Asp Trp Val Arg Gln Ala Pro Gly Lys Gly Leu Glu Trp Val
        35                  40                  45

Gly Arg Ile Arg Asn Lys Pro Asn Ser Tyr Thr Thr Asp Tyr Ala Ala
    50                  55                  60

Tyr Val Lys Gly Arg Phe Ser Ile Ser Arg Asp Asp Ser Lys Asn Ser
65                  70                  75                  80

Leu Phe Leu Gln Met Asn Ser Leu Lys Thr Glu Asp Thr Ala Val Tyr
                85                  90                  95

Tyr Cys Ala Arg Val Val Asn Gly Leu Asp Val Trp Gly Gln Gly Thr
            100                 105                 110

Thr Val Thr Val Ser Ser
        115
```

<210> SEQ ID NO 426
<211> LENGTH: 114
<212> TYPE: PRT

<213> ORGANISM: Artificial sequence
<220> FEATURE:
<223> OTHER INFORMATION: Synthetic polypeptide

<400> SEQUENCE: 426

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Leu Ser Ser Tyr
            20                  25                  30

Val Met His Trp Val Arg Gln Ala Pro Gly Lys Gly Leu Glu Trp Val
        35                  40                  45

Ala Val Ile Ser Ser Asp Gly Thr Asn Lys Tyr Tyr Ala Asp Ser Val
    50                  55                  60

Lys Gly Arg Phe Thr Ile Ser Arg Asp Ser Lys Asn Thr Leu Tyr
65                  70                  75                  80

Leu Gln Met Asn Ser Leu Arg Pro Glu Asp Ser Ala Val Tyr Tyr Cys
                85                  90                  95

Ala Arg Gly Gln Pro Asp Tyr Trp Gly Gln Gly Thr Leu Val Thr Val
            100                 105                 110

Ser Ser

<210> SEQ ID NO 427
<211> LENGTH: 121
<212> TYPE: PRT
<213> ORGANISM: Artificial sequence
<220> FEATURE:
<223> OTHER INFORMATION: Synthetic polypeptide

<400> SEQUENCE: 427

Glu Val Gln Leu Val Glu Ser Gly Pro Gly Leu Val Lys Pro Ser Gly
1               5                   10                  15

Thr Leu Ser Leu Thr Cys Ala Val Ser Gly Gly Ser Ile Ser Ser Asp
            20                  25                  30

Asn Trp Trp Ser Trp Val Arg Gln Ala Pro Gly Lys Gly Leu Glu Trp
        35                  40                  45

Ile Gly Glu Ile Tyr His Thr Gly Ser Thr Ser Tyr Asn Pro Ser Leu
    50                  55                  60

Lys Ser Arg Val Thr Ile Ser Leu Asp Lys Ser Lys Asn His Phe Ser
65                  70                  75                  80

Leu Lys Leu Asn Ser Leu Thr Ala Ala Asp Thr Ala Val Tyr Tyr Cys
                85                  90                  95

Ala Gly Lys Lys Trp Glu Leu Leu Gly Phe Arg Phe Asp Pro Trp Gly
            100                 105                 110

Gln Gly Thr Leu Val Thr Val Ser Ser
        115                 120

<210> SEQ ID NO 428
<211> LENGTH: 117
<212> TYPE: PRT
<213> ORGANISM: Artificial sequence
<220> FEATURE:
<223> OTHER INFORMATION: Synthetic polypeptide

<400> SEQUENCE: 428

Gln Val Gln Leu Val Glu Ser Gly Ala Glu Glu Lys Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Arg Leu Glu Trp Met
        35                  40                  45

Gly Trp Ile Asn Ala Gly Asn Gly Asn Thr Lys Tyr Ser Gln Lys Phe
 50                  55                  60

Gln Gly Arg Val Thr Ile Thr Arg Asp Thr Ser Ala Ser Thr Ala Tyr
65                   70                  75                  80

Met Glu Leu Ser Ser Leu Arg Ser Glu Asp Thr Ala Val Tyr Tyr Cys
                85                  90                  95

Ala Arg Gln Trp Leu Gly His Phe Asp Tyr Trp Gly Gln Gly Thr Leu
            100                 105                 110

Val Thr Val Ser Ser
        115

<210> SEQ ID NO 429
<211> LENGTH: 119
<212> TYPE: PRT
<213> ORGANISM: Artificial sequence
<220> FEATURE:
<223> OTHER INFORMATION: Synthetic polypeptide

<400> SEQUENCE: 429

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Phe Ser Asp His
            20                  25                  30

Tyr Met Ala Trp Val Arg Gln Ala Pro Gly Lys Gly Leu Glu Trp Val
        35                  40                  45

Gly His Val Gly Asn Lys Ala Asn Thr Tyr Thr Thr Glu Tyr Ala Ala
 50                  55                  60

Ser Val Lys Gly Arg Phe Thr Ile Ser Arg Asp Asp Ser Lys Lys Ser
65                  70                  75                  80

Leu Tyr Leu Gln Met Asn Arg Leu Lys Ser Glu Asp Thr Ala Val Tyr
                85                  90                  95

Tyr Cys Ala Arg Val Phe Ser Tyr Tyr Leu Asp Tyr Trp Gly Gln Gly
            100                 105                 110

Thr Pro Val Thr Val Ser Ser
        115

<210> SEQ ID NO 430
<211> LENGTH: 126
<212> TYPE: PRT
<213> ORGANISM: Artificial sequence
<220> FEATURE:
<223> OTHER INFORMATION: Synthetic polypeptide

<400> SEQUENCE: 430

Gln Val Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Thr Arg Gln Pro Pro Gly Lys Ala Leu Glu
        35                  40                  45

Trp Leu Ala Leu Ile Tyr Trp Asp Asp Asp Lys Arg Tyr Ser Pro Ser
 50                  55                  60

Leu Lys Ser Arg Leu Thr Ile Thr Lys Asp Thr Ser Lys Asn Gln Val
65                  70                  75                  80

Val Leu Thr Met Thr Lys Met Asp Pro Val Asp Thr Ala Thr Tyr Tyr
                85                  90                  95

-continued

Cys Ala His Arg His Ile Ala Ala Arg Leu Tyr Arg Asp Asp Val
            100                 105                 110

Phe Asp Val Trp Gly Gln Gly Thr Met Val Thr Val Ser Ser
            115                 120                 125

<210> SEQ ID NO 431
<211> LENGTH: 119
<212> TYPE: PRT
<213> ORGANISM: Artificial sequence
<220> FEATURE:
<223> OTHER INFORMATION: Synthetic polypeptide

<400> SEQUENCE: 431

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Asp Ile Asn Trp Val Arg Gln Ala Thr Gly Gln Gly Leu Glu Trp Met
            35                  40                  45

Gly Trp Met Asn Pro Asn Ser Gly Asn Thr Gly Tyr Ala Gln Lys Phe
        50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Leu Asn Thr Val Thr Asn Ser Asp Tyr Trp Gly Gln Gly
            100                 105                 110

Thr Leu Val Thr Val Ser Ser
        115

<210> SEQ ID NO 432
<211> LENGTH: 120
<212> TYPE: PRT
<213> ORGANISM: Artificial sequence
<220> FEATURE:
<223> OTHER INFORMATION: Synthetic polypeptide

<400> SEQUENCE: 432

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
        50                  55                  60

Gln Gly Trp Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Ser Gly Leu Ser Pro Asp Phe Ser Val Leu Asp Val Trp Gly Gln
            100                 105                 110

Gly Thr Thr Val Thr Val Ser Ser
        115                 120

<210> SEQ ID NO 433
<211> LENGTH: 133
<212> TYPE: PRT

<213> ORGANISM: Artificial sequence
<220> FEATURE:
<223> OTHER INFORMATION: Synthetic polypeptide

<400> SEQUENCE: 433

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Thr Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Leu Ser Val Lys Ser Arg Ile Thr Ile Lys Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Glu Gly Ala Gly Tyr Tyr Asp Ser Ser Gly Tyr
            100                 105                 110

Tyr Pro Leu Ser Tyr Asp Ala Phe Asp Ile Trp Gly Arg Gly Thr Met
        115                 120                 125

Val Thr Val Ser Ser
    130

<210> SEQ ID NO 434
<211> LENGTH: 119
<212> TYPE: PRT
<213> ORGANISM: Artificial sequence
<220> FEATURE:
<223> OTHER INFORMATION: Synthetic polypeptide

<400> SEQUENCE: 434

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp His
            20                  25                  30

Tyr Met Asp Trp Val Arg Gln Ala Pro Gly Lys Gly Leu Glu Trp Val
        35                  40                  45

Gly Arg Ala Arg Asn Arg Ala Asn Ser Tyr Thr Thr Glu Tyr Ala Ala
    50                  55                  60

Ser Val Lys Gly Arg Phe Ala Ala Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Val Arg Gly Ser Tyr Trp Asp Tyr Trp Gly Gln Gly
            100                 105                 110

Thr Leu Val Thr Val Ser Ser
        115

<210> SEQ ID NO 435
<211> LENGTH: 118
<212> TYPE: PRT
<213> ORGANISM: Artificial sequence
<220> FEATURE:
<223> OTHER INFORMATION: Synthetic polypeptide

<400> SEQUENCE: 435

Gln Val Gln Leu Val Gln Ser Gly Gly Gly Leu Val Gln Pro Gly Gly
1               5                   10                  15

```
Ser Leu Arg Leu Ser Cys Ala Ala Ser Gly Phe Thr Phe Ser Asp His
            20                  25                  30

Tyr Met Asp Trp Val Arg Gln Ala Pro Gly Lys Gly Leu Glu Trp Val
        35                  40                  45

Gly Arg Ile Arg Asn Lys Val Asn Ser Tyr Thr Thr Glu Tyr Ala Ala
 50                  55                  60

Ser Val Lys Gly Arg Phe Thr Ile Ser Arg Asp Asp Ser Lys Asn Ser
 65                  70                  75                  80

Leu Tyr Leu Gln Met Asn Ser Leu Lys Thr Glu Asp Thr Ala Val Tyr
                85                  90                  95

Tyr Cys Gly Arg Asp Arg Gly Trp Leu Asp Ile Trp Gly Gln Gly Thr
            100                 105                 110

Met Val Thr Val Ser Ser
        115
```

<210> SEQ ID NO 436
<211> LENGTH: 130
<212> TYPE: PRT
<213> ORGANISM: Artificial sequence
<220> FEATURE:
<223> OTHER INFORMATION: Synthetic polypeptide

<400> SEQUENCE: 436

```
Gln Val Gln Leu Gln Glu Ser Gly Pro Gly Leu Val Glu Pro Ser Gly
 1               5                  10                  15

Thr Leu Ser Leu Thr Cys Val Val Thr Gly Asp Ser Ile Ser Ser Arg
            20                  25                  30

Ser Trp Trp Ser Trp Val Arg Gln Pro Pro Gly Lys Gly Leu Glu Trp
        35                  40                  45

Ile Gly Glu Ile Tyr His Ser Gly Thr Thr Thr Tyr Ser Pro Ser Leu
 50                  55                  60

Lys Ser Arg Val Ile Ile Ser Leu Asp Lys Ser Glu Asn His Phe Ser
 65                  70                  75                  80

Leu Lys Met Thr Ser Val Thr Ala Ala Asp Thr Ala Val Tyr Tyr Cys
                85                  90                  95

Ala Arg Val Ile Arg Asp Leu Arg Asp Tyr Tyr Asp Gly Ser Gly Tyr
            100                 105                 110

Gly Pro Asp Ala Phe Asp Ile Trp Gly Gln Gly Thr Thr Val Thr Val
            115                 120                 125

Ser Ser
    130
```

<210> SEQ ID NO 437
<211> LENGTH: 123
<212> TYPE: PRT
<213> ORGANISM: Artificial sequence
<220> FEATURE:
<223> OTHER INFORMATION: Synthetic polypeptide

<400> SEQUENCE: 437

```
Glu Val Gln Leu Val Glu Ser Gly Pro Gly Leu Val Lys Pro Ser Gly
 1               5                  10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
```

```
                    50                  55                  60

Lys Ser Arg Val Thr Ile Ser Val Asp Lys Ser Lys Asn Gln Phe Ser
 65                  70                  75                  80

Leu Lys Leu Ser Ser Val Thr Ala Ala Asp Thr Ala Val Tyr Tyr Cys
                    85                  90                  95

Ala Arg Ala Arg Trp Glu Asp Gly Asn Tyr Tyr Gly Met Asp Val
                100                 105                 110

Trp Gly Gln Gly Thr Thr Val Thr Val Ser Ser
            115                 120
```

<210> SEQ ID NO 438
<211> LENGTH: 124
<212> TYPE: PRT
<213> ORGANISM: Artificial sequence
<220> FEATURE:
<223> OTHER INFORMATION: Synthetic polypeptide

<400> SEQUENCE: 438

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
                35                  40                  45

Ser Ala Ile Ser Gly Ser Gly Gly Ser Thr Tyr Tyr Ala Asp Ser Val
                50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Asp Gln Ser Ser Gly Trp Pro Asn Tyr Tyr Gly Met Asp
                100                 105                 110

Val Trp Gly Gln Gly Thr Thr Val Thr Val Ser Ser
            115                 120
```

<210> SEQ ID NO 439
<211> LENGTH: 126
<212> TYPE: PRT
<213> ORGANISM: Artificial sequence
<220> FEATURE:
<223> OTHER INFORMATION: Synthetic polypeptide

<400> SEQUENCE: 439

```
Gln Val Gln Leu Val Glu Ser Gly Ser Glu Leu Lys Lys Pro Gly Ala
 1               5                  10                  15

Ser Val Lys Val Ser Cys Lys Ala Ser Gly Tyr Thr Phe Thr Ser Tyr
                20                  25                  30

Ala Met Asn Trp Val Arg Gln Ala Pro Gly Gln Gly Leu Glu Trp Met
                35                  40                  45

Gly Trp Ile Asn Thr Asn Thr Gly Asn Pro Thr Tyr Ala Gln Gly Phe
            50                  55                  60

Thr Gly Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Val Tyr Tyr Cys
                85                  90                  95

Val Arg Gly Tyr Cys Ser Ser Thr Ser Cys Tyr Gly Gly Leu Tyr Trp
                100                 105                 110
```

```
Phe Asp Pro Trp Gly Gln Gly Thr Leu Val Thr Val Ser Ser
        115                 120                 125
```

<210> SEQ ID NO 440
<211> LENGTH: 126
<212> TYPE: PRT
<213> ORGANISM: Artificial sequence
<220> FEATURE:
<223> OTHER INFORMATION: Synthetic polypeptide

<400> SEQUENCE: 440

```
Glu Val Gln Leu Val Glu Ser Gly Gly Gly Val Val Gln Pro Gly Arg
1               5                   10                  15

Ser Leu Arg Leu Ser Cys Ala Asp Ser Gly Phe Thr Phe Ser Tyr Ser
            20                  25                  30

Ala Ile His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Arg His Ser Gly Gly Tyr Ser Ser Lys Asp Lys Pro Thr Glu Tyr
            100                 105                 110

Phe Gln His Trp Gly Gln Gly Thr Leu Val Thr Val Ser Ser
        115                 120                 125
```

<210> SEQ ID NO 441
<211> LENGTH: 122
<212> TYPE: PRT
<213> ORGANISM: Artificial sequence
<220> FEATURE:
<223> OTHER INFORMATION: Synthetic polypeptide

<400> SEQUENCE: 441

```
Glu Val Gln Leu Leu Glu Ser Gly Pro Gly Leu Val Lys Pro Ser Gly
1               5                   10                  15

Thr Leu Ser Leu Thr Cys Ala Val Ser Gly Ala Ser Ile Ser Ser Asn
            20                  25                  30

Asn Trp Trp Ser Trp Val Arg Gln Ser Pro Gly Lys Gly Leu Glu Trp
        35                  40                  45

Ile Gly Glu Ile Phe His Ser Gly Thr Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Asn Ser Val Thr Ala Ala Asp Thr Ala Val Tyr Tyr Cys
                85                  90                  95

Ala Arg Asp Val Gly Val Ala Val Ile Thr Gly Ser Val Arg Trp
            100                 105                 110

Gly Gln Gly Thr Leu Val Thr Val Ser Ser
        115                 120
```

<210> SEQ ID NO 442
<211> LENGTH: 126
<212> TYPE: PRT
<213> ORGANISM: Artificial sequence
<220> FEATURE:
<223> OTHER INFORMATION: Synthetic polypeptide

```
<400> SEQUENCE: 442

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Ser Tyr
            20                  25                  30

Ala Met Asn Trp Val Arg Gln Ala Pro Gly Gln Gly Leu Glu Trp Met
        35                  40                  45

Gly Trp Ile Asn Thr Asn Thr Gly Asn Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Gly Tyr Cys Ser Ser Ser Cys Tyr Gly Leu Tyr Trp
            100                 105                 110

Phe Asp Pro Trp Gly Gln Gly Thr Leu Val Thr Val Ser Ser
        115                 120                 125

<210> SEQ ID NO 443
<211> LENGTH: 133
<212> TYPE: PRT
<213> ORGANISM: Artificial sequence
<220> FEATURE:
<223> OTHER INFORMATION: Synthetic polypeptide

<400> SEQUENCE: 443

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Ala Gly Asp Tyr Ile Trp Gly Ser Tyr Arg His Lys
            100                 105                 110

Gly Leu His Tyr Tyr Gly Met Asp Val Trp Gly Gln Gly Thr Thr
        115                 120                 125

Val Thr Val Ser Ser
    130

<210> SEQ ID NO 444
<211> LENGTH: 124
<212> TYPE: PRT
<213> ORGANISM: Artificial sequence
<220> FEATURE:
<223> OTHER INFORMATION: Synthetic polypeptide

<400> SEQUENCE: 444

Glu Val Gln Leu Val Glu Ser Gly Pro Gly Leu Val Met Pro Ser Gly
1               5                   10                  15

Thr Leu Ser Leu Thr Cys Thr Val Ser Gly Ile Ser Ile Ser Ser Ser
            20                  25                  30
```

```
Asn Trp Trp Ser Trp Val Arg Gln Ser Pro Gly Lys Gly Leu Glu Trp
             35                  40                  45

Ile Gly Glu Val Tyr His Ser Gly Ser Thr Lys Tyr Asn Pro Ser Leu
 50                      55                  60

Lys Ser Arg Val Thr Ile Ser Val Asp Lys Ser Arg Asn Gln Phe Ser
 65                  70                  75                  80

Leu Lys Leu Asn Ser Val Thr Ala Ala Asp Thr Ala Val Tyr Tyr Cys
                 85                  90                  95

Ala Lys Asp Pro Arg Thr Phe Tyr Gly Val Val Met Leu Leu Asp Asp
                100                 105                 110

Pro Trp Gly Gln Gly Thr Leu Val Thr Val Ser Ser
            115                 120

<210> SEQ ID NO 445
<211> LENGTH: 119
<212> TYPE: PRT
<213> ORGANISM: Artificial sequence
<220> FEATURE:
<223> OTHER INFORMATION: Synthetic polypeptide

<400> SEQUENCE: 445

Glu Val Gln Leu Val Glu Ser Gly Gly Gly Val Val Gln Pro Gly Arg
 1               5                  10                  15

Ser Leu Arg Leu Ser Cys Ala Val Ser Gly Phe Thr Phe Ser Thr Ser
                 20                  25                  30

Pro Leu His Trp Val Arg Gln Ala Pro Gly Lys Gly Leu Glu Trp Val
             35                  40                  45

Ala Val Ser Ser Phe Val Ala Thr Asp Lys Tyr Tyr Ala Asp Ser Val
 50                  55                  60

Lys Gly Arg Phe Thr Val Ser Arg Asp Asn Ser Lys Asn Thr Leu Tyr
 65                  70                  75                  80

Leu Gln Met Asn Ser Leu Arg Pro Glu Asp Thr Ala Val Tyr Tyr Cys
                 85                  90                  95

Ala Arg Gly Phe Gly Glu Leu Pro Gly Phe Asp Ile Trp Gly Gln Gly
                100                 105                 110

Thr Met Val Thr Val Ser Ser
            115

<210> SEQ ID NO 446
<211> LENGTH: 117
<212> TYPE: PRT
<213> ORGANISM: Artificial sequence
<220> FEATURE:
<223> OTHER INFORMATION: Synthetic polypeptide

<400> SEQUENCE: 446

Glu Val Gln Leu Leu Glu Ser Gly Gly Gly Leu Val Lys Pro Gly Gly
 1               5                  10                  15

Ser Leu Arg Leu Ser Cys Ala Ala Ser Gly Phe Thr Phe Ser Ser Tyr
                 20                  25                  30

Ser Met Asn Trp Val Arg Gln Ala Pro Gly Lys Gly Leu Glu Trp Val
             35                  40                  45

Ser Ser Ile Ser Ser Ser Ser Ser Tyr Ile Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95
```

Ala Arg Asp Ser Trp Gly Pro Phe Asp Tyr Trp Gly Gln Gly Thr Leu
            100                 105                 110

Val Thr Val Ser Ser
        115

<210> SEQ ID NO 447
<211> LENGTH: 121
<212> TYPE: PRT
<213> ORGANISM: Artificial sequence
<220> FEATURE:
<223> OTHER INFORMATION: Synthetic polypeptide

<400> SEQUENCE: 447

Glu Val Gln Leu Val Glu Ser Gly Gly Ala Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Ser Val
        35                  40                  45

Ala Val Ile Trp Tyr Asp Gly Ser Asn Lys Asn Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Ser Ala Met Tyr Tyr Cys
                85                  90                  95

Ala Lys Thr Tyr Asp Ser Arg Ala Tyr Tyr Tyr Leu Asp Tyr Trp Gly
            100                 105                 110

Gln Gly Thr Leu Val Thr Val Ser Ser
        115                 120

<210> SEQ ID NO 448
<211> LENGTH: 123
<212> TYPE: PRT
<213> ORGANISM: Artificial sequence
<220> FEATURE:
<223> OTHER INFORMATION: Synthetic polypeptide

<400> SEQUENCE: 448

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Leu Val
        35                  40                  45

Ser Ala Ile Ser Ser Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Leu Tyr Tyr Cys
                85                  90                  95

Ala Lys Asp Leu Phe Tyr Asp Phe Trp Thr Gly Ile Thr Ile Asp Tyr
            100                 105                 110

Trp Gly Gln Gly Thr Leu Val Thr Val Ser Ser
        115                 120

<210> SEQ ID NO 449
<211> LENGTH: 120
<212> TYPE: PRT

<213> ORGANISM: Artificial sequence
<220> FEATURE:
<223> OTHER INFORMATION: Synthetic polypeptide

<400> SEQUENCE: 449

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ile Phe Ser Asn Tyr
            20                  25                  30

Trp Met Ser Trp Val Arg Gln Ala Pro Gly Lys Gly Leu Glu Trp Val
        35                  40                  45

Ala Asn Ile Lys Pro Asp Gly Ser Glu Lys Tyr Tyr Val Glu Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Phe Tyr Cys
                85                  90                  95

Ala Arg Asp Gly Gly Thr Val Ser Asp Gly Leu Asp Val Trp Gly Gln
            100                 105                 110

Gly Thr Thr Val Thr Val Ser Ser
        115                 120
```

<210> SEQ ID NO 450
<211> LENGTH: 122
<212> TYPE: PRT
<213> ORGANISM: Artificial sequence
<220> FEATURE:
<223> OTHER INFORMATION: Synthetic polypeptide

<400> SEQUENCE: 450

```
Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Val Val Trp Tyr Ser Ser Ser His Leu Phe Asp Tyr Trp
            100                 105                 110

Gly Gln Gly Thr Leu Val Thr Val Ser Ser
        115                 120
```

<210> SEQ ID NO 451
<211> LENGTH: 117
<212> TYPE: PRT
<213> ORGANISM: Artificial sequence
<220> FEATURE:
<223> OTHER INFORMATION: Synthetic polypeptide

<400> SEQUENCE: 451

```
Glu Val Gln Leu Val Glu Ser Gly Gly Gly Val Val Gln Thr Gly Arg
1               5                   10                  15

Ser Leu Arg Leu Ser Cys Ala Ala Ser Gly Phe Thr Phe Ser Ile Ser
            20                  25                  30
```

```
Gly Met His Trp Val Arg Gln Ala Pro Gly Lys Gly Leu Glu Trp Val
        35                  40                  45

Ala Leu Ile Trp Tyr Asp Gly Thr Lys Lys Tyr Tyr Ala Asp Ser Val
 50                  55                  60

Lys Gly Arg Phe Thr Ile Ser Arg Asp Asp Phe Lys Asn Thr Val Tyr
 65                  70                  75                  80

Leu Gln Met Asn Ser Leu Arg Ala Asp Asp Thr Ala Val Tyr Tyr Cys
                85                  90                  95

Ala Arg Ile Lys Ser Asp Ala Phe Asp Leu Trp Gly Gln Gly Thr Thr
                100                 105                 110

Val Thr Val Ser Ser
        115

<210> SEQ ID NO 452
<211> LENGTH: 123
<212> TYPE: PRT
<213> ORGANISM: Artificial sequence
<220> FEATURE:
<223> OTHER INFORMATION: Synthetic polypeptide

<400> SEQUENCE: 452

Glu Val Gln Leu Leu Glu Ser Gly Gly Gly Val Val Gln Pro Gly Lys
 1               5                  10                  15

Ser Leu Arg Leu Ser Cys Ala Ala Ser Gly Phe Ser Phe Gly Asp Tyr
                20                  25                  30

Gly Met His Trp Val Arg Gln Thr Pro Asp Lys Gly Leu Glu Trp Val
        35                  40                  45

Ala Val Ile Leu Phe Asp Gly Ser Lys Lys Phe Tyr Ala Asp Ser Val
 50                  55                  60

Arg Gly Arg Phe Thr Ile Ser Arg Asp Asn Ser Lys Asn Asn Leu Tyr
 65                  70                  75                  80

Leu Gln Met Ser Ser Leu Arg Pro Glu Asp Thr Ala Val Tyr Tyr Cys
                85                  90                  95

Ala Lys Phe Pro Leu Arg Asp Gly Ser Gly Glu Gly Phe Asp Tyr
                100                 105                 110

Trp Gly Gln Gly Thr Leu Val Thr Val Ser Ser
        115                 120

<210> SEQ ID NO 453
<211> LENGTH: 121
<212> TYPE: PRT
<213> ORGANISM: Artificial sequence
<220> FEATURE:
<223> OTHER INFORMATION: Synthetic polypeptide

<400> SEQUENCE: 453

Glu Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
                20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
```

```
                        85                  90                  95

Ala Arg Asn Thr Tyr Tyr Asp Arg Arg Thr Phe Asp Tyr Trp Gly
                100                 105                 110

Gln Gly Thr Leu Val Thr Val Ser Ser
            115                 120

<210> SEQ ID NO 454
<211> LENGTH: 122
<212> TYPE: PRT
<213> ORGANISM: Artificial sequence
<220> FEATURE:
<223> OTHER INFORMATION: Synthetic polypeptide

<400> SEQUENCE: 454

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Asp His
            20                  25                  30

Tyr Met Asp Trp Val Arg Gln Ala Pro Gly Lys Gly Leu Glu Trp Val
        35                  40                  45

Gly Arg Thr Arg Asn Lys Ala Asn Ser Tyr Thr Thr Glu Tyr Ala Ala
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Gly Val Gly Ile Thr Gly Thr Thr Gly Ile Asp Tyr Trp
            100                 105                 110

Gly Gln Gly Thr Leu Val Thr Val Ser Ser
        115                 120

<210> SEQ ID NO 455
<211> LENGTH: 125
<212> TYPE: PRT
<213> ORGANISM: Artificial sequence
<220> FEATURE:
<223> OTHER INFORMATION: Synthetic polypeptide

<400> SEQUENCE: 455

Glu Val Gln Leu Leu Glu Ser Gly Gly Asp Leu Val Gln Pro Gly Arg
1               5                   10                  15

Ser Leu Arg Leu Ser Cys Ala Ala Ser Gly Phe Asn Leu Ile Asp Tyr
            20                  25                  30

Ala Met His Trp Val Arg Gln Val Pro Gly Lys Gly Leu Glu Trp Val
        35                  40                  45

Ser Gly Ile Ser Trp Asn Ser Arg Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asp Ser Leu Lys His Glu Asp Thr Ala Leu Phe Tyr Cys
                85                  90                  95

Ala Lys Gly Ala Ala Ala Gly Pro Phe Pro Tyr Phe Tyr Tyr Ala Met
            100                 105                 110

Asp Val Trp Gly Gln Gly Thr Thr Val Thr Val Ser Ser
        115                 120                 125

<210> SEQ ID NO 456
<211> LENGTH: 110
```

```
<212> TYPE: PRT
<213> ORGANISM: Artificial sequence
<220> FEATURE:
<223> OTHER INFORMATION: Synthetic polypeptide

<400> SEQUENCE: 456

Gln Ser Val Leu Thr Gln Pro Pro Ser Val Ser Ala Ala Pro Gly Gln
1               5                   10                  15

Lys Val Thr Ile Ser Cys Ser Gly Ser Ser Asn Ile Gly Asn Asn
            20                  25                  30

Tyr Val Ser Trp Tyr Gln Gln Leu Pro Gly Ala Ala Pro Lys Leu Leu
        35                  40                  45

Ile Tyr Asp Asn Lys Lys Arg Pro Ser Gly Ile Pro Asp Arg Phe Ser
50                  55                  60

Gly Ser Ala Ser Gly Thr Ser Ala Thr Met Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Trp Val Phe Gly Gly Gly Thr Lys Val Thr Val Leu
            100                 105                 110

<210> SEQ ID NO 457
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 457

Asp Ile Arg Val Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Val Arg Phe Ser Gly
    50                  55                  60

Ser Gly Ser Gly Thr Asp Phe Thr Leu Thr Ile Ser Ser Leu Gln Ser
65                  70                  75                  80

Glu Asp Phe Ala Val Tyr Tyr Cys Gln Gln Tyr Asp Asn Trp Pro Leu
                85                  90                  95

Thr Phe Gly Gly Gly Thr Lys Val Glu Ile Lys
            100                 105

<210> SEQ ID NO 458
<211> LENGTH: 110
<212> TYPE: PRT
<213> ORGANISM: Artificial sequence
<220> FEATURE:
<223> OTHER INFORMATION: Synthetic polypeptide

<400> SEQUENCE: 458

Gln Ser Val Val Thr Gln Pro Pro Ser Val Ser Ala Ala Pro Gly Gln
1               5                   10                  15

Lys Val Thr Ile Ser Cys Ser Gly Ser Ser Asn Ile Gly Asn Asn
            20                  25                  30

Tyr Val Ser Trp Tyr Gln Gln Phe Pro Arg Thr Ala Pro Lys Leu Leu
        35                  40                  45

Ile Tyr Asp Asn Lys Lys Arg Pro Ser Gly Ile Pro Asp Arg Phe Ser
```

Gly Ser Ala Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Trp Val Phe Gly Gly Gly Thr Lys Val Thr Val Leu
            100                 105                 110

<210> SEQ ID NO 459
<211> LENGTH: 110
<212> TYPE: PRT
<213> ORGANISM: Artificial sequence
<220> FEATURE:
<223> OTHER INFORMATION: Synthetic polypeptide

<400> SEQUENCE: 459

Gln Pro Val Leu Thr Gln Pro Pro Ser Ala Ser Gly Thr Pro Gly Gln
1               5                   10                  15

Arg Val Thr Ile Phe Cys Ser Gly Ser Arg Ser Asn Ile Gly Thr Tyr
            20                  25                  30

Thr Ile Asn Trp Tyr Gln Lys Leu Pro Gly Thr Ala Pro Lys Leu Leu
        35                  40                  45

Ile Tyr Ser Asn Asn Arg Gly Pro Ser Gly Val Pro Asp Arg Phe Ser
    50                  55                  60

Gly Ser Gln Ser Gly Thr Ser Ala Ser Leu Ala Ile Ser Gly Leu Gln
65                  70                  75                  80

Pro Glu Asp Glu Ala Asp Tyr Tyr Cys Ala Ala Trp Asp Asp Ser Leu
                85                  90                  95

Asn Gly Trp Val Phe Gly Gly Gly Thr Lys Val Thr Val Leu
            100                 105                 110

<210> SEQ ID NO 460
<211> LENGTH: 110
<212> TYPE: PRT
<213> ORGANISM: Artificial sequence
<220> FEATURE:
<223> OTHER INFORMATION: Synthetic polypeptide

<400> SEQUENCE: 460

Gln Ser Val Val Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ala Trp Tyr Gln Gln Leu Pro Gly Arg Ala Pro Lys Leu Leu
        35                  40                  45

Ile His Asp Asn Lys Lys Arg Pro Ser Gly Ile Pro Asp Arg Phe Ser
    50                  55                  60

Gly Ser Ala Ser Gly Thr Ser Ala Thr Leu Gly Ile Thr Gly Leu Gln
65                  70                  75                  80

Thr Gly Asp Glu Ala Asp Tyr Tyr Cys Glu Thr Trp Asp Ser Ser Leu
                85                  90                  95

Asn Ala Val Val Phe Gly Gly Gly Thr Lys Leu Thr Val Leu
            100                 105                 110

<210> SEQ ID NO 461
<211> LENGTH: 108
<212> TYPE: PRT
<213> ORGANISM: Artificial sequence
<220> FEATURE:

<223> OTHER INFORMATION: Synthetic polypeptide

<400> SEQUENCE: 461

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Thr Ile Ser Val Asp
            20                  25                  30

Leu Asn Trp Tyr Gln His Lys Pro Gly Lys Ala Pro Lys Leu Leu Ile
        35                  40                  45

Phe Ala Ala Ser Thr Leu Gln Ser Gly Val Pro Ser Arg Phe Ser Gly
    50                  55                  60

Ser Gly Ser Gly Thr Asp Phe Thr Leu Thr Ile Arg Ser Leu Gln Pro
65                  70                  75                  80

Glu Asp Phe Ala Thr Tyr Tyr Cys Gln Gln Ser Tyr Ser Ile Pro Arg
                85                  90                  95

Ile Thr Phe Gly Gln Gly Thr Arg Leu Glu Ile Lys
            100                 105

<210> SEQ ID NO 462
<211> LENGTH: 108
<212> TYPE: PRT
<213> ORGANISM: Artificial sequence
<220> FEATURE:
<223> OTHER INFORMATION: Synthetic polypeptide

<400> SEQUENCE: 462

Glu Ile Val Met Thr Gln Ser Pro Ser Ala Leu Ser Ala Ser Val Arg
1               5                   10                  15

Asp Arg Val Thr Ile Thr Cys Arg Ala Ser Gln Ser Ile Gly Ser Asp
            20                  25                  30

Leu Asn Trp Tyr Gln Gln Arg Pro Gly Lys Ala Pro Met Leu Leu Ile
        35                  40                  45

Tyr Ala Ala Thr Gly Leu Gln Ser Gly Val Pro Ser Arg Phe Ser Gly
    50                  55                  60

Ser Gly Ser Gly Thr Asp Phe Thr Leu Thr Ile Ser Asn Leu Gln Pro
65                  70                  75                  80

Glu Asp Phe Ala Thr Tyr Tyr Cys Gln Gln Ser Tyr Ser Pro Pro Met
                85                  90                  95

Tyr Thr Phe Gly Gln Gly Thr Lys Val Asp Ile Lys
            100                 105

<210> SEQ ID NO 463
<211> LENGTH: 110
<212> TYPE: PRT
<213> ORGANISM: Artificial sequence
<220> FEATURE:
<223> OTHER INFORMATION: Synthetic polypeptide

<400> SEQUENCE: 463

Gln Pro Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Thr Asn
            20                  25                  30

Thr Val Ser Trp Tyr Gln Gln Leu Pro Gly Thr Ala Pro Gln Leu Leu
        35                  40                  45

Val Phe Ser Arg Thr Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln

```
                65                  70                  75                  80
Ser Asp Asp Glu Ala Asp Tyr Tyr Cys Ala Ala Trp Asp Asp Ser Arg
                    85                  90                  95

Asn Gly Trp Val Phe Gly Gly Gly Thr Lys Leu Thr Val Leu
            100                 105                 110

<210> SEQ ID NO 464
<211> LENGTH: 112
<212> TYPE: PRT
<213> ORGANISM: Artificial sequence
<220> FEATURE:
<223> OTHER INFORMATION: Synthetic polypeptide

<400> SEQUENCE: 464

Gln Pro Val Leu Thr Gln Pro Pro Ser Val Ser Ala Ala Pro Gly Gln
1               5                   10                  15

Lys Val Thr Ile Ser Cys Ser Gly Ser Asn Ser Asn Ile Gly Asn Tyr
                20                  25                  30

Tyr Val Ser Trp Tyr Gln Gln Phe Pro Gly Thr Ala Pro Lys Leu Leu
            35                  40                  45

Ile Tyr Asp Asn Asn Lys Arg Pro Ser Gly Ile Pro Asp Arg Phe Ser
50                  55                  60

Gly Ser Lys Ser Gly Thr Ser Ala Thr Leu Ala Ile Thr Gly Leu Gln
65                  70                  75                  80

Thr Gly Asp Glu Ala His Tyr Tyr Cys Gly Thr Trp Asp Thr Ser Ser
                85                  90                  95

Leu Ser Ala Gly Arg Val Phe Gly Gly Gly Thr Lys Leu Thr Val Leu
            100                 105                 110

<210> SEQ ID NO 465
<211> LENGTH: 111
<212> TYPE: PRT
<213> ORGANISM: Artificial sequence
<220> FEATURE:
<223> OTHER INFORMATION: Synthetic polypeptide

<400> SEQUENCE: 465

Gln Ser Ala Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Ser
                20                  25                  30

Tyr Val Ser Trp Tyr Gln Gln Val Pro Gly Thr Ala Pro Lys Leu Leu
            35                  40                  45

Ile Tyr Asp Asn Asn Lys Arg Pro Ser Gly Ile Pro Asp Arg Phe Ser
50                  55                  60

Gly Ser Lys Ser Gly Thr Ser Ala Thr Leu Gly Ile Thr Gly Leu Gln
65                  70                  75                  80

Ala Gly Asp Glu Ala Asp Tyr Tyr Cys Gly Thr Trp Asp Thr Ser Leu
                85                  90                  95

Ser Ala Gly Arg Val Phe Gly Arg Gly Thr Lys Leu Thr Val Leu
            100                 105                 110

<210> SEQ ID NO 466
<211> LENGTH: 109
<212> TYPE: PRT
<213> ORGANISM: Artificial sequence
<220> FEATURE:
<223> OTHER INFORMATION: Synthetic polypeptide

<400> SEQUENCE: 466
```

Gln Ser Val Leu Thr Gln Pro Pro Ser Val Ala Ala Pro Gly Gln
1               5                   10                  15

Lys Val Thr Ile Ser Cys Ser Gly Ser Ser Asn Ile Gly Tyr Ser
                20                  25                  30

His Val Ser Trp Tyr Gln Gln Leu Pro Gly Thr Ala Pro Lys Val Leu
            35                  40                  45

Ile Tyr Asp Asn Asp Lys Arg Pro Ser Gly Ile Pro Asp Arg Phe Ser
50                      55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Thr Ser Leu
                85                  90                  95

Gly Val Val Phe Gly Gly Gly Thr Lys Leu Thr Val Leu
            100                 105

<210> SEQ ID NO 467
<211> LENGTH: 112
<212> TYPE: PRT
<213> ORGANISM: Artificial sequence
<220> FEATURE:
<223> OTHER INFORMATION: Synthetic polypeptide

<400> SEQUENCE: 467

Gln Ser Val Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Ala Tyr
                20                  25                  30

Asn Phe Val Ser Trp Tyr Gln Gln Tyr Pro Gly Lys Ala Pro Lys Leu
            35                  40                  45

Met Ile Tyr Asp Val Asn Lys Arg Pro Ser Gly Val Pro Asp Arg Phe
50                      55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr His Cys Cys Ser Tyr Ala Gly Thr
                85                  90                  95

Tyr Thr Ser Asn Tyr Val Phe Gly Ser Gly Thr Lys Val Thr Val Leu
            100                 105                 110

<210> SEQ ID NO 468
<211> LENGTH: 110
<212> TYPE: PRT
<213> ORGANISM: Artificial sequence
<220> FEATURE:
<223> OTHER INFORMATION: Synthetic polypeptide

<400> SEQUENCE: 468

Gln Ser Val Val Thr Gln Pro Pro Ser Val Ala Ala Pro Gly Gln
1               5                   10                  15

Lys Val Thr Ile Ser Cys Ser Gly Ser Ser Asn Ile Gly Asn Asn
                20                  25                  30

Tyr Val Ser Trp Tyr Gln Gln Leu Ser Glu Thr Ala Pro Lys Leu Leu
            35                  40                  45

Ile Tyr Asp Asn Asn Lys Arg Pro Ser Gly Ile Pro Asn Arg Phe Ser
50                      55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Asn Ser Leu

```
                85                  90                  95
Gly Ala Val Val Phe Gly Gly Gly Thr Lys Val Thr Val Leu
                100                 105                 110

<210> SEQ ID NO 469
<211> LENGTH: 110
<212> TYPE: PRT
<213> ORGANISM: Artificial sequence
<220> FEATURE:
<223> OTHER INFORMATION: Synthetic polypeptide

<400> SEQUENCE: 469

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Ser Asn
                20                  25                  30

Tyr Val Ser Trp Tyr Gln Gln Phe Pro Gly Thr Ala Pro Lys Leu Leu
            35                  40                  45

Ile Tyr Asp Asn Ser Lys Arg Pro Ser Gly Ile Pro Asp Arg Phe Ser
        50                  55                  60

Gly Ser Met Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Val Val Phe Gly Gly Gly Thr Lys Val Thr Val Leu
                100                 105                 110

<210> SEQ ID NO 470
<211> LENGTH: 111
<212> TYPE: PRT
<213> ORGANISM: Artificial sequence
<220> FEATURE:
<223> OTHER INFORMATION: Synthetic polypeptide

<400> SEQUENCE: 470

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
                20                  25                  30

Tyr Val Ser Trp Tyr Gln Gln Leu Pro Gly Thr Ala Pro Lys Leu Leu
            35                  40                  45

Ile Tyr Asp Asn Asn Lys Arg Pro Ser Gly Ile Pro Asp Arg Phe Ser
        50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Thr Ser Leu
                85                  90                  95

Ser Ala Gly Arg Val Phe Gly Gly Gly Thr Lys Leu Thr Val Leu
                100                 105                 110

<210> SEQ ID NO 471
<211> LENGTH: 108
<212> TYPE: PRT
<213> ORGANISM: Artificial sequence
<220> FEATURE:
<223> OTHER INFORMATION: Synthetic polypeptide

<400> SEQUENCE: 471

Glu Ile Val Leu Thr Gln Ser Pro Ala Thr Leu Ser Val Ser Pro Gly
1               5                   10                  15
```

Glu Arg Ala Thr Leu Ser Cys Arg Ala Ser Arg Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Thr Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Pro
                85                  90                  95

Arg Thr Phe Gly Gln Gly Thr Lys Val Asp Ile Lys
            100                 105

<210> SEQ ID NO 472
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 472

Asp Ile Gln Leu Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

His Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Lys Ser Phe Pro Pro
                85                  90                  95

Thr Phe Gly Gln Gly Thr Arg Leu Glu Ile Lys
            100                 105

<210> SEQ ID NO 473
<211> LENGTH: 110
<212> TYPE: PRT
<213> ORGANISM: Artificial sequence
<220> FEATURE:
<223> OTHER INFORMATION: Synthetic polypeptide

<400> SEQUENCE: 473

Gln Pro Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Leu Ile Tyr Asp Val Ser Asn Arg Pro Ser Gly Val Ser Asn Arg Phe
    50                  55                  60

Ser Gly Ser Lys Ser Ala Asn Ser Ala Ser Leu Thr Ile Ser Gly Leu
65                  70                  75                  80

Gln Ala Glu Asp Glu Ala Asp Tyr Tyr Cys Asn Ser Tyr Thr Ser Ser
                85                  90                  95

Ser Thr Leu Val Phe Gly Gly Gly Thr Lys Leu Thr Val Leu

<210> SEQ ID NO 474
<211> LENGTH: 106
<212> TYPE: PRT
<213> ORGANISM: Artificial sequence
<220> FEATURE:
<223> OTHER INFORMATION: Synthetic polypeptide

<400> SEQUENCE: 474

Glu Ile Val Met Thr Gln Ser Pro Ala Thr Leu Ser Val Ser Pro Gly
1               5                   10                  15
Glu Arg Ala Thr Leu Ser Cys Arg Ala Ser Gln Ser Val Ser Ser Asn
            20                  25                  30
Leu Ala Trp Tyr Gln Gln Lys Pro Gly Gln Ala Pro Arg Leu Leu Ile
        35                  40                  45
Tyr Gly Ala Ser Thr Arg Ala Thr Gly Ile Pro Ala Arg Phe Ser Gly
    50                  55                  60
Ser Gly Ser Gly Thr Glu Phe Thr Leu Thr Ile Ser Ser Leu Gln Ser
65                  70                  75                  80
Glu Asp Phe Ala Leu Tyr Tyr Cys Gln Gln Tyr Asp Asp Trp Pro Leu
                85                  90                  95
Phe Gly Gln Gly Thr Arg Leu Glu Ile Lys
            100                 105

<210> SEQ ID NO 475
<211> LENGTH: 111
<212> TYPE: PRT
<213> ORGANISM: Artificial sequence
<220> FEATURE:
<223> OTHER INFORMATION: Synthetic polypeptide

<400> SEQUENCE: 475

Gln Ser Val Leu Thr Gln Pro Pro Ser Val Ser Ala Ala Pro Gly Gln
1               5                   10                  15
Lys Val Thr Ile Ser Cys Ser Gly Ser Ser Ser Asn Ile Gly Asn Asn
            20                  25                  30
Tyr Val Ser Trp Tyr Gln Gln Leu Pro Gly Thr Ala Pro Lys Leu Leu
        35                  40                  45
Ile Tyr Asp Asn Asn Lys Arg Pro Ser Gly Ile Pro Asp Arg Phe Ser
    50                  55                  60
Gly Ser Lys Ser Gly Thr Ser Ala Thr Leu Gly Ile Thr Gly Leu Gln
65                  70                  75                  80
Thr Gly Asp Glu Ala Asp Tyr Ile Cys Gly Thr Trp Asp Thr Ser Leu
                85                  90                  95
Ser Ala Gly Gly Val Phe Gly Gly Gly Thr Lys Leu Thr Val Leu
            100                 105                 110

<210> SEQ ID NO 476
<211> LENGTH: 110
<212> TYPE: PRT
<213> ORGANISM: Artificial sequence
<220> FEATURE:
<223> OTHER INFORMATION: Synthetic polypeptide

<400> SEQUENCE: 476

Gln Ser Val Leu Thr Gln Pro Ala Ser Val Ser Gly Ser Pro Gly Gln
1               5                   10                  15
Ser Ile Thr Ile Ser Cys Thr Gly Thr Ser Ser Asp Ile Gly Ala Tyr
            20                  25                  30

```
Asn Tyr Val Ser Trp Tyr Gln Gln His Pro Gly Lys Ala Pro Lys Leu
            35                  40                  45

Met Ile Tyr Asp Val Thr Asn Arg Pro Ser Gly Val Ser Asn Arg Phe
 50                  55                  60

Ser Gly Ser Lys Ser Gly Ser Ala Ser Leu Thr Ile Ser Gly Leu
 65                  70                  75                  80

Gln Thr Glu Asp Glu Ala Asp Tyr Tyr Cys Ser Ser Tyr Thr Arg Arg
                 85                  90                  95

Ser Thr Leu Val Phe Gly Gly Gly Thr Lys Leu Thr Val Leu
            100                 105                 110

<210> SEQ ID NO 477
<211> LENGTH: 109
<212> TYPE: PRT
<213> ORGANISM: Artificial sequence
<220> FEATURE:
<223> OTHER INFORMATION: Synthetic polypeptide

<400> SEQUENCE: 477

Gln Ser Val Leu Thr Gln Pro Pro Ser Val Ser Ala Ala Pro Gly Gln
 1               5                  10                  15

Lys Val Thr Ile Ser Cys Ser Gly Ser Ser Ser Asn Ile Gly Asn Asn
                20                  25                  30

Tyr Val Ser Trp Tyr Gln Gln Leu Pro Gly Thr Ala Pro Lys Leu Leu
            35                  40                  45

Ile Tyr Asp Asn Asn Lys Arg Pro Ser Gly Ile Pro Asp Arg Phe Ser
 50                  55                  60

Gly Ser Lys Ser Gly Thr Ser Ala Thr Leu Gly Ile Thr Gly Leu Gln
 65                  70                  75                  80

Thr Gly Asp Glu Ala Asn Tyr Tyr Cys Gly Thr Trp Asp Thr Ser Leu
                 85                  90                  95

Ser Thr Val Phe Gly Gly Gly Thr Lys Leu Thr Val Leu
            100                 105

<210> SEQ ID NO 478
<211> LENGTH: 111
<212> TYPE: PRT
<213> ORGANISM: Artificial sequence
<220> FEATURE:
<223> OTHER INFORMATION: Synthetic polypeptide

<400> SEQUENCE: 478

Gln Ser Ala Leu Thr Gln Pro Ala Ser Val Ser Gly Ser Pro Gly Gln
 1               5                  10                  15

Ser Ile Thr Ile Ser Cys Thr Gly Thr Gly Ser Asp Val Gly Gly Tyr
                20                  25                  30

Asn Phe Val Ser Trp Tyr Gln Gln His Pro Gly Lys Ala Pro Lys Leu
            35                  40                  45

Met Leu Tyr Asp Val Asn Asn Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Pro Gly Thr
                 85                  90                  95

Ser Ala Leu Val Ile Phe Gly Gly Gly Thr Arg Leu Thr Val Leu
            100                 105                 110
```

```
<210> SEQ ID NO 479
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 479
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Glu Ala Pro Asn Leu Leu Ile
        35                  40                  45

Phe Ala Ala Ser Ile Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Val Glu Ile Lys
            100                 105

```
<210> SEQ ID NO 480
<211> LENGTH: 112
<212> TYPE: PRT
<213> ORGANISM: Artificial sequence
<220> FEATURE:
<223> OTHER INFORMATION: Synthetic polypeptide

<400> SEQUENCE: 480
```

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly His Val Val Phe Gly Gly Gly Thr Lys Leu Thr Val Leu
            100                 105                 110

```
<210> SEQ ID NO 481
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 481
```

Glu Ile Val Leu Thr Gln Ser Pro Ala Thr Leu Ser Ser Pro Gly
1               5                   10                  15

Glu Arg Ala Thr Leu Ser Cys Arg Ala Ser Gln Ser Val Asn Ser Tyr
            20                  25                  30

Leu Val Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Thr Gly
            50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Thr Asn Trp Pro Phe
                 85                  90                  95

Thr Phe Gly Gln Gly Thr Lys Val Asp Ile Lys
            100                 105

<210> SEQ ID NO 482
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 482

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Asn Arg Tyr
             20                  25                  30

Leu Ala Trp Tyr Gln Gln Lys Pro Gly Gln Ala Pro Arg Leu Leu Ile
         35                  40                  45

Tyr Asp Ala Ser Asn Arg Ala Thr Gly Ile Pro Ala Arg Phe Ser Gly
     50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys His Gln Arg Thr Asn Trp Pro Trp
                 85                  90                  95

Thr Phe Gly Gln Gly Thr Lys Val Glu Ile Lys
            100                 105

<210> SEQ ID NO 483
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 483

Glu Ile Val Met Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Asn Tyr
             20                  25                  30

Leu Ala Trp Tyr Gln Gln Lys Pro Gly Gln Ala Pro Arg Leu Leu Ile
         35                  40                  45

Ser Asp Ala Ser Ser Arg Ala Thr Gly Ile Pro Ala Arg Phe Arg Gly
     50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Leu Gln Arg Thr Asn Trp Pro Phe
                 85                  90                  95

Thr Phe Gly Pro Gly Thr Lys Val Glu Ile Lys
            100                 105

<210> SEQ ID NO 484
<211> LENGTH: 111
<212> TYPE: PRT

-continued

<213> ORGANISM: Artificial sequence
<220> FEATURE:
<223> OTHER INFORMATION: Synthetic polypeptide

<400> SEQUENCE: 484

Gln Ser Val Leu Thr Gln Pro Ala Ser Val Ser Gly Ser Pro Gly Gln
1               5                   10                  15

Ser Ile Thr Ile Ser Cys Thr Gly Thr Ser Ser Asp Ile Gly Gly Tyr
            20                  25                  30

Asn Tyr Val Ser Trp Tyr Gln Gln His Pro Gly Lys Val Pro Lys Leu
        35                  40                  45

Val Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Gly
                85                  90                  95

Thr Thr Leu Gly Val Phe Gly Thr Gly Thr Lys Leu Thr Val Leu
            100                 105                 110

<210> SEQ ID NO 485
<211> LENGTH: 110
<212> TYPE: PRT
<213> ORGANISM: Artificial sequence
<220> FEATURE:
<223> OTHER INFORMATION: Synthetic polypeptide

<400> SEQUENCE: 485

Gln Ser Val Val Thr Gln Pro Pro Ser Val Ser Ala Ala Pro Gly Gln
1               5                   10                  15

Lys Val Thr Ile Ser Cys Ser Gly Arg Ser Ser Asn Ile Gly Asn Ser
            20                  25                  30

Asp Val Ser Trp Tyr Gln Gln Phe Pro Gly Arg Ala Pro Lys Leu Leu
        35                  40                  45

Ile Tyr Asp Asn Asp Glu Arg Pro Ser Gly Ile Pro Asp Arg Phe Ser
    50                  55                  60

Gly Ser Lys Ser Gly Thr Ser Ala Thr Leu Asp Ile Thr Gly Leu Gln
65                  70                  75                  80

Thr Gly Asp Glu Ala Asp Tyr Tyr Cys Gly Thr Trp Asp Ser Ser Leu
                85                  90                  95

Gly Gly Val Ile Phe Gly Gly Gly Thr Lys Val Thr Val Leu
            100                 105                 110

<210> SEQ ID NO 486
<211> LENGTH: 110
<212> TYPE: PRT
<213> ORGANISM: Artificial sequence
<220> FEATURE:
<223> OTHER INFORMATION: Synthetic polypeptide

<400> SEQUENCE: 486

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Glu Thr Trp Asp Ser Ser Leu
                85                  90                  95

Gly Val Val Phe Gly Gly Gly Thr Lys Leu Thr Val Leu
            100                 105                 110

<210> SEQ ID NO 487
<211> LENGTH: 108
<212> TYPE: PRT
<213> ORGANISM: Artificial sequence
<220> FEATURE:
<223> OTHER INFORMATION: Synthetic polypeptide

<400> SEQUENCE: 487

Asp Ile Gln Val Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln His Lys Pro Gly Arg Ala Pro Lys Leu Leu Ile
        35                  40                  45

Tyr Asp Ala Ser Asn Leu Glu Arg Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Ser Arg
                85                  90                  95

Leu Thr Phe Gly Gly Gly Thr Lys Leu Glu Ile Lys
            100                 105

<210> SEQ ID NO 488
<211> LENGTH: 111
<212> TYPE: PRT
<213> ORGANISM: Artificial sequence
<220> FEATURE:
<223> OTHER INFORMATION: Synthetic polypeptide

<400> SEQUENCE: 488

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Thr Ser Leu
                85                  90                  95

Ser Ala Gly Arg Val Phe Gly Gly Gly Thr Lys Leu Thr Val Leu
            100                 105                 110

<210> SEQ ID NO 489
<211> LENGTH: 109
<212> TYPE: PRT
<213> ORGANISM: Artificial sequence
<220> FEATURE:
<223> OTHER INFORMATION: Synthetic polypeptide

<400> SEQUENCE: 489

Gln Ser Val Leu Thr Gln Pro Pro Ser Met Ser Ala Ala Pro Gly Gln
1               5                   10                  15

Lys Val Thr Ile Ser Cys Ser Gly Ser Ser Asn Ile Gly Asn Asn
            20                  25                  30

Tyr Val Ser Trp Tyr Arg Gln Leu Pro Gly Thr Ala Pro Lys Leu Leu
        35                  40                  45

Ile Tyr Asp Asn Asp Lys Arg Pro Ser Gly Ile Pro Asp Arg Phe Ser
50                  55                  60

Gly Ser Lys Ser Gly Thr Thr Ala Thr Leu Gly Ile Thr Gly Leu Gln
65                  70                  75                  80

Thr Gly Asp Glu Ala Val Tyr Tyr Cys Gly Thr Trp Asp Phe Arg Leu
                85                  90                  95

Ser Ala Leu Phe Gly Gly Gly Thr Lys Leu Thr Val Leu
            100                 105

<210> SEQ ID NO 490
<211> LENGTH: 111
<212> TYPE: PRT
<213> ORGANISM: Artificial sequence
<220> FEATURE:
<223> OTHER INFORMATION: Synthetic polypeptide

<400> SEQUENCE: 490

Gln Ser Val Leu Ile Gln Pro Ala Ser Val Ser Gly Ser Pro Gly Gln
1               5                   10                  15

Ser Ile Thr Ile Ser Cys Thr Gly Thr Ser Ser Asp Val Gly Gly Asp
            20                  25                  30

Lys Tyr Val Ser Trp Tyr Gln Gln His Pro Gly Lys Ala Pro Lys Leu
        35                  40                  45

Val Ile Tyr Glu Val Ser Asn Arg Pro Ser Gly Val Ser Asn Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Gly Thr Pro Val Val Cys Gly Gly Thr Lys Val Thr Val Leu
            100                 105                 110

<210> SEQ ID NO 491
<211> LENGTH: 111
<212> TYPE: PRT
<213> ORGANISM: Artificial sequence
<220> FEATURE:
<223> OTHER INFORMATION: Synthetic polypeptide

<400> SEQUENCE: 491

Gln Ser Val Leu Thr Gln Pro Pro Ser Val Ser Ala Ala Pro Gly Gln
1               5                   10                  15

Lys Val Thr Ile Ser Cys Ser Gly Ser Ser Asn Ile Gly Asn Tyr
            20                  25                  30

Tyr Val Ser Trp Tyr Gln Gln Val Pro Gly Thr Ala Pro Lys Leu Leu
        35                  40                  45

Ile Tyr Asp Asn Asn Lys Arg Pro Ser Gly Ile Pro Asp Arg Phe Ser
50                  55                  60

Gly Ser Lys Ser Gly Thr Ser Ala Thr Leu Gly Ile Thr Gly Leu His
65                  70                  75                  80

```
Thr Gly Asp Glu Ala Glu Tyr Tyr Cys Gly Thr Trp Asp Ser Ser Pro
                85                  90                  95

Ser Ala Gly Arg Val Phe Gly Gly Thr Lys Leu Thr Val Leu
            100                 105                 110

<210> SEQ ID NO 492
<211> LENGTH: 113
<212> TYPE: PRT
<213> ORGANISM: Artificial sequence
<220> FEATURE:
<223> OTHER INFORMATION: Synthetic polypeptide

<400> SEQUENCE: 492

Asp Ile Val Leu Thr Gln Ser Pro Asp Ser Leu Ala Val Ser Leu Gly
1               5                   10                  15

Glu Arg Ala Thr Ile Asn Cys Lys Ser Ser Gln Ser Val Leu Phe Gly
            20                  25                  30

Ser Asn Gln Lys Ser Cys Leu Ala Trp Tyr Gln Gln Lys Pro Gly Gln
        35                  40                  45

Ser Pro Lys Leu Leu Ile His Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Arg Thr Phe Gly Gln Gly Thr Lys Val Glu Ile
            100                 105                 110

Lys

<210> SEQ ID NO 493
<211> LENGTH: 109
<212> TYPE: PRT
<213> ORGANISM: Artificial sequence
<220> FEATURE:
<223> OTHER INFORMATION: Synthetic polypeptide

<400> SEQUENCE: 493

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Ser Asn
            20                  25                  30

Phe Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Ala Ile Thr Gly Leu Gln
65                  70                  75                  80

Thr Gly Asp Glu Ala Asp Tyr Tyr Cys Gly Thr Trp Asp Thr Arg Leu
                85                  90                  95

Ser Ala Leu Phe Gly Gly Gly Thr Lys Val Thr Val Leu
            100                 105

<210> SEQ ID NO 494
<211> LENGTH: 111
<212> TYPE: PRT
<213> ORGANISM: Artificial sequence
<220> FEATURE:
<223> OTHER INFORMATION: Synthetic polypeptide
```

<400> SEQUENCE: 494

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Phe Gly Asn Asp
            20                  25                  30

Tyr Val Ser Trp Tyr Gln Gln Leu Pro Gly Thr Ala Pro Lys Leu Leu
        35                  40                  45

Ile Tyr Asp Asn Asp Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Thr Ser Leu
                85                  90                  95

Ser Ala Ala Trp Val Phe Gly Gly Gly Thr Lys Val Thr Val Leu
            100                 105                 110

<210> SEQ ID NO 495
<211> LENGTH: 111
<212> TYPE: PRT
<213> ORGANISM: Artificial sequence
<220> FEATURE:
<223> OTHER INFORMATION: Synthetic polypeptide

<400> SEQUENCE: 495

Gln Ser Val Val Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Thr Ser Gly Thr Ser Ala Thr Leu Gly Ile Thr Gly Leu Gln
65                  70                  75                  80

Thr Gly Asp Glu Ala Val Tyr Tyr Cys Gly Thr Trp Asp Thr Ser Pro
                85                  90                  95

Ser Ala Gly Gly Val Phe Gly Gly Gly Thr Lys Val Thr Val Leu
            100                 105                 110

<210> SEQ ID NO 496
<211> LENGTH: 111
<212> TYPE: PRT
<213> ORGANISM: Artificial sequence
<220> FEATURE:
<223> OTHER INFORMATION: Synthetic polypeptide

<400> SEQUENCE: 496

Gln Pro Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

```
Gln Ala Glu Asp Glu Ala Asp Tyr Tyr Cys Ser Ser Tyr Thr Ser Ser
                85                  90                  95

Ser Thr Leu Ala Val Phe Gly Gly Gly Thr Lys Leu Thr Val Leu
            100                 105                 110
```

<210> SEQ ID NO 497
<211> LENGTH: 111
<212> TYPE: PRT
<213> ORGANISM: Artificial sequence
<220> FEATURE:
<223> OTHER INFORMATION: Synthetic polypeptide

<400> SEQUENCE: 497

```
Gln Pro Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asp
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Gly Asp Tyr Tyr Cys Gly Thr Trp Asp Ser Ser Leu
                85                  90                  95

Ser Ala Ala Trp Val Phe Gly Gly Gly Thr Lys Val Thr Val Leu
            100                 105                 110
```

<210> SEQ ID NO 498
<211> LENGTH: 111
<212> TYPE: PRT
<213> ORGANISM: Artificial sequence
<220> FEATURE:
<223> OTHER INFORMATION: Synthetic polypeptide

<400> SEQUENCE: 498

```
Gln Pro Val Leu Thr Gln Ser Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Lys Tyr Val Ser Trp Tyr Gln Gln His Pro Gly Lys Ala Pro Lys Leu
        35                  40                  45

Met Ile Tyr Glu Val Ser Asn Arg Pro Ser Gly Val Ser Ile Arg Phe
    50                  55                  60

Ser Gly Ser Lys Ser Gly Asn Thr Ala Ser Leu Thr Ile Ser Gly Leu
65                  70                  75                  80

Gln Ala Ala Asp Glu Ala Asp Tyr Tyr Cys Ser Ser Tyr Arg Ser Ser
                85                  90                  95

Gly Thr Pro Tyr Val Phe Gly Thr Gly Thr Lys Val Thr Val Leu
            100                 105                 110
```

<210> SEQ ID NO 499
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 499

```
Glu Ile Val Leu Thr Gln Ser Pro Ser Ser Leu Ser Ala Ser Val Gly
```

```
1               5                   10                  15
Asp Arg Val Thr Ile Thr Cys Gln Ala Ser Gln Asp Ile Ser Asn Phe
                20                  25                  30

Leu Asn Trp Tyr Gln Gln Lys Pro Gly Lys Ala Pro Lys Leu Leu Ile
            35                  40                  45

Tyr Asp Ala Ser Ser Leu Glu Thr Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro Leu
                85                  90                  95

Thr Phe Gly Gly Gly Thr Lys Leu Glu Ile Lys
                100                 105
```

<210> SEQ ID NO 500
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 500

```
Asp Ile Arg Leu Thr Gln Ser Pro Ser Thr Leu Ser Ala Ser Val Gly
1               5                   10                  15

Asp Arg Val Thr Val Thr Cys Arg Ala Ser Gln Asn Ile Asn Thr Tyr
                20                  25                  30

Leu Ala Trp Tyr Gln Gln Ile Pro Gly Lys Ala Pro Arg Leu Leu Ile
            35                  40                  45

Tyr Arg Ala Ser Thr Leu Glu Ser Gly Val Pro Ser Arg Phe Ser Gly
        50                  55                  60

Ser Gly Ser Gly Thr Glu Phe Thr Leu Thr Ile Asn Ser Leu Gln Pro
65                  70                  75                  80

Asp Asp Tyr Ala Thr Tyr Tyr Cys Gln His Tyr Glu Thr Tyr Ser Val
                85                  90                  95

Arg Phe Gly Gln Gly Thr Lys Val Glu Ile Lys
                100                 105
```

<210> SEQ ID NO 501
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 501

```
Asp Ile Gln Val Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
                20                  25                  30

Leu Ala Trp Tyr Gln Gln Lys Pro Gly Lys Val Pro Lys Leu Leu Ile
            35                  40                  45

Phe Ala Ala Ser Thr Leu Arg Ser Gly Val Pro Ser Arg Phe Arg Gly
        50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro Leu
                85                  90                  95
```

```
Thr Phe Gly Gly Gly Thr Lys Val Glu Ile Lys
            100                 105
```

<210> SEQ ID NO 502
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 502

```
Asp Ile Val Met Thr Gln Thr Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Leu Gln Arg Thr Asn Trp Pro Phe
                85                  90                  95

Thr Phe Gly Pro Gly Thr Lys Val Glu Ile Lys
            100                 105
```

<210> SEQ ID NO 503
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 503

```
Asp Ile Val Leu Thr Gln Ser Pro Ser Thr Leu Ser Ala Ser Val Gly
1               5                   10                  15

Asp Arg Val Thr Val Thr Cys Arg Ala Ser Gln Asn Ile Asn Thr Tyr
            20                  25                  30

Leu Ala Trp Tyr Gln Gln Ile Pro Gly Lys Ala Pro Arg Leu Leu Ile
        35                  40                  45

Tyr Arg Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln His Tyr Asn Ser Phe Ser Val
                85                  90                  95

Lys Phe Gly Gln Gly Thr Lys Val Glu Ile Lys
            100                 105
```

<210> SEQ ID NO 504
<211> LENGTH: 109
<212> TYPE: PRT
<213> ORGANISM: Artificial sequence
<220> FEATURE:
<223> OTHER INFORMATION: Synthetic polypeptide

<400> SEQUENCE: 504

```
Ser Tyr Glu Leu Thr Gln Pro Pro Ser Val Ser Val Ala Pro Gly Gln
1               5                   10                  15

Thr Ala Arg Ile Thr Cys Gly Gly His Asn Val Gly Ser Lys Ser Val
```

```
                20                  25                  30

His Trp Tyr Gln Gln Lys Pro Gly Gln Ala Pro Val Leu Val Val Tyr
            35                  40                  45

Asp Asp Ser Asp Arg Pro Ser Gly Ile Pro Glu Arg Phe Ser Gly Ser
        50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Ser Ser Asp His
                85                  90                  95

Pro Trp Val Phe Gly Gly Gly Thr Lys Val Thr Val Leu
            100                 105

<210> SEQ ID NO 505
<211> LENGTH: 111
<212> TYPE: PRT
<213> ORGANISM: Artificial sequence
<220> FEATURE:
<223> OTHER INFORMATION: Synthetic polypeptide

<400> SEQUENCE: 505

Gln Ser Val Val Thr Gln Pro Pro Ser Val Ser Ala Ala Pro Gly Gln
 1               5                  10                  15

Lys Val Thr Ile Ser Cys Ser Gly Ser Ser Ser Asn Ile Gly Asn Asn
                20                  25                  30

Tyr Val Ser Trp Tyr Gln Gln Leu Pro Gly Thr Ala Pro Lys Leu Leu
            35                  40                  45

Ile Tyr Asp Asn Asn Lys Arg Pro Ser Gly Ile Pro Asp Arg Phe Ser
        50                  55                  60

Gly Ser Lys Ser Gly Thr Ser Ala Thr Leu Gly Ile Thr Gly Leu Gln
 65                  70                  75                  80

Thr Gly Asp Glu Ala Asp Tyr Tyr Cys Gly Thr Trp Asp Thr Ser Leu
                85                  90                  95

Ser Ala Gly Arg Val Phe Gly Gly Gly Thr Lys Leu Thr Val Leu
            100                 105                 110

<210> SEQ ID NO 506
<211> LENGTH: 109
<212> TYPE: PRT
<213> ORGANISM: Artificial sequence
<220> FEATURE:
<223> OTHER INFORMATION: Synthetic polypeptide

<400> SEQUENCE: 506

Gln Pro Val Leu Thr Gln Pro Pro Ser Val Ser Val Ala Pro Gly Gln
 1               5                  10                  15

Thr Ala Arg Ile Thr Cys Gly Gly Asn Asn Ile Gly Ser Lys Ser Val
                20                  25                  30

His Trp Tyr Gln Gln Lys Pro Gly Gln Ala Pro Met Leu Val Ile Tyr
            35                  40                  45

Ser Asn Ser Asp Arg Pro Ser Gly Ile Pro Glu Arg Phe Ser Gly Ser
        50                  55                  60

Asn Ser Gly Ile Thr Ala Thr Leu Thr Ile Ser Arg Val Glu Ala Gly
 65                  70                  75                  80

Asp Glu Ala Asp Tyr His Cys Gln Val Trp Asp Thr Ser Ile Asp His
                85                  90                  95

His Trp Val Phe Gly Gly Gly Thr Lys Leu Thr Val Leu
            100                 105
```

<210> SEQ ID NO 507
<211> LENGTH: 111
<212> TYPE: PRT
<213> ORGANISM: Artificial sequence
<220> FEATURE:
<223> OTHER INFORMATION: Synthetic polypeptide

<400> SEQUENCE: 507

Gln Ser Val Leu Ile Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Gly Ala Asp Tyr Tyr Cys Ser Ser Tyr Ala Gly Ser
                85                  90                  95

Asn Asn Trp Val Val Phe Gly Gly Gly Thr Lys Leu Thr Val Leu
            100                 105                 110

<210> SEQ ID NO 508
<211> LENGTH: 110
<212> TYPE: PRT
<213> ORGANISM: Artificial sequence
<220> FEATURE:
<223> OTHER INFORMATION: Synthetic polypeptide

<400> SEQUENCE: 508

Gln Pro Val Leu Thr Gln Pro Ala Ser Val Ser Gly Ser Pro Gly Gln
1               5                   10                  15

Ser Ile Thr Ile Ser Cys Thr Gly Thr Ser Thr Asp Val Gly Gly Tyr
            20                  25                  30

Asn Tyr Val Ser Trp Tyr Gln Gln Tyr Pro Gly Lys Ala Pro Lys Leu
        35                  40                  45

Ile Ile Tyr Asp Val Thr Asn Arg Pro Ser Gly Val Ser His Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Thr Thr
                85                  90                  95

Ser Leu Val Ile Phe Gly Gly Gly Thr Lys Leu Thr Val Leu
            100                 105                 110

<210> SEQ ID NO 509
<211> LENGTH: 113
<212> TYPE: PRT
<213> ORGANISM: Artificial sequence
<220> FEATURE:
<223> OTHER INFORMATION: Synthetic polypeptide

<400> SEQUENCE: 509

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser

```
                35                  40                  45
Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Pro Arg Thr Phe Gly Gln Gly Thr Arg Leu Glu Ile
                100                 105                 110

Lys

<210> SEQ ID NO 510
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 510

Asp Ile Gln Val Thr Gln Ser Pro Ser Ser Leu Ser Ala Ser Val Gly
1               5                   10                  15

Gly Arg Val Thr Ile Thr Cys Arg Ala Ser Gln Gly Ile Arg Asn Asp
                20                  25                  30

Leu Gly Trp Tyr Gln Arg Lys Pro Gly Lys Ala Pro Lys Arg Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Leu
                85                  90                  95

Thr Phe Gly Gly Gly Thr Lys Val Asp Ile Lys
            100                 105

<210> SEQ ID NO 511
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 511

Asp Ile Gln Leu Thr Gln Ser Pro Ser Thr Leu Ser Ala Ser Val Gly
1               5                   10                  15

Asp Arg Val Thr Ile Thr Cys Arg Ala Ser Gln Ser Ile Ser Thr Trp
                20                  25                  30

Leu Ala Trp Tyr Gln Gln Lys Pro Gly Lys Ala Pro Lys Leu Leu Ile
            35                  40                  45

Tyr Arg Ala Ser Ser Leu Glu Ser Gly Val Pro Ser Arg Phe Ser Ala
        50                  55                  60

Ser Gly Ser Gly Thr Glu Phe Thr Leu Ser Ile Ser Ser Leu Gln Pro
65                  70                  75                  80

Asp Asp Phe Ala Thr Tyr Tyr Cys Lys Gln Tyr Asn Arg Asn Pro Tyr
                85                  90                  95

Thr Phe Gly Gln Gly Thr Lys Val Glu Ile Lys
            100                 105
```

<210> SEQ ID NO 512
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 512

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Phe Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro Gln
                85                  90                  95

Thr Phe Gly Gln Gly Thr Lys Val Asp Ile Lys
            100                 105
```

<210> SEQ ID NO 513
<211> LENGTH: 108
<212> TYPE: PRT
<213> ORGANISM: Artificial sequence
<220> FEATURE:
<223> OTHER INFORMATION: Synthetic polypeptide

<400> SEQUENCE: 513

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Phe Asn
            20                  25                  30

Leu Ala Trp Tyr Gln Gln Lys Pro Gly Gln Ala Pro Arg Leu Leu Ile
        35                  40                  45

Ser Arg Ala Ser Thr Arg Ala Ala Gly Val Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Pro
                85                  90                  95

Leu Thr Phe Gly Gly Gly Thr Lys Leu Glu Ile Lys
            100                 105
```

<210> SEQ ID NO 514
<211> LENGTH: 113
<212> TYPE: PRT
<213> ORGANISM: Artificial sequence
<220> FEATURE:
<223> OTHER INFORMATION: Synthetic polypeptide

<400> SEQUENCE: 514

```
Asp Ile Gln Met Thr Gln Ser Pro Asp Ser Leu Thr Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Ser Leu Ala Trp Tyr Gln Gln Lys Pro Gly Gln
        35                  40                  45
```

```
Pro Pro Lys Leu Leu Ile Tyr Trp Ala Ser Thr Arg Glu Ser Gly Val
         50                  55                  60

Pro Asp Arg Phe Ser Gly Ser Gly Ser Gly Thr Asp Phe Thr Leu Thr
 65                  70                  75                  80

Ile Ser Ser Leu Gln Ala Ala Asp Val Ala Val Tyr Tyr Cys Gln Gln
                 85                  90                  95

Tyr Tyr Arg Thr Pro Trp Thr Phe Gly Gln Gly Thr Lys Val Glu Ile
            100                 105                 110

Lys

<210> SEQ ID NO 515
<211> LENGTH: 110
<212> TYPE: PRT
<213> ORGANISM: Artificial sequence
<220> FEATURE:
<223> OTHER INFORMATION: Synthetic polypeptide

<400> SEQUENCE: 515

Gln Ser Val Leu Thr Gln Pro Pro Ser Val Ser Ala Ala Pro Gly Gln
 1               5                  10                  15

Lys Val Thr Ile Ser Cys Ser Gly Ser Ser Ser Asn Ile Gly Asn Asn
                 20                  25                  30

Tyr Val Ser Trp Tyr Gln Gln Leu Pro Gly Thr Ala Pro Lys Val Leu
             35                  40                  45

Ile Tyr Asp Asn Asn Lys Arg Pro Ser Gly Ile Pro Asp Arg Phe Ser
         50                  55                  60

Gly Ser Lys Ser Gly Thr Ser Ala Thr Leu Gly Ile Thr Gly Leu Gln
 65                  70                  75                  80

Thr Gly Asp Glu Ala Asp Tyr Tyr Cys Gly Thr Trp Asp Ser Ala Leu
                 85                  90                  95

Gly Ala Ala Val Phe Gly Gly Gly Thr Lys Leu Thr Val Leu
            100                 105                 110

<210> SEQ ID NO 516
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 516

Asp Ile Gln Leu Thr Gln Ser Pro Ser Thr Leu Ser Ala Ser Val Gly
 1               5                  10                  15

Asp Arg Val Thr Ile Thr Cys Arg Ala Ser Gln Ser Val Ser Ser Trp
                 20                  25                  30

Leu Ala Trp Tyr Gln Gln Lys Pro Gly Lys Ala Pro Arg Leu Leu Ile
             35                  40                  45

Tyr Arg Ala Ser Ser Leu Glu Ser Gly Val Pro Ser Arg Phe Ser Gly
         50                  55                  60

Ser Gly Ser Gly Thr Glu Phe Thr Leu Thr Ile Ser Ser Leu Gln Pro
 65                  70                  75                  80

Asp Asp Phe Ala Ala Tyr Tyr Cys Gln Gln Tyr Asn Arg Asp Pro Tyr
                 85                  90                  95

Thr Phe Gly Gln Gly Thr Lys Val Glu Ile Lys
            100                 105

<210> SEQ ID NO 517
```

```
<211> LENGTH: 105
<212> TYPE: PRT
<213> ORGANISM: Artificial sequence
<220> FEATURE:
<223> OTHER INFORMATION: Synthetic polypeptide

<400> SEQUENCE: 517

Ser Tyr Glu Leu Thr Gln Leu Pro Ser Val Ser Val Ser Pro Gly Gln
1               5                   10                  15

Thr Ala Arg Val Thr Cys Ser Gly Asp Ala Leu Gln Tyr Val Tyr Trp
            20                  25                  30

Tyr Gln Gln Lys Pro Gly Gln Ala Pro Val Val Val Ile Tyr Lys Asp
        35                  40                  45

Thr Glu Arg Pro Ser Gly Ile Pro Glu Arg Phe Ser Gly Ser Ser Ser
    50                  55                  60

Gly Thr Thr Val Thr Leu Thr Ile Thr Gly Val Gln Ala Glu Asp Glu
65                  70                  75                  80

Ala Asp Tyr Tyr Cys Gln Ser Ala Asp Arg Ser Gly Ser Val Ile Phe
                85                  90                  95

Gly Gly Gly Thr Lys Val Thr Val Leu
            100                 105

<210> SEQ ID NO 518
<211> LENGTH: 106
<212> TYPE: PRT
<213> ORGANISM: Artificial sequence
<220> FEATURE:
<223> OTHER INFORMATION: Synthetic polypeptide

<400> SEQUENCE: 518

Asp Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Ser
                85                  90                  95

Phe Gly Gln Gly Thr Lys Leu Glu Ile Lys
            100                 105

<210> SEQ ID NO 519
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 519

Asp Ile Arg Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45
```

-continued

```
Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Leu
                 85                  90                  95

Thr Phe Gly Gly Gly Thr Lys Val Glu Ile Lys
                100                 105
```

<210> SEQ ID NO 520
<211> LENGTH: 108
<212> TYPE: PRT
<213> ORGANISM: Artificial sequence
<220> FEATURE:
<223> OTHER INFORMATION: Synthetic polypeptide

<400> SEQUENCE: 520

```
Glu Thr Thr Leu Thr Gln Ser Pro Gly Thr Leu Ser Leu Ser Pro Gly
 1               5                  10                  15

Glu Arg Ala Thr Leu Ser Cys Arg Ala Ser Arg Ser Val Ser Gly Asn
                20                  25                  30

Tyr Leu Ala Trp Tyr Gln Gln Lys Pro Gly Gln Ala Pro Arg Leu Leu
             35                  40                  45

Ile Tyr Ala Ala Ser Ser Arg Ala Thr Gly Ile Pro Asp Arg Phe Ser
    50                  55                  60

Gly Gly Gly Ser Gly Thr His Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Arg Ala Phe Gly Gln Gly Thr Lys Val Glu Ile Lys
                100                 105
```

<210> SEQ ID NO 521
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 521

```
Glu Ile Val Met Thr Gln Ser Pro Ser Ser Leu Ser Ala Ser Val Gly
 1               5                  10                  15

Asp Arg Val Thr Ile Thr Cys Arg Ala Ser Gln Ser Ile Arg Ser Tyr
                20                  25                  30

Leu Asn Trp Tyr Gln Gln Lys Pro Gly Lys Ala Pro Lys Leu Leu Ile
             35                  40                  45

Tyr Ala Ala Ser Ser Leu Gln Ser Gly Val Pro Leu Arg Phe Ser Gly
    50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Ser Ile Thr Pro Pro
                 85                  90                  95

Thr Phe Gly Gln Gly Thr Lys Leu Glu Ile Lys
                100                 105
```

<210> SEQ ID NO 522
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 522

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Gln Ala Ser Ser Leu Glu Ser Gly Val Pro Ser Arg Phe Ser Gly
50                  55                  60

Ser Glu Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Phe Pro Phe
                85                  90                  95

Thr Phe Gly Pro Gly Thr Lys Val Glu Ile Lys
            100                 105

<210> SEQ ID NO 523
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 523

Asp Ile Val Leu Thr Gln Ser Pro Ser Ser Leu Ser Ala Ser Val Gly
1               5                   10                  15

Asp Arg Val Thr Ile Thr Cys Arg Ala Ser Gln Ser Ile Asn Asn Tyr
            20                  25                  30

Leu Asn Trp Tyr Gln Gln Lys Pro Gly Lys Ala Pro Asn Leu Leu Ile
        35                  40                  45

Phe Gly Ala Ser Thr Leu Gln Ser Gly Val Pro Ser Arg Phe Thr Gly
50                  55                  60

Ser Gly Ser Gly Thr Val Phe Thr Leu Thr Ile Ser Ser Leu Gln Arg
65                  70                  75                  80

Asp Asp Phe Val Ile Tyr Tyr Cys Gln Gln Thr Tyr Ser Ala Ser Gly
                85                  90                  95

Ser Phe Gly Gln Gly Thr Lys Val Glu Ile Lys
            100                 105

<210> SEQ ID NO 524
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 524

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Trp
                85                  90                  95

Thr Phe Gly Gln Gly Thr Lys Val Glu Ile Lys
            100                 105

<210> SEQ ID NO 525
<211> LENGTH: 109
<212> TYPE: PRT
<213> ORGANISM: Artificial sequence
<220> FEATURE:
<223> OTHER INFORMATION: Synthetic polypeptide

<400> SEQUENCE: 525

Gln Ser Ala Leu Ile Gln Pro Pro Ser Val Ser Ala Ala Pro Gly Gln
1               5                   10                  15

Lys Val Thr Ile Ser Cys Ser Gly Ser Ser Asn Ile Gly Asn Asn
            20                  25                  30

Tyr Val Ser Trp Tyr Gln Gln Leu Pro Gly Thr Ala Pro Lys Leu Leu
                35                  40                  45

Ile Tyr Asp Asn Asn Lys Arg Pro Ser Gly Ile Pro Asp Arg Phe Ser
        50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Asn Ser Leu
                85                  90                  95

Gly Val Val Phe Gly Gly Gly Thr Gln Leu Thr Val Leu
            100                 105

<210> SEQ ID NO 526
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 526

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
                35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Ser Ile Asn Arg Leu Glu
65                  70                  75                  80

Pro Glu Asp Phe Ala Val Tyr Tyr Cys Gln Gln Tyr Gly Ser Ser Pro
                85                  90                  95

Gly Phe Gly Gln Gly Thr Lys Val Glu Ile Lys
            100                 105

<210> SEQ ID NO 527
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 527

Asp Ile Val Leu Thr Gln Ser Pro Ser Thr Leu Ser Ala Ser Val Gly
1               5                   10                  15

Asp Arg Val Thr Ile Thr Cys Arg Ala Ser Gln Ser Ile Ser Asp Trp
            20                  25                  30

Leu Ala Trp Tyr Gln Gln Lys Pro Gly Lys Ala Pro Gly Leu Leu Ile
        35                  40                  45

Tyr Arg Ala Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys His Gln Tyr Lys Asp Phe Pro Trp
                85                  90                  95

Thr Phe Gly Gln Gly Thr Lys Val Asp Ile Lys
                100                 105

<210> SEQ ID NO 528
<211> LENGTH: 106
<212> TYPE: PRT
<213> ORGANISM: Artificial sequence
<220> FEATURE:
<223> OTHER INFORMATION: Synthetic polypeptide

<400> SEQUENCE: 528

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Thr Trp
            20                  25                  30

Leu Ala Trp Tyr Gln Leu Lys Pro Gly Lys Ala Pro Lys Leu Leu Ile
        35                  40                  45

Tyr Lys Ala Ser Asn Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Pro
                85                  90                  95

Trp Gly Gln Gly Thr Lys Leu Glu Ile Lys
                100                 105

<210> SEQ ID NO 529
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 529

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Arg
            20                  25                  30

Tyr Leu Ala Trp Tyr Arg Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
            85                  90                  95

Phe Phe Gly Gly Gly Thr Lys Leu Glu Ile Lys
            100                 105

<210> SEQ ID NO 530
<211> LENGTH: 111
<212> TYPE: PRT
<213> ORGANISM: Artificial sequence
<220> FEATURE:
<223> OTHER INFORMATION: Synthetic polypeptide

<400> SEQUENCE: 530

Gln Ser Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Asp
                20                  25                  30

Lys Tyr Val Ser Trp Tyr Gln Gln His Pro Gly Lys Ala Pro Lys Pro
            35                  40                  45

Met Ile Tyr Glu Val Ser Asn Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Pro Val Val Phe Gly Gly Gly Thr Lys Leu Thr Val Leu
            100                 105                 110

<210> SEQ ID NO 531
<211> LENGTH: 110
<212> TYPE: PRT
<213> ORGANISM: Artificial sequence
<220> FEATURE:
<223> OTHER INFORMATION: Synthetic polypeptide

<400> SEQUENCE: 531

Gln Pro Val Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Ser Asp Val Ser Lys Arg Pro Ser Gly Val Pro Asp Arg Phe
        50                  55                  60

Ser Gly Ser Lys Ser Gly Asn Thr Ala Ser Leu Thr Ile Ser Gly Leu
65                  70                  75                  80

Gln Ala Asp Asp Glu Ala Asp Tyr Tyr Cys Cys Ser Tyr Ala Thr Asn
                85                  90                  95

Tyr Gly Val Val Phe Gly Gly Gly Thr Lys Val Thr Val Leu
            100                 105                 110

<210> SEQ ID NO 532
<211> LENGTH: 110
<212> TYPE: PRT
<213> ORGANISM: Artificial sequence
<220> FEATURE:
<223> OTHER INFORMATION: Synthetic polypeptide

<400> SEQUENCE: 532

Asn Phe Met Leu Thr Gln Pro His Ser Val Ser Glu Ser Pro Gly Lys

-continued

```
                1               5                  10                 15
            Thr Val Thr Ile Ser Cys Thr Arg Ser Ser Gly Ser Ile Ala Ser Asn
                            20                 25                 30

Tyr Val Gln Trp Tyr Gln Gln Arg Pro Gly Ser Ser Pro Thr Thr Val
                        35                 40                 45

Ile Tyr Glu Asp Asn Gln Arg Pro Ser Gly Val Pro Asp Arg Phe Ser
                50                 55                 60

Gly Ser Ile Asp Ser Ser Asn Ser Ala Ser Leu Thr Ile Ser Gly
            65                 70                 75                 80

Leu Lys Thr Glu Asp Glu Ala Asp Tyr Tyr Cys Gln Ser Tyr Asp Ser
                            85                 90                 95

Ser Asn Val Val Phe Gly Gly Gly Thr Lys Val Thr Val Leu
                        100                105                110
```

<210> SEQ ID NO 533
<211> LENGTH: 111
<212> TYPE: PRT
<213> ORGANISM: Artificial sequence
<220> FEATURE:
<223> OTHER INFORMATION: Synthetic polypeptide

<400> SEQUENCE: 533

```
            Gln Ser Val Leu Thr Gln Pro Pro Ser Val Ser Ala Ala Pro Gly Gln
            1               5                  10                 15

Lys Val Thr Ile Ser Cys Ser Gly Ser Ser Asn Ile Gly Asn Asn
                            20                 25                 30

Asp Val Ser Trp Tyr Gln Gln Leu Pro Gly Arg Ala Pro Lys Leu Leu
                        35                 40                 45

Ile Tyr Asp Asn Asn Lys Arg Pro Ser Gly Ile Pro Asp Arg Phe Ser
                50                 55                 60

Gly Ser Lys Ser Gly Thr Ser Ala Thr Leu Gly Ile Thr Gly Leu Gln
            65                 70                 75                 80

Thr Gly Asp Glu Ala Asp Tyr Tyr Cys Gly Ala Trp Asp Ser Ser Leu
                            85                 90                 95

Ser Ala His Val Val Phe Gly Gly Gly Thr Lys Val Thr Val Leu
                        100                105                110
```

<210> SEQ ID NO 534
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 534

```
            Asp Ile Val Met Thr Gln Thr Pro Ser Thr Leu Ser Ala Ser Val Gly
            1               5                  10                 15

Asp Arg Val Thr Val Thr Cys Arg Ala Ser Gln Ser Ile Ser Asp Trp
                            20                 25                 30

Leu Ala Trp Tyr Gln Gln Lys Ala Gly Lys Ala Pro Lys Leu Leu Ile
                        35                 40                 45

Tyr Arg Ala Ser Ser Leu Glu Ser Gly Val Pro Pro Arg Phe Ser Gly
                50                 55                 60

Ser Gly Ser Gly Thr Glu Phe Thr Leu Thr Ile Ser Ser Leu Arg Pro
            65                 70                 75                 80

Asp Asp Phe Ala Thr Tyr Tyr Cys Gln Gln Tyr Asn Arg Tyr Pro Tyr
                            85                 90                 95
```

```
Thr Phe Gly Gln Gly Thr Lys Val Asp Ile Lys
            100                 105
```

<210> SEQ ID NO 535
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 535

```
Asp Ile Gln Val Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Ala Trp Tyr Gln Gln Arg Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His His Ser Tyr Pro Trp
                85                  90                  95

Thr Phe Gly Gln Gly Thr Lys Val Glu Ile Lys
            100                 105
```

<210> SEQ ID NO 536
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 536

```
Asp Ile Arg Met Thr Gln Ser Pro Ser Thr Leu Ser Ala Ser Ile Gly
1               5                   10                  15

Asp Arg Val Thr Ile Thr Cys Arg Ala Ser Gln Ser Ile Ser Asp Trp
            20                  25                  30

Leu Ala Trp Tyr Leu Gln Lys Pro Gly Lys Ala Pro Ser Leu Leu Ile
        35                  40                  45

Tyr Arg Ala Ser Ser Leu Glu Thr Gly Val Pro Ser Arg Phe Ser Gly
    50                  55                  60

Arg Gly Ser Gly Thr Glu Phe Thr Leu Thr Ile Ser Ser Leu Gln Pro
65                  70                  75                  80

Asp Asp Phe Gly Thr Tyr Tyr Cys Gln Gln Tyr Asn Arg Asp Pro Tyr
                85                  90                  95

Thr Phe Gly Gln Gly Thr Lys Val Asp Ile Lys
            100                 105
```

<210> SEQ ID NO 537
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 537

```
Asp Ile Gln Leu Thr Gln Ser Pro Ser Thr Leu Ser Ala Ser Val Gly
1               5                   10                  15

Asp Arg Val Thr Val Thr Cys Arg Ala Ser Gln Asn Val Gly Gly Trp
```

```
                    20                  25                  30
Leu Ala Trp Tyr Gln Gln Lys Pro Gly Lys Ala Pro Lys Leu Leu Ile
            35                  40                  45
Phe Gln Ala Ser Arg Leu Glu Asn Gly Val Pro Ser Arg Phe Ser Ala
 50                  55                  60
Asn Ala Ser Gly Thr Glu Phe Thr Leu Thr Ile Gly Ser Leu Gln Pro
 65                  70                  75                  80
Asp Asp Phe Ala Thr Tyr Tyr Cys Gln Gln Tyr Asn Thr Tyr Pro Tyr
                 85                  90                  95
Thr Phe Gly Gln Gly Thr Lys Val Asp Ile Lys
            100                 105

<210> SEQ ID NO 538
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 538

Asp Ile Gln Leu Thr Gln Ser Pro Ser Ser Leu Ser Ala Ser Val Gly
 1               5                  10                  15
Asp Arg Val Thr Ile Thr Cys Arg Ala Ser Gln Ser Ile Ser Gln Tyr
                20                  25                  30
Leu Asn Trp Tyr Gln Gln Lys Pro Gly Lys Ala Pro Lys Leu Leu Ile
            35                  40                  45
Ser Pro Ala Ser Ser Phe Gln Ser Gly Val Pro Ser Arg Phe Ser Gly
 50                  55                  60
Ser Gly Ser Gly Thr Asp Phe Thr Leu Thr Ile Thr Ser Leu Gln Pro
 65                  70                  75                  80
Glu Asp Phe Ala Thr Tyr Tyr Cys Gln Gln Ser Tyr Ser Thr Pro Trp
                 85                  90                  95
Thr Phe Gly Gln Gly Thr Lys Val Asp Ile Lys
            100                 105

<210> SEQ ID NO 539
<211> LENGTH: 110
<212> TYPE: PRT
<213> ORGANISM: Artificial sequence
<220> FEATURE:
<223> OTHER INFORMATION: Synthetic polypeptide

<400> SEQUENCE: 539

Gln Ser Val Leu Thr Gln Pro Ala Ser Val Ser Gly Ser Pro Gly Gln
 1               5                  10                  15
Ser Ile Thr Ile Ser Cys Thr Gly Thr Ser Ser Asp Val Gly Gly Tyr
                20                  25                  30
Asn Tyr Val Ser Trp Tyr Gln Gln His Pro Gly Lys Ala Pro Lys Leu
            35                  40                  45
Met Ile Tyr Asp Val Ser Asn Arg Pro Ser Gly Val Ser Asn Arg Phe
         50                  55                  60
Ser Gly Ser Lys Ser Gly Asn Thr Ala Ser Leu Thr Ile Ser Gly Leu
 65                  70                  75                  80
Gln Ala Glu Asp Glu Ala Asp Tyr Tyr Cys Ser Ser Tyr Thr Ser Ser
                 85                  90                  95
Ser Thr Leu Val Phe Gly Gly Gly Thr Gln Leu Thr Val Leu
            100                 105                 110
```

```
<210> SEQ ID NO 540
<211> LENGTH: 108
<212> TYPE: PRT
<213> ORGANISM: Artificial sequence
<220> FEATURE:
<223> OTHER INFORMATION: Synthetic polypeptide

<400> SEQUENCE: 540

Ser Tyr Glu Leu Thr Gln Pro Pro Ser Val Ser Val Ala Pro Gly Gln
1               5                   10                  15

Thr Ala Arg Ile Ile Cys Gly Gly Asn Tyr Ile Gly Gly Lys Ser Val
            20                  25                  30

His Trp Tyr Gln Gln Lys Pro Gly Gln Ala Pro Val Leu Val Val Tyr
        35                  40                  45

Asn Asp Asn Asp Arg Pro Ser Gly Ile Pro Glu Arg Phe Ser Gly Ser
    50                  55                  60

Asn Ser Gly Asn Thr Ala Thr Leu Thr Ile Ser Arg Val Ala Ala Gly
65                  70                  75                  80

Asp Glu Ala Asp Tyr Tyr Cys Gln Val Trp Asp Asn Ser Ser Asp Arg
                85                  90                  95

Arg Val Phe Gly Gly Gly Thr Lys Leu Thr Val Leu
            100                 105

<210> SEQ ID NO 541
<211> LENGTH: 106
<212> TYPE: PRT
<213> ORGANISM: Artificial sequence
<220> FEATURE:
<223> OTHER INFORMATION: Synthetic polypeptide

<400> SEQUENCE: 541

Asp Ile Arg Val Thr Gln Ser Pro Ala Thr Leu Ser Val Ser Pro Gly
1               5                   10                  15

Glu Arg Ala Thr Leu Ser Cys Arg Ala Ser Gln Arg Val Asn Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Val Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Thr Trp Trp Thr
                85                  90                  95

Phe Gly Gln Gly Thr Lys Val Glu Ile Lys
            100                 105

<210> SEQ ID NO 542
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 542

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
```

```
                35                  40                  45

Tyr Ala Ala Ser Ser Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Leu
                 85                  90                  95

Thr Phe Gly Gly Gly Thr Lys Val Asp Ile Lys
                100                 105
```

<210> SEQ ID NO 543
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 543

```
Asp Ile Val Met Thr Gln Ser Pro Ala Thr Leu Ser Val Ser Pro Gly
 1               5                  10                  15

Glu Arg Ala Thr Leu Ser Cys Arg Ala Ser Gln Ser Val Ser Ser Asn
                 20                  25                  30

Leu Ala Trp Tyr Gln Gln Lys Pro Gly Gln Ala Pro Arg Leu Leu Ile
             35                  40                  45

Tyr Gly Ala Ser Thr Arg Ala Thr Gly Ile Pro Ala Arg Phe Ser Gly
         50                  55                  60

Ser Gly Ser Gly Thr Glu Phe Thr Leu Thr Ile Ser Ser Leu Gln Ser
 65                  70                  75                  80

Glu Asp Phe Ala Val Tyr Ser Cys Gln Gln Tyr Asn Thr Trp Pro Lys
                 85                  90                  95

Thr Phe Gly Gln Gly Thr Lys Val Glu Ile Lys
                100                 105
```

<210> SEQ ID NO 544
<211> LENGTH: 108
<212> TYPE: PRT
<213> ORGANISM: Artificial sequence
<220> FEATURE:
<223> OTHER INFORMATION: Synthetic polypeptide

<400> SEQUENCE: 544

```
Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
                 20                  25                  30

Phe Leu Ala Trp Tyr Gln Gln Lys Pro Gly Gln Ala Pro Arg Leu Leu
             35                  40                  45

Ile Tyr Gly Ala Ser Ser Arg Ala Thr Gly Ile Pro Asp Arg Phe Ser
         50                  55                  60

Gly Ser Gly Ser Gly Thr Asp Phe Thr Leu Thr Ile Arg Arg Leu Glu
 65                  70                  75                  80

Pro Glu Asp Phe Ala Val Tyr Tyr Cys Gln Gln Tyr Gly Ser Ser Arg
                 85                  90                  95

Arg Thr Phe Gly Gln Gly Thr Lys Val Glu Ile Lys
                100                 105
```

<210> SEQ ID NO 545
<211> LENGTH: 107

```
<212> TYPE: PRT
<213> ORGANISM: Artificial sequence
<220> FEATURE:
<223> OTHER INFORMATION: Synthetic polypeptide

<400> SEQUENCE: 545

Asp Ile Arg Val Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Arg Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Arg Tyr Pro Tyr
                85                  90                  95

Thr Phe Gly Gln Gly Thr Lys Val Glu Ile Lys
            100                 105

<210> SEQ ID NO 546
<211> LENGTH: 112
<212> TYPE: PRT
<213> ORGANISM: Artificial sequence
<220> FEATURE:
<223> OTHER INFORMATION: Synthetic polypeptide

<400> SEQUENCE: 546

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Leu Asp Val Val Phe Gly Gly Gly Thr Lys Leu Thr Val Leu
            100                 105                 110

<210> SEQ ID NO 547
<211> LENGTH: 108
<212> TYPE: PRT
<213> ORGANISM: Artificial sequence
<220> FEATURE:
<223> OTHER INFORMATION: Synthetic polypeptide

<400> SEQUENCE: 547

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Ser Ile Pro Ala Arg Phe Ser Gly
```

```
                    50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Tyr Asn Ser Trp Pro Pro
                     85                  90                  95

Ile Thr Phe Gly Gln Gly Thr Arg Leu Glu Ile Lys
                100                 105

<210> SEQ ID NO 548
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 548

Asp Ile Arg Leu Thr Gln Ser Pro Ser Thr Leu Ser Ala Ser Val Gly
 1               5                  10                  15

Asp Arg Val Ser Ile Thr Cys Arg Ala Ser Gln Ser Ile Ser Asp Trp
                20                  25                  30

Leu Ala Trp Tyr Gln Gln Lys Pro Gly Lys Ala Pro Lys Leu Leu Ile
            35                  40                  45

Tyr Arg Ala Ser Gly Leu Glu Thr Gly Val Pro Ser Arg Phe Ser Gly
        50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Asn Arg Tyr Pro Tyr
                     85                  90                  95

Thr Phe Gly Gln Gly Thr Lys Val Asp Ile Lys
                100                 105

<210> SEQ ID NO 549
<211> LENGTH: 111
<212> TYPE: PRT
<213> ORGANISM: Artificial sequence
<220> FEATURE:
<223> OTHER INFORMATION: Synthetic polypeptide

<400> SEQUENCE: 549

Gln Pro Val Leu Ile Gln Pro Ser Ala Ser Gly Thr Pro Gly Gln
 1               5                  10                  15

Arg Val Thr Ile Ser Cys Ser Gly Ser Ser Ser Asn Phe Gly Ser Asn
                20                  25                  30

Phe Val Tyr Trp Tyr Gln Gln Leu Pro Gly Thr Ala Pro Lys Leu Leu
            35                  40                  45

Ile Tyr Arg Val Asn Gln Arg Pro Ser Gly Val Pro Asp Arg Phe Ser
        50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Ala Thr Trp Asp Val Ser Leu
                     85                  90                  95

Ser Asn Asp Val Leu Phe Gly Gly Gly Thr Lys Leu Thr Val Leu
                100                 105                 110

<210> SEQ ID NO 550
<211> LENGTH: 109
<212> TYPE: PRT
<213> ORGANISM: Artificial sequence
<220> FEATURE:
```

<223> OTHER INFORMATION: Synthetic polypeptide

<400> SEQUENCE: 550

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ser Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Pro Ile Thr Phe Gly Gly Gly Thr Lys Val Glu Ile Lys
            100                 105

<210> SEQ ID NO 551
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 551

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Thr Ile Thr Arg Tyr
            20                  25                  30

Met Asn Trp Tyr Gln Gln Lys Pro Gly Glu Ala Pro Lys Leu Leu Ile
        35                  40                  45

Tyr Ala Thr Ser Ser Leu Gln Ser Gly Val Pro Ser Arg Phe Ser Gly
    50                  55                  60

Ser Gly Ser Gly Thr Asp Phe Thr Leu Thr Ile Thr Asn Leu Gln Pro
65                  70                  75                  80

Ala Asp Phe Ala Thr Tyr Tyr Cys Gln Gln Ser Ser Thr Thr Arg Trp
                85                  90                  95

Thr Phe Gly Gln Gly Thr Lys Val Asp Ile Lys
            100                 105

<210> SEQ ID NO 552
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 552

Asp Ile Arg Leu Thr Gln Ser Pro Ser Ser Leu Ser Ala Ser Val Gly
1               5                   10                  15

Asp Arg Val Thr Ile Thr Cys Arg Ala Ser Gln Asp Ile Arg Lys Phe
            20                  25                  30

Leu Asn Trp Tyr Gln Gln Lys Leu Gly Lys Ala Pro Ser Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro

```
                65                  70                  75                  80
Glu Asp Phe Ala Ile Tyr Tyr Cys Gln His Ala Ser Thr Thr Pro Trp
                    85                  90                  95
Thr Phe Gly Gln Gly Thr Lys Val Glu Ile Lys
            100                 105
```

<210> SEQ ID NO 553
<211> LENGTH: 108
<212> TYPE: PRT
<213> ORGANISM: Artificial sequence
<220> FEATURE:
<223> OTHER INFORMATION: Synthetic polypeptide

<400> SEQUENCE: 553

```
Ser Tyr Glu Leu Thr Gln Pro Pro Ser Val Ser Val Ser Pro Gly Gln
1               5                   10                  15
Thr Ala Thr Ile Thr Cys Ser Gly Asp Lys Leu Gly Tyr Thr Tyr Thr
                20                  25                  30
Cys Trp Tyr Gln Gln Lys Pro Gly Gln Ser Pro Val Leu Val Ile Tyr
            35                  40                  45
Gln Asp Thr Lys Arg Pro Ser Gly Ile Pro Glu Arg Phe Ser Gly Ser
        50                  55                  60
Asn Ser Gly Asn Thr Ala Thr Leu Thr Ile Thr Gly Thr Gln Ala Met
65                  70                  75                  80
Asp Glu Ala Asp Tyr Tyr Cys Gln Ala Trp Asp Thr Thr Ala Gly
                85                  90                  95
Gly Val Phe Gly Gly Gly Thr Lys Leu Thr Val Leu
            100                 105
```

<210> SEQ ID NO 554
<211> LENGTH: 108
<212> TYPE: PRT
<213> ORGANISM: Artificial sequence
<220> FEATURE:
<223> OTHER INFORMATION: Synthetic polypeptide

<400> SEQUENCE: 554

```
Asp Ile Val Leu Thr Gln Ser Pro Gly Thr Leu Ser Leu Ser Pro Gly
1               5                   10                  15
Glu Arg Ala Thr Leu Ser Cys Arg Ala Ser Gln Ser Val Ser Ser Ser
                20                  25                  30
Tyr Leu Ala Trp Tyr Gln Gln Lys Pro Gly Gln Ala Pro Arg Leu Leu
            35                  40                  45
Ile Tyr Gly Ala Ser Ser Arg Ala Thr Gly Ile Pro Asp Arg Phe Ser
        50                  55                  60
Gly Ser Gly Ser Gly Thr Asp Phe Thr Leu Thr Ile Ser Arg Leu Glu
65                  70                  75                  80
Pro Glu Asp Phe Ala Val Tyr Tyr Cys Gln Gln Tyr Gly Ser Ser Pro
                85                  90                  95
Arg Ala Phe Gly Pro Gly Thr Lys Val Glu Ile Lys
            100                 105
```

<210> SEQ ID NO 555
<211> LENGTH: 110
<212> TYPE: PRT
<213> ORGANISM: Artificial sequence
<220> FEATURE:
<223> OTHER INFORMATION: Synthetic polypeptide

<400> SEQUENCE: 555

```
Gln Ser Val Leu Thr Gln Pro Pro Ser Ala Gly Ser Pro Gly Gln
1               5                   10                  15

Ser Val Thr Ile Ser Cys Ala Gly Thr Arg Ser Asp Val Gly Gly Tyr
                20                  25                  30

Asn Phe Val Ser Trp Tyr Gln Gln His Pro Gly Lys Ala Pro Lys Leu
                35                  40                  45

Leu Ile Tyr Glu Val Asn Lys Arg Pro Ser Gly Val Pro Asp Arg Phe
        50                  55                  60

Ser Gly Ser Lys Ser Ala Asn Thr Ala Ser Leu Thr Val Ser Gly Leu
65                  70                  75                  80

Gln Ala Glu Asp Glu Ala Glu Tyr Phe Cys Ser Ser Tyr Gly Gly Asn
                85                  90                  95

Asn Asp Leu Val Phe Gly Gly Gly Thr Lys Val Thr Val Leu
                100                 105                 110

<210> SEQ ID NO 556
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 556

Glu Ile Val Met Thr Gln Ser Pro Ala Thr Leu Ser Leu Ser Pro Gly
1               5                   10                  15

Glu Arg Gly Thr Leu Ser Cys Arg Thr Ser Gln Ser Val Ser Ser Phe
                20                  25                  30

Leu Ala Trp Tyr Gln Gln Lys Pro Gly Gln Ala Pro Arg Leu Leu Met
                35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Tyr
                85                  90                  95

Thr Phe Gly Gln Gly Thr Lys Val Asp Ile Lys
                100                 105

<210> SEQ ID NO 557
<211> LENGTH: 106
<212> TYPE: PRT
<213> ORGANISM: Artificial sequence
<220> FEATURE:
<223> OTHER INFORMATION: Synthetic polypeptide

<400> SEQUENCE: 557

Gly Ile Gln Leu Thr Gln Ser Pro Ser Thr Leu Ser Ala Ser Val Gly
1               5                   10                  15

Asp Arg Val Thr Ile Thr Cys Arg Ala Ser Gln Ser Val Ser Asp Trp
                20                  25                  30

Leu Ala Trp Tyr Gln Gln Lys Pro Gly Arg Ala Pro Asn Leu Leu Ile
                35                  40                  45

Tyr Arg Ala Ser Ser Leu Gln Ser Gly Val Pro Ser Arg Phe Ser Gly
        50                  55                  60

Ser Gly Ser Gly Thr Glu Phe Thr Leu Thr Ile Asn Ser Leu Gln Pro
65                  70                  75                  80

Asp Asp Phe Ala Thr Tyr Tyr Cys Gln Gln Tyr Lys Thr Tyr Trp Thr
```

```
                85                  90                  95
Phe Gly Gln Gly Thr Lys Val Glu Ile Lys
            100                 105

<210> SEQ ID NO 558
<211> LENGTH: 110
<212> TYPE: PRT
<213> ORGANISM: Artificial sequence
<220> FEATURE:
<223> OTHER INFORMATION: Synthetic polypeptide

<400> SEQUENCE: 558

Gln Ser Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Gly Thr Asn Ile Phe Gly Thr Gly Thr Lys Leu Thr Val Leu
            100                 105                 110

<210> SEQ ID NO 559
<211> LENGTH: 108
<212> TYPE: PRT
<213> ORGANISM: Artificial sequence
<220> FEATURE:
<223> OTHER INFORMATION: Synthetic polypeptide

<400> SEQUENCE: 559

Asp Ile Val Met Thr Gln Thr Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Val Ala Trp Tyr Gln Gln Lys Pro Gly Gln Ala Pro Arg Leu Leu Ile
        35                  40                  45

His Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Pro
                85                  90                  95

Leu Thr Phe Gly Gly Gly Thr Lys Leu Glu Ile Lys
            100                 105

<210> SEQ ID NO 560
<211> LENGTH: 108
<212> TYPE: PRT
<213> ORGANISM: Artificial sequence
<220> FEATURE:
<223> OTHER INFORMATION: Synthetic polypeptide

<400> SEQUENCE: 560

Ser Tyr Glu Leu Thr Gln Pro Pro Ser Val Ser Val Ser Pro Gly Gln
1               5                   10                  15
```

```
Thr Ala Arg Ile Thr Cys Ser Gly Asp Ala Leu Pro Lys Lys Tyr Val
            20                  25                  30

Tyr Trp Phe Gln Gln Lys Ser Gly Gln Ala Pro Val Leu Val Ile Tyr
        35                  40                  45

Glu Asp Arg Arg Gly Pro Ser Gly Ile Pro Glu Arg Phe Ser Gly Ser
50                  55                  60

Thr Ser Gly Thr Met Ala Thr Leu Thr Ile Arg Gly Ala Gln Val Glu
65                  70                  75                  80

Asp Glu Ala Asp Tyr Phe Cys Tyr Ser Thr Asp Ser Ser Gly Leu Leu
                85                  90                  95

Gly Val Phe Gly Gly Gly Thr Lys Leu Thr Val Leu
            100                 105
```

<210> SEQ ID NO 561
<211> LENGTH: 113
<212> TYPE: PRT
<213> ORGANISM: Artificial sequence
<220> FEATURE:
<223> OTHER INFORMATION: Synthetic polypeptide

<400> SEQUENCE: 561

```
Asp Ile Gln Met Thr Gln Ser Pro Asp Ser Leu Ala Val Ser Leu Gly
1               5                   10                  15

Glu Arg Ala Thr Ile Asn Cys Lys Ser Ser Gln Ser Val Phe Tyr Ser
            20                  25                  30

Ser Asn Ser Gln Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Ala Thr Asp Phe Ser Leu Thr
65                  70                  75                  80

Ile Ser Ser Leu Gln Ala Glu Asp Val Ala Val Tyr Tyr Cys Gln Gln
                85                  90                  95

Phe His Ser Pro Pro Trp Thr Phe Gly Gln Gly Thr Lys Leu Glu Ile
            100                 105                 110

Lys
```

<210> SEQ ID NO 562
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 562

```
Asp Ile Val Met Thr Gln Ser Pro Ser Thr Leu Ser Ala Ser Val Gly
1               5                   10                  15

Asp Arg Val Val Ile Thr Cys Arg Ala Ser Gln Ser Ile Ser Asn Trp
            20                  25                  30

Leu Ala Trp Tyr Gln Gln Lys Ser Gly Lys Ala Pro Lys Leu Leu Ile
        35                  40                  45

Tyr Lys Ala Ser Arg Leu Glu Ser Gly Val Pro Ser Thr Phe Ser Gly
50                  55                  60

Ser Gly Ser Gly Thr Glu Phe Thr Leu Thr Ile Ser Ser Leu Gln Ala
65                  70                  75                  80

Asp Asp Phe Ala Ser Tyr Tyr Cys Gln Gln Tyr Asn Asp Tyr Pro Trp
                85                  90                  95
```

```
Thr Phe Gly Gln Gly Thr Lys Val Glu Ile Lys
            100                 105
```

<210> SEQ ID NO 563
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 563

```
Glu Ile Val Met Thr Gln Ser Pro Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Arg Glu Phe Thr Leu Thr Ile Ser Ser Leu Gln Pro
65                  70                  75                  80

Glu Asp Phe Ala Thr Tyr Tyr Cys Leu Gln His Asn Thr Tyr Pro Trp
                85                  90                  95

Thr Phe Gly Gln Gly Thr Lys Val Glu Ile Lys
            100                 105
```

<210> SEQ ID NO 564
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 564

```
Asp Ile Gln Val Thr Gln Ser Pro Ser Thr Leu Ser Ala Ser Val Gly
1               5                   10                  15

Asp Arg Val Ser Ile Thr Cys Arg Ala Ser Gln Thr Ile Ser Ser Trp
            20                  25                  30

Leu Ala Trp Tyr Gln Gln Lys Pro Gly Lys Ala Pro Lys Leu Leu Met
        35                  40                  45

Tyr Lys Ala Ser Asn Leu Gln Ser Gly Val Pro Ser Arg Phe Thr Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Tyr Ser Tyr Pro Tyr
                85                  90                  95

Thr Phe Gly Pro Gly Thr Lys Val Asp Ile Lys
            100                 105
```

<210> SEQ ID NO 565
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 565

```
Ser Tyr Val Leu Thr Gln Pro Pro Ser Val Ser Val Pro Gly Gln
1               5                   10                  15
```

```
Thr Ala Arg Ile Thr Cys Ser Gly Asp Ala Leu Pro Lys Gln Tyr Gly
                20                  25                  30

Tyr Trp Tyr Gln Gln Lys Pro Gly Gln Ala Pro Val Leu Val Ile Tyr
            35                  40                  45

Lys Asp Ser Glu Arg Pro Ser Gly Ile Pro Glu Arg Phe Ser Gly Ser
50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Arg Ser Gly Thr Val
                85                  90                  95

Val Phe Gly Gly Gly Thr Lys Leu Thr Val Leu
            100                 105
```

<210> SEQ ID NO 566
<211> LENGTH: 110
<212> TYPE: PRT
<213> ORGANISM: Artificial sequence
<220> FEATURE:
<223> OTHER INFORMATION: Synthetic polypeptide

<400> SEQUENCE: 566

```
Gln Ala Val Val Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Val Tyr Glu Val Thr Lys Arg Pro Ser Gly Val Pro Asp Arg Phe
        50                  55                  60

Ser Gly Ser Lys Ser Gly Asn Ala Ala Ser Leu Thr Val Ser Gly Leu
65                  70                  75                  80

Gln Ala Glu Asp Glu Ala Glu Tyr Tyr Cys Ser Ser Tyr Ala Gly Ser
                85                  90                  95

Asn Ala Leu Val Phe Ser Gly Gly Thr Lys Leu Thr Val Leu
            100                 105                 110
```

<210> SEQ ID NO 567
<211> LENGTH: 110
<212> TYPE: PRT
<213> ORGANISM: Artificial sequence
<220> FEATURE:
<223> OTHER INFORMATION: Synthetic polypeptide

<400> SEQUENCE: 567

```
Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Asn
                20                  25                  30

Tyr Val Gln Trp Tyr Gln Gln Arg Pro Gly Ser Ala Pro Thr Thr Val
            35                  40                  45

Ile Tyr Glu Asp Asn Gln Arg Pro Ser Gly Val Pro Asp Arg Phe Ser
        50                  55                  60

Gly Ser Ile Asp Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Ser Asn Trp Val Phe Gly Gly Gly Thr Lys Leu Thr Val Leu
            100                 105                 110
```

<210> SEQ ID NO 568
<211> LENGTH: 105
<212> TYPE: PRT
<213> ORGANISM: Artificial sequence
<220> FEATURE:
<223> OTHER INFORMATION: Synthetic polypeptide

<400> SEQUENCE: 568

Gln Pro Glu Leu Thr Gln Pro Pro Ser Val Ser Val Ser Pro Gly Gln
1               5                   10                  15

Thr Ala Arg Ile Thr Cys Ser Gly Asp Ala Leu Ser Lys Gln Tyr Ala
            20                  25                  30

Tyr Trp Tyr Gln Gln Lys Pro Gly Gln Ala Pro Val Val Val Ile Tyr
        35                  40                  45

Lys Asp Ser Glu Arg Pro Ser Gly Ile Pro Glu Arg Phe Ser Gly Ser
    50                  55                  60

Arg Ser Gly Thr Thr Val Thr Leu Thr Ile Ser Gly Val Gln Ala Glu
65                  70                  75                  80

Asp Glu Ala Asp Tyr Tyr Cys His Ser Pro Asp Ser His Val Val Phe
                85                  90                  95

Gly Gly Gly Thr Lys Leu Thr Val Leu
            100                 105

<210> SEQ ID NO 569
<211> LENGTH: 108
<212> TYPE: PRT
<213> ORGANISM: Artificial sequence
<220> FEATURE:
<223> OTHER INFORMATION: Synthetic polypeptide

<400> SEQUENCE: 569

Ser Tyr Glu Leu Ile Gln Leu Pro Ser Ala Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Glu Val Phe Gly Gly Gly Thr Lys Leu Thr Val Leu
            100                 105

<210> SEQ ID NO 570
<211> LENGTH: 103
<212> TYPE: PRT
<213> ORGANISM: Artificial sequence
<220> FEATURE:
<223> OTHER INFORMATION: Synthetic polypeptide

<400> SEQUENCE: 570

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

```
Leu Asn Trp Tyr Gln Gln Lys Pro Gly Lys Ala Pro Lys Leu Leu Ile
        35                  40                  45

Tyr Asp Val Ser Lys Leu Lys Thr Gly Val Pro Pro Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Trp Gly Thr Phe Gly Gln
                 85                  90                  95

Gly Thr Lys Val Asp Ile Lys
            100
```

<210> SEQ ID NO 571
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 571

```
Glu Ile Val Leu Thr Gln Ser Pro Ser Thr Leu Ser Ala Ser Val Gly
 1               5                  10                  15

Asp Arg Val Thr Ile Thr Cys Arg Ala Ser Gln Ser Ile Ser Asp Trp
                20                  25                  30

Leu Ala Trp Tyr Gln Gln Lys Pro Gly Lys Ala Pro Asn Leu Leu Ile
        35                  40                  45

Tyr Arg Ala Ser Ser Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Asn Arg Tyr Pro Tyr
                 85                  90                  95

Thr Phe Gly Gln Gly Thr Lys Val Glu Ile Lys
            100                 105
```

<210> SEQ ID NO 572
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 572

```
Asp Ile Gln Leu Thr Gln Ser Pro Ser Thr Leu Ser Ala Ser Val Gly
 1               5                  10                  15

Asp Arg Val Thr Ile Thr Cys Arg Ala Ser Gln Ser Ile Ser Asp Trp
                20                  25                  30

Leu Ala Trp Phe Gln Gln Lys Pro Gly Lys Ala Pro Lys Leu Leu Ile
        35                  40                  45

Tyr Arg Ala Ser Gly Leu Glu Thr Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Asn Arg Tyr Ser Tyr
                 85                  90                  95

Thr Phe Gly Gln Gly Thr Lys Val Glu Ile Lys
            100                 105
```

<210> SEQ ID NO 573

```
<211> LENGTH: 106
<212> TYPE: PRT
<213> ORGANISM: Artificial sequence
<220> FEATURE:
<223> OTHER INFORMATION: Synthetic polypeptide

<400> SEQUENCE: 573

Asp Ile Arg Leu Thr Gln Ser Pro Ser Thr Leu Ser Ala Ser Val Gly
1               5                   10                  15

Asp Arg Val Thr Ile Thr Cys Arg Ala Ser Gln Ser Ile Ser Gly Trp
            20                  25                  30

Leu Ala Trp Tyr Gln Gln Lys Pro Gly Lys Ala Pro Lys Leu Leu Ile
        35                  40                  45

Tyr Lys Ala Ser Ile Leu Glu Ser Gly Val Pro Ser Arg Phe Ser Gly
50                  55                  60

Ser Gln Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Asn Phe Trp Thr
                85                  90                  95

Phe Gly Gln Gly Thr Lys Leu Glu Ile Lys
            100                 105

<210> SEQ ID NO 574
<211> LENGTH: 111
<212> TYPE: PRT
<213> ORGANISM: Artificial sequence
<220> FEATURE:
<223> OTHER INFORMATION: Synthetic polypeptide

<400> SEQUENCE: 574

Gln Ser Val Leu Thr Gln Pro Pro Ser Val Ser Gly Ala Pro Gly Gln
1               5                   10                  15

Arg Val Thr Ile Ser Cys Thr Gly Asn Ser Ser Asn Ile Gly Ala Gly
            20                  25                  30

Tyr Glu Val His Trp Tyr Gln Gln Leu Pro Gly Thr Ala Pro Lys Leu
        35                  40                  45

Leu Ile Tyr Gly Asn Asn Asn Arg Pro Ser Gly Val Pro Asp Arg Phe
50                  55                  60

Ser Gly Ser Lys Ser Gly Ala Ser Gly Ser Leu Ala Val Thr Gly Leu
65                  70                  75                  80

Arg Ala Glu Asp Glu Ala Asp Tyr Tyr Cys His Ser Tyr Asp Ser Asn
                85                  90                  95

Met Ser Gly Ser Val Phe Gly Gly Thr Lys Val Thr Val Leu
            100                 105                 110

<210> SEQ ID NO 575
<211> LENGTH: 108
<212> TYPE: PRT
<213> ORGANISM: Artificial sequence
<220> FEATURE:
<223> OTHER INFORMATION: Synthetic polypeptide

<400> SEQUENCE: 575

Glu Ile Val Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Ala Pro Lys Leu Leu Ile
        35                  40                  45
```

Tyr Ala Ala Ser Thr Leu Gln Ser Gly Val Pro Ser Arg Phe Ser Gly
            50                  55                  60

Ser Gly Ser Gly Thr Asp Phe Ile Leu Thr Ile Ser Ser Leu Gln Pro
65                  70                  75                  80

Glu Asp Val Ala Thr Tyr Tyr Cys Gln Lys Tyr Tyr Ser Ala Pro Leu
                85                  90                  95

Ile Thr Phe Gly Pro Gly Thr Lys Val Glu Ile Lys
            100                 105

<210> SEQ ID NO 576
<211> LENGTH: 110
<212> TYPE: PRT
<213> ORGANISM: Artificial sequence
<220> FEATURE:
<223> OTHER INFORMATION: Synthetic polypeptide

<400> SEQUENCE: 576

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Gln Tyr Ala
            20                  25                  30

Tyr Trp Tyr Gln Gln Lys Pro Gly Gln Ala Pro Val Leu Val Ile Tyr
        35                  40                  45

Lys Asp Thr Glu Arg Pro Ser Gly Ile Pro Glu Arg Phe Ser Gly Ser
    50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Ser Ser Val Ala Asp
                85                  90                  95

Ser Ser Val Val Phe Gly Gly Gly Thr Lys Leu Thr Val Leu
            100                 105                 110

<210> SEQ ID NO 577
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 577

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Asn Tyr
            20                  25                  30

Phe Ala Trp Tyr Gln Gln Lys Pro Gly Gln Ala Pro Arg Leu Leu Ile
        35                  40                  45

Tyr Gly Ala Ser Asn Arg Ala Thr Gly Val Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Tyr
                85                  90                  95

Thr Phe Gly Gln Gly Thr Lys Val Glu Ile Lys
            100                 105

<210> SEQ ID NO 578
<211> LENGTH: 110
<212> TYPE: PRT
<213> ORGANISM: Artificial sequence -continued
<220> FEATURE:
<223> OTHER INFORMATION: Synthetic polypeptide

<400> SEQUENCE: 578

Asn Phe Met Leu Thr Gln Pro Pro Ser Val Ser Ala Ala Pro Gly Gln
1               5                   10                  15

Lys Val Thr Ile Ser Cys Ser Gly Ser Asn Ser Asn Ile Gly Asn Asn
            20                  25                  30

Phe Val Ser Trp Tyr Gln Gln Leu Pro Gly Thr Ala Pro Lys Leu Leu
        35                  40                  45

Ile Tyr Asp Asn Asn Glu Arg Pro Ser Gly Ile Pro Asp Arg Phe Ser
    50                  55                  60

Gly Ser Lys Ser Val Thr Ser Ala Thr Leu Gly Ile Thr Gly Leu Gln
65                  70                  75                  80

Thr Gly Asp Glu Ala Asp Tyr Tyr Cys Gly Thr Trp Asn Ser Leu
                85                  90                  95

Gly Met Val Val Phe Gly Gly Gly Thr Lys Leu Thr Val Leu
            100                 105                 110

<210> SEQ ID NO 579
<211> LENGTH: 110
<212> TYPE: PRT
<213> ORGANISM: Artificial sequence
<220> FEATURE:
<223> OTHER INFORMATION: Synthetic polypeptide

<400> SEQUENCE: 579

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Tyr Val Phe Gly Thr Gly Thr Lys Val Thr Val Leu
            100                 105                 110

<210> SEQ ID NO 580
<211> LENGTH: 109
<212> TYPE: PRT
<213> ORGANISM: Artificial sequence
<220> FEATURE:
<223> OTHER INFORMATION: Synthetic polypeptide

<400> SEQUENCE: 580

Glu Ile Val Leu Thr Gln Ser Pro Gly Thr Leu Ala Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ser Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Pro Gly Asn Trp Pro Pro
                85                  90                  95

Ala Phe Thr Phe Gly Gly Gly Thr Lys Leu Glu Ile Lys
            100                 105

<210> SEQ ID NO 581
<211> LENGTH: 106
<212> TYPE: PRT
<213> ORGANISM: Artificial sequence
<220> FEATURE:
<223> OTHER INFORMATION: Synthetic polypeptide

<400> SEQUENCE: 581

Asp Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Thr Ser Lys
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Ile Thr
                85                  90                  95

Phe Gly Gln Gly Thr Arg Leu Glu Ile Lys
            100                 105

<210> SEQ ID NO 582
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 582

Asp Ile Gln Leu Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Trp
                85                  90                  95

Thr Phe Gly Gln Gly Thr Lys Val Asp Ile Lys
            100                 105

<210> SEQ ID NO 583
<211> LENGTH: 112
<212> TYPE: PRT
<213> ORGANISM: Artificial sequence
<220> FEATURE:
<223> OTHER INFORMATION: Synthetic polypeptide

<400> SEQUENCE: 583

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Ser Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Tyr Thr Phe Gly Gln Gly Thr Lys Leu Glu Ile Lys
            100                 105                 110

<210> SEQ ID NO 584
<211> LENGTH: 110
<212> TYPE: PRT
<213> ORGANISM: Artificial sequence
<220> FEATURE:
<223> OTHER INFORMATION: Synthetic polypeptide

<400> SEQUENCE: 584

Gln Pro Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val His Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Leu Ser
    50                  55                  60

Gly Ser Arg Ser Gly Thr Ser Ala Ser Leu Ala Ile Ser Gly Leu Gln
65                  70                  75                  80

Ser Glu Asp Glu Ala Glu Tyr Tyr Cys Ala Ala Trp Asp Asp Asn Leu
                85                  90                  95

Ile Gly Val Val Phe Gly Gly Gly Thr Lys Leu Thr Val Leu
            100                 105                 110

<210> SEQ ID NO 585
<211> LENGTH: 111
<212> TYPE: PRT
<213> ORGANISM: Artificial sequence
<220> FEATURE:
<223> OTHER INFORMATION: Synthetic polypeptide

<400> SEQUENCE: 585

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Phe Ala Gly Ser
                85                  90                  95

Asn Asn Leu Tyr Val Phe Gly Thr Gly Thr Lys Val Thr Val Leu
            100                 105                 110

<210> SEQ ID NO 586
<211> LENGTH: 110
<212> TYPE: PRT
<213> ORGANISM: Artificial sequence
<220> FEATURE:
<223> OTHER INFORMATION: Synthetic polypeptide

<400> SEQUENCE: 586

Gln Ser Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Thr Asn Arg Pro Ser Gly Val Ser Asn Arg Phe
    50                  55                  60

Ser Gly Ser Arg Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Arg Ser
                85                  90                  95

Ser Thr Arg Val Phe Gly Gly Gly Thr Lys Leu Thr Val Leu
            100                 105                 110

<210> SEQ ID NO 587
<211> LENGTH: 109
<212> TYPE: PRT
<213> ORGANISM: Artificial sequence
<220> FEATURE:
<223> OTHER INFORMATION: Synthetic polypeptide

<400> SEQUENCE: 587

Gln Pro Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Ser Asn
            20                  25                  30

Phe Val Ser Trp Tyr Gln Gln Phe Pro Gly Thr Ala Pro Lys Leu Leu
        35                  40                  45

Ile Tyr Asp Asp Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Glu Thr Trp Asp Ser Arg Leu
                85                  90                  95

Ser Val Val Phe Gly Gly Gly Thr Lys Leu Thr Val Leu
            100                 105

<210> SEQ ID NO 588
<211> LENGTH: 110
<212> TYPE: PRT
<213> ORGANISM: Artificial sequence
<220> FEATURE:
<223> OTHER INFORMATION: Synthetic polypeptide

<400> SEQUENCE: 588

Gln Pro Val Leu Thr Gln Pro Pro Ser Val Ser Ala Ala Pro Gly Gln

```
1               5                   10                  15
Lys Val Thr Ile Ser Cys Ser Gly Ser Ser Asn Ile Gly Asn Asn
                    20                  25                  30

Tyr Val Ser Trp Tyr Gln Gln Leu Pro Gly Thr Ala Pro Lys Leu Leu
            35                  40                  45

Ile Tyr Asp Asn Asn Lys Arg Pro Ser Gly Ile Pro Asp Arg Phe Ser
        50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Val Val Phe Gly Gly Gly Thr Lys Val Thr Val Leu
            100                 105                 110
```

<210> SEQ ID NO 589
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 589

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Trp
                85                  90                  95

Thr Phe Gly Gln Gly Thr Lys Val Asp Ile Lys
            100                 105
```

<210> SEQ ID NO 590
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 590

```
Asp Ile Arg Val Thr Gln Ser Pro Ser Ser Leu Ser Ala Ser Val Gly
1               5                   10                  15

Asp Arg Val Thr Ile Thr Ser Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Arg
                85                  90                  95
```

Thr Phe Gly Gly Gly Thr Lys Val Asp Ile Lys
            100                 105

<210> SEQ ID NO 591
<211> LENGTH: 111
<212> TYPE: PRT
<213> ORGANISM: Artificial sequence
<220> FEATURE:
<223> OTHER INFORMATION: Synthetic polypeptide

<400> SEQUENCE: 591

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asp Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Thr Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Val Val Phe Gly Gly Gly Thr Lys Leu Thr Val Leu
            100                 105                 110

<210> SEQ ID NO 592
<211> LENGTH: 113
<212> TYPE: PRT
<213> ORGANISM: Artificial sequence
<220> FEATURE:
<223> OTHER INFORMATION: Synthetic polypeptide

<400> SEQUENCE: 592

Asp Ile Val Leu Thr Gln Ser Pro Asp Ser Leu Ala Val Ser Leu Gly
1               5                   10                  15

Glu Arg Ala Ala Ile Asn Cys Lys Ser Ser Gln Ser Val Phe Phe Ser
            20                  25                  30

Ser Asp Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Phe Tyr Thr Thr Pro Ser Thr Phe Gly Gln Gly Thr Lys Val Glu Ile
            100                 105                 110

Lys

<210> SEQ ID NO 593
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 593

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Arg
                85                  90                  95

Thr Phe Gly Gly Gly Thr Lys Val Glu Ile Lys
            100                 105

<210> SEQ ID NO 594
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 594

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Leu
                85                  90                  95

Thr Phe Gly Gly Gly Thr Lys Val Glu Ile Lys
            100                 105

<210> SEQ ID NO 595
<211> LENGTH: 110
<212> TYPE: PRT
<213> ORGANISM: Artificial sequence
<220> FEATURE:
<223> OTHER INFORMATION: Synthetic polypeptide

<400> SEQUENCE: 595

Asn Phe Met Leu Thr Gln Pro His Ser Val Ser Glu Ser Pro Gly Asn
1               5                   10                  15

Thr Val Thr Ile Ser Cys Thr Arg Ser Ser Gly Ser Ile Ala Ser Thr
            20                  25                  30

Tyr Val Gln Trp Tyr Gln Gln Arg Pro Gly Ser Ala Pro Ser Thr Val
        35                  40                  45

Ile Tyr Glu Asp Asn Gln Arg Pro Pro Gly Val Pro Ala Arg Phe Ser
    50                  55                  60

Gly Ser Ile Asp Ser Ser Ser Asn Ser Ala Ser Leu Thr Ile Ser Gly
65                  70                  75                  80

Leu Glu Thr Glu Asp Glu Ala Asp Tyr Tyr Cys Gln Ser Tyr Asp Ser
                85                  90                  95

Thr Thr Val Val Phe Gly Gly Gly Thr Lys Val Thr Val Leu

<210> SEQ ID NO 596
<211> LENGTH: 111
<212> TYPE: PRT
<213> ORGANISM: Artificial sequence
<220> FEATURE:
<223> OTHER INFORMATION: Synthetic polypeptide

<400> SEQUENCE: 596

```
Ser Tyr Val Leu Thr Gln Pro Pro Ser Ala Ser Gly Ser Pro Gly Gln
1               5                   10                  15

Ser Val Thr Ile Ser Cys Thr Gly Thr Ser Ser Asp Phe Gly Gly Tyr
            20                  25                  30

Asn Tyr Val Ser Trp Tyr Gln Gln His Pro Gly Lys Ala Pro Lys Leu
        35                  40                  45

Met Val Tyr Glu Val Ala Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Ser
                85                  90                  95

Asn Asn Phe Val Val Phe Gly Gly Gly Thr Lys Leu Thr Val Leu
            100                 105                 110
```

<210> SEQ ID NO 597
<211> LENGTH: 110
<212> TYPE: PRT
<213> ORGANISM: Artificial sequence
<220> FEATURE:
<223> OTHER INFORMATION: Synthetic polypeptide

<400> SEQUENCE: 597

```
Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Lys Val Phe Gly Gly Gly Thr Lys Leu Thr Val Leu
            100                 105                 110
```

<210> SEQ ID NO 598
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 598

```
Glu Thr Thr Leu Thr Gln Ser Pro Ser Thr Leu Ser Thr Ser Val Gly
1               5                   10                  15

Asp Arg Val Thr Ile Thr Cys Arg Ala Ser Gln Ser Ile Ser Ser Trp
            20                  25                  30
```

Leu Ala Trp Tyr Gln Gln Lys Pro Gly Lys Ala Pro Lys Leu Leu Ile
        35                  40                  45

Tyr Arg Ala Ser Ser Leu Glu Thr Glu Val Pro Ser Arg Phe Ser Gly
    50                  55                  60

Ser Gly Ser Gly Thr Asp Phe Thr Leu Thr Ile Ser Arg Leu Gln Pro
65                  70                  75                  80

Asp Asp Phe Ala Thr Tyr Phe Cys Gln Gln Tyr Asn Arg Tyr Pro Tyr
                85                  90                  95

Thr Phe Gly Gln Gly Thr Lys Leu Glu Ile Lys
            100                 105

<210> SEQ ID NO 599
<211> LENGTH: 111
<212> TYPE: PRT
<213> ORGANISM: Artificial sequence
<220> FEATURE:
<223> OTHER INFORMATION: Synthetic polypeptide

<400> SEQUENCE: 599

Gln Pro Val Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Asp Val Ser Lys Arg Pro Ser Gly Val Pro Asp Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Tyr Thr Phe Val Leu Phe Gly Gly Gly Thr Lys Leu Thr Val Leu
            100                 105                 110

<210> SEQ ID NO 600
<211> LENGTH: 106
<212> TYPE: PRT
<213> ORGANISM: Artificial sequence
<220> FEATURE:
<223> OTHER INFORMATION: Synthetic polypeptide

<400> SEQUENCE: 600

Asp Ile Arg Val Thr Gln Ser Pro Ser Ser Leu Ser Ala Ser Val Gly
1               5                   10                  15

Asp Arg Val Thr Ile Ser Cys Arg Ala Ser Glu Ser Ile Ser Ile Tyr
                20                  25                  30

Leu Asn Trp Tyr Gln Gln Lys Pro Gly Lys Ala Pro Asn Leu Leu Ile
            35                  40                  45

Tyr Ala Ala Ser Ser Leu Gln Arg Gly Val Pro Ser Arg Phe Ser Gly
        50                  55                  60

Ser Gly Ser Gly Thr Asp Phe Thr Leu Thr Ile Thr Ser Leu Gln Ala
65                  70                  75                  80

Glu Asp Phe Ala Thr Tyr Tyr Cys Gln Gln Thr Phe Ser Ile Trp Thr
                85                  90                  95

Phe Gly Gln Gly Thr Lys Val Glu Ile Lys
            100                 105

<210> SEQ ID NO 601
<211> LENGTH: 111
<212> TYPE: PRT
<213> ORGANISM: Artificial sequence
<220> FEATURE:
<223> OTHER INFORMATION: Synthetic polypeptide

<400> SEQUENCE: 601

Gln Pro Val Leu Thr Gln Pro Pro Ser Val Ser Ala Ala Pro Gly Gln
1               5                   10                  15

Lys Val Thr Ile Ser Cys Ser Gly Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Gly Lys Val Phe Gly Gly Gly Thr Lys Leu Thr Val Leu
            100                 105                 110

<210> SEQ ID NO 602
<211> LENGTH: 110
<212> TYPE: PRT
<213> ORGANISM: Artificial sequence
<220> FEATURE:
<223> OTHER INFORMATION: Synthetic polypeptide

<400> SEQUENCE: 602

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Phe
            20                  25                  30

Asn Tyr Val Ser Trp Tyr Gln Gln His Pro Gly Arg Ala Pro Lys Leu
        35                  40                  45

Val Ile Tyr Glu Val Asn Arg Arg Pro Ser Gly Val Pro Asp Arg Phe
    50                  55                  60

Ser Gly Ser Lys Ser Gly Tyr Thr Ala Ser Leu Thr Val Ser Gly Leu
65                  70                  75                  80

Gln Ala Glu Asp Glu Ala Asp Tyr Tyr Cys Phe Ser Tyr Ala Gly Ser
                85                  90                  95

Asn Asn Tyr Val Phe Gly Thr Gly Thr Lys Val Thr Val Leu
            100                 105                 110

<210> SEQ ID NO 603
<211> LENGTH: 112
<212> TYPE: PRT
<213> ORGANISM: Artificial sequence
<220> FEATURE:
<223> OTHER INFORMATION: Synthetic polypeptide

<400> SEQUENCE: 603

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

```
Pro Arg Phe Leu Ile Tyr Lys Ile Ser Asn Arg Phe Ser Gly Val Pro
    50                  55                  60

Asp Arg Phe Ser Gly Gly Gly Ala Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Ser Gln Phe Pro Leu Thr Phe Gly Gly Gly Thr Lys Val Glu Ile Lys
                100                 105                 110
```

<210> SEQ ID NO 604
<211> LENGTH: 108
<212> TYPE: PRT
<213> ORGANISM: Artificial sequence
<220> FEATURE:
<223> OTHER INFORMATION: Synthetic polypeptide

<400> SEQUENCE: 604

```
Glu Ile Val Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
                20                  25                  30

Leu Asn Trp Tyr Gln Gln Lys Pro Gly Lys Ala Pro Lys Leu Leu Ile
            35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro Pro
                85                  90                  95

Val Thr Phe Gly Gln Gly Thr Arg Leu Glu Ile Lys
                100                 105
```

<210> SEQ ID NO 605
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 605

```
Gln Pro Val Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
                20                  25                  30

Cys Trp Tyr Gln Gln Lys Pro Gly Gln Ser Pro Val Leu Val Ile Tyr
            35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Asp Val
                85                  90                  95

Val Phe Gly Gly Gly Thr Lys Val Thr Val Leu
                100                 105
```

<210> SEQ ID NO 606
<211> LENGTH: 107
<212> TYPE: PRT

<213> ORGANISM: Artificial sequence
<220> FEATURE:
<223> OTHER INFORMATION: Synthetic polypeptide

<400> SEQUENCE: 606

```
Asp Ile Gln Val Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Asn
            20                  25                  30

Leu Ala Trp Tyr Gln Gln Lys Pro Gly Ile Phe Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Ile Leu Thr Ile Ser Ser Leu Gln Pro
65                  70                  75                  80

Glu Asp Val Ala Thr Tyr Tyr Cys Gln Lys Tyr Gln Ser Ala Pro Pro
                85                  90                  95

Thr Phe Gly Gly Gly Thr Lys Leu Glu Ile Lys
            100                 105
```

<210> SEQ ID NO 607
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 607

```
Tyr Ser Ile Ser Ser Gly Phe Tyr Trp Gly
1               5                   10
```

<210> SEQ ID NO 608
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 608

```
Ser Met Tyr Gln Ser Gly Ile Thr Tyr Tyr Asn Pro Ser Leu Lys Ser
1               5                   10                  15
```

<210> SEQ ID NO 609
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 609

```
Phe Thr Phe Ser Asn Tyr Ala Met Asn
1               5
```

<210> SEQ ID NO 610
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 610

```
Ala Ile Asn Arg Gly Gly Asp Ser Thr Tyr Tyr Ala Asp Ser Val Lys
1               5                   10                  15
```

Gly

<210> SEQ ID NO 611
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 611

Ser Met Tyr His Ser Gly Ile Thr Tyr Tyr Asn Pro Ser Leu Lys Ser
1               5                   10                  15

<210> SEQ ID NO 612
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 612

Phe Ala Phe Ser Ser Tyr Gly Met His
1               5

<210> SEQ ID NO 613
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 613

Leu Ile Arg Phe Asp Gly Thr Ile Lys Tyr Tyr Ala Asp Ser Val Lys
1               5                   10                  15
Gly

<210> SEQ ID NO 614
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 614

Phe Thr Phe Asn Ser His Gly Met His
1               5

<210> SEQ ID NO 615
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 615

Val Ile Ser Tyr Asp Gly Thr Lys Lys Tyr Phe Ala Asp Ser Val Lys
1               5                   10                  15
Gly

<210> SEQ ID NO 616
<211> LENGTH: 9
<212> TYPE: PRT
<213> ORGANISM: Artificial sequence
<220> FEATURE:
<223> OTHER INFORMATION: Synthetic polypeptide

```
<400> SEQUENCE: 616

Phe Thr Phe Arg Asn Tyr Ala Met Asn
1               5

<210> SEQ ID NO 617
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 617

Gly Ile Ser Gly Gly Gly Asp Ser Thr Asn Tyr Ala Asp Ser Val Lys
1               5                   10                  15

Gly

<210> SEQ ID NO 618
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 618

Leu Ile Phe Arg Asn Tyr Ala Met Ser
1               5

<210> SEQ ID NO 619
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 619

Ser Phe Ser Gly Ser Gly Gly Ser Ala Tyr Tyr Ala Asp Ser Val Lys
1               5                   10                  15

Gly

<210> SEQ ID NO 620
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 620

Gly Met Arg Phe Asp Gly Thr Lys Ile Tyr Tyr Ala Asp Ser Val Lys
1               5                   10                  15

Gly

<210> SEQ ID NO 621
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 621

Gly Ser Ile Ser Ser Asp Tyr Trp Trp Ser
1               5                   10

<210> SEQ ID NO 622
<211> LENGTH: 16
```

<212> TYPE: PRT
<213> ORGANISM: Artificial sequence
<220> FEATURE:
<223> OTHER INFORMATION: Synthetic polypeptide

<400> SEQUENCE: 622

Glu Ile Tyr His Thr Gly Ser Thr Asn Tyr Asn Pro Ser Leu Lys Ser
1               5                   10                  15

<210> SEQ ID NO 623
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 623

Gly Ser Ile Thr Ser Ser Asn Trp Trp Ser
1               5                   10

<210> SEQ ID NO 624
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 624

Asp Ile Tyr His Ser Gly Ser Thr Ser Tyr Asn Pro Ser Leu Lys Ser
1               5                   10                  15

<210> SEQ ID NO 625
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 625

Asp Ser Ile Ser Ser Asn Asn Trp Trp Ser
1               5                   10

<210> SEQ ID NO 626
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 626

Glu Ile Tyr His Ser Gly Ser Thr Ser Tyr Asn Pro Ser Leu Lys Ser
1               5                   10                  15

<210> SEQ ID NO 627
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 627

Phe Thr Phe Gly Asp Tyr Tyr Met Ser
1               5

<210> SEQ ID NO 628
<211> LENGTH: 17
<212> TYPE: PRT

```
<213> ORGANISM: Artificial sequence
<220> FEATURE:
<223> OTHER INFORMATION: Synthetic polypeptide

<400> SEQUENCE: 628

Tyr Ile Ser Ser Ser Gly Ser Ser Ile Tyr Tyr Thr Asp Ser Val Arg
1               5                   10                  15

Gly

<210> SEQ ID NO 629
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 629

Gly Ser Ile Ser Ser Ser Asp Trp Trp Ser
1               5                   10

<210> SEQ ID NO 630
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 630

Glu Ile Tyr His Ser Gly Ser Thr Ser Tyr Asn Pro Ser Val Lys Ser
1               5                   10                  15

<210> SEQ ID NO 631
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 631

Asp Ser Ile Ser Ser Ser His Trp Trp Cys
1               5                   10

<210> SEQ ID NO 632
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 632

Gly Ser Ile Ser Ser Ser Tyr Trp Trp Ser
1               5                   10

<210> SEQ ID NO 633
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 633

Glu Val Tyr His Ser Gly Ser Thr His Tyr Asn Pro Ser Leu Lys Ser
1               5                   10                  15

<210> SEQ ID NO 634
<211> LENGTH: 10
```

```
<212> TYPE: PRT
<213> ORGANISM: Artificial sequence
<220> FEATURE:
<223> OTHER INFORMATION: Synthetic polypeptide

<400> SEQUENCE: 634

Gly Ser Ile Ser Ser Ser Asn Trp Trp Ser
1               5                   10

<210> SEQ ID NO 635
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 635

Asp Ile Tyr His Thr Gly Ser Thr Ser Tyr Asn Pro Ser Leu Lys Ser
1               5                   10                  15

<210> SEQ ID NO 636
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 636

Phe Ile Phe Ser Asp Tyr Tyr Met Asn
1               5

<210> SEQ ID NO 637
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 637

Thr Ile Ser Gly Ser Gly Lys Ser Ile Tyr Tyr Ala Asp Ser Val Lys
1               5                   10                  15

Gly

<210> SEQ ID NO 638
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 638

Phe Thr Phe Ser Asp Tyr Tyr Met Ser
1               5

<210> SEQ ID NO 639
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 639

Tyr Ile Thr Ser Ser Gly Asn Thr Lys Tyr Tyr Ala Asp Ser Val Lys
1               5                   10                  15

Gly
```

<210> SEQ ID NO 640
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 640

Phe Thr Phe Asp Asp Tyr Ala Met His
1               5

<210> SEQ ID NO 641
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 641

Gly Ile Ser Trp Asn Gly Gly Ile Gly Tyr Ala Asp Ser Val Lys
1               5                   10                  15

Gly

<210> SEQ ID NO 642
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 642

Phe Thr Phe Ser Ser Tyr Ala Met Ser
1               5

<210> SEQ ID NO 643
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 643

Ala Ile Ser Gly Ser Gly Gly Ser Thr Tyr Tyr Ala Asp Ser Val Lys
1               5                   10                  15

Gly

<210> SEQ ID NO 644
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 644

Gly Ser Ile Ser Ser Asn Lys Trp Trp Ser
1               5                   10

<210> SEQ ID NO 645
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 645

```
Phe Thr Phe Ser Asp Asp Tyr Met Ser
1               5
```

<210> SEQ ID NO 646
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 646

```
Tyr Ile Ser Gly Ser Gly Arg Ala Met Tyr Tyr Ala Asp Ser Val Gln
1               5                   10                  15
Gly
```

<210> SEQ ID NO 647
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 647

```
Ser Ser Ile Thr Ser Ser His Trp Trp Ser
1               5                   10
```

<210> SEQ ID NO 648
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 648

```
Asp Ile Tyr His Ser Gly Gly Thr Thr Tyr Asn Pro Ser Leu Lys Ser
1               5                   10                  15
```

<210> SEQ ID NO 649
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 649

```
Phe Thr Phe Asn Asn Tyr Tyr Met Arg
1               5
```

<210> SEQ ID NO 650
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 650

```
Gln Ile Ser Ser Ser Gly Ser Ile Lys Asp Tyr Ala Asp Ser Val Lys
1               5                   10                  15
Gly
```

<210> SEQ ID NO 651
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 651

Phe Thr Leu Arg Ser Tyr Gly Met His
1               5

<210> SEQ ID NO 652
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 652

Val Ser Trp Tyr Asp Gly Ser Asn Lys His Tyr Ala Asp Ser Val Lys
1               5                   10                  15
Gly

<210> SEQ ID NO 653
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 653

Phe Thr Phe Ser Ser Tyr Thr Met His
1               5

<210> SEQ ID NO 654
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 654

Val Ile Ser Tyr Asp Gly Ser Asn Lys Tyr Tyr Ala Asp Ser Val Lys
1               5                   10                  15
Gly

<210> SEQ ID NO 655
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 655

Asp Ser Ile Ser Val Ser Tyr Trp Ser
1               5

<210> SEQ ID NO 656
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 656

Tyr Ile Tyr Asn Ser Gly Asn Ala Asn Tyr Asn Pro Ser Leu Glu Ser
1               5                   10                  15

<210> SEQ ID NO 657
<211> LENGTH: 11
<212> TYPE: PRT

```
<213> ORGANISM: Artificial sequence
<220> FEATURE:
<223> OTHER INFORMATION: Synthetic polypeptide

<400> SEQUENCE: 657

Gly Ser Leu Ser Ser Asp Ser His Phe Trp Gly
1               5                   10

<210> SEQ ID NO 658
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 658

Tyr Ile Tyr Tyr Ser Gly Asn Ala Asn Tyr Asn Pro Ser Leu Gln Ser
1               5                   10                  15

<210> SEQ ID NO 659
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 659

Gly Ser Val Ser Ser Gly Ser Tyr Tyr Trp Ser
1               5                   10

<210> SEQ ID NO 660
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 660

Tyr Ile Tyr Asp Ser Gly Asn Thr Asn Tyr Asn Pro Ser Leu Lys Ser
1               5                   10                  15

<210> SEQ ID NO 661
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 661

Cys Ile Ser Ser Ser Gly Ser Met Ile Tyr Tyr Ala Asp Ser Val Lys
1               5                   10                  15

Gly

<210> SEQ ID NO 662
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 662

Gly Ser Ile Ser Thr Thr Asp Trp Trp Ser
1               5                   10

<210> SEQ ID NO 663
<211> LENGTH: 16
```

```
<212> TYPE: PRT
<213> ORGANISM: Artificial sequence
<220> FEATURE:
<223> OTHER INFORMATION: Synthetic polypeptide

<400> SEQUENCE: 663

Glu Ile Asn Gln Ser Gly Ser Thr Ser Tyr Ser Pro Ser Phe Lys Ser
1               5                   10                  15

<210> SEQ ID NO 664
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 664

Gly Ser Ile Ser Ser Gly Asn Trp Trp Ser
1               5                   10

<210> SEQ ID NO 665
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 665

Glu Ile Tyr His Ser Gly Ser Ala Asn Tyr Asn Pro Ser Leu Lys Ser
1               5                   10                  15

<210> SEQ ID NO 666
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 666

Phe Thr Phe Thr Thr Tyr Ala Met His
1               5

<210> SEQ ID NO 667
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 667

Ala Val Ser Tyr Asp Gly Asn Asn Lys Tyr Tyr Ala Asp Ser Val Lys
1               5                   10                  15

Gly

<210> SEQ ID NO 668
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 668

Asp Ser Ile Ser Ser Thr Asn Trp Trp Ser
1               5                   10

<210> SEQ ID NO 669
```

```
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 669

Glu Ile Phe His Ser Gly Ser Thr Asn Tyr Asn Pro Phe Leu Lys Ser
1               5                   10                  15

<210> SEQ ID NO 670
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 670

Gly Ser Ile Ser Ser Asn Asn Trp Trp Ser
1               5                   10

<210> SEQ ID NO 671
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 671

Asp Thr Tyr His Ser Gly Ser Pro Ser Tyr Asn Pro Ser Leu Lys Ser
1               5                   10                  15

<210> SEQ ID NO 672
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 672

Phe Thr Phe Ser Asn Phe Gly Met His
1               5

<210> SEQ ID NO 673
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 673

Ile Ile Ser Tyr Asp Arg Ser Asn Lys Asp Tyr Ala Asp Ser Val Lys
1               5                   10                  15

Gly

<210> SEQ ID NO 674
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 674

Ala Ser Ile Ser Ser Asn His Trp Trp Thr
1               5                   10
```

```
<210> SEQ ID NO 675
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 675

Glu Ile Tyr His Ser Gly Ser Pro Thr Tyr Asn Pro Ser Leu Lys Ser
1               5                   10                  15

<210> SEQ ID NO 676
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 676

Phe Thr Phe Ser Asn Ser Gly Met His
1               5

<210> SEQ ID NO 677
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 677

Leu Ile Ser Tyr Thr Gly Glu Thr Lys Tyr Tyr Ser Asp Ser Leu Lys
1               5                   10                  15

Ala

<210> SEQ ID NO 678
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 678

Gly Ser Ile Ser Ser Ile Ser Trp Trp Ser
1               5                   10

<210> SEQ ID NO 679
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 679

Glu Ile Asn His Ser Gly Ser Thr Val Tyr Asn Pro Ser Leu Lys Ser
1               5                   10                  15

<210> SEQ ID NO 680
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 680

Phe Thr Phe Thr Asp Tyr Tyr Met Ser
1               5
```

<210> SEQ ID NO 681
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 681

Tyr Ile Ser Ser Ser Gly Asn Thr Arg Tyr Tyr Ala Asp Ser Val Lys
1               5                   10                  15

Gly

<210> SEQ ID NO 682
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 682

Gly Ser Ile Thr Gly Ser Asn Trp Trp Ser
1               5                   10

<210> SEQ ID NO 683
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 683

Glu Ile Tyr His Thr Gly Ser Thr Ser Tyr Asn Pro Ser Leu Lys Ser
1               5                   10                  15

<210> SEQ ID NO 684
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 684

Phe Ser Leu Ser Thr Ser Gly Val Gly Val Gly
1               5                   10

<210> SEQ ID NO 685
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 685

Leu Ile Tyr Trp Asp Asp Asp Lys Arg Tyr Ser Pro Ser Leu Lys Ser
1               5                   10                  15

<210> SEQ ID NO 686
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 686

Val Ile Trp Tyr Asp Glu Ser Asn Lys Tyr Tyr Ala Asp Ser Val Lys
1               5                   10                  15

Gly

<210> SEQ ID NO 687
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 687

Val Ile Ser Asp Ser Gly Gly Ser Thr Tyr Tyr Ala Asp Ser Val Lys
1               5                   10                  15

Gly

<210> SEQ ID NO 688
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 688

Phe Thr Phe Ile Asn Tyr Ala Met Thr
1               5

<210> SEQ ID NO 689
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 689

Ala Ile Ser Gly Asn Gly Asp Gly Thr Tyr Tyr Ala Asp Ser Val Lys
1               5                   10                  15

Gly

<210> SEQ ID NO 690
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 690

Phe Thr Phe Ser Ser Tyr Ala Met His
1               5

<210> SEQ ID NO 691
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 691

Val Ile Ser His Asp Gly Ser Asn Lys Tyr Tyr Ala Asp Ser Val Lys
1               5                   10                  15

Gly

<210> SEQ ID NO 692
<211> LENGTH: 11
<212> TYPE: PRT
<213> ORGANISM: Artificial sequence

```
<220> FEATURE:
<223> OTHER INFORMATION: Synthetic polypeptide

<400> SEQUENCE: 692

Gly Ser Val Arg Gly Gly Ser His Tyr Trp Ser
1               5                   10

<210> SEQ ID NO 693
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 693

Tyr Val Tyr Asp Ser Gly Ser Thr Asn Tyr Asn Pro Ser Leu Lys Ser
1               5                   10                  15

<210> SEQ ID NO 694
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 694

Phe Thr Phe Ser Asn Tyr Ala Met Ser
1               5

<210> SEQ ID NO 695
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 695

Ala Ile Ser Gly Ser Gly Asp Ser Thr Tyr Tyr Ala Asp Ser Val Lys
1               5                   10                  15

Gly

<210> SEQ ID NO 696
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 696

Tyr Ile Thr Ser Ser Gly Asn Thr Met Tyr Tyr Ala Asp Ser Val Lys
1               5                   10                  15

Gly

<210> SEQ ID NO 697
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 697

Glu Ile Tyr His Ser Gly Ser Thr Thr Tyr Asn Pro Ser Leu Lys Ser
1               5                   10                  15

<210> SEQ ID NO 698
```

```
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 698

Tyr Ile Ser Ser Ser Gly Asn Thr Ile Tyr Tyr Ala Asp Ser Val Lys
1               5                   10                  15

Gly

<210> SEQ ID NO 699
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 699

Phe Thr Phe Ser Asn Tyr Gly Met His
1               5

<210> SEQ ID NO 700
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 700

Tyr Thr Phe Asn Thr Tyr Ala Met Thr
1               5

<210> SEQ ID NO 701
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 701

Trp Ile Ser Thr Tyr Asn Gly Asn Thr Val Phe Gly Gln Lys Phe Gln
1               5                   10                  15

Gly

<210> SEQ ID NO 702
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 702

Phe Thr Phe Ser Thr Tyr Trp Met Ser
1               5

<210> SEQ ID NO 703
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 703

Asn Ile Lys Gln Asp Gly Ser Glu Lys Tyr Tyr Val Asp Ser Val Lys
1               5                   10                  15
```

Gly

<210> SEQ ID NO 704
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 704

Val Ile Trp Tyr Asp Ser Arg Asn Gln Asn Tyr Ala Asp Ser Val Lys
1               5                   10                  15

Gly

<210> SEQ ID NO 705
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 705

Thr Phe Ser Gly Arg Gly Gly Ser Thr Tyr Tyr Ala Asp Phe Val Lys
1               5                   10                  15

Gly

<210> SEQ ID NO 706
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 706

Phe Thr Phe Ser Ser Tyr Gly Met His
1               5

<210> SEQ ID NO 707
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 707

Val Ile Ser Tyr Asp Gly Ser Lys Lys Tyr Ser Ala Asp Ser Val Lys
1               5                   10                  15

Gly

<210> SEQ ID NO 708
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 708

Phe Thr Phe Ala Glu Tyr Ala Met His
1               5

<210> SEQ ID NO 709
<211> LENGTH: 17
<212> TYPE: PRT
<213> ORGANISM: Artificial sequence

```
<220> FEATURE:
<223> OTHER INFORMATION: Synthetic polypeptide

<400> SEQUENCE: 709

Ser Ile Ser Trp Asn Ser Gly Arg Ile Gly Tyr Val Asp Ser Val Arg
1               5                   10                  15
Gly

<210> SEQ ID NO 710
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 710

Gly Ser Ile Ser Ser Tyr Tyr Trp Ser
1               5

<210> SEQ ID NO 711
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 711

Arg Ile Tyr Thr Ser Gly Ser Gly Asn Tyr Asn Pro Ser Leu Lys Arg
1               5                   10                  15

<210> SEQ ID NO 712
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 712

Phe Thr Phe Ser Asp Tyr Glu Met Asn
1               5

<210> SEQ ID NO 713
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 713

His Ile Ser Ser Ser Gly Asn Ile Ile Tyr Tyr Ala Asp Ser Val Lys
1               5                   10                  15
Gly

<210> SEQ ID NO 714
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 714

Phe Thr Phe Ser Ala Tyr Ala Met Ser
1               5

<210> SEQ ID NO 715
```

```
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 715

Ala Ile Ser Gly Ser Asp Arg Arg Ile Tyr Tyr Ala Asp Ser Val Lys
1               5                   10                  15

Gly

<210> SEQ ID NO 716
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 716

Phe Thr Phe Ser Asp His Tyr Met Ala
1               5

<210> SEQ ID NO 717
<211> LENGTH: 19
<212> TYPE: PRT
<213> ORGANISM: Artificial sequence
<220> FEATURE:
<223> OTHER INFORMATION: Synthetic polypeptide

<400> SEQUENCE: 717

Arg Ile Arg Asn Lys Pro Asn Ser Tyr Thr Thr Glu Tyr Ala Ala Ser
1               5                   10                  15

Val Lys Gly

<210> SEQ ID NO 718
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 718

Tyr Ser Phe Thr Thr Tyr Gly Ile Ser
1               5

<210> SEQ ID NO 719
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 719

Trp Ile Ser Gly Tyr Ser Gly Asp Thr Asn Tyr Ala Gln Lys Val Gln
1               5                   10                  15

Gly

<210> SEQ ID NO 720
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 720
```

```
Gly Ser Ile Ser Ser Ser Ser Tyr Tyr Trp Gly
1               5                   10

<210> SEQ ID NO 721
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 721

Ser Ile Tyr Tyr Ser Gly Ser Thr Tyr Tyr Asn Pro Ser Leu Lys Ser
1               5                   10                  15

<210> SEQ ID NO 722
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 722

Phe Thr Phe Ser Arg Tyr Ser Met Asn
1               5

<210> SEQ ID NO 723
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 723

Ser Ile Ser His Ser Gly Arg Tyr Ile Tyr Tyr Ala Asp Ser Glu Lys
1               5                   10                  15

Gly

<210> SEQ ID NO 724
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 724

Phe Thr Phe Ser Asp His Tyr Met Asp
1               5

<210> SEQ ID NO 725
<211> LENGTH: 19
<212> TYPE: PRT
<213> ORGANISM: Artificial sequence
<220> FEATURE:
<223> OTHER INFORMATION: Synthetic polypeptide

<400> SEQUENCE: 725

Arg Thr Arg Asn Lys Pro Asn Ser His Thr Thr Glu Tyr Ala Ala Ser
1               5                   10                  15

Val Lys Gly

<210> SEQ ID NO 726
<211> LENGTH: 9
<212> TYPE: PRT
<213> ORGANISM: Artificial sequence
<220> FEATURE:
<223> OTHER INFORMATION: Synthetic polypeptide
```

<400> SEQUENCE: 726

Phe Ile Tyr Thr Asn Tyr Ala Met Tyr
1               5

<210> SEQ ID NO 727
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 727

Ala Ile Ser Gly Ser Gly Gly Ile Thr Tyr Tyr Ala Asp Ser Val Lys
1               5                   10                  15
Gly

<210> SEQ ID NO 728
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 728

Phe Ile Phe Ser Asp Tyr Tyr Met Asp
1               5

<210> SEQ ID NO 729
<211> LENGTH: 19
<212> TYPE: PRT
<213> ORGANISM: Artificial sequence
<220> FEATURE:
<223> OTHER INFORMATION: Synthetic polypeptide

<400> SEQUENCE: 729

Arg Ile Thr Asn Arg Pro Asn Ser Tyr Thr Thr Glu Tyr Ala Ala Ser
1               5                   10                  15
Val Lys Gly

<210> SEQ ID NO 730
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 730

Gly Ser Ile Ser Ser Gly Ser Tyr Tyr Trp Ser
1               5                   10

<210> SEQ ID NO 731
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 731

Arg Ile Tyr Thr Ser Gly Ser Thr Asn Tyr Asn Pro Ser Leu Lys Ser
1               5                   10                  15

<210> SEQ ID NO 732
<211> LENGTH: 16
<212> TYPE: PRT

```
<213> ORGANISM: Artificial sequence
<220> FEATURE:
<223> OTHER INFORMATION: Synthetic polypeptide

<400> SEQUENCE: 732

Glu Ile Tyr His Ser Glu Ser Thr Asn Tyr Asn Pro Ser Leu Lys Ser
1               5                   10                  15

<210> SEQ ID NO 733
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 733

Gly Ile Ser Trp Asn Ser Gly Ser Ile Gly Tyr Ala Asp Ser Val Lys
1               5                   10                  15

Gly

<210> SEQ ID NO 734
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 734

Ser Ile Arg Ser Ser Gly Gly Arg Thr Glu Tyr Ala Asp Ser Val Lys
1               5                   10                  15

Gly

<210> SEQ ID NO 735
<211> LENGTH: 19
<212> TYPE: PRT
<213> ORGANISM: Artificial sequence
<220> FEATURE:
<223> OTHER INFORMATION: Synthetic polypeptide

<400> SEQUENCE: 735

Arg Ile Arg Asn Lys Pro Asn Ser Tyr Ala Thr Gln Tyr Ala Ala Ser
1               5                   10                  15

Val Lys Gly

<210> SEQ ID NO 736
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 736

Phe Thr Phe Ser Ser Tyr Ser Met Asn
1               5

<210> SEQ ID NO 737
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 737

Ser Ile Ser Ser Arg Ser Ser Phe Met Tyr Tyr Ala Asp Ser Val Lys
1               5                   10                  15
```

Gly

<210> SEQ ID NO 738
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 738

Leu Ile Ser Tyr Asp Gly Ser Asn Lys Tyr Tyr Ala Asp Ser Val Lys
1               5                   10                  15

Gly

<210> SEQ ID NO 739
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 739

Phe Thr Phe Ser Ser Leu Ala Met His
1               5

<210> SEQ ID NO 740
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 740

Thr Ile Ser Tyr Asp Val Ser Asn Lys Tyr Tyr Ala Asp Ser Val Lys
1               5                   10                  15

Gly

<210> SEQ ID NO 741
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 741

Tyr Thr Phe Thr Ser Tyr Gly Ile Ser
1               5

<210> SEQ ID NO 742
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 742

Trp Ile Ser Ala Tyr Asn Gly Asn Thr Asn Tyr Ala Gln Lys Leu Gln
1               5                   10                  15

Gly

<210> SEQ ID NO 743
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 743

Gly Ala Ile Ser Ser Gly Asp Tyr Tyr Trp Ser
1               5                   10

<210> SEQ ID NO 744
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 744

Tyr Ile His Tyr Ser Gly Thr Thr Tyr Asn Asn Pro Ser Leu Lys Ser
1               5                   10                  15

<210> SEQ ID NO 745
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 745

Val Ile Arg Phe Asp Gly Ser Asn Thr Val Tyr Ala Asp Ser Val Lys
1               5                   10                  15

Gly

<210> SEQ ID NO 746
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 746

Val Ile Ser Tyr Asp Gly Ser Tyr Lys Trp Tyr Ala Asp Ser Val Lys
1               5                   10                  15

Gly

<210> SEQ ID NO 747
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 747

Phe Ser Phe Ser Ser His Ala Met Thr
1               5

<210> SEQ ID NO 748
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 748

Ser Ile Arg Gly Ser Asp Arg Thr Thr Asn Tyr Ala Asp Ser Val Lys
1               5                   10                  15

Gly

```
<210> SEQ ID NO 749
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 749

Phe Thr Phe Gly Thr His Ala Met Ser
1               5

<210> SEQ ID NO 750
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 750

Thr Phe Ser Gly Ser Gly Gly Arg Thr Tyr Tyr Ala Asp Ser Val Lys
1               5                   10                  15

Gly

<210> SEQ ID NO 751
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 751

Phe Thr Phe Ser Asp Tyr Tyr Met Asp
1               5

<210> SEQ ID NO 752
<211> LENGTH: 19
<212> TYPE: PRT
<213> ORGANISM: Artificial sequence
<220> FEATURE:
<223> OTHER INFORMATION: Synthetic polypeptide

<400> SEQUENCE: 752

Gly Ile Arg Asn Lys Pro Asn Ser Tyr Thr Thr Glu Tyr Ala Ala Ser
1               5                   10                  15

Val Lys Gly

<210> SEQ ID NO 753
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 753

Ala Ser Ile Arg Ser Tyr Leu Trp Ser
1               5

<210> SEQ ID NO 754
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 754
```

Ser Ile Tyr His Ser Gly Ser Thr Lys Tyr Asn Pro Ser Leu Lys Ser
1               5                   10                  15

<210> SEQ ID NO 755
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 755

Phe Thr Phe Ser Gly Asn Ala Met His
1               5

<210> SEQ ID NO 756
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 756

Val Ile Leu Tyr Asp Gly Ser Asn Gln Tyr Tyr Ala Asp Ser Val Lys
1               5                   10                  15
Gly

<210> SEQ ID NO 757
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 757

Gly Ser Ile Ser Ser Ser Asn Trp Trp Thr
1               5                   10

<210> SEQ ID NO 758
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 758

Glu Ile Tyr His Ser Gly Ser Thr Asn Tyr Asn Pro Ser Leu Glu Ser
1               5                   10                  15

<210> SEQ ID NO 759
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 759

Phe Thr Phe Thr Tyr Tyr Ala Met Ser
1               5

<210> SEQ ID NO 760
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 760

```
Gly Ile Ser Gly Ser Gly Asp Ser Thr Tyr Asn Ala Asp Ser Val Lys
1               5                   10                  15

Gly

<210> SEQ ID NO 761
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 761

Val Ile Ser Tyr Asp Gly Ser Lys Lys Tyr Phe Ala Asp Ser Val Lys
1               5                   10                  15

Gly

<210> SEQ ID NO 762
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 762

Val Ile Trp Tyr Asp Gly Ser Asn Lys Tyr Tyr Ala Asp Ser Val Lys
1               5                   10                  15

Gly

<210> SEQ ID NO 763
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 763

Gly Ser Ile Ser Ser Gly Gly Tyr Tyr Trp Thr
1               5                   10

<210> SEQ ID NO 764
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 764

Tyr Ile Tyr Tyr Thr Gly Ser Thr Tyr Tyr Asn Pro Ser Leu Lys Ser
1               5                   10                  15

<210> SEQ ID NO 765
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 765

Phe Thr Phe Ser Ser Tyr Ala Met Thr
1               5

<210> SEQ ID NO 766
<211> LENGTH: 17
<212> TYPE: PRT
```

```
<213> ORGANISM: Artificial sequence
<220> FEATURE:
<223> OTHER INFORMATION: Synthetic polypeptide

<400> SEQUENCE: 766

Asp Met Asn His Ser Gly Asp Arg Thr Asn Tyr Ala Asp Ser Val Arg
1               5                   10                  15

Gly

<210> SEQ ID NO 767
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 767

Phe Ile Phe Ser Asp His Tyr Met Ala
1               5

<210> SEQ ID NO 768
<211> LENGTH: 19
<212> TYPE: PRT
<213> ORGANISM: Artificial sequence
<220> FEATURE:
<223> OTHER INFORMATION: Synthetic polypeptide

<400> SEQUENCE: 768

Arg Ser Arg Asn Arg Pro Asn Ser Tyr Thr Thr Glu Tyr Ala Ala Ser
1               5                   10                  15

Ala Lys Gly

<210> SEQ ID NO 769
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 769

Tyr Thr Phe Thr Gly Tyr Tyr Met His
1               5

<210> SEQ ID NO 770
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 770

Arg Ile Asn Pro Asn Ser Gly Gly Thr Asn Tyr Ala Gln Lys Phe Gln
1               5                   10                  15

Gly

<210> SEQ ID NO 771
<211> LENGTH: 19
<212> TYPE: PRT
<213> ORGANISM: Artificial sequence
<220> FEATURE:
<223> OTHER INFORMATION: Synthetic polypeptide

<400> SEQUENCE: 771

Arg Ile Arg Asn Lys Pro Asn Gly Tyr Thr Thr Glu Tyr Ala Ala Ser
1               5                   10                  15
```

Val Lys Gly

<210> SEQ ID NO 772
<211> LENGTH: 19
<212> TYPE: PRT
<213> ORGANISM: Artificial sequence
<220> FEATURE:
<223> OTHER INFORMATION: Synthetic polypeptide

<400> SEQUENCE: 772

Arg Ser Arg Asn Lys Pro Asn Ser Tyr Ile Thr Glu Tyr Ala Ala Ser
1               5                   10                  15

Val Lys Gly

<210> SEQ ID NO 773
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 773

Phe Ser Leu Ser Asn Thr Lys Leu Gly Val Ser
1               5                   10

<210> SEQ ID NO 774
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 774

His Ile Phe Ser Asn Ala Glu Lys Ser Ser Ser Lys Ser Leu Lys Ser
1               5                   10                  15

<210> SEQ ID NO 775
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 775

Leu Thr Phe Ser Thr Tyr Thr Leu His
1               5

<210> SEQ ID NO 776
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 776

Val Ile Ser Ser Asp Gly Gly Asn Lys Tyr Tyr Ala Asp Ser Val Lys
1               5                   10                  15

Gly

<210> SEQ ID NO 777
<211> LENGTH: 17
<212> TYPE: PRT
<213> ORGANISM: Artificial sequence
<220> FEATURE:
<223> OTHER INFORMATION: Synthetic polypeptide

```
<400> SEQUENCE: 777

Met Met Ser Tyr Asp Gly Gly Asp Lys Asn Tyr Ala Asp Ser Val Lys
1               5                   10                  15

Gly

<210> SEQ ID NO 778
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 778

Trp Ile Ser Thr Tyr Asn Gly Asn Thr Asn Tyr Ala Gln Lys Leu Gln
1               5                   10                  15

Gly

<210> SEQ ID NO 779
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 779

Phe Thr Phe Ser Asn Tyr Trp Met Asn
1               5

<210> SEQ ID NO 780
<211> LENGTH: 19
<212> TYPE: PRT
<213> ORGANISM: Artificial sequence
<220> FEATURE:
<223> OTHER INFORMATION: Synthetic polypeptide

<400> SEQUENCE: 780

Arg Ser Thr Asn Lys Pro Asn Ser Tyr Thr Thr Thr Tyr Ala Ala Ser
1               5                   10                  15

Val Arg Gly

<210> SEQ ID NO 781
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 781

Gly Ser Phe Ser Gly Tyr Tyr Trp Ser
1               5

<210> SEQ ID NO 782
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 782

Glu Ile Asn His Arg Gly Ser Thr Asp Tyr Asn Pro Ser Leu Lys Ser
1               5                   10                  15

<210> SEQ ID NO 783
```

```
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 783

Phe Thr Phe Ser His Ala Trp Met Thr
1               5

<210> SEQ ID NO 784
<211> LENGTH: 19
<212> TYPE: PRT
<213> ORGANISM: Artificial sequence
<220> FEATURE:
<223> OTHER INFORMATION: Synthetic polypeptide

<400> SEQUENCE: 784

Arg Ile Lys Ser Glu Thr Asp Gly Gly Thr Ala Asn Tyr Ala Ala Pro
1               5                   10                  15

Val Lys Gly

<210> SEQ ID NO 785
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 785

Gly Thr Phe Ser Ser Tyr Val Ile Ser
1               5

<210> SEQ ID NO 786
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 786

Gly Ile Ile Pro Ile Phe Gly Thr Pro Asn Tyr Ala Gln Lys Phe Gln
1               5                   10                  15

Gly

<210> SEQ ID NO 787
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 787

Phe Ile Phe Ser Ser Asn Ser Met His
1               5

<210> SEQ ID NO 788
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 788

Ile Ile Ser Asn Asp Gly Arg Asn Lys Phe Tyr Ala Asp Ala Val Lys
1               5                   10                  15
```

Gly

<210> SEQ ID NO 789
<211> LENGTH: 19
<212> TYPE: PRT
<213> ORGANISM: Artificial sequence
<220> FEATURE:
<223> OTHER INFORMATION: Synthetic polypeptide

<400> SEQUENCE: 789

Arg Thr Arg Asn Lys Ala Asn Ser Tyr Thr Thr Lys Tyr Ala Ala Ser
1               5                   10                  15

Val Lys Gly

<210> SEQ ID NO 790
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 790

Phe Ser Leu Ser Asn Thr Lys Met Gly Val Thr
1               5                   10

<210> SEQ ID NO 791
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 791

His Ile Phe Ser Asn Asp Glu Lys Ser Cys Asn Thr Ser Leu Lys Ser
1               5                   10                  15

<210> SEQ ID NO 792
<211> LENGTH: 19
<212> TYPE: PRT
<213> ORGANISM: Artificial sequence
<220> FEATURE:
<223> OTHER INFORMATION: Synthetic polypeptide

<400> SEQUENCE: 792

Arg Ser Arg Asn Lys Val Asn Ser Tyr Thr Thr Asp Tyr Ala Ala Ser
1               5                   10                  15

Val Lys Gly

<210> SEQ ID NO 793
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 793

Tyr Ile Tyr Tyr Ser Gly Ser Thr Asn Tyr Asn Pro Ser Leu Lys Ser
1               5                   10                  15

<210> SEQ ID NO 794
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 794

Phe Thr Phe Asp Asp Tyr Asp Met His
1               5

<210> SEQ ID NO 795
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 795

Gly Ile Ser Trp Asn Ser Gly Gly Arg Gly Tyr Ala Asp Ser Val Lys
1               5                   10                  15
Gly

<210> SEQ ID NO 796
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 796

Val Met Ser Tyr Asp Gly Ser Asn Lys Tyr Tyr Ala Asp Ser Leu Lys
1               5                   10                  15
Gly

<210> SEQ ID NO 797
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 797

Phe Asn Phe Ser Ser Tyr Gly Met His
1               5

<210> SEQ ID NO 798
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 798

Leu Thr Leu Ser Ser Ser Ala Met Ser
1               5

<210> SEQ ID NO 799
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 799

Gly Ile Thr Gly Ser Gly Ser Asp Ser Ser Tyr Ala Ala Ser Val Lys
1               5                   10                  15
Gly

<210> SEQ ID NO 800

```
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 800

Val Ile Ser Glu Asp Gly Asn Lys Asp His Tyr Val Asp Ser Val Lys
1               5                   10                  15

Gly

<210> SEQ ID NO 801
<211> LENGTH: 19
<212> TYPE: PRT
<213> ORGANISM: Artificial sequence
<220> FEATURE:
<223> OTHER INFORMATION: Synthetic polypeptide

<400> SEQUENCE: 801

Arg Ser Arg Asn Lys Val Asn Ser Tyr Ile Thr Glu Tyr Ala Ala Ser
1               5                   10                  15

Val Lys Gly

<210> SEQ ID NO 802
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 802

Phe Ile Phe Ser Asp His Tyr Met Asp
1               5

<210> SEQ ID NO 803
<211> LENGTH: 19
<212> TYPE: PRT
<213> ORGANISM: Artificial sequence
<220> FEATURE:
<223> OTHER INFORMATION: Synthetic polypeptide

<400> SEQUENCE: 803

Arg Ile Arg Asn Lys Pro Asn Ser Tyr Thr Thr Asp Tyr Ala Ala Tyr
1               5                   10                  15

Val Lys Gly

<210> SEQ ID NO 804
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 804

Phe Thr Leu Ser Ser Tyr Val Met His
1               5

<210> SEQ ID NO 805
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 805
```

```
Val Ile Ser Ser Asp Gly Thr Asn Lys Tyr Tyr Ala Asp Ser Val Lys
1               5                   10                  15

Gly

<210> SEQ ID NO 806
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 806

Gly Ser Ile Ser Ser Asp Asn Trp Trp Ser
1               5                   10

<210> SEQ ID NO 807
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 807

Tyr Thr Phe Thr Ser Tyr Ala Met His
1               5

<210> SEQ ID NO 808
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 808

Trp Ile Asn Ala Gly Asn Gly Asn Thr Lys Tyr Ser Gln Lys Phe Gln
1               5                   10                  15

Gly

<210> SEQ ID NO 809
<211> LENGTH: 19
<212> TYPE: PRT
<213> ORGANISM: Artificial sequence
<220> FEATURE:
<223> OTHER INFORMATION: Synthetic polypeptide

<400> SEQUENCE: 809

His Val Gly Asn Lys Ala Asn Thr Tyr Thr Thr Glu Tyr Ala Ala Ser
1               5                   10                  15

Val Lys Gly

<210> SEQ ID NO 810
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 810

Tyr Thr Phe Thr Ser Tyr Asp Ile Asn
1               5

<210> SEQ ID NO 811
<211> LENGTH: 17
<212> TYPE: PRT
<213> ORGANISM: Artificial sequence
```

```
<220> FEATURE:
<223> OTHER INFORMATION: Synthetic polypeptide

<400> SEQUENCE: 811

Trp Met Asn Pro Asn Ser Gly Asn Thr Gly Tyr Ala Gln Lys Phe Gln
1               5                   10                  15
Gly

<210> SEQ ID NO 812
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 812

Trp Ile Asn Pro Asn Ser Gly Gly Thr Asn Tyr Ala Gln Lys Phe Gln
1               5                   10                  15
Gly

<210> SEQ ID NO 813
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 813

Asp Ser Val Ser Thr Asn Ser Ala Ala Trp Asn
1               5                   10

<210> SEQ ID NO 814
<211> LENGTH: 18
<212> TYPE: PRT
<213> ORGANISM: Artificial sequence
<220> FEATURE:
<223> OTHER INFORMATION: Synthetic polypeptide

<400> SEQUENCE: 814

Arg Thr Tyr Tyr Arg Ser Lys Trp Tyr Asn Asp Tyr Ala Leu Ser Val
1               5                   10                  15
Lys Ser

<210> SEQ ID NO 815
<211> LENGTH: 19
<212> TYPE: PRT
<213> ORGANISM: Artificial sequence
<220> FEATURE:
<223> OTHER INFORMATION: Synthetic polypeptide

<400> SEQUENCE: 815

Arg Ala Arg Asn Arg Ala Asn Ser Tyr Thr Thr Glu Tyr Ala Ala Ser
1               5                   10                  15
Val Lys Gly

<210> SEQ ID NO 816
<211> LENGTH: 19
<212> TYPE: PRT
<213> ORGANISM: Artificial sequence
<220> FEATURE:
<223> OTHER INFORMATION: Synthetic polypeptide

<400> SEQUENCE: 816

Arg Ile Arg Asn Lys Val Asn Ser Tyr Thr Thr Glu Tyr Ala Ala Ser
```

```
1               5                   10                  15

Val Lys Gly

<210> SEQ ID NO 817
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 817

Asp Ser Ile Ser Ser Arg Ser Trp Trp Ser
1               5                   10

<210> SEQ ID NO 818
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 818

Glu Ile Tyr His Ser Gly Thr Thr Thr Tyr Ser Pro Ser Leu Lys Ser
1               5                   10                  15

<210> SEQ ID NO 819
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 819

Glu Ile Tyr His Ser Gly Ser Thr Asn Tyr Asn Pro Ser Leu Lys Ser
1               5                   10                  15

<210> SEQ ID NO 820
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 820

Tyr Thr Phe Thr Ser Tyr Ala Met Asn
1               5

<210> SEQ ID NO 821
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 821

Trp Ile Asn Thr Asn Thr Gly Asn Pro Thr Tyr Ala Gln Gly Phe Thr
1               5                   10                  15
Gly

<210> SEQ ID NO 822
<211> LENGTH: 9
<212> TYPE: PRT
<213> ORGANISM: Artificial sequence
<220> FEATURE:
<223> OTHER INFORMATION: Synthetic polypeptide
```

```
<400> SEQUENCE: 822

Phe Thr Phe Ser Tyr Ser Ala Ile His
1               5

<210> SEQ ID NO 823
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 823

Ala Ser Ile Ser Ser Asn Asn Trp Trp Ser
1               5                   10

<210> SEQ ID NO 824
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 824

Glu Ile Phe His Ser Gly Thr Thr Asn Tyr Asn Pro Ser Leu Lys Ser
1               5                   10                  15

<210> SEQ ID NO 825
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 825

Ile Ser Ile Ser Ser Ser Asn Trp Trp Ser
1               5                   10

<210> SEQ ID NO 826
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 826

Glu Val Tyr His Ser Gly Ser Thr Lys Tyr Asn Pro Ser Leu Lys Ser
1               5                   10                  15

<210> SEQ ID NO 827
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 827

Phe Thr Phe Ser Thr Ser Pro Leu His
1               5

<210> SEQ ID NO 828
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 828
```

Val Ser Ser Phe Val Ala Thr Asp Lys Tyr Tyr Ala Asp Ser Val Lys
1               5                   10                  15

Gly

<210> SEQ ID NO 829
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 829

Ser Ile Ser Ser Ser Ser Ser Tyr Ile Tyr Tyr Ala Asp Ser Val Lys
1               5                   10                  15

Gly

<210> SEQ ID NO 830
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 830

Val Ile Trp Tyr Asp Gly Ser Asn Lys Asn Tyr Ala Asp Ser Val Lys
1               5                   10                  15

Gly

<210> SEQ ID NO 831
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 831

Ala Ile Ser Ser Ser Gly Gly Ser Thr Tyr Tyr Ala Asp Ser Val Lys
1               5                   10                  15

Gly

<210> SEQ ID NO 832
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 832

Phe Ile Phe Ser Asn Tyr Trp Met Ser
1               5

<210> SEQ ID NO 833
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 833

Asn Ile Lys Pro Asp Gly Ser Glu Lys Tyr Tyr Val Glu Ser Val Arg
1               5                   10                  15

Gly

```
<210> SEQ ID NO 834
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 834

Phe Thr Phe Ser Ile Ser Gly Met His
1               5

<210> SEQ ID NO 835
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 835

Leu Ile Trp Tyr Asp Gly Thr Lys Lys Tyr Tyr Ala Asp Ser Val Lys
1               5                   10                  15

Gly

<210> SEQ ID NO 836
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 836

Phe Ser Phe Gly Asp Tyr Gly Met His
1               5

<210> SEQ ID NO 837
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 837

Val Ile Leu Phe Asp Gly Ser Lys Lys Phe Tyr Ala Asp Ser Val Arg
1               5                   10                  15

Gly

<210> SEQ ID NO 838
<211> LENGTH: 19
<212> TYPE: PRT
<213> ORGANISM: Artificial sequence
<220> FEATURE:
<223> OTHER INFORMATION: Synthetic polypeptide

<400> SEQUENCE: 838

Arg Thr Arg Asn Lys Ala Asn Ser Tyr Thr Thr Glu Tyr Ala Ala Ser
1               5                   10                  15

Val Lys Gly

<210> SEQ ID NO 839
<211> LENGTH: 9
<212> TYPE: PRT
<213> ORGANISM: Artificial sequence
<220> FEATURE:
<223> OTHER INFORMATION: Synthetic polypeptide
```

```
<400> SEQUENCE: 839

Phe Asn Leu Ile Asp Tyr Ala Met His
1               5

<210> SEQ ID NO 840
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 840

Gly Ile Ser Trp Asn Ser Arg Ser Ile Gly Tyr Ala Asp Ser Val Lys
1               5                   10                  15

Gly

<210> SEQ ID NO 841
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 841

Ser Gly Ser Ser Ser Asn Ile Gly Asn Asn Tyr Val Ser
1               5                   10

<210> SEQ ID NO 842
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 842

Asp Asn Lys Lys Arg Pro Ser
1               5

<210> SEQ ID NO 843
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 843

Arg Ala Ser Gln Ser Val Ser Ser Asn Leu Ala
1               5                   10

<210> SEQ ID NO 844
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 844

Asp Ala Ser Asn Arg Ala Thr
1               5

<210> SEQ ID NO 845
<211> LENGTH: 13
<212> TYPE: PRT
<213> ORGANISM: Artificial sequence
<220> FEATURE:
<223> OTHER INFORMATION: Synthetic polypeptide
```

<400> SEQUENCE: 845

Ser Gly Ser Arg Ser Asn Ile Gly Thr Tyr Thr Ile Asn
1               5                   10

<210> SEQ ID NO 846
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 846

Ser Asn Asn Arg Gly Pro Ser
1               5

<210> SEQ ID NO 847
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 847

Ser Gly Ser Ser Ser Asn Ile Gly Asn Asn Tyr Val Ala
1               5                   10

<210> SEQ ID NO 848
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 848

Arg Ala Ser Gln Thr Ile Ser Val Asp Leu Asn
1               5                   10

<210> SEQ ID NO 849
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 849

Ala Ala Ser Thr Leu Gln Ser
1               5

<210> SEQ ID NO 850
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 850

Arg Ala Ser Gln Ser Ile Gly Ser Asp Leu Asn
1               5                   10

<210> SEQ ID NO 851
<211> LENGTH: 7
<212> TYPE: PRT
<213> ORGANISM: Artificial sequence
<220> FEATURE:
<223> OTHER INFORMATION: Synthetic polypeptide

```
<400> SEQUENCE: 851

Ala Ala Thr Gly Leu Gln Ser
1               5

<210> SEQ ID NO 852
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 852

Ser Gly Ser Ser Ser Asn Ile Gly Thr Asn Thr Val Ser
1               5                   10

<210> SEQ ID NO 853
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 853

Ser Arg Thr Gln Arg Pro Ser
1               5

<210> SEQ ID NO 854
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 854

Ser Gly Ser Asn Ser Asn Ile Gly Asn Tyr Tyr Val Ser
1               5                   10

<210> SEQ ID NO 855
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 855

Asp Asn Asn Lys Arg Pro Ser
1               5

<210> SEQ ID NO 856
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 856

Ser Gly Ser Ser Ser Asn Ile Gly Asn Ser Tyr Val Ser
1               5                   10

<210> SEQ ID NO 857
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 857
```

```
Ser Gly Ser Ser Ser Asn Ile Gly Tyr Ser His Val Ser
1               5                   10

<210> SEQ ID NO 858
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 858

Asp Asn Asp Lys Arg Pro Ser
1               5

<210> SEQ ID NO 859
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 859

Thr Gly Thr Ser Ser Asp Val Gly Ala Tyr Asn Phe Val Ser
1               5                   10

<210> SEQ ID NO 860
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 860

Asp Val Asn Lys Arg Pro Ser
1               5

<210> SEQ ID NO 861
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 861

Ser Gly Ser Ser Ser Asn Ile Gly Ser Asn Tyr Val Ser
1               5                   10

<210> SEQ ID NO 862
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 862

Asp Asn Ser Lys Arg Pro Ser
1               5

<210> SEQ ID NO 863
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 863
```

Arg Ala Ser Arg Ser Val Ser Ser Asn Leu Ala
1               5                   10

<210> SEQ ID NO 864
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 864

Gly Ala Ser Thr Arg Ala Thr
1               5

<210> SEQ ID NO 865
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 865

Arg Ala Ser Gln Gly Ile Ser Ser Trp Leu Ala
1               5                   10

<210> SEQ ID NO 866
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 866

Ala Ala Ser Ser Leu Gln Ser
1               5

<210> SEQ ID NO 867
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 867

Thr Gly Thr Ser Ser Asp Val Gly Gly Tyr Asn Tyr Val Ser
1               5                   10

<210> SEQ ID NO 868
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 868

Asp Val Ser Asn Arg Pro Ser
1               5

<210> SEQ ID NO 869
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 869

Thr Gly Thr Ser Ser Asp Ile Gly Ala Tyr Asn Tyr Val Ser

```
1               5                  10

<210> SEQ ID NO 870
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 870

Asp Val Thr Asn Arg Pro Ser
1               5

<210> SEQ ID NO 871
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 871

Thr Gly Thr Gly Ser Asp Val Gly Gly Tyr Asn Phe Val Ser
1               5                  10

<210> SEQ ID NO 872
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 872

Asp Val Asn Asn Arg Pro Ser
1               5

<210> SEQ ID NO 873
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 873

Arg Ala Ser Gln Ser Ile Ser Ser Tyr Leu Asn
1               5                  10

<210> SEQ ID NO 874
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 874

Ala Ala Ser Ile Leu Gln Ser
1               5

<210> SEQ ID NO 875
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 875

Thr Gly Ser Ser Ser Asn Ile Gly Ala Gly Tyr Asp Val
1               5                  10
```

<210> SEQ ID NO 876
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 876

Gly Asn Ser Asn Arg Pro Ser
1               5

<210> SEQ ID NO 877
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 877

Arg Ala Ser Gln Ser Val Asn Ser Tyr Leu Val
1               5                   10

<210> SEQ ID NO 878
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 878

Arg Ala Ser Gln Ser Val Asn Arg Tyr Leu Ala
1               5                   10

<210> SEQ ID NO 879
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 879

Arg Ala Ser Gln Ser Val Ser Asn Tyr Leu Ala
1               5                   10

<210> SEQ ID NO 880
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 880

Asp Ala Ser Ser Arg Ala Thr
1               5

<210> SEQ ID NO 881
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 881

Thr Gly Thr Ser Ser Asp Ile Gly Gly Tyr Asn Tyr Val Ser
1               5                   10

<210> SEQ ID NO 882
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 882

Ser Gly Arg Ser Ser Asn Ile Gly Asn Ser Asp Val Ser
1               5                   10

<210> SEQ ID NO 883
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 883

Asp Asn Asp Glu Arg Pro Ser
1               5

<210> SEQ ID NO 884
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 884

Gln Ala Ser Gln Asp Ile Ser Asn Tyr Leu Asn
1               5                   10

<210> SEQ ID NO 885
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 885

Asp Ala Ser Asn Leu Glu Arg
1               5

<210> SEQ ID NO 886
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 886

Thr Gly Thr Ser Ser Asp Val Gly Gly Asp Lys Tyr Val Ser
1               5                   10

<210> SEQ ID NO 887
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 887

Glu Val Ser Asn Arg Pro Ser
1               5

```
<210> SEQ ID NO 888
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 888

Ser Gly Ser Ser Ser Asn Ile Gly Asn Tyr Tyr Val Ser
1               5                   10

<210> SEQ ID NO 889
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 889

Lys Ser Ser Gln Ser Val Leu Phe Gly Ser Asn Gln Lys Ser Cys Leu
1               5                   10                  15

Ala

<210> SEQ ID NO 890
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 890

Trp Ala Ser Thr Arg Glu Ser
1               5

<210> SEQ ID NO 891
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 891

Ser Gly Ser Ser Ser Asn Ile Gly Ser Asn Phe Val Ser
1               5                   10

<210> SEQ ID NO 892
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 892

Ser Gly Ser Ser Ser Asn Phe Gly Asn Asp Tyr Val Ser
1               5                   10

<210> SEQ ID NO 893
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 893

Ser Gly Ser Ser Ser Asn Ile Gly Asn Asp Tyr Val Ser
1               5                   10
```

```
<210> SEQ ID NO 894
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 894

Thr Gly Thr Ser Ser Asp Val Gly Gly Tyr Lys Tyr Val Ser
1               5                   10

<210> SEQ ID NO 895
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 895

Gln Ala Ser Gln Asp Ile Ser Asn Phe Leu Asn
1               5                   10

<210> SEQ ID NO 896
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 896

Asp Ala Ser Ser Leu Glu Thr
1               5

<210> SEQ ID NO 897
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 897

Arg Ala Ser Gln Asn Ile Asn Thr Tyr Leu Ala
1               5                   10

<210> SEQ ID NO 898
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 898

Arg Ala Ser Thr Leu Glu Ser
1               5

<210> SEQ ID NO 899
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 899

Arg Ala Ser Gln Gly Ile Ser Asn Tyr Leu Ala
1               5                   10
```

```
<210> SEQ ID NO 900
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 900

Ala Ala Ser Thr Leu Arg Ser
1               5

<210> SEQ ID NO 901
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 901

Arg Ala Ser Gln Ser Val Ser Ser Tyr Leu Ala
1               5                   10

<210> SEQ ID NO 902
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 902

Gly Ala Ser Asn Arg Ala Thr
1               5

<210> SEQ ID NO 903
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 903

Arg Ala Ser Ser Leu Glu Ser
1               5

<210> SEQ ID NO 904
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 904

Gly Gly His Asn Val Gly Ser Lys Ser Val His
1               5                   10

<210> SEQ ID NO 905
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 905

Asp Asp Ser Asp Arg Pro Ser
1               5

<210> SEQ ID NO 906
```

```
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 906

Gly Gly Asn Asn Ile Gly Ser Lys Ser Val His
1               5                   10

<210> SEQ ID NO 907
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 907

Ser Asn Ser Asp Arg Pro Ser
1               5

<210> SEQ ID NO 908
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 908

Glu Val Ser Lys Arg Pro Ser
1               5

<210> SEQ ID NO 909
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 909

Thr Gly Thr Ser Thr Asp Val Gly Gly Tyr Asn Tyr Val Ser
1               5                   10

<210> SEQ ID NO 910
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 910

Arg Ser Ser Gln Ser Leu Leu His Ser Asn Gly Tyr Asn Tyr Leu Asp
1               5                   10                  15

<210> SEQ ID NO 911
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 911

Leu Gly Ser Asn Arg Ala Ser
1               5

<210> SEQ ID NO 912
<211> LENGTH: 11
```

```
<212> TYPE: PRT
<213> ORGANISM: Artificial sequence
<220> FEATURE:
<223> OTHER INFORMATION: Synthetic polypeptide

<400> SEQUENCE: 912

Arg Ala Ser Gln Gly Ile Arg Asn Asp Leu Gly
1               5                   10

<210> SEQ ID NO 913
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 913

Arg Ala Ser Gln Ser Ile Ser Thr Trp Leu Ala
1               5                   10

<210> SEQ ID NO 914
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 914

Arg Ala Ser Gln Gly Ile Ser Ser Tyr Leu Ala
1               5                   10

<210> SEQ ID NO 915
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 915

Arg Ala Ser Gln Ser Val Ser Phe Asn Leu Ala
1               5                   10

<210> SEQ ID NO 916
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 916

Arg Ala Ser Thr Arg Ala Ala
1               5

<210> SEQ ID NO 917
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 917

Lys Ser Ser Gln Ser Val Leu Tyr Ser Ser Asn Asn Lys Asn Ser Leu
1               5                   10                  15

Ala

<210> SEQ ID NO 918
```

```
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 918

Arg Ala Ser Gln Ser Val Ser Ser Trp Leu Ala
1               5                   10

<210> SEQ ID NO 919
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 919

Ser Gly Asp Ala Leu Gln Tyr Val Tyr
1               5

<210> SEQ ID NO 920
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 920

Lys Asp Thr Glu Arg Pro Ser
1               5

<210> SEQ ID NO 921
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 921

Arg Ala Ser Arg Ser Val Ser Gly Asn Tyr Leu Ala
1               5                   10

<210> SEQ ID NO 922
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 922

Ala Ala Ser Ser Arg Ala Thr
1               5

<210> SEQ ID NO 923
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 923

Arg Ala Ser Gln Ser Ile Arg Ser Tyr Leu Asn
1               5                   10

<210> SEQ ID NO 924
<211> LENGTH: 11
```

```
<212> TYPE: PRT
<213> ORGANISM: Artificial sequence
<220> FEATURE:
<223> OTHER INFORMATION: Synthetic polypeptide

<400> SEQUENCE: 924

Arg Ala Ser Gln Ser Ile Ser Ser Trp Leu Ala
1               5                   10

<210> SEQ ID NO 925
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 925

Gln Ala Ser Ser Leu Glu Ser
1               5

<210> SEQ ID NO 926
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 926

Arg Ala Ser Gln Ser Ile Asn Asn Tyr Leu Asn
1               5                   10

<210> SEQ ID NO 927
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 927

Gly Ala Ser Thr Leu Gln Ser
1               5

<210> SEQ ID NO 928
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 928

Arg Ala Ser Gln Ser Val Ser Ser Tyr Leu Ala
1               5                   10

<210> SEQ ID NO 929
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 929

Gly Ala Ser Ser Arg Ala Thr
1               5

<210> SEQ ID NO 930
<211> LENGTH: 11
<212> TYPE: PRT
```

```
<213> ORGANISM: Artificial sequence
<220> FEATURE:
<223> OTHER INFORMATION: Synthetic polypeptide

<400> SEQUENCE: 930

Arg Ala Ser Gln Ser Ile Ser Asp Trp Leu Ala
1               5                   10

<210> SEQ ID NO 931
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 931

Arg Ala Ser Gly Leu Glu Ser
1               5

<210> SEQ ID NO 932
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 932

Lys Ala Ser Asn Leu Gln Ser
1               5

<210> SEQ ID NO 933
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 933

Arg Ala Ser Gln Ser Val Ser Ser Arg Tyr Leu Ala
1               5                   10

<210> SEQ ID NO 934
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 934

Asp Val Ser Lys Arg Pro Ser
1               5

<210> SEQ ID NO 935
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 935

Thr Arg Ser Ser Gly Ser Ile Ala Ser Asn Tyr Val Gln
1               5                   10

<210> SEQ ID NO 936
<211> LENGTH: 7
<212> TYPE: PRT
<213> ORGANISM: Artificial sequence
```

```
<220> FEATURE:
<223> OTHER INFORMATION: Synthetic polypeptide

<400> SEQUENCE: 936

Glu Asp Asn Gln Arg Pro Ser
1               5

<210> SEQ ID NO 937
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 937

Ser Gly Ser Ser Ser Asn Ile Gly Asn Asn Asp Val Ser
1               5                   10

<210> SEQ ID NO 938
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 938

Arg Ala Ser Gln Gly Ile Arg Asn Asp Leu Ala
1               5                   10

<210> SEQ ID NO 939
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 939

Arg Ala Ser Ser Leu Glu Thr
1               5

<210> SEQ ID NO 940
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 940

Arg Ala Ser Gln Asn Val Gly Gly Trp Leu Ala
1               5                   10

<210> SEQ ID NO 941
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 941

Gln Ala Ser Arg Leu Glu Asn
1               5

<210> SEQ ID NO 942
<211> LENGTH: 11
<212> TYPE: PRT
<213> ORGANISM: Artificial sequence
<220> FEATURE:
```

<223> OTHER INFORMATION: Synthetic polypeptide

<400> SEQUENCE: 942

Arg Ala Ser Gln Ser Ile Ser Gln Tyr Leu Asn
1               5                   10

<210> SEQ ID NO 943
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 943

Pro Ala Ser Ser Phe Gln Ser
1               5

<210> SEQ ID NO 944
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 944

Gly Gly Asn Tyr Ile Gly Gly Lys Ser Val His
1               5                   10

<210> SEQ ID NO 945
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 945

Asn Asp Asn Asp Arg Pro Ser
1               5

<210> SEQ ID NO 946
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 946

Arg Ala Ser Gln Arg Val Asn Ser Asn Leu Ala
1               5                   10

<210> SEQ ID NO 947
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 947

Arg Ala Ser Gln Ser Val Ser Ser Ser Phe Leu Ala
1               5                   10

<210> SEQ ID NO 948
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 948

Arg Ala Ser Gly Leu Glu Thr
1               5

<210> SEQ ID NO 949
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 949

Ser Gly Ser Ser Ser Asn Phe Gly Ser Asn Phe Val Tyr
1               5                   10

<210> SEQ ID NO 950
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 950

Arg Val Asn Gln Arg Pro Ser
1               5

<210> SEQ ID NO 951
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 951

Arg Ala Ser Gln Ser Val Ser Ser Ser Tyr Leu Ser
1               5                   10

<210> SEQ ID NO 952
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 952

Arg Ala Ser Gln Thr Ile Thr Arg Tyr Met Asn
1               5                   10

<210> SEQ ID NO 953
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 953

Ala Thr Ser Ser Leu Gln Ser
1               5

<210> SEQ ID NO 954
<211> LENGTH: 11
<212> TYPE: PRT
<213> ORGANISM: Artificial sequence
<220> FEATURE:
<223> OTHER INFORMATION: Synthetic polypeptide

```
<400> SEQUENCE: 954

Arg Ala Ser Gln Asp Ile Arg Lys Phe Leu Asn
1               5                   10

<210> SEQ ID NO 955
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 955

Gly Ala Ser Ser Leu Gln Ser
1               5

<210> SEQ ID NO 956
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 956

Ser Gly Asp Lys Leu Gly Tyr Thr Tyr Thr Cys
1               5                   10

<210> SEQ ID NO 957
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 957

Gln Asp Thr Lys Arg Pro Ser
1               5

<210> SEQ ID NO 958
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 958

Ala Gly Thr Arg Ser Asp Val Gly Gly Tyr Asn Phe Val Ser
1               5                   10

<210> SEQ ID NO 959
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 959

Glu Val Asn Lys Arg Pro Ser
1               5

<210> SEQ ID NO 960
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 960
```

Arg Thr Ser Gln Ser Val Ser Ser Phe Leu Ala
1               5                   10

<210> SEQ ID NO 961
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 961

Arg Ala Ser Gln Ser Val Ser Asp Trp Leu Ala
1               5                   10

<210> SEQ ID NO 962
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 962

Arg Ala Ser Ser Leu Gln Ser
1               5

<210> SEQ ID NO 963
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 963

Arg Ala Ser Gln Ser Val Ser Ser Asn Val Ala
1               5                   10

<210> SEQ ID NO 964
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 964

Ser Gly Asp Ala Leu Pro Lys Lys Tyr Val Tyr
1               5                   10

<210> SEQ ID NO 965
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 965

Glu Asp Arg Arg Gly Pro Ser
1               5

<210> SEQ ID NO 966
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 966

```
Lys Ser Ser Gln Ser Val Phe Tyr Ser Ser Asn Ser Gln Asn Tyr Leu
1               5                   10                  15
Ala
```

<210> SEQ ID NO 967
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 967

```
Arg Ala Ser Gln Ser Ile Ser Asn Trp Leu Ala
1               5                   10
```

<210> SEQ ID NO 968
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 968

```
Lys Ala Ser Arg Leu Glu Ser
1               5
```

<210> SEQ ID NO 969
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 969

```
Arg Ala Ser Gln Thr Ile Ser Ser Trp Leu Ala
1               5                   10
```

<210> SEQ ID NO 970
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 970

```
Ser Gly Asp Ala Leu Pro Lys Gln Tyr Gly Tyr
1               5                   10
```

<210> SEQ ID NO 971
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 971

```
Lys Asp Ser Glu Arg Pro Ser
1               5
```

<210> SEQ ID NO 972
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 972

```
Glu Val Thr Lys Arg Pro Ser
1               5

<210> SEQ ID NO 973
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 973

Ser Gly Asp Ala Leu Ser Lys Gln Tyr Ala Tyr
1               5                   10

<210> SEQ ID NO 974
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 974

Asp Val Ser Lys Leu Lys Thr
1               5

<210> SEQ ID NO 975
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 975

Arg Ala Ser Gln Ser Ile Ser Gly Trp Leu Ala
1               5                   10

<210> SEQ ID NO 976
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 976

Lys Ala Ser Ile Leu Glu Ser
1               5

<210> SEQ ID NO 977
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 977

Thr Gly Asn Ser Ser Asn Ile Gly Ala Gly Tyr Glu Val His
1               5                   10

<210> SEQ ID NO 978
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 978
```

Gly Asn Asn Asn Arg Pro Ser
1               5

<210> SEQ ID NO 979
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 979

Ser Gly Asp Ala Leu Pro Lys Gln Tyr Ala Tyr
1               5                   10

<210> SEQ ID NO 980
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 980

Arg Ala Ser Gln Ser Val Ser Asn Tyr Phe Ala
1               5                   10

<210> SEQ ID NO 981
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 981

Ser Gly Ser Asn Ser Asn Ile Gly Asn Asn Phe Val Ser
1               5                   10

<210> SEQ ID NO 982
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 982

Asp Asn Asn Glu Arg Pro Ser
1               5

<210> SEQ ID NO 983
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 983

Asp Ser Ser Asn Arg Ala Thr
1               5

<210> SEQ ID NO 984
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 984

Arg Ala Ser Gln Ser Val Thr Ser Lys Leu Ala

```
<210> SEQ ID NO 985
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 985

Arg Ser Ser Gln Ser Leu Leu His Ser Asn Gly Tyr Asn Ser Leu Asp
1               5                   10                  15

<210> SEQ ID NO 986
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 986

Ser Gly Ser Ser Ser Asn Ile Gly Ser Asn Thr Val His
1               5                   10

<210> SEQ ID NO 987
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 987

Ser Asn Asn Gln Arg Pro Ser
1               5

<210> SEQ ID NO 988
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 988

Asp Asp Asn Lys Arg Pro Ser
1               5

<210> SEQ ID NO 989
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 989

Thr Gly Ser Ser Ser Asp Ile Gly Ala Gly Tyr Asp Val His
1               5                   10

<210> SEQ ID NO 990
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 990

Gly Asn Thr Asn Arg Pro Ser
1               5
```

<210> SEQ ID NO 991
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 991

Lys Ser Ser Gln Ser Val Phe Phe Ser Ser Asp Asn Lys Asn Tyr Leu
1               5                   10                  15

Ala

<210> SEQ ID NO 992
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 992

Thr Arg Ser Ser Gly Ser Ile Ala Ser Thr Tyr Val Gln
1               5                   10

<210> SEQ ID NO 993
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 993

Glu Asp Asn Gln Arg Pro Pro
1               5

<210> SEQ ID NO 994
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 994

Thr Gly Thr Ser Ser Asp Phe Gly Gly Tyr Asn Tyr Val Ser
1               5                   10

<210> SEQ ID NO 995
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 995

Glu Val Ala Lys Arg Pro Ser
1               5

<210> SEQ ID NO 996
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 996

Arg Ala Ser Glu Ser Ile Ser Ile Tyr Leu Asn

```
1               5                   10
```

<210> SEQ ID NO 997
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 997

```
Ala Ala Ser Ser Leu Gln Arg
1               5
```

<210> SEQ ID NO 998
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 998

```
Thr Gly Thr Ser Ser Asp Val Gly Gly Phe Asn Tyr Val Ser
1               5                   10
```

<210> SEQ ID NO 999
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 999

```
Glu Val Asn Arg Arg Pro Ser
1               5
```

<210> SEQ ID NO 1000
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 1000

```
Arg Ser Ser Gln Ser Leu Val His Ser Asp Gly Asn Thr Tyr Leu Ser
1               5                   10                  15
```

<210> SEQ ID NO 1001
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 1001

```
Lys Ile Ser Asn Arg Phe Ser
1               5
```

<210> SEQ ID NO 1002
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 1002

```
Asp Ala Ser Asn Leu Glu Thr
1               5
```

```
<210> SEQ ID NO 1003
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 1003

Ser Gly Asp Lys Leu Gly Asp Lys Tyr Ala Cys
1               5                   10

<210> SEQ ID NO 1004
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 1004

Gln Asp Ser Lys Arg Pro Ser
1               5

<210> SEQ ID NO 1005
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 1005

Arg Ala Ser Gln Gly Ile Ser Asn Asn Leu Ala
1               5                   10

<210> SEQ ID NO 1006
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (5)..(5)
<223> OTHER INFORMATION: is S or T
<220> FEATURE:
<221> NAME/KEY: MISC_FEATURE
<222> LOCATION: (7)..(7)
<223> OTHER INFORMATION: is S or no amino acid
<220> FEATURE:
<221> NAME/KEY: MISC_FEATURE
<222> LOCATION: (8)..(8)
<223> OTHER INFORMATION: is L or P
<220> FEATURE:
<221> NAME/KEY: MISC_FEATURE
<222> LOCATION: (12)..(13)
<223> OTHER INFORMATION: is K, G, or R
<220> FEATURE:
<221> NAME/KEY: MISC_FEATURE
<222> LOCATION: (12)..(12)
<223> OTHER INFORMATION: is K, G, or R

<400> SEQUENCE: 1006

Gly Thr Trp Asp Xaa Ser Xaa Xaa Ser Ala Gly Xaa Val
1               5                   10

<210> SEQ ID NO 1007
<211> LENGTH: 14
<212> TYPE: PRT
<213> ORGANISM: Artificial Sequence
<220> FEATURE:
```

```
<223> OTHER INFORMATION: Synthetic polypeptide
<220> FEATURE:
<221> NAME/KEY: MISC_FEATURE
<222> LOCATION: (2)..(2)
<223> OTHER INFORMATION: is K or R
<220> FEATURE:
<221> NAME/KEY: MISC_FEATURE
<222> LOCATION: (3)..(3)
<223> OTHER INFORMATION: is Y, F, T, A, G, Y
<220> FEATURE:
<221> NAME/KEY: MISC_FEATURE
<222> LOCATION: (7)..(7)
<223> OTHER INFORMATION: is S, N, or R
<220> FEATURE:
<221> NAME/KEY: MISC_FEATURE
<222> LOCATION: (8)..(8)
<223> OTHER INFORMATION: is A or G
<220> FEATURE:
<221> NAME/KEY: MISC_FEATURE
<222> LOCATION: (11)..(11)
<223> OTHER INFORMATION: is W or Y
<220> FEATURE:
<221> NAME/KEY: MISC_FEATURE
<222> LOCATION: (12)..(12)
<223> OTHER INFORMATION: is F, L, I, A, or E
<220> FEATURE:
<221> NAME/KEY: MISC_FEATURE
<222> LOCATION: (13)..(13)
<223> OTHER INFORMATION: is D, E, or H
<220> FEATURE:
<221> NAME/KEY: MISC_FEATURE
<222> LOCATION: (14)..(14)
<223> OTHER INFORMATION: is Y, H, or S

<400> SEQUENCE: 1007

Ala Xaa Xaa Tyr Asp Ser Xaa Xaa Tyr Tyr Xaa Xaa Xaa Xaa
1               5                   10

<210> SEQ ID NO 1008
<211> LENGTH: 7
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: is D, E, or R
<220> FEATURE:
<221> NAME/KEY: MISC_FEATURE
<222> LOCATION: (3)..(3)
<223> OTHER INFORMATION: is S, T, N, or A
<220> FEATURE:
<221> NAME/KEY: MISC_FEATURE
<222> LOCATION: (4)..(4)
<223> OTHER INFORMATION: is N, K, or Q
<220> FEATURE:
<221> NAME/KEY: MISC_FEATURE
<222> LOCATION: (4)..(4)
<223> OTHER INFORMATION: is N, K, or Q

<400> SEQUENCE: 1008

Xaa Val Xaa Xaa Arg Pro Ser
1               5

<210> SEQ ID NO 1009
<211> LENGTH: 7
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: is R, Q, or K
```

```
<220> FEATURE:
<221> NAME/KEY: MISC_FEATURE
<222> LOCATION: (4)..(4)
<223> OTHER INFORMATION: is T, S, G, R, or I
<220> FEATURE:
<221> NAME/KEY: MISC_FEATURE
<222> LOCATION: (7)..(7)
<223> OTHER INFORMATION: is T or S

<400> SEQUENCE: 1009

Xaa Ala Ser Xaa Leu Glu Xaa
1               5

<210> SEQ ID NO 1010
<211> LENGTH: 16
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: is D, E, or S
<220> FEATURE:
<221> NAME/KEY: MISC_FEATURE
<222> LOCATION: (2)..(2)
<223> OTHER INFORMATION: is I or V
<220> FEATURE:
<221> NAME/KEY: MISC_FEATURE
<222> LOCATION: (3)..(3)
<223> OTHER INFORMATION: is F or Y
<220> FEATURE:
<221> NAME/KEY: MISC_FEATURE
<222> LOCATION: (5)..(5)
<223> OTHER INFORMATION: is X or T
<220> FEATURE:
<221> NAME/KEY: MISC_FEATURE
<222> LOCATION: (6)..(6)
<223> OTHER INFORMATION: is G or E
<220> FEATURE:
<221> NAME/KEY: MISC_FEATURE
<222> LOCATION: (7)..(7)
<223> OTHER INFORMATION: is S, G, or T
<220> FEATURE:
<221> NAME/KEY: MISC_FEATURE
<222> LOCATION: (8)..(8)
<223> OTHER INFORMATION: is T or A
<220> FEATURE:
<221> NAME/KEY: MISC_FEATURE
<222> LOCATION: (9)..(9)
<223> OTHER INFORMATION: is N, S, H, K, or T
<220> FEATURE:
<221> NAME/KEY: MISC_FEATURE
<222> LOCATION: (11)..(11)
<223> OTHER INFORMATION: is N or S
<220> FEATURE:
<221> NAME/KEY: MISC_FEATURE
<222> LOCATION: (13)..(13)
<223> OTHER INFORMATION: S or F
<220> FEATURE:
<221> NAME/KEY: MISC_FEATURE
<222> LOCATION: (14)..(14)
<223> OTHER INFORMATION: is L or V
<220> FEATURE:
<221> NAME/KEY: MISC_FEATURE
<222> LOCATION: (15)..(15)
<223> OTHER INFORMATION: K or E

<400> SEQUENCE: 1010

Xaa Xaa Xaa His Xaa Xaa Xaa Xaa Tyr Xaa Pro Xaa Xaa Xaa Ser
1               5                   10                  15

<210> SEQ ID NO 1011
<211> LENGTH: 17
<212> TYPE: PRT
```

```
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: is V or L
<220> FEATURE:
<221> NAME/KEY: MISC_FEATURE
<222> LOCATION: (2)..(2)
<223> OTHER INFORMATION: is I or M
<220> FEATURE:
<221> NAME/KEY: MISC_FEATURE
<222> LOCATION: (3)..(3)
<223> OTHER INFORMATION: is S, W, or L
<220> FEATURE:
<221> NAME/KEY: MISC_FEATURE
<222> LOCATION: (4)..(4)
<223> OTHER INFORMATION: is F or Y
<220> FEATURE:
<221> NAME/KEY: MISC_FEATURE
<222> LOCATION: (6)..(6)
<223> OTHER INFORMATION: is E or G
<220> FEATURE:
<221> NAME/KEY: MISC_FEATURE
<222> LOCATION: (7)..(7)
<223> OTHER INFORMATION: is S or T
<220> FEATURE:
<221> NAME/KEY: MISC_FEATURE
<222> LOCATION: (8)..(8)
<223> OTHER INFORMATION: is K, N, or Y
<220> FEATURE:
<221> NAME/KEY: MISC_FEATURE
<222> LOCATION: (10)..(10)
<223> OTHER INFORMATION: is F, W, or Y
<220> FEATURE:
<221> NAME/KEY: MISC_FEATURE
<222> LOCATION: (11)..(11)
<223> OTHER INFORMATION: is Y or F
<220> FEATURE:
<221> NAME/KEY: MISC_FEATURE
<222> LOCATION: (15)..(15)
<223> OTHER INFORMATION: is V or L
<220> FEATURE:
<221> NAME/KEY: MISC_FEATURE
<222> LOCATION: (16)..(16)
<223> OTHER INFORMATION: is K or R

<400> SEQUENCE: 1011

Xaa Xaa Xaa Xaa Asp Xaa Xaa Xaa Lys Xaa Xaa Ala Asp Ser Xaa Xaa
1               5                   10                  15

Gly

<210> SEQ ID NO 1012
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (4)..(4)
<223> OTHER INFORMATION: is N or S
<220> FEATURE:
<221> NAME/KEY: MISC_FEATURE
<222> LOCATION: (7)..(7)
<223> OTHER INFORMATION: is I or F
<220> FEATURE:
<221> NAME/KEY: MISC_FEATURE
<222> LOCATION: (9)..(9)
<223> OTHER INFORMATION: is S or N
<220> FEATURE:
<221> NAME/KEY: MISC_FEATURE
<222> LOCATION: (10)..(10)
<223> OTHER INFORMATION: is N, Y, S, or D
<220> FEATURE:
```

```
<221> NAME/KEY: MISC_FEATURE
<222> LOCATION: (11)..(11)
<223> OTHER INFORMATION: is Y, F, or D
<220> FEATURE:
<221> NAME/KEY: MISC_FEATURE
<222> LOCATION: (13)..(13)
<223> OTHER INFORMATION: is S or A

<400> SEQUENCE: 1012

Ser Gly Ser Xaa Ser Asn Xaa Gly Xaa Xaa Xaa Val Xaa
1               5                   10

<210> SEQ ID NO 1013
<211> LENGTH: 14
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: is A or T
<220> FEATURE:
<221> NAME/KEY: MISC_FEATURE
<222> LOCATION: (4)..(4)
<223> OTHER INFORMATION: is S, G, or R
<220> FEATURE:
<221> NAME/KEY: MISC_FEATURE
<222> LOCATION: (5)..(5)
<223> OTHER INFORMATION: is S or T
<220> FEATURE:
<221> NAME/KEY: MISC_FEATURE
<222> LOCATION: (7)..(7)
<223> OTHER INFORMATION: is V, F, or I
<220> FEATURE:
<221> NAME/KEY: MISC_FEATURE
<222> LOCATION: (9)..(9)
<223> OTHER INFORMATION: is G or A
<220> FEATURE:
<221> NAME/KEY: MISC_FEATURE
<222> LOCATION: (10)..(10)
<223> OTHER INFORMATION: is Y, D, or F
<220> FEATURE:
<221> NAME/KEY: MISC_FEATURE
<222> LOCATION: (11)..(11)
<223> OTHER INFORMATION: K or N
<220> FEATURE:
<221> NAME/KEY: MISC_FEATURE
<222> LOCATION: (12)..(12)
<223> OTHER INFORMATION: is Y or F

<400> SEQUENCE: 1013

Xaa Gly Thr Xaa Xaa Asp Xaa Gly Xaa Xaa Xaa Xaa Val Ser
1               5                   10

<210> SEQ ID NO 1014
<211> LENGTH: 9
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (2)..(2)
<223> OTHER INFORMATION: is I or T
<220> FEATURE:
<221> NAME/KEY: MISC_FEATURE
<222> LOCATION: (6)..(6)
<223> OTHER INFORMATION: is H or Y
<220> FEATURE:
<221> NAME/KEY: MISC_FEATURE
<222> LOCATION: (9)..(9)
<223> OTHER INFORMATION: is A or D

<400> SEQUENCE: 1014
```

```
Phe Xaa Phe Ser Asp Xaa Tyr Met Xaa
1               5
```